US008183011B2

(12) United States Patent
Inouye et al.

(10) Patent No.: US 8,183,011 B2
(45) Date of Patent: May 22, 2012

(54) RNA INTERFERASES AND METHODS OF USE THEREOF

(75) Inventors: Masayori Inouye, Piscataway, NJ (US); Junjie Zhang, Edison, NJ (US); Yong Long Zhang, Highland Park, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 1311 days.

(21) Appl. No.: 10/560,303

(22) PCT Filed: Jun. 14, 2004

(86) PCT No.: PCT/US2004/018571

§ 371 (c)(1),
(2), (4) Date: Mar. 29, 2007

(87) PCT Pub. No.: WO2004/113498

PCT Pub. Date: Dec. 29, 2004

(65) Prior Publication Data

US 2008/0058275 A1 Mar. 6, 2008

Related U.S. Application Data

(60) Provisional application No. 60/478,515, filed on Jun. 13, 2003, provisional application No. 60/543,693, filed on Feb. 11, 2004.

(51) Int. Cl.

| | |
|---|---|
| ***C12P 21/06*** | (2006.01) |
| ***C12P 21/04*** | (2006.01) |
| ***C12N 15/00*** | (2006.01) |
| *C07H 21/02* | (2006.01) |

(52) U.S. Cl. ...... 435/69.1; 435/71.1; 435/440; 536/23.1

(58) Field of Classification Search ........................ None
See application file for complete search history.

(56) References Cited

U.S. PATENT DOCUMENTS

| | | | |
|---|---|---|---|
| 2004/0220123 | A1 | 11/2004 | Norris et al. |
| 2005/0260585 | A1 | 11/2005 | Szpirer et al. |

OTHER PUBLICATIONS

Christensen and Gerdes in "RelE toxins from Bacteria and Archaea cleave mRNAs on translating ribosomes, which are rescued by tmRNA" Molecular Microbiology vol. 48, Issue 5, pp. 1389-1400, publishes online May 7, 2003.*

Christensen et al, "Toxin-antitoxin Loci as Stress-response-elements: ChpAk/MazF and ChpBK Cleave Translated RNAs and are Counteracted by tmRNA" (Journal of Molecular Biology, 2003, vol. 332, pp. 809-819).*

Zhang et al, "MazF Cleaves Cellular mRNAs Specifically at ACA to Block Protein Synthesis in *Escherichia coli*" (Molecular Cell, vol. 12, pp. 913-923, Oct. 2003).*

Zhang et al "Interference of mRNA Function by Sequence-specific Endoribonuclease PemK" (The Journal of Biological Chemistry, vol. 279, No. 20, pp. 20678-20684, May 14, 2004).*

Munoz-Gomez, A. J. et al., "Insights into the specificity of RNA cleavage by the *Escherichia coli* MazF toxin", FEBS Letters, No. 567, pp. 316-320.*

* cited by examiner

*Primary Examiner* — Nancy Vogel
*Assistant Examiner* — Catherine Hibbert
(74) *Attorney, Agent, or Firm* — Lowenstein Sandler PC

(57) ABSTRACT

The present invention is directed to the discovery of a novel family of enzymes designated herein as mRNA interferases that exhibit endoribonuclease activity. The novel finding of the present inventors, therefore, presents new applications for which mRNA interferase nucleic and amino acid sequences, and compositions thereof may be used to advantage. The invention also encompasses screening methods to identify compounds/agents capable of modulating mRNA interferase activity and methods for using such compounds/agents. Also provided is a kit comprising mRNA interferase nucleic and/or amino acid sequences, mRNA interferase activity compatible buffers, and instruction materials.

8 Claims, 52 Drawing Sheets

FIG. 1B

```
                                                   S
                                                   ▲
E.coli             1 -----MVSRYVPDMGDLIWVDFDPTKGSEQAGHRPAVVLSPFMYNNKTG-----MCLCVP
B.halodurans       1 --------MPVPDRGNLVYVDFNPQSGHDQAGTRPALVLSPKLFNKNTG-----FAVVCP
S.epidermidis      1 ----------MIRRGDVYLADLSPVQGSEQGGVRPVVIIQNDTGNKYSP-----TVIVAA
S.aureus           1 ----------MIRRGDVYLADLSPVQGSEQGGVRPVVIIQNDTGNKYSP-----TVIVAA
B.subtilis         1 ---------MIVKRGDVYFADLSPVVGSEQGGVRPVLVIQNDIGNRFSP-----TAIVAA
N.meningitidis     1 --------MYIPDKGDIIHLNFDPSSGKEIKGGRFALALSPKAFHRATG-----LVFACP
M.morganii         1 MRRRLVRRKSDMEKGEIWLVSLDPTAGHEQQGTPIVLIVTPAAFNRVTR-----LPVVVP
M.tuberculosis     1 ----------MMRRGEIWQVDLDPARGSEANNQRPAVVVSNDRANATATRLGRGVITVVP

                                                                G
                                                                ▲
E.coli            51 CTTQS--KGYPFEVVLS----GQERDGVALADQVKSIAWRARGATKKGTVAPEELQLIKA
B.halodurans      48 ITRQQ--KGYPFEIEIPP---GLPIEGVILTDQVKSLDWRARNFHIKGQAPEETVTDCLQ
S.epidermidis     46 ITDGINKAKIPTHVEIEKKKYKLDKDSVILLEQIPTLDK-KRLKEKLTFLSESKMIEVDN
S.aureus          46 ITGRINKAKIPTHVEIEKKKYKLDKDSVILLEQIRTLDK-KRLKEKLTYLSDDKMKEVDN
B.subtilis        47 ITAQIQKAKLPTHVEIDAKRYGFERDSVILLEQIRTIDK-QRLTDKITHLDDEMMDKVDE
N.meningitidis    48 ISQGNAAAARSSGMISTLLGAGTETQGNVHCHALKSLIWQIRKASFKETVPDYVLDDVLA
M.morganii        56 VTSGGN-FARTAGFAVSLDGAGIRTTGVVRCDQPPTILMKARGGKRLERVPETIMDDVLG
M.tuberculosis    51 VTSNIA-KVYPFQVLLSATTTGLQVDCKAQAEQIRSIAT-ERLLRPIGRVSAAELAQLDE

E.coli           105 KINVLIG-----------------------
B.halodurans     103 LIHTFLS-----------------------
S.epidermidis    105 ALDISLGLNNFDHHKS--------------
S.aureus         105 ALMISLGLNAVAQPEKLGVYYMYFSEINKILI
B.subtilis       106 ALQISLALIDF-------------------
N.meningitidis   108 RIGAVLFD----------------------
M.morganii       115 RLATILT-----------------------
M.tuberculosis   109 ALKLHLDLWS--------------------
```

FIG. 3B
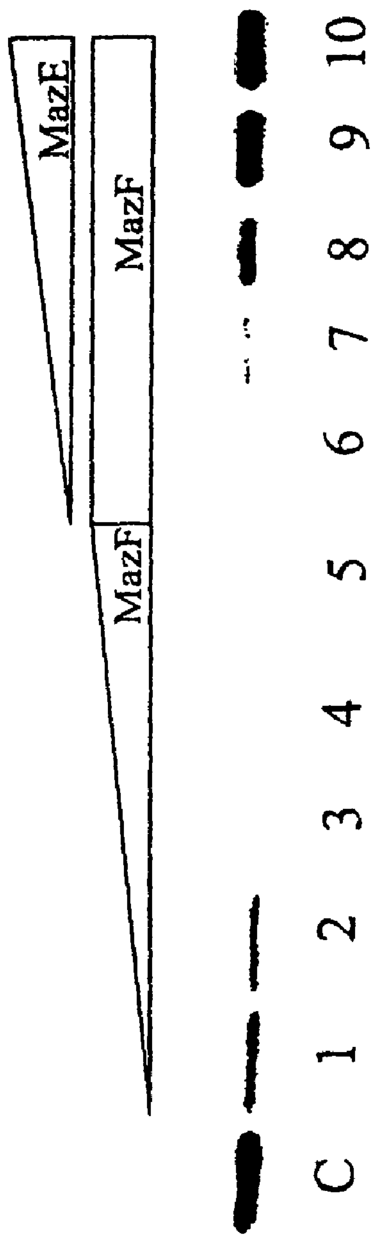
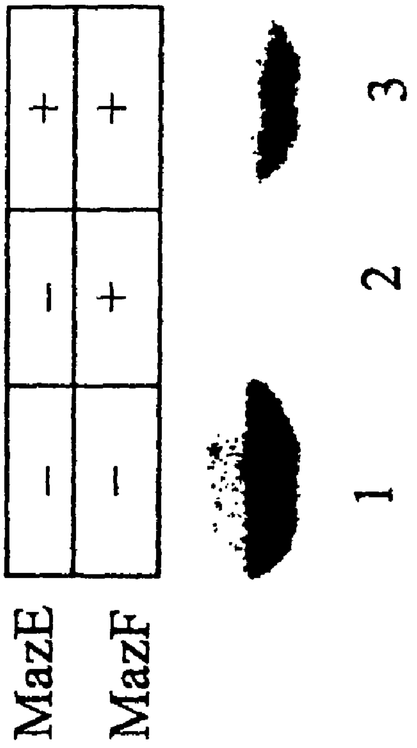
FIG. 3C

```
MazE_D.radiodurans    1 ------------MTSQIQKWGNSLALPIPKAIAQVGLTQSSEVELLIQS---DGQIVER
MazE_B.halodurans     1 ------------MTLMTTIQKWGNSLAVPIFNHYAKHINVTQGSEIELSLG--SDQTILK
PemI_R100             1 -----------MHTTRLKFVSGSVMLTVFPALLNALSLGTDNEVGMVIDNGRLIVEPYR
PemI_R446b            1 MLYLNITFMEGKMHTTRLKKVGGSVMLTVFPLLNALSLGTENEVGMVIDNGRLIVEPHR
MazE_E.coli           1 ------------MIHSSVKFRSHSPAVRFATMQANINIDDEVKIDVDGKLIEPVR
ChpB_E.coli           1 ------------MQMRITIKWGSAGMVEFNIVMKENLQPGQSVEAQVSNNQLILTPIS
MazE_P.putida         1 ------------MQIKIQQWGKSAAIRLEAAVIKQMRLGVGSTLSLDTTGETMVLKPVR
MazE_P.profundum      1 ------------AMRTQIRIGNSLGS-II-ATFIRQEL-EGAEIDVKT-DGKIVIEPI
consensus               m  stikrwgnslalrip  allq l l l  d ev lll        liv pir

                                                    N-Box

MazE_D.radiodurans   46 VPA-R-Q-DLAALLAEM-P-----ENLGE--TDWGA----SREEW-
MazE_B.halodurans    48 K-K-R--KPLEELVAKIT------ENRHE--IDFGR--T--ELL-
PemI_R100            49 R-P---QYSLAE-LAQCDPNAEISAEEREWLDAPA--TGQEEI-
PemI_R446b           61 R-P---QYSLAE-LAQCDPNAEISAEEREWLDAPA--AGQEEI-
MazE_E.coli          49 KEP---VFTLAELVNDITP-----ENLHENIDWGE--PKDKEVW
ChpB_E.coli          50 P----RYSLDE-LAQCDMN----AAELSEQDVWGKSTPAGDEIW
MazE_P.putida        48 SKP---KVTLEELMAQCLS----APEPEDMADWNAMRPVGREV-
MazE_P.profundum     44 -KMKKRFPFSRELLSGLDA----TAHAD--LVVISTQEL--E--
consensus               k p   yslaellaqcdp        e  re dw             eei

                                    Hp-Box
```

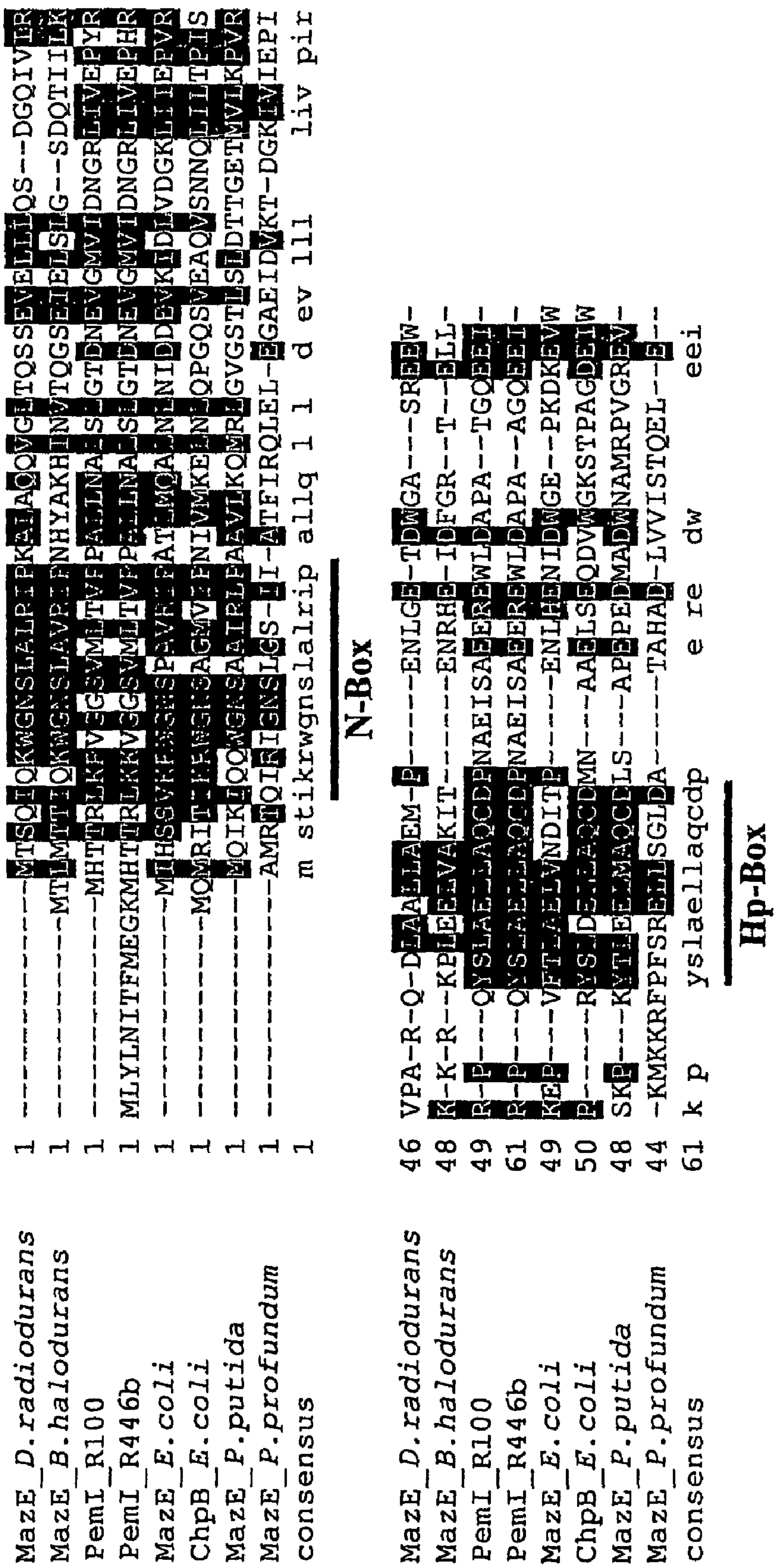

Nucleic acid sequence of *Escherichia coli MazF* gene (NP_289336.1)

atggta agccgatacg tacccgatat gggcgatctg atttgggttg attttgaccc gacaaaaggt agcgagcaag ctggacatcg tccagctgtt gtcctgagtc ctttcatgta caacaacaaa acaggtatgt gtctgtgtgt tccttgtaca acgcaatcaa aaggatatcc gttcgaagtt gttttatccg gtcaggaacg tgatggcgta gcgttagctg atcaggtaaa aagtatcgcc tggcgggcaa gaggagcaac gaagaaagga acagttgccc cagaggaatt acaactcatt aaagccaaaa ttaacgtact gattgggtag

FIG. 20B

Amino acid sequence of *Escherichia coli* MazF protein (NP_289336.1)

MVSRYVPDMG DLIWVDFDPT KGSEQAGHRP AVVLSPFMYN NKTGMCLCVP CTTQSKGYPF EVVLSGQERD GVALADQVKS IAWRARGATK KGTVAPEELQ LIKAKINVLI G

FIG. 21A

Nucleic acid sequence of *Escherichia coli MazE* gene atgatccacagtagcgtaaagcgttggggaaattcaccggcggtgcggatcccggctacgttaatgcaggcg
ctcaatctgaatattgatgatgaagtgaagattgacctggtggatggcaaattaattattgagccagtgcgt
aaagagcccgtatttacgcttgctgaactggtcaacgacatcacgccggaaaacctccacgagaatatcgac
tggggagagccgaaagataaggaagtctggtaa

FIG. 21B

Amino acid sequence of *Escherichia coli* MazE protein

MIHSSVKRWGNSPAVRIPATLMQALNLNIDDEVKIDLVDGKLIIEPVRKEPVFTLAELVN
DITPENLHENIDWGEPKDKEVW

FIG. 22A: Nucleic acid sequence of *Bacillus halodurans* MazF gene (SEQ ID NO: 39)

atgccagtac cggatagagg gaatcttgtt tatgtagact ttaacccaca atcgggtcat
gaccaagccg ggacacgacc ggctattgtt ttgtccccta aattatttaa taaaaacaca
ggttttgcgg tggtttgtcc aattaccaga caacaaaaag gttatccttt tgaaatagaa
ataccaccgg ggttacctat tgaaggggtt attcttactg accaagtaaa aagtctggat
tggagagcaa gaaactttca cattaaagga caagcaccag aggaaactgt tactgattgt
ttacaactta ttcatacatt tttatcttaa FIG. 22B: Nucleic acid sequence of *Staphylococcus epidermidis* MazF gene (SEQ ID NO: 40)

atgattagaag aggagatgtt tatttagcgg atttatcacc agttcaaggg tctgaacaag
ggggagtaag acctgtagtt atcattcaaa atgatactgg taataaatat agtccaactg
taattgtagc tgcgattact gatgggatta ataaagcgaa aataccaacc cacgtagaaa
ttgaaaagaa aaagtataaa ttagacaaag attcagttat tcttcttgaa caaattagaa
cactagataa aaagcgttta aaagaaaaat taacattttt atcagagagt aaaatgatag
aggttgataa tgccttagat attagtttgg gattaaataa ctttgatcat cataaatcttaa FIG. 22C: Nucleic acid sequence of *Staphylococcus aureus* MazF gene (SEQ ID NO: 41)

atgattagac gaggagatgt ttatttagca gatttatcac cagtacaggg atctgaacaa
gggggagtca gacctgtagt cataattcaa aatgatactg gtaataaata tagtcctaca
gttattgttg cggcaataac tggtaggatt aataaagcga aaataccgac acatgtagag
attgaaaaga aaaagtataa gttggataaa gactcagtta tattattaga acaaattcgt
acacttgata aaaaacgatt gaaagaaaaa ctgacgtact tatccgatga taaaatgaaa
gaagtagata atgcactaat gattagttta ggctgaatg cagtagctca accagaaaaa
ttaggcgtct attatatgta tttttcagag ataaataaaa tattgatataa FIG. 22D: Nucleic acid sequence of *Bacillus subtilis* MazF gene (SEQ ID NO: 42)

ttgattgtgaa acgcggcgat gtttattttg ctgatttatc tcctgttgtt ggctcagagc
aaggcggggt gcgcccggtt ttagtgatcc aaaatgacat cggaaatcgc ttcagcccaa
ctgctattgt tgcagccata acagcacaaa tacagaaagc gaaattacca acccacgtcg
aaatcgatgc aaaacgctac ggttttgaaa gagattccgt tattttgctg gagcaaattc
ggacgattga caagcaaagg ttaacggata agattactca tctggatgat gaaatgatgg
ataaggttga tgaagcctta caaatcagtt tggcactcat tgattttttag FIG. 22E: Nucleic acid sequence of *Neisseria meningitides* MC58 MazF gene (SEQ ID NO: 43)

atggat atggtagtac gcggcggaat ctatctggtc tccttagacc cgaccgtagg aagcgaaatc
aaaaagacac gtccttgtgt cgtagtctct cctcctgaaa tacacaacta tctcaagact
gtgctgatcg ttcccatgac gagcggaagc cgtcctgccc cgttccgcgt caatgtccgc
tttcaggata aagacggttt gcttttgccc gaacagatta gggctgtgga taaagccgga
ttggtcaaac atcttggcaa tttagacaac agtacggctg aaaaactgtt tgcagtattg
caggagatgt ttgcctga FIG. 22F: Nucleic acid sequence of *Morganella morgani* MazF gene (SEQ ID NO: 44)

atgcgccgg cggctggtca ggaggaaatc tgacatggaa agaggggaaa tctggcttgt
ctcgcttgac cctaccgcag gtcatgagca gcagggaacg cggccggtac tgattgtcac
gccggctgct tttaaccgcg tgacccgcct gcctgttgtt gtgcccgtga ccagcggagg
taattttgcc cgcacagcag gctttgctgt gtcgcttgac ggcgccggca tacgtaccac
cggcgttgtg cgttgcgatc aaccccggac gatcgatatg aaagcccgcg gcggcaaacg
actcgaacgg gtgccagaga ctatcatgga cgacgttctt ggccgtctgg ccaccatcct
gacctga FIG. 22G: Nucleic acid sequence of *Mycobacterium tuberculosis* MazF gene (SEQ ID NO: 45)

gtggtgattc ggggagcggt ctacagggtc gacttcggcg atgcgaagcg aggccacgag
caacgcgggc ggcgctacgc cgtggtcatc agccccggct cgatgccgtg gagtgtagta
accgtggtgc cgacgtcgac aagcgcccaa cctgcggttt tccgaccaga gctggaagtc
atgggaacaa agacacggtt cctggtggat cagatccgga cgatcggcat cgtctatgtg
cacggcgatc cggtcgacta tctggaccgt gaccaaatgg ccaaggtgga acacgccgtg
gcacgatacc ttggtctgtga FIG. 22H: Nucleic acid sequence of *Bacillus anthracis* MazF gene (SEQ ID NO: 79)

tt gattgtaaaa cgcggcgacg tgtattttgc agacctttcc ccagttgttg
gttctgagca aggaggtgtt cgtccggttc ttgtcattca aaatgacatc ggaaatcgtt
ttagtccaac ggtgattgta gcggctatta ctgcacagat tcaaaaagcg aaattaccca
ctcatgtgga aattgatgcg aaaaagtacg gttttgagag agattctgtt attttacttg
agcagattcg aacaatcgat aagcagcgct taacggacaa aatcactcac ttagatgaag
tgatgatgat tcgtgtagat gaagcgctac aaattagttt aggactaata gatttttaa FIG. 23A: Amino acid sequence of *Bacillus halodurans* MazF (NP_244588.1)(SEQ ID NO: 46)

MPVPDRGNLV YVDFNPQSGH DQAGTRPAIV LSPKLFNKNT GFAVVCPITR QQKGYPFEIE
IPPGLPIEGV ILTDQVKSLD WRARNFHIKG QAPEETVTDC LQLIHTFLS

FIG. 23B: Amino acid sequence of *Staphylococcus epidermidis* MazF (AAG23809.1) (SEQ ID NO: 47)

MIRRGDVYLA DLSPVQGSEQ GGVRPVVIIQ NDTGNKYSPT VIVAAITDGI NKAKIPTHVE
IEKKKYKLDK DSVILLEQIR TLDKKRLKEK LTFLSESKMI EVDNALDISL GLNNFDHHKS

FIG. 23C: Amino acid sequence of *Staphylococcus aureus* MazF (NP_372592.1) (SEQ ID NO: 48)

MIRRGDVYLA DLSPVQGSEQ GGVRPVVIIQ NDTGNKYSPT VIVAAITGRI NKAKIPTHVE
IEKKKYKLDK DSVILLEQIR TLDKKRLKEK LTYLSDDKMK EVDNALMISL GLNAVAQPEK
LGVYYMYFSE INKILI

FIG. 23D: Amino acid sequence of *Bacillus subtilis* (1NE8_A) MazF (SEQ ID NO: 49)

MIVKRGDVYF ADLSPVVGSE QGGVRPVLVI QNDIGNRFSP TAIVAAITAQ IQKAKLPTHV
EIDAKRYGFE RDSVILLEQI RTIDKQRLTD KITHLDDEMM DKVDEALQIS LALIDF

FIG. 23E: Amino acid sequence of *Neisseria meningitides* MC58 MazF (NP_266040.1) (SEQ ID NO: 50)

MYIPDKGDIF HLNFDPSSGK EIKGGRFALA LSPKAFNRAT GLVFACPISQ GNAAAARSSG
MISTLLGAGT ETQGNVHCHQ LKSLDWQIRK ASFKETVPDY VLDDVLARIG AVLFD

FIG. 23F: Amino acid sequence of *Morganella morgani* MazF (AAC82516.1) (SEQ ID NO: 51)

MRRRLVRRKS DMERGEIWLV SLDPTAGHEQ QGTRPVLIVT PAAFNRVTRL PVVVPVTSGG
NFARTAGFAV SLDGAGIRTT GVVRCDQPRT IDMKARGGKR LERVPETIMD DVLGRLATILT

FIG. 23G: Amino acid sequence of *Mycobacterium tuberculosis* MazF (NP_217317.1) (SEQ ID NO: 52)

MMRRGEIWQV DLDPARGSEA NNQRPAVVVS NDRANATATR LGRGVITVVP VTSNIAKVYP
FQVLLSATTT GLQVDCKAQA EQIRSIATER LLRPIGRVSA AELAQLDEAL KLHLDLWS

FIG. 23H: Amino acid sequence of *Bacillus anthracis* MazF (NP 842807) (SEQ ID NO: 80)

MIVKRGDVYF ADLSPVVGSE QGGVRPVLVI QNDIGNRFSP TVIVAAITAQ IQKAKLPTHV
EIDAKKYGFE RDSVILLEQI RTIDKQRLTD KITHLDEVMM IRVDEALQIS LGLIDF

FIG. 24A: Nucleic acid sequence of *Deinococcus radiodurans mazE* gene (SEQ ID NO: 53)

atgacgagtcaaattcagaaatggggcaacagcctcgcgctccgcattcccaaagctctggcgcagcaggtg
ggactgacgcagagttcagaagtggagctgcttcttcaggacggtcagattgtcatccggccagttcctgct
cggcagtacgatctcgccgcgctgctggccgaaatgacacctgaaaatctgcatggggaaacagactggggc
gcactggaaggacgcgaggaatggtaa FIG. 24B: Nucleic acid sequence of *Bacillus halodurans mazE* gene (SEQ ID NO: 54)

gtgacactcatgactactatacaaaagtggggaaatagtttagctgttcgtattccgaaccattatgctaaa
catattaacgttacgcaaggatctgaaattgaactaagcttagggagtgatcaaacgattattttaaagcct
aaaaaaagaaagccaacattagaggaattagtggcaaaaatcactcctgaaaacagacataacgaaattgat
ttcgggagaacaggaaaggaattgttgtaa FIG. 24C: Nucleic acid sequence of Plasmid R100 *pemI* gene (SEQ ID NO: 55)

atgcataccacccgactgaagagggttggcggctcagttatgctgaccgtcccaccggcactgctgaatgcg
ctgtctctgggcacagataatgaagttggcatggtcattgataatggccggctgattgttgagccgtacaga
cgcccgcaatattcactggctgagctactggcacagtgtgatccgaatgctgaaatatcagctgaagaacga
gaatggctggatgcaccggcgactggtcaggaggaaatctga FIG. 24D: Nucleic acid sequence of Plasmid R466b *pemI* gene (SEQ ID NO: 56)

atgttatatttaaatataactttttatggagggaaaaatgcataccactcgactgaagaaggttggcggctca
gtcatgctgaccgtcccaccggcactgctgaatgcgctgtcgctgggtacagataatgaagttggcatggtc
attgataatggccggctgattgtggagccgcacagacgcccgcagtattcactggctgagctgttggcacag
tgcgatccgaacgctgaaatctcggcagaagaacgtgaatggctggatgcgccggcggctggtcaggaggaa
atctga FIG. 24E: Nucleic acid sequence of *Escherichia coli chps* gene (SEQ ID NO: 57)

gtgcagatgcgtattaccataaaaagatggggaacagtgcaggtatggtcattcccaatatcgtaatgaaa
gaacttaacttacagccggggcagagcgtggaagtgcaggtgagcaacaaccaactgattctgacacccatc
tccaggcgctactcgcttgatgaactgctggcacagtgtgacatgaacgccgcggaacttagcgagcaggat
gtctggggtaaatccacccctgcgggtgacgaaatatggtaa FIG. 24F: Nucleic acid sequence of *Pseudomonas putida* KT2440 *mazE* gene (SEQ ID NO: 58)

atgcagatcaagattcaacagtggggcaacagcgccgcgatccgcttgcccgccgcagtactcaagcagatg
cgcctcggtgtcggctccaccctgagccttgacacaacgggtgagacgatggtgctcaaacccgtcaggtcg
aaacccaagtacacccttgaggaactgatggcccagtgtgacctgagtgcaccggagccagaggacatggcc
gactggaatgccatgcgcccagtggggcgtgaagtgtga FIG. 24G: Nucleic acid sequence of *Photobacterium profundum mazE* gene (SEQ ID NO: 59)

gtgcaatgagaactcagataagaaagatcggtaactcacttggttcaattattcctgccacttttattcgtc
agcttgaactggcagagggcgcagaaattgatgttaaaacggttgatggaaaaattgtgattgagccaatta
gaaaaatgaaaaaacgtttcccattcagtgagcgtgaattactaagtggattggatgcacacactgctcatg
ctgacgaactggttgtaatttctacccaggagctaggcgaataa FIG. 25A: Amino acid sequence of *Deinococcus radiodurans* MazE (GenBank Accession No. NP_294139) (SEQ ID NO: 60)

MTSQIQKWGN SLALRIPKAL AQQVGLTQSS EVELLLQDGQ IVIRPVPARQ YDLAALLAEM
TPENLHGETD WGALEGREEW

FIG. 25B: Amino acid sequence of *Bacillus halodurans* MazE (GenBank Accession No. NP_244587)(SEQ ID NO: 61)

MTLMTTIQKW GNSLAVRIPN HYAKHINVTQ GSEIELSLGS DQTIILKPKK RKPTLEELVA
KITPENRHNE IDFGRTGKEL L

FIG. 25C: Amino acid sequence of PemI plasmid R100 (GenBank Accession No. NP_052993) (SEQ ID NO: 62)

MHTTRLKRVG GSVMLTVPPA LLNALSLGTD NEVGMVIDNG RLIVEPYRRP QYSLAELLAQ
CDPNAEISAE EREWLDAPAT GQEEI

FIG. 25D: Amino acid sequence of PemI plasmid R466b (GenBank Accession No. AAC82515) (SEQ ID NO: 63)

MLYLNITFME GKMHTTRLKK VGGSVMLTVP PALLNALSLG TDNEVGMVID NGRLIVEPHR
RPQYSLAELL AQCDPNAEIS AEEREWLDAP AAGQEEI

FIG. 25E: Amino acid sequence of *Escherichia coli* ChpS (GenBank Accession No. NP_290856) (SEQ ID NO: 64)

MQMRITIKRW GNSAGMVIPN IVMKELNLQP GQSVEAQVSN NQLILTPISR RYSLDELLAQ
CDMNAAELSE QDVWGKSTPA GDEIW

FIG. 25F: Amino acid sequence of *Pseudomonas putida* MazE KT2440 (GenBank Accession No. NP_742931) (SEQ ID NO: 65)

MQIKIQQWGN SAAIRLPAAV LKQMRLGVGS TLSLDTTGET MVLKPVRSKP KYTLEELMAQ
CDLSAPEPED MADWNAMRPV GREV

FIG. 25G: Amino acid sequence of *Photobacterium profundum* MazE (GenBank Accession No. AAG34554) (SEQ ID NO: 66)

AMRTQIRKIG NSLGSIIPAT FIRQLELAEG AEIDVKTVDG KIVIEPIRKM KKRFPFSERE
LLSGLDAHTA HADELVVIST QELGE

```
atggaaagag gggaaatctg gcttgtctcg cttgatccta
ccgcaggtca tgagcagcag ggaacgcggc cggtgctgat
tgtcacaccg gcggccttta atcgcgtgac ccgcctgcct
gttgttgtgc ccgtaaccag cggaggcaat tttgcccgca
ctgccggctt tgcggtgtcg ttggatggtg ttggcatacg
taccacaggt gttgtacgtt gcgatcaacc ccggacaatt
gatatgaaag cacggggcgg aaaacgactc gaacgggttc
cggagactat catgaacgaa gttcttggcc gcctgtccac
tattctgact tga
```

FIG. 31A

```
MERGEIWLVS LDPTAGHEQ QGTRPVLIVT PAAFNRVTRL
PVVVPVTSGG NFARTAGFAV SLDGVGIRTT GVVRCDQPRT
IDMKARGGKR LERVPETIMN EVLGRLSTILT
```

FIG. 31B atgcatacca cccgactgaa gagggttggc ggctcagtta
tgctgaccgt cccaccggca ctgctgaatg cgctgtctct
gggcacagat aatgaagttg gcatggtcat tgataatggc
cggctgattg ttgagccgta cagacgcccg caatattcac
tggctgagct actggcacag tgtgatccga atgctgaaat
atcagctgaa gaacgagaat ggctggatgc accggcgact
ggtcaggagg aaatctga

FIG. 32A

MHTTRLKRVG GSVMLTVPPA LLNALSLGTD NEVGMVIDNG
RLIVEPYRRP GYSLAELLAQ CDPNAEISAE EREWLDAPAT
GQEEI

FIG. 32B

```
PemKR100_E.coli    1  -------MERGEIWLVSLDPTAGHEQQG-TRPVLIVTPAAFNRVTRLPVVVPVTSGGNFARTAGFAVSLDGVGIRT---TG
PemK_M.celatum     1  ------MTERGDIYLVSLDPTSGHEQSG-TRPVLVVSPGAFNRLTKTPVVLPITRGGNFARTAGFAVSLTDAGTRT---AG
PemK_P.putida      1  -MKRLKFARGDIVRVNLDPTVGREQQGSGRPALVLTPAAFN-ASGLAVTIIPITQGGDFARHAGFAVTLSGAGTQT---QG
ChpBK_E.coli       1  MVKKSEFERGDIVLVGFDPASGHEQQGAGRPALVLSVQAFN-QLGMTLVAPITQGGNFARYAGFSVPLHCEEGDV---HG
PemK_S.flexneri    1  MVKARTPHRGEIWYFNPDPVAGHELQG-PHYCIVVTDKKLNNVLKVAMCCPISTGANAARSTGVTVNVLPRDTQTGNLHG
MazF_E.coli        1  MVSRYVPDMGDLIWVDFDPTKGSEQAG-HRPAVVLSPFMYNNKTGMCLCVPCTTQ-----SKGYPFEVVLSGQER---DG

PemKR100_E.coli   71  VVRCDQPRTIDMKARGGKRLERVPETIMNEVLGRLSTILT--
PemK_M.celatum    72  VIRCDQPRSIDIRARKGRKVERVPSGVLDEALAKLATILT--
PemK_P.putida     76  VMLCNQVRTVDLEARFAKRIESVPEAVILDALARVQTLFD--
ChpBK_E.coli      77  VVLVNQVRMMDLHARLAKRIGLAADEVVEEALLRLQAVVE--
PemK_S.flexneri   80  VVLCHQLKAVDLIARGAKFHTVADEKLISEVISKLVNLIDPQ
MazF_E.coli       72  VALADQVKSIAWRARGATKKGTVAPEELQLIKAKINVLIG--
```

FIG. 34

Human Eotaxin Sequence

```
    G   P   A   S   V   P   T   T   C   C   F   N   L   A
AUG GGU CCA GCA UCU GUU CCG ACU ACC UGU UGC UUU AAC CUG GCG

 N   R   K   I   P   L   Q   R   L   E   S   Y   R   R   I
AAC CGC AAA AUU CCG CUG CAG CGC CUG GAA AGC UAU CGC CGU AUU

 T   S   G   K   C   P   Q   K   A   V   I   F   K   T   K
ACC UCU GGC AAA UGC CCG CAG AAA GCG GUG AUC UUU AAA ACC AAA

 L   A   K   D   I   C   A   D   P   K   K   K   W   V   Q
CUG GCG AAA GAU AUU UGC GCG GAU CCG AAA AAA AAA UGG GUG CAG

 D   S   M   K   Y   L   D   Q   K   S   P   T   P   K   P
GAU UCU AUG AAA UAU CUG GAU CAG AAA UCU CCG ACC CCG AAA CCG

UAA
```

FIG. 35

Thrombin

MGSSHHHHHHSSGLVPRGSH(MazF)

FIG.41A

```
Rv0456A      1  ------MLRGEIWQVDLDPARGSAANMRRPAVIVSNDRANAAAIRLDRGV
Rv2801c      1  -----MMRRGEIWQVDLDPARGSEANNQRPAVVVSNDRANATATRLGRGV
MazF         1  MVSRYVPDMGDLIWVDFDPTKGSEQAGHRPAVVLSPFMYNN-----KTGM
Rv1991c      1  ----MVISRAEIYWADLGPPSGSQPAKRRPVLVIQSDPYNAS----RLAT
Rv0659c      1  ------MRRGELWFAAT-------PGGDRPVLVLTRDPVAD-----RIGA
Rv1942c      1  --MTALPARGEVWWCEMA------EIGRRPVVVLSRDAAIP-----RLRR
consensus    1  --   l  rgevww em         grRPvvvls d a  -----rl

Rv0456A     45  VPVVPVTSNTEKVPIPGVVAGSERWPGRRFEGAGPAGWIRRCATSPLPS-
Rv2801c     46  ITVVPVTSNIAKV-YPFQVLLSATTTGLQVDCKAQAEQIRSIATERLLRP
MazF        46  CLCVPCTTQSKGY--PFEVVLS----GQERDGVALADQVKSIAWRARGAT
Rv1991c     43  VIAAVITSNTALAAMPGNVFLPATTTRLPRDSVVNVTAIVTLNKTDLTDR
Rv0659c     33  VVVVALTRTRRGLVSELELTAVEN--RVPSDCVVNFDNIHTLPRTAFRRR
Rv1942c     38  ALVAPCTTTIRGLASEVVLEPGSD--PIPRRSAVNLDSVESVSVAVLVNR
consensus   51   lv p Tt  rgl     l   s -- ipr   vn d v svs   l  r

Rv0456A         ------------------------
Rv2801c     95  IGRVSAAELAQLDEALKLHLDLWS
MazF        90  KKGTVAPEELQLIKAKINVLIG--
Rv1991c     93  VGEVPASLMHEVDRGLRRVLDL--
Rv0659c     81  ITRLSPARLHEACQTLRASTGC--
Rv1942c     86  LGRLADIRMRAICTALEVAVDCSR
consensus  101  lgrla   mr i  al   vd
```

FIG.41B

```
B.subtilis     1  ----MIVKRGDVYFADLSPVVGSEQGGVRPVLVIQNDIGNRFSPTAIVAA
B.anthracis    1  ----MIVKRGDVYFADLSPVVGSEQGGVRPVLVIQNDIGNRFSPTVIVAA
S.aureus       1  -----MIRRGDVYLADLSPVQGSEQGGVRPVVIIQNDTGNKYSPTVIVAA
E.coli         1  MVSRYVPDMGDLIWVDFDPTKGSEQAGHRPAVVLSPFMYN--NKTGMCLC
consensus      1       v   GDl w D  P  GSEQaG RP vvl   m N    Tgm

B.subtilis    47  ITAQIQKAKLPTHVEIDAKRYGFERDSVILLEQIRTIDK-QRLTDKITHL
B.anthracis   47  ITAQIQKAKLPTHVEIDAKKYGFERDSVILLEQIRTIDK-QRLTDKITHL
S.aureus      46  ITGRINKAKIPTHVEIEKKKYKLDKDSVILLEQIRTLDK-KRLKEKLTYL
E.coli        49  VPCTTQSKGYPFEVVLS----GQERDGVALADQVKSIAWRARGATKKGTV
consensus     51  v    q    P  V l     g erD V L dQvksi    R   K   v

B.subtilis    96  DDEMMDKVDEALQISLALIDF---------------------
B.anthracis   96  DEVMMIRVDEALQISLGLIDF---------------------
S.aureus      95  SDDKMKEVDNALMISLGLNAVAQPEKLGVYYMYFSEINKILI
E.coli        95  APEELQLIKAKINVLIG-------------------------
consensus    101  a e l  i   inv ig    ---------------------
```

```
 M   V   S   R   Y   V   P   D   M   G   D   L   I   W   V   D   F   D   P   T
AUG GUA AGC CGA UAC GUA CCC GAU AUG GGC GAU CUG AUU UGG GUU GAU UUU GAC CCG ACC
                                                                              A
 K   G   S   E   Q   A   G   H   R   P   A   V   V   L   S   P   F   M   Y   N
AAA GGU AGC GAG CAA GCU GGU CAU CGU CCA GCU GUU GUC CUG AGU CCU UUC AUG UAU AAU
                          A                                               C   C
 N   K   T   G   M   C   L   C   V   P   C   T   T   Q   S   K   G   Y   P   F
AAU AAA ACC GGU AUG UGU CUG UGU GUU CCU UGU ACC ACG CAA UCA AAA GGA UAU CCG UUC
  C       A                                   A
 E   V   V   L   S   G   Q   E   R   D   G   V   A   L   A   D   Q   V   K   S
GAA GUU GUU UUA UCC GGU CAG GAA CGU GAU GGC GUA GCG UUA GCU GAU CAG GUA AAA AGU

 I   A   W   R   A   R   G   A   T   K   K   G   T   V   A   P   E   E   L   Q
AUC GCC UGG CGG GCA AGA GGA GCA ACG AAG AAA GGA ACC GUU GCC CCA GAG GAA CUG CAA
                                                  A                 U A
 L   I   K   A   K   I   N   V   L   I   G
CUC AUU AAA GCC AAA AUU AAC GUA CUG AUU GGG UAG
```

FIG.42

FIG. 43A nucleic acid sequence of Mazf-mt1 (NP_217317) (SEQ ID NO: 69)

gtgatgcgcc gcggtgagat ttggcaggtc gatctcgacc ccgctcgagg tagcgaagcg
aacaaccagc gccccgccgt cgtcgtcagc aacgaccggg ccaacgcgac cgccacgcgt
cttgggcgcg gcgtcatcac cgtcgtgccg gtgacgagca acatcgccaa ggtctatccg
tttcaggtgt tgttgtcggc caccactact ggtctccagg tcgactgcaa ggcgcaggcc
gagcaaatca gatcgattgc taccgagcgg ttgctccggc caatcggccg agtttcagcc
gccgaacttg cccagctcga tgaggctttg aaactgcatc tcgacttatg gtcgtag FIG. 43B nucleic acid sequence of Mazf-mt2 (CAE55283) (SEQ ID NO: 70)

atgctgcgcg gtgagatctg gcaggtcgac ctggatccgg cccgcggcag cgcggcaaat
atgcggcggc cagcggtaat tgtcagcaac gacagggcca acgctgccgc gatacgtctc
gaccgaggcg tggtgccggt tgtcccggtt accagcaaca ccgaaaaggt ccccattcca
ggtgttgttg ccggcagcga gcggtggcct ggccgtcgat tcgaaggcgc aggcccagca
ggttggatcc gtcgctgcgc aacgtctccc ctgccgagct ga FIG. 43C nucleic acid sequence of Mazf-mt3 (CAA98393) (SEQ ID NO: 71)

gtggtgatta gtcgtgccga gatctactgg gctgacctcg ggccgccatc aggcagtcag
ccggcgaagc gccgcccggt gctcgtaatc cagtcagatc cgtacaacgc aagtcgcctt
gccactgtga tcgcagcggt gatcacgtcc aatacggcgc tggcggcaat gcccggcaac
gtgttcttgc ccgcgaccac aacgcgactg ccacgtgact cggtcgtcaa cgtcacggcg
attgtcacgc tcaacaagac tgacctcacc gaccgagttg ggaggtgcc agcgagcttg
atgcacgagg ttgaccgagg acttcgtcgc gtactggacc tttga FIG. 43D nucleic acid sequence of Mazf-mt4 (CAB09387) (SEQ ID NO: 72)

atgcggcgcg gtgaattgtg gtttgccgcc acacctggtg gtgacagacc agtacttgtc
cttaccagag atccggtggc agaccgcatc ggcgcggtcg ttgtggtggc cctaacccgc
acccgccgag gcctggtgtc ggaattggag ctcacggccg tcgaaaaccg tgttccgagc
gactgcgtcg tcaacttcga caacattcat acgttgccac gcaccgcatt ccgacgccgc
atcacccggc tgtccccggc ccgcctgcac gaagcctgtc aaacactccg ggcgagcacg
gggtgttga FIG. 43E nucleic acid sequence of Mazf-mt5 (CAB06519) (SEQ ID NO: 73)

gtgaccgcac ttccggcgcg cggagaggtg tggtggtgtg agatggctga gatcggtcgg
cgaccagtcg tcgtgctgtc gcgcgatgcc gcgatccctc ggctgcgacg cgcacttgtc
gcgccctgca ccacgaccat ccgagggcta gccagtgagg ttgttcttga acccggttcc
gacccgatcc cgcgccgttc cgcggtgaat ttggactcag tcgaaagtgt ctcggtcgcg
gtattggtga atcggcttgg ccgcctcgcc gacatccgga tgcgcgccat ctgcacggcc
ctcgaggtcg ccgtcgattg ctctcgatga FIG. 44A amino acid sequence of Mazf-mt1 (NP_217317) (SEQ ID NO:74)

MMRRGEIWQV DLDPARGSEA NNQRPAVVVS NDRANATATR LGRGVITVVP VTSNIAKVYP
FQVLLSATTT GLQVDCKAQA EQIRSIATER LLRPIGRVSA AELAQLDEAL KLHLDLWS

FIG. 44B amino acid sequence of Mazf-mt2 (CAE55283) (SEQ ID NO:75)

MLRGEIWQVD LDPARGSAAN MRRPAVIVSN DRANAAAIRL DRGVVPVVPV TSNTEKVPIP
GVVAGSERWP GRRFEGAGPA GWIRRCATSP LPS

FIG. 44C amino acid sequence of Mazf-mt3 (CAA98393) (SEQ ID NO:76)

MVISRAEIYW ADLGPPSGSQ PAKRRPVLVI QSDPYNASRL ATVIAAVITS NTALAAMPGN
VFLPATTTRL PRDSVVNVTA IVTLNKTDLT DRVGEVPASL MHEVDRGLRR VLDL

FIG. 44D amino acid sequence of Mazf-mt4 (CAB09387) (SEQ ID NO:77)

MRRGELWFAA TPGGDRPVLV LTRDPVADRI GAVVVVALTR TRRGLVSELE LTAVENRVPS
DCVVNFDNIH TLPRTAFRRR ITRLSPARLH EACQTLRAST GC

FIG. 44E amino acid sequence of Mazf-mt5 (CAB06519) (SEQ ID NO:78)

MTALPARGEV WWCEMAEIGR RPVVVLSRDA AIPRLRRALV APCTTTIRGL ASEVVLEPGS
DPIPRRSAVN LDSVESVSVA VLVNRLGRLA DIRMRAICTA LEVAVDCSR

Figure 45A nucleic acid sequence of *Pseudomonas putida* Pem-like gene (KT2440) (SEQ ID NO: 81)

```
                         gtgaa acggttgaaa ttcgccaggg gtgatattgt
tcgcgtcaac ctggacccaa cagtcgggcg ggaacagcag ggctccggcc gacctgcact
ggtacttact ccggctgcgt tcaatgcttc aggcctggct gtaatcatcc cgatcactca
aggtggggat ttcgcgaggc atgcgggttt cgctgtcacg ctcagcggtg cgggcacgca
gactcagggg gtgatgcttt gcaaccaggt gcgcacagtc gaccttgaag cacgatttgc
caagcgcata gagtcggtgc ctgaagctgt catcctggat gcactggcgc gtgtgcaaac
cctattcgat taa
```

Figure 45B nucleic acid sequence of *Mycobacterium celatum* Pem-like gene(SEQ ID NO: 82)

```
                                            t gaattgctct gacggaacgc
ggcgacatct acatcgtttc gcttgacccg acgtcgggac atgagcagag cggcacgcgc
ccagtattgg tcgtgtcccc gggcgcgttt aatcgcctga cgaaaacacc ggtcgtgcta
cctataacac gcggcgggaa ctttgcccga acggcagggt tcgctgtctc gctgaccgat
gcgggtactc gcaccgccgg cgtaatacgc tgcgatcagc ctcgctcgat tgatatccgc
gcccgtaaag gccgcaaggt tgaacgtgtg ccgtctgggg ttcttgacga agcgttggcc
aagctcgcca cgatcttgac ttga
```

Figure 45C nucleic acid sequence of *Shigella flexneri* 2a str. 301 Pem-like gene(SEQ ID NO: 83)

```
                                                atggtaaag gcacggacgc
cacatcgtgg tgagatctgg tattttaacc ctgatccggt tgccgggcat gaacttcagg
ggccacatta ttgcattgtg gtaacggaca aaaaactcaa caatgtttta aaagttgcta
tgtgctgccc gatttcaaca ggggcaaatg cagcacgttc cacaggggtg acggtgaacg
tcctcccccg tgatacgcaa accggtaacc tgcatggcgt tgtactttgt caccagctaa
aagccgtcga tcttattgcc cgtggcgcta aatttcatac cgttgccgat gaaaaattga
ttagtgaagt tatcagtaaa ctggtgaatt taatcgaccc acaataa
```

Figure 45D nucleic acid sequence of *E. coli* ChpBK (SEQ ID NO: 84)

```
                                   atggt aaagaaaagt gaatttgaac
ggggagacat tgtgctggtt ggctttgatc cagcaagcgg ccatgaacag caaggtgctg
gtcgacctgc gcttgtgctc tccgttcaag cctttaatca actgggaatg acgctggtgg
cccccattac gcagggcgga aattttgccc gttatgccgg atttagcgtt cctttacatt
gcgaagaagg cgatgtgcac ggcgtggtgc tggtgaatca ggtgcggatg atggatctac
acgcccggct ggcaaagcgt attggtctgg ctgcggatga ggtggtggaa gaggcgttat
tacgcttgca ggcggtggtg gaataa
```

FIG. 46A amino acid sequence of *Pseudomonas putida* KT2440 Pem-like protein (SEQ ID NO: 85)

MKRLKFARGD IVRVNLDPTV GREQQGSGRP ALVLTPAAFN ASGLAVIIPI TQGGDFARHA
GFAVTLSGAG TQTQGVMLCN QVRTVDLEAR FAKRIESVPE AVILDALARV QTLFD

FIG. 46B amino acid sequence of *Mycobacterium celatum* Pem-like protein (SEQ ID NO: 86)

MTERGDIYIV SLDPTSGHEQ SGTRPVLVVS PGAFNRLTKT PVVLPITRGG NFARTAGFAV
SLTDAGTRTA GVIRCDQPRS IDIRARKGRK VERVPSGVLD EALAKLATIL T

FIG. 46C amino acid sequence of *Shigella flexneri* 2a str. 301 Pem-like protein (SEQ ID NO: 87)

MVKARTPHRG EIWYFNPDPV AGHELQGPHY CIVVTDKKLN NVLKVAMCCP ISTGANAARS
TGVTVNVLPR DTQTGNLHGV VLCHQLKAVD LIARGAKFHT VADEKLISEV ISKLVNLIDP
Q

FIG. 46D amino acid sequence of *E. coli* ChpBK (SEQ ID NO: 88)

MVKKSEFERGDIVLVGFDPASGHEQQGAGRPALVLSVQAFNQLGMTLVAPITQGGNFARYAGFSVPLHCEEG
DVHGVVLVNQVRMMDLHARLAKRIGLAADEVVEEALLRLQAVVE

SEQUENCE LISTING

```
<160> NUMBER OF SEQ ID NOS: 120

<210> SEQ ID NO 1
<211> LENGTH: 336
<212> TYPE: DNA
<213> ORGANISM: E. coli

<400> SEQUENCE: 1
```

```
atggtaagcc gatacgtacc cgatatgggc gatctgattt gggttgattt tgacccgaca     60

aaaggtagcg agcaagctgg acatcgtcca gctgttgtcc tgagtccttt catgtacaac    120

aacaaaacag gtatgtgtct gtgtgttcct tgtacaacgc aatcaaaagg atatccgttc    180

gaagttgttt tatccggtca ggaacgtgat ggcgtagcgt tagctgatca ggtaaaaagt    240

atcgcctggc gggcaagagg agcaacgaag aaaggaacag ttgccccaga ggaattacaa    300

ctcattaaag ccaaaattaa cgtactgatt gggtag                              336


<210> SEQ ID NO 2
<211> LENGTH: 111
<212> TYPE: PRT
<213> ORGANISM: E. coli

<400> SEQUENCE: 2

Met Val Ser Arg Tyr Val Pro Asp Met Gly Asp Leu Ile Trp Val Asp
 1               5                  10                  15

Phe Asp Pro Thr Lys Gly Ser Glu Gln Ala Gly His Arg Pro Ala Val
            20                  25                  30

Val Leu Ser Pro Phe Met Tyr Asn Asn Lys Thr Gly Met Cys Leu Cys
        35                  40                  45

Val Pro Cys Thr Thr Gln Ser Lys Gly Tyr Pro Phe Glu Val Val Leu
    50                  55                  60

Ser Gly Gln Glu Arg Asp Gly Val Ala Leu Ala Asp Gln Val Lys Ser
65                  70                  75                  80

Ile Ala Trp Arg Ala Arg Gly Ala Thr Lys Lys Gly Thr Val Ala Pro
                85                  90                  95

Glu Glu Leu Gln Leu Ile Lys Ala Lys Ile Asn Val Leu Ile Gly
            100                 105                 110


<210> SEQ ID NO 3
<211> LENGTH: 333
<212> TYPE: DNA
<213> ORGANISM: E. coli

<400> SEQUENCE: 3

atggaaagag gggaaatctg gcttgtctcg cttgatccta ccgcaggtca tgagcagcag     60

ggaacgcggc cggtgctgat tgtcacaccg gcggccttta atcgcgtgac ccgcctgcct    120

gttgttgtgc ccgtaaccag cggaggcaat tttgcccgca ctgccggctt tgcggtgtcg    180

ttggatggtg ttggcatacg taccacaggt gttgtacgtt gcgatcaacc ccggacaatt    240

gatatgaaag cacggggcgg aaaacgactc gaacgggttc cggagactat catgaacgaa    300

gttcttggcc gcctgtccac tattctgact tga                                 333


<210> SEQ ID NO 4
<211> LENGTH: 110
<212> TYPE: PRT
<213> ORGANISM: E. coli

<400> SEQUENCE: 4

Met Glu Arg Gly Glu Ile Trp Leu Val Ser Leu Asp Pro Thr Ala Gly
 1               5                  10                  15

His Glu Gln Gln Gly Thr Arg Pro Val Leu Ile Val Thr Pro Ala Ala
            20                  25                  30

Phe Asn Arg Val Thr Arg Leu Pro Val Val Val Pro Val Thr Ser Gly
        35                  40                  45

Gly Asn Phe Ala Arg Thr Ala Gly Phe Ala Val Ser Leu Asp Gly Val
```

-continued

```
    50                  55                  60

Gly Ile Arg Thr Thr Gly Val Val Arg Cys Asp Gln Pro Arg Thr Ile
65                  70                  75                  80

Asp Met Lys Ala Arg Gly Gly Lys Arg Leu Glu Arg Val Pro Glu Thr
                85                  90                  95

Ile Met Asn Glu Val Leu Gly Arg Leu Ser Thr Ile Leu Thr
            100                 105                 110


<210> SEQ ID NO 5
<211> LENGTH: 249
<212> TYPE: DNA
<213> ORGANISM: E. coli

<400> SEQUENCE: 5

atgatccaca gtagcgtaaa gcgttgggga aattcaccgg cggtgcggat cccggctacg      60

ttaatgcagg cgctcaatct gaatattgat gatgaagtga agattgacct ggtggatggc     120

aaattaatta ttgagccagt gcgtaaagag cccgtattta cgcttgctga actggtcaac     180

gacatcacgc cggaaaacct ccacgagaat atcgactggg gagagccgaa agataaggaa     240

gtctggtaa                                                             249


<210> SEQ ID NO 6
<211> LENGTH: 82
<212> TYPE: PRT
<213> ORGANISM: E. coli

<400> SEQUENCE: 6

Met Ile His Ser Ser Val Lys Arg Trp Gly Asn Ser Pro Ala Val Arg
 1               5                  10                  15

Ile Pro Ala Thr Leu Met Gln Ala Leu Asn Leu Asn Ile Asp Asp Glu
            20                  25                  30

Val Lys Ile Asp Leu Val Asp Gly Lys Leu Ile Ile Glu Pro Val Arg
        35                  40                  45

Lys Glu Pro Val Phe Thr Leu Ala Glu Leu Val Asn Asp Ile Thr Pro
    50                  55                  60

Glu Asn Leu His Glu Asn Ile Asp Trp Gly Glu Pro Lys Asp Lys Glu
65                  70                  75                  80

Val Trp


<210> SEQ ID NO 7
<211> LENGTH: 258
<212> TYPE: DNA
<213> ORGANISM: E. coli

<400> SEQUENCE: 7

atgcatacca cccgactgaa gagggttggc ggctcagtta tgctgaccgt cccaccggca      60

ctgctgaatg cgctgtctct gggcacagat aatgaagttg gcatggtcat tgataatggc     120

cggctgattg ttgagccgta cagacgcccg caatattcac tggctgagct actggcacag     180

tgtgatccga atgctgaaat atcagctgaa gaacgagaat ggctggatgc accggcgact     240

ggtcaggagg aaatctga                                                   258


<210> SEQ ID NO 8
<211> LENGTH: 85
<212> TYPE: PRT
<213> ORGANISM: E. coli

<400> SEQUENCE: 8
```

-continued

```
Met His Thr Thr Arg Leu Lys Arg Val Gly Gly Ser Val Met Leu Thr
 1               5                  10                  15

Val Pro Pro Ala Leu Leu Asn Ala Leu Ser Leu Gly Thr Asp Asn Glu
            20                  25                  30

Val Gly Met Val Ile Asp Asn Gly Arg Leu Ile Val Glu Pro Tyr Arg
        35                  40                  45

Arg Pro Gln Tyr Ser Leu Ala Glu Leu Leu Ala Gln Cys Asp Pro Asn
    50                  55                  60

Ala Glu Ile Ser Ala Glu Glu Arg Glu Trp Leu Asp Ala Pro Ala Thr
65                  70                  75                  80

Gly Gln Glu Glu Ile
                85


<210> SEQ ID NO 9
<211> LENGTH: 24
<212> TYPE: PRT
<213> ORGANISM: Artificial Sequence
<220> FEATURE:
<223> OTHER INFORMATION: T54 to K77 fragment of E. coli MazE

<400> SEQUENCE: 9

Thr Leu Ala Glu Leu Val Asn Asp Ile Thr Pro Glu Asn Leu His Glu
 1               5                  10                  15

Asn Ile Asp Trp Gly Glu Pro Lys
            20


<210> SEQ ID NO 10
<211> LENGTH: 18
<212> TYPE: PRT
<213> ORGANISM: Artificial Sequence
<220> FEATURE:
<223> OTHER INFORMATION: N60 to K77 fragment of E. coli MazE

<400> SEQUENCE: 10

Asn Asp Ile Thr Pro Glu Asn Leu His Glu Asn Ile Asp Trp Gly Glu
 1               5                  10                  15

Pro Lys


<210> SEQ ID NO 11
<211> LENGTH: 30
<212> TYPE: RNA
<213> ORGANISM: Artificial Sequence
<220> FEATURE:
<223> OTHER INFORMATION: synthetic RNA substrate

<400> SEQUENCE: 11

uaagaaggag auauacauau gaaucaaauc                                       30


<210> SEQ ID NO 12
<211> LENGTH: 50
<212> TYPE: DNA
<213> ORGANISM: Artificial Sequence
<220> FEATURE:
<223> OTHER INFORMATION: single stranded oligonucleotide

<400> SEQUENCE: 12

gctcgtatct acaatgtaga ttgatatata ctgtatctac atatgatagc                 50


<210> SEQ ID NO 13
<211> LENGTH: 50
<212> TYPE: DNA
<213> ORGANISM: Artificial Sequence
<220> FEATURE:
<223> OTHER INFORMATION: single stranded oligonucleotide
```

<400> SEQUENCE: 13
cgagcataga tgttacatct aactatatat gacatagatg tatactatcg 50

<210> SEQ ID NO 14
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 14
agatctcgat cccgcaaatt aat 23

<210> SEQ ID NO 15
<211> LENGTH: 27
<212> TYPE: DNA
<213> ORGANISM: Artificial Sequence
<220> FEATURE:
<223> OTHER INFORMATION: DNA primer

<400> SEQUENCE: 15
ttagagatca atttcctgcc gttttac 27

<210> SEQ ID NO 16
<211> LENGTH: 22
<212> TYPE: DNA
<213> ORGANISM: Artificial Sequence
<220> FEATURE:
<223> OTHER INFORMATION: DNA primer

<400> SEQUENCE: 16
ttaaagatcg tcaacgtaac cg 22

<210> SEQ ID NO 17
<211> LENGTH: 22
<212> TYPE: DNA
<213> ORGANISM: Artificial Sequence
<220> FEATURE:
<223> OTHER INFORMATION: DNA primer

<400> SEQUENCE: 17
tgctctttat cccacgggca gc 22

<210> SEQ ID NO 18
<211> LENGTH: 24
<212> TYPE: DNA
<213> ORGANISM: Artificial Sequence
<220> FEATURE:
<223> OTHER INFORMATION: DNA primer

<400> SEQUENCE: 18
gcccagttca ccgcgaagat cgtc 24

<210> SEQ ID NO 19
<211> LENGTH: 27
<212> TYPE: DNA
<213> ORGANISM: Artificial Sequence
<220> FEATURE:
<223> OTHER INFORMATION: DNA primer

<400> SEQUENCE: 19
ggttttgatt tgctcccaac gggcaag 27

<210> SEQ ID NO 20
<211> LENGTH: 27

<212> TYPE: DNA
<213> ORGANISM: Artificial Sequence
<220> FEATURE:
<223> OTHER INFORMATION: DNA primer

<400> SEQUENCE: 20
catttcctcc tccagtttag cctggtc 27

<210> SEQ ID NO 21
<211> LENGTH: 27
<212> TYPE: DNA
<213> ORGANISM: Artificial Sequence
<220> FEATURE:
<223> OTHER INFORMATION: DNA primer

<400> SEQUENCE: 21
ttgccagact tcttccattg tttcgag 27

<210> SEQ ID NO 22
<211> LENGTH: 24
<212> TYPE: DNA
<213> ORGANISM: Artificial Sequence
<220> FEATURE:
<223> OTHER INFORMATION: DNA primer

<400> SEQUENCE: 22
gatccccaca atgcggtgac gagt 24

<210> SEQ ID NO 23
<211> LENGTH: 24
<212> TYPE: DNA
<213> ORGANISM: Artificial Sequence
<220> FEATURE:
<223> OTHER INFORMATION: DNA primer

<400> SEQUENCE: 23
cacgttgtcc actttgttca ccgc 24

<210> SEQ ID NO 24
<211> LENGTH: 24
<212> TYPE: DNA
<213> ORGANISM: Artificial Sequence
<220> FEATURE:
<223> OTHER INFORMATION: DNA primer

<400> SEQUENCE: 24
cagttcagcg ccgaggaaac gcat 24

<210> SEQ ID NO 25
<211> LENGTH: 24
<212> TYPE: DNA
<213> ORGANISM: Artificial Sequence
<220> FEATURE:
<223> OTHER INFORMATION: DNA primer

<400> SEQUENCE: 25
gcgttcgtcg tcggcccaac cgga 24

<210> SEQ ID NO 26
<211> LENGTH: 30
<212> TYPE: RNA
<213> ORGANISM: Artificial Sequence
<220> FEATURE:
<223> OTHER INFORMATION: antisense RNA

<400> SEQUENCE: 26
gauuugauuc auauguauau cuccuucuua 30

<210> SEQ ID NO 27
<211> LENGTH: 30
<212> TYPE: DNA
<213> ORGANISM: Artificial Sequence
<220> FEATURE:
<223> OTHER INFORMATION: complementary DNA

<400> SEQUENCE: 27
gatttgattc atatgtatat ctccttctta 30

<210> SEQ ID NO 28
<211> LENGTH: 22
<212> TYPE: DNA
<213> ORGANISM: Artificial Sequence
<220> FEATURE:
<223> OTHER INFORMATION: DNA primer

<400> SEQUENCE: 28
agaatgtgcg ccatttttca ct 22

<210> SEQ ID NO 29
<211> LENGTH: 9
<212> TYPE: DNA
<213> ORGANISM: Artificial Sequence
<220> FEATURE:
<223> OTHER INFORMATION: DNA fragment from pCold I vector

<400> SEQUENCE: 29 taatacacc 9

<210> SEQ ID NO 30
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 30
atgaatcaca aagtg 15

<210> SEQ ID NO 31
<211> LENGTH: 18
<212> TYPE: DNA
<213> ORGANISM: Artificial Sequence
<220> FEATURE:
<223> OTHER INFORMATION: DNA fragment from pCold I vector

<400> SEQUENCE: 31
catcatcatc atcatcat 18

<210> SEQ ID NO 32
<211> LENGTH: 12
<212> TYPE: DNA
<213> ORGANISM: Artificial Sequence
<220> FEATURE:
<223> OTHER INFORMATION: DNA fragment from pCold I vector

<400> SEQUENCE: 32
atcgaaggta gg 12

<210> SEQ ID NO 33
<211> LENGTH: 60
<212> TYPE: DNA
<213> ORGANISM: Artificial Sequence
<220> FEATURE:
<223> OTHER INFORMATION: multiple cloning site

<400> SEQUENCE: 33
catatggagc tcggtaccct cgagggatcc gaattcaagc ttgtcgacct gcagtctaga 60

<210> SEQ ID NO 34
<211> LENGTH: 21
<212> TYPE: DNA
<213> ORGANISM: Artificial Sequence
<220> FEATURE:
<223> OTHER INFORMATION: DNA primer

<400> SEQUENCE: 34
caggagauac cucaaugauc a 21

<210> SEQ ID NO 35
<211> LENGTH: 21
<212> TYPE: DNA
<213> ORGANISM: Artificial Sequence
<220> FEATURE:
<223> OTHER INFORMATION: DNA primer

<400> SEQUENCE: 35
ctcaatgatc acaggagata c 21

<210> SEQ ID NO 36
<211> LENGTH: 21
<212> TYPE: DNA
<213> ORGANISM: Artificial Sequence
<220> FEATURE:
<223> OTHER INFORMATION: DNA primer

<400> SEQUENCE: 36
tcctctatgg agttactagt g 21

<210> SEQ ID NO 37
<211> LENGTH: 16
<212> TYPE: DNA
<213> ORGANISM: Artificial Sequence
<220> FEATURE:
<223> OTHER INFORMATION: DNA primer

<400> SEQUENCE: 37
gggacaggag atacct 16

<210> SEQ ID NO 38
<211> LENGTH: 23
<212> TYPE: DNA
<213> ORGANISM: Artificial Sequence
<220> FEATURE:
<223> OTHER INFORMATION: DNA primer

<400> SEQUENCE: 38
tgtcctctat ggagttacta gtg 23

<210> SEQ ID NO 39
<211> LENGTH: 330
<212> TYPE: DNA
<213> ORGANISM: Bacillus halodurans

<400> SEQUENCE: 39
atgccagtac cggatagagg gaatcttgtt tatgtagact ttaacccaca atcgggtcat 60
gaccaagccg ggacacgacc ggctattgtt ttgtccccta aattatttaa taaaaacaca 120
ggttttgcgg tggtttgtcc aattaccaga caacaaaaag gttatccttt tgaaatagaa 180
ataccaccgg ggttacctat tgaaggggtt attcttactg accaagtaaa aagtctggat 240
tggagagcaa gaaactttca cattaaagga caagcaccag aggaaactgt tactgattgt 300
ttacaactta ttcatacatt tttatcttaa 330

<210> SEQ ID NO 40
<211> LENGTH: 363
<212> TYPE: DNA
<213> ORGANISM: Staphylococcus epidermidis

<400> SEQUENCE: 40
atgattagaa gaggagatgt ttatttagcg gatttatcac cagttcaagg gtctgaacaa 60
gggggagtaa gacctgtagt tatcattcaa aatgatactg gtaataaata tagtccaact 120
gtaattgtag ctgcgattac tgatgggatt aataaagcga aaataccaac ccacgtagaa 180
attgaaaaga aaaagtataa attagacaaa gattcagtta ttcttcttga acaaattaga 240
acactagata aaaagcgttt aaaagaaaaa ttaacatttt tatcagagag taaaatgata 300
gaggttgata atgccttaga tattagtttg ggattaaata actttgatca tcataaatct 360
taa 363

<210> SEQ ID NO 41
<211> LENGTH: 411
<212> TYPE: DNA
<213> ORGANISM: Staphylococcus aureus

<400> SEQUENCE: 41
atgattagac gaggagatgt ttatttagca gatttatcac cagtacaggg atctgaacaa 60
gggggagtca gacctgtagt cataattcaa aatgatactg gtaataaata tagtcctaca 120
gttattgttg cggcaataac tggtaggatt aataaagcga aaataccgac acatgtagag 180
attgaaaaga aaaagtataa gttggataaa gactcagtta tattattaga acaaattcgt 240
acacttgata aaaaacgatt gaaagaaaaa ctgacgtact tatccgatga taaaatgaaa 300
gaagtagata atgcactaat gattagttta gggctgaatg cagtagctca accagaaaaa 360
ttaggcgtct attatatgta tttttcagag ataaataaaa tattgatata a 411

<210> SEQ ID NO 42
<211> LENGTH: 351
<212> TYPE: DNA
<213> ORGANISM: Bacillus subtilis

<400> SEQUENCE: 42
ttgattgtga aacgcggcga tgtttatttt gctgatttat ctcctgttgt tggctcagag 60
caaggcgggg tgcgcccggt tttagtgatc caaaatgaca tcggaaatcg cttcagccca 120
actgctattg ttgcagccat aacagcacaa atacagaaag cgaaattacc aacccacgtc 180
gaaatcgatg caaaacgcta cggttttgaa agagattccg ttattttgct ggagcaaatt 240
cggacgattg acaagcaaag gttaacggat aagattactc atctggatga tgaaatgatg 300
gataaggttg atgaagcctt acaaatcagt ttggcactca ttgattttta g 351

<210> SEQ ID NO 43
<211> LENGTH: 324
<212> TYPE: DNA
<213> ORGANISM: Neisseria meningitides

<400> SEQUENCE: 43
atggatatgg tagtacgcgg cggaatctat ctggtctcct tagacccgac cgtaggaagc 60
gaaatcaaaa agacacgtcc ttgtgtcgta gtctctcctc ctgaaataca caactatctc 120

```
aagactgtgc tgatcgttcc catgacgagc ggaagccgtc ctgccccgtt ccgcgtcaat    180

gtccgctttc aggataaaga cggtttgctt ttgcccgaac agattagggc tgtggataaa    240

gccggattgg tcaaacatct tggcaattta gacaacagta cggctgaaaa actgtttgca    300

gtattgcagg agatgtttgc ctga                                           324


<210> SEQ ID NO 44
<211> LENGTH: 366
<212> TYPE: DNA
<213> ORGANISM: Morganella morgani

<400> SEQUENCE: 44

atgcgccggc ggctggtcag gaggaaatct gacatggaaa gaggggaaat ctggcttgtc     60

tcgcttgacc ctaccgcagg tcatgagcag cagggaacgc ggccggtact gattgtcacg    120

ccggctgctt ttaaccgcgt gacccgcctg cctgttgttg tgcccgtgac cagcggaggt    180

aattttgccc gcacagcagg ctttgctgtg tcgcttgacg gcgccggcat acgtaccacc    240

ggcgttgtgc gttgcgatca accccggacg atcgatatga aagcccgcgg cggcaaacga    300

ctcgaacggg tgccagagac tatcatggac gacgttcttg gccgtctggc caccatcctg    360

acctga                                                               366


<210> SEQ ID NO 45
<211> LENGTH: 321
<212> TYPE: DNA
<213> ORGANISM: Mycobacterium tuberculosis

<400> SEQUENCE: 45

gtggtgattc ggggagcggt ctacagggtc gacttcggcg atgcgaagcg aggccacgag     60

caacgcgggc ggcgctacgc cgtggtcatc agccccggct cgatgccgtg gagtgtagta    120

accgtggtgc cgacgtcgac aagcgcccaa cctgcggttt tccgaccaga gctggaagtc    180

atgggaacaa agacacggtt cctggtggat cagatccgga cgatcggcat cgtctatgtg    240

cacggcgatc cggtcgacta tctggaccgt gaccaaatgg ccaaggtgga acacgccgtg    300

gcacgatacc ttggtctgtg a                                              321


<210> SEQ ID NO 46
<211> LENGTH: 109
<212> TYPE: PRT
<213> ORGANISM: Bacillus halodurans

<400> SEQUENCE: 46

Met Pro Val Pro Asp Arg Gly Asn Leu Val Tyr Val Asp Phe Asn Pro
 1               5                  10                  15

Gln Ser Gly His Asp Gln Ala Gly Thr Arg Pro Ala Ile Val Leu Ser
            20                  25                  30

Pro Lys Leu Phe Asn Lys Asn Thr Gly Phe Ala Val Val Cys Pro Ile
        35                  40                  45

Thr Arg Gln Gln Lys Gly Tyr Pro Phe Glu Ile Glu Ile Pro Pro Gly
    50                  55                  60

Leu Pro Ile Glu Gly Val Ile Leu Thr Asp Gln Val Lys Ser Leu Asp
65                  70                  75                  80

Trp Arg Ala Arg Asn Phe His Ile Lys Gly Gln Ala Pro Glu Glu Thr
                85                  90                  95

Val Thr Asp Cys Leu Gln Leu Ile His Thr Phe Leu Ser
            100                 105
```

<210> SEQ ID NO 47
<211> LENGTH: 120
<212> TYPE: PRT
<213> ORGANISM: Staphylococcus epidermidis

<400> SEQUENCE: 47

Met Ile Arg Arg Gly Asp Val Tyr Leu Ala Asp Leu Ser Pro Val Gln
1 5 10 15

Gly Ser Glu Gln Gly Gly Val Arg Pro Val Val Ile Ile Gln Asn Asp
20 25 30

Thr Gly Asn Lys Tyr Ser Pro Thr Val Ile Val Ala Ala Ile Thr Asp
35 40 45

Gly Ile Asn Lys Ala Lys Ile Pro Thr His Val Glu Ile Glu Lys Lys
50 55 60

Lys Tyr Lys Leu Asp Lys Asp Ser Val Ile Leu Leu Glu Gln Ile Arg
65 70 75 80

Thr Leu Asp Lys Lys Arg Leu Lys Glu Lys Leu Thr Phe Leu Ser Glu
85 90 95

Ser Lys Met Ile Glu Val Asp Asn Ala Leu Asp Ile Ser Leu Gly Leu
100 105 110

Asn Asn Phe Asp His His Lys Ser
115 120

<210> SEQ ID NO 48
<211> LENGTH: 136
<212> TYPE: PRT
<213> ORGANISM: Staphylococcus aureus

<400> SEQUENCE: 48

Met Ile Arg Arg Gly Asp Val Tyr Leu Ala Asp Leu Ser Pro Val Gln
1 5 10 15

Gly Ser Glu Gln Gly Gly Val Arg Pro Val Val Ile Ile Gln Asn Asp
20 25 30

Thr Gly Asn Lys Tyr Ser Pro Thr Val Ile Val Ala Ala Ile Thr Gly
35 40 45

Arg Ile Asn Lys Ala Lys Ile Pro Thr His Val Glu Ile Glu Lys Lys
50 55 60

Lys Tyr Lys Leu Asp Lys Asp Ser Val Ile Leu Leu Glu Gln Ile Arg
65 70 75 80

Thr Leu Asp Lys Lys Arg Leu Lys Glu Lys Leu Thr Tyr Leu Ser Asp
85 90 95

Asp Lys Met Lys Glu Val Asp Asn Ala Leu Met Ile Ser Leu Gly Leu
100 105 110

Asn Ala Val Ala Gln Pro Glu Lys Leu Gly Val Tyr Tyr Met Tyr Phe
115 120 125

Ser Glu Ile Asn Lys Ile Leu Ile
130 135

<210> SEQ ID NO 49
<211> LENGTH: 116
<212> TYPE: PRT
<213> ORGANISM: Bacillus subtilis

<400> SEQUENCE: 49

Met Ile Val Lys Arg Gly Asp Val Tyr Phe Ala Asp Leu Ser Pro Val
1 5 10 15

Val Gly Ser Glu Gln Gly Gly Val Arg Pro Val Leu Val Ile Gln Asn
20 25 30

Asp Ile Gly Asn Arg Phe Ser Pro Thr Ala Ile Val Ala Ala Ile Thr
35 40 45

Ala Gln Ile Gln Lys Ala Lys Leu Pro Thr His Val Glu Ile Asp Ala
50 55 60

Lys Arg Tyr Gly Phe Glu Arg Asp Ser Val Ile Leu Leu Glu Gln Ile
65 70 75 80

Arg Thr Ile Asp Lys Gln Arg Leu Thr Asp Lys Ile Thr His Leu Asp
85 90 95

Asp Glu Met Met Asp Lys Val Asp Glu Ala Leu Gln Ile Ser Leu Ala
100 105 110

Leu Ile Asp Phe
115

<210> SEQ ID NO 50
<211> LENGTH: 115
<212> TYPE: PRT
<213> ORGANISM: Neisseria meningitides

<400> SEQUENCE: 50

Met Tyr Ile Pro Asp Lys Gly Asp Ile Phe His Leu Asn Phe Asp Pro
1 5 10 15

Ser Ser Gly Lys Glu Ile Lys Gly Gly Arg Phe Ala Leu Ala Leu Ser
20 25 30

Pro Lys Ala Phe Asn Arg Ala Thr Gly Leu Val Phe Ala Cys Pro Ile
35 40 45

Ser Gln Gly Asn Ala Ala Ala Ala Arg Ser Ser Gly Met Ile Ser Thr
50 55 60

Leu Leu Gly Ala Gly Thr Glu Thr Gln Gly Asn Val His Cys His Gln
65 70 75 80

Leu Lys Ser Leu Asp Trp Gln Ile Arg Lys Ala Ser Phe Lys Glu Thr
85 90 95

Val Pro Asp Tyr Val Leu Asp Asp Val Leu Ala Arg Ile Gly Ala Val
100 105 110

Leu Phe Asp
115

<210> SEQ ID NO 51
<211> LENGTH: 121
<212> TYPE: PRT
<213> ORGANISM: Morganella morgani

<400> SEQUENCE: 51

Met Arg Arg Arg Leu Val Arg Arg Lys Ser Asp Met Glu Arg Gly Glu
1 5 10 15

Ile Trp Leu Val Ser Leu Asp Pro Thr Ala Gly His Glu Gln Gln Gly
20 25 30

Thr Arg Pro Val Leu Ile Val Thr Pro Ala Ala Phe Asn Arg Val Thr
35 40 45

Arg Leu Pro Val Val Val Pro Val Thr Ser Gly Gly Asn Phe Ala Arg
50 55 60

Thr Ala Gly Phe Ala Val Ser Leu Asp Gly Ala Gly Ile Arg Thr Thr
65 70 75 80

Gly Val Val Arg Cys Asp Gln Pro Arg Thr Ile Asp Met Lys Ala Arg
85 90 95

Gly Gly Lys Arg Leu Glu Arg Val Pro Glu Thr Ile Met Asp Asp Val
100 105 110

```
Leu Gly Arg Leu Ala Thr Ile Leu Thr
        115                 120


<210> SEQ ID NO 52
<211> LENGTH: 118
<212> TYPE: PRT
<213> ORGANISM: Mycobacterium tuberculosis

<400> SEQUENCE: 52

Met Met Arg Arg Gly Glu Ile Trp Gln Val Asp Leu Asp Pro Ala Arg
 1               5                  10                  15

Gly Ser Glu Ala Asn Asn Gln Arg Pro Ala Val Val Val Ser Asn Asp
            20                  25                  30

Arg Ala Asn Ala Thr Ala Thr Arg Leu Gly Arg Gly Val Ile Thr Val
        35                  40                  45

Val Pro Val Thr Ser Asn Ile Ala Lys Val Tyr Pro Phe Gln Val Leu
    50                  55                  60

Leu Ser Ala Thr Thr Thr Gly Leu Gln Val Asp Cys Lys Ala Gln Ala
65                  70                  75                  80

Glu Gln Ile Arg Ser Ile Ala Thr Glu Arg Leu Leu Arg Pro Ile Gly
                85                  90                  95

Arg Val Ser Ala Ala Glu Leu Ala Gln Leu Asp Glu Ala Leu Lys Leu
            100                 105                 110

His Leu Asp Leu Trp Ser
        115


<210> SEQ ID NO 53
<211> LENGTH: 243
<212> TYPE: DNA
<213> ORGANISM: Deinococcus radiodurans

<400> SEQUENCE: 53

atgacgagtc aaattcagaa atggggcaac agcctcgcgc tccgcattcc caaagctctg     60

gcgcagcagg tgggactgac gcagagttca gaagtggagc tgcttcttca ggacggtcag    120

attgtcatcc ggccagttcc tgctcggcag tacgatctcg ccgcgctgct ggccgaaatg    180

acacctgaaa atctgcatgg ggaaacagac tggggcgcac tggaaggacg cgaggaatgg    240

taa                                                                  243


<210> SEQ ID NO 54
<211> LENGTH: 246
<212> TYPE: DNA
<213> ORGANISM: Bacillus halodurans

<400> SEQUENCE: 54

gtgacactca tgactactat acaaaagtgg ggaaatagtt tagctgttcg tattccgaac     60

cattatgcta aacatattaa cgttacgcaa ggatctgaaa ttgaactaag cttagggagt    120

gatcaaacga ttattttaaa gcctaaaaaa agaaagccaa cattagagga attagtggca    180

aaaatcactc ctgaaaacag acataacgaa attgatttcg ggagaacagg aaaggaattg    240

ttgtaa                                                               246


<210> SEQ ID NO 55
<211> LENGTH: 258
<212> TYPE: DNA
<213> ORGANISM: E. coli Plasmid R100

<400> SEQUENCE: 55

atgcatacca cccgactgaa gagggttggc ggctcagtta tgctgaccgt cccaccggca     60
```

ctgctgaatg cgctgtctct gggcacagat aatgaagttg gcatggtcat tgataatggc 120
cggctgattg ttgagccgta cagacgcccg caatattcac tggctgagct actggcacag 180
tgtgatccga atgctgaaat atcagctgaa gaacgagaat ggctggatgc accggcgact 240
ggtcaggagg aaatctga 258

<210> SEQ ID NO 56
<211> LENGTH: 294
<212> TYPE: DNA
<213> ORGANISM: E. coli Plasmid R466b

<400> SEQUENCE: 56
atgttatatt taaatataac ttttatggag ggaaaaatgc ataccactcg actgaagaag 60
gttggcggct cagtcatgct gaccgtccca ccggcactgc tgaatgcgct gtcgctgggt 120
acagataatg aagttggcat ggtcattgat aatggccggc tgattgtgga gccgcacaga 180
cgcccgcagt attcactggc tgagctgttg gcacagtgcg atccgaacgc tgaaatctcg 240
gcagaagaac gtgaatggct ggatgcgccg gcggctggtc aggaggaaat ctga 294

<210> SEQ ID NO 57
<211> LENGTH: 258
<212> TYPE: DNA
<213> ORGANISM: Escherichia coli

<400> SEQUENCE: 57
gtgcagatgc gtattaccat aaaaagatgg gggaacagtg caggtatggt cattcccaat 60
atcgtaatga aagaacttaa cttacagccg gggcagagcg tggaagtgca ggtgagcaac 120
aaccaactga ttctgacacc catctccagg cgctactcgc ttgatgaact gctggcacag 180
tgtgacatga acgccgcgga acttagcgag caggatgtct ggggtaaatc cacccctgcg 240
ggtgacgaaa tatggtaa 258

<210> SEQ ID NO 58
<211> LENGTH: 255
<212> TYPE: DNA
<213> ORGANISM: Pseudomonas putida

<400> SEQUENCE: 58
atgcagatca agattcaaca gtggggcaac agcgccgcga tccgcttgcc cgccgcagta 60
ctcaagcaga tgcgcctcgg tgtcggctcc accctgagcc ttgacacaac gggtgagacg 120
atggtgctca aacccgtcag gtcgaaaccc aagtacaccc ttgaggaact gatggcccag 180
tgtgacctga gtgcaccgga gccagaggac atggccgact ggaatgccat gcgcccagtg 240
gggcgtgaag tgtga 255

<210> SEQ ID NO 59
<211> LENGTH: 260
<212> TYPE: DNA
<213> ORGANISM: Photobacterium profundum

<400> SEQUENCE: 59
gtgcaatgag aactcagata agaaagatcg gtaactcact tggttcaatt attcctgcca 60
cttttattcg tcagcttgaa ctggcagagg gcgcagaaat tgatgttaaa acggttgatg 120
gaaaaattgt gattgagcca attagaaaaa tgaaaaaacg tttcccattc agtgagcgtg 180
aattactaag tggattggat gcacacactg ctcatgctga cgaactggtt gtaatttcta 240
cccaggagct aggcgaataa 260

<210> SEQ ID NO 60
<211> LENGTH: 80
<212> TYPE: PRT
<213> ORGANISM: Deinococcus radiodurans

<400> SEQUENCE: 60

Met Thr Ser Gln Ile Gln Lys Trp Gly Asn Ser Leu Ala Leu Arg Ile
1 5 10 15

Pro Lys Ala Leu Ala Gln Gln Val Gly Leu Thr Gln Ser Ser Glu Val
20 25 30

Glu Leu Leu Leu Gln Asp Gly Gln Ile Val Ile Arg Pro Val Pro Ala
35 40 45

Arg Gln Tyr Asp Leu Ala Ala Leu Leu Ala Glu Met Thr Pro Glu Asn
50 55 60

Leu His Gly Glu Thr Asp Trp Gly Ala Leu Glu Gly Arg Glu Glu Trp
65 70 75 80

<210> SEQ ID NO 61
<211> LENGTH: 81
<212> TYPE: PRT
<213> ORGANISM: Bacillus halodurans

<400> SEQUENCE: 61

Met Thr Leu Met Thr Thr Ile Gln Lys Trp Gly Asn Ser Leu Ala Val
1 5 10 15

Arg Ile Pro Asn His Tyr Ala Lys His Ile Asn Val Thr Gln Gly Ser
20 25 30

Glu Ile Glu Leu Ser Leu Gly Ser Asp Gln Thr Ile Ile Leu Lys Pro
35 40 45

Lys Lys Arg Lys Pro Thr Leu Glu Glu Leu Val Ala Lys Ile Thr Pro
50 55 60

Glu Asn Arg His Asn Glu Ile Asp Phe Gly Arg Thr Gly Lys Glu Leu
65 70 75 80

Leu

<210> SEQ ID NO 62
<211> LENGTH: 85
<212> TYPE: PRT
<213> ORGANISM: E. coli PemI plasmid R100

<400> SEQUENCE: 62

Met His Thr Thr Arg Leu Lys Arg Val Gly Gly Ser Val Met Leu Thr
1 5 10 15

Val Pro Pro Ala Leu Leu Asn Ala Leu Ser Leu Gly Thr Asp Asn Glu
20 25 30

Val Gly Met Val Ile Asp Asn Gly Arg Leu Ile Val Glu Pro Tyr Arg
35 40 45

Arg Pro Gln Tyr Ser Leu Ala Glu Leu Leu Ala Gln Cys Asp Pro Asn
50 55 60

Ala Glu Ile Ser Ala Glu Glu Arg Glu Trp Leu Asp Ala Pro Ala Thr
65 70 75 80

Gly Gln Glu Glu Ile
85

<210> SEQ ID NO 63
<211> LENGTH: 97
<212> TYPE: PRT
<213> ORGANISM: E. coli PemI plasmid R466b

<400> SEQUENCE: 63

```
Met Leu Tyr Leu Asn Ile Thr Phe Met Glu Gly Lys Met His Thr Thr
 1               5                  10                  15

Arg Leu Lys Lys Val Gly Gly Ser Val Met Leu Thr Val Pro Pro Ala
            20                  25                  30

Leu Leu Asn Ala Leu Ser Leu Gly Thr Asp Asn Glu Val Gly Met Val
        35                  40                  45

Ile Asp Asn Gly Arg Leu Ile Val Glu Pro His Arg Arg Pro Gln Tyr
    50                  55                  60

Ser Leu Ala Glu Leu Leu Ala Gln Cys Asp Pro Asn Ala Glu Ile Ser
65                  70                  75                  80

Ala Glu Glu Arg Glu Trp Leu Asp Ala Pro Ala Ala Gly Gln Glu Glu
                85                  90                  95

Ile
```

<210> SEQ ID NO 64
<211> LENGTH: 85
<212> TYPE: PRT
<213> ORGANISM: Escherichia coli

<400> SEQUENCE: 64

```
Met Gln Met Arg Ile Thr Ile Lys Arg Trp Gly Asn Ser Ala Gly Met
 1               5                  10                  15

Val Ile Pro Asn Ile Val Met Lys Glu Leu Asn Leu Gln Pro Gly Gln
            20                  25                  30

Ser Val Glu Ala Gln Val Ser Asn Asn Gln Leu Ile Leu Thr Pro Ile
        35                  40                  45

Ser Arg Arg Tyr Ser Leu Asp Glu Leu Leu Ala Gln Cys Asp Met Asn
    50                  55                  60

Ala Ala Glu Leu Ser Glu Gln Asp Val Trp Gly Lys Ser Thr Pro Ala
65                  70                  75                  80

Gly Asp Glu Ile Trp
                85
```

<210> SEQ ID NO 65
<211> LENGTH: 84
<212> TYPE: PRT
<213> ORGANISM: Pseudomonas putida

<400> SEQUENCE: 65

```
Met Gln Ile Lys Ile Gln Gln Trp Gly Asn Ser Ala Ala Ile Arg Leu
 1               5                  10                  15

Pro Ala Ala Val Leu Lys Gln Met Arg Leu Gly Val Gly Ser Thr Leu
            20                  25                  30

Ser Leu Asp Thr Thr Gly Glu Thr Met Val Leu Lys Pro Val Arg Ser
        35                  40                  45

Lys Pro Lys Tyr Thr Leu Glu Glu Leu Met Ala Gln Cys Asp Leu Ser
    50                  55                  60

Ala Pro Glu Pro Glu Asp Met Ala Asp Trp Asn Ala Met Arg Pro Val
65                  70                  75                  80

Gly Arg Glu Val
```

<210> SEQ ID NO 66
<211> LENGTH: 85
<212> TYPE: PRT
<213> ORGANISM: Photobacterium profundum -continued

<400> SEQUENCE: 66

Ala Met Arg Thr Gln Ile Arg Lys Ile Gly Asn Ser Leu Gly Ser Ile
 1               5                  10                  15

Ile Pro Ala Thr Phe Ile Arg Gln Leu Glu Leu Ala Glu Gly Ala Glu
            20                  25                  30

Ile Asp Val Lys Thr Val Asp Gly Lys Ile Val Ile Glu Pro Ile Arg
        35                  40                  45

Lys Met Lys Lys Arg Phe Pro Phe Ser Glu Arg Glu Leu Leu Ser Gly
    50                  55                  60

Leu Asp Ala His Thr Ala His Ala Asp Glu Leu Val Val Ile Ser Thr
65                  70                  75                  80

Gln Glu Leu Gly Glu
                85

<210> SEQ ID NO 67
<211> LENGTH: 228
<212> TYPE: DNA
<213> ORGANISM: Homo sapiens

<400> SEQUENCE: 67
atgggtccag catctgttcc gactacctgt tgctttaacc tggcgaaccg caaaattccg 60
ctgcagcgcc tggaaagcta tcgccgtatt acctctggca aatgcccgca gaaagcggtg 120
atctttaaaa ccaaactggc gaaagatatt tgcgcggatc cgaaaaaaaa atgggtgcag 180
gattctatga aatatctgga tcagaaatct ccgaccccga aaccgtaa 228

<210> SEQ ID NO 68
<211> LENGTH: 73
<212> TYPE: PRT
<213> ORGANISM: Homo sapiens

<400> SEQUENCE: 68

Gly Pro Ala Ser Pro Thr Thr Cys Cys Phe Asn Leu Ala Asn Arg Lys
 1               5                  10                  15

Ile Pro Leu Gln Arg Leu Glu Ser Tyr Arg Arg Ile Thr Ser Gly Lys
            20                  25                  30

Cys Pro Gln Lys Ala Val Ile Phe Lys Thr Lys Leu Ala Lys Asp Ile
        35                  40                  45

Cys Ala Asp Pro Lys Lys Lys Trp Val Gln Asp Ser Met Lys Tyr Leu
    50                  55                  60

Asp Gln Lys Ser Pro Thr Pro Lys Pro
65                  70

<210> SEQ ID NO 69
<211> LENGTH: 357
<212> TYPE: DNA
<213> ORGANISM: Mycobacterium tuberculosis

<400> SEQUENCE: 69
gtgatgcgcc gcggtgagat ttggcaggtc gatctcgacc ccgctcgagg tagcgaagcg 60
aacaaccagc gccccgccgt cgtcgtcagc aacgaccggg ccaacgcgac cgccacgcgt 120
cttgggcgcg gcgtcatcac cgtcgtgccg gtgacgagca acatcgccaa ggtctatccg 180
tttcaggtgt tgttgtcggc caccactact ggtctccagg tcgactgcaa ggcgcaggcc 240
gagcaaatca gatcgattgc taccgagcgg ttgctccggc caatcggccg agtttcagcc 300
gccgaacttg cccagctcga tgaggctttg aaactgcatc tcgacttatg gtcgtag 357

<210> SEQ ID NO 70
<211> LENGTH: 282
<212> TYPE: DNA
<213> ORGANISM: Mycobacterium tuberculosis

<400> SEQUENCE: 70
atgctgcgcg gtgagatctg gcaggtcgac ctggatccgg cccgcggcag cgcggcaaat 60
atgcggcggc cagcggtaat tgtcagcaac gacagggcca acgctgccgc gatacgtctc 120
gaccgaggcg tggtgccggt tgtcccggtt accagcaaca ccgaaaaggt ccccattcca 180
ggtgttgttg ccggcagcga gcggtggcct ggccgtcgat tcgaaggcgc aggcccagca 240
ggttggatcc gtcgctgcgc aacgtctccc ctgccgagct ga 282

<210> SEQ ID NO 71
<211> LENGTH: 345
<212> TYPE: DNA
<213> ORGANISM: Mycobacterium tuberculosis

<400> SEQUENCE: 71
gtggtgatta gtcgtgccga gatctactgg gctgacctcg ggccgccatc aggcagtcag 60
ccggcgaagc gccgcccggt gctcgtaatc cagtcagatc cgtacaacgc aagtcgcctt 120
gccactgtga tcgcagcggt gatcacgtcc aatacggcgc tggcggcaat gcccggcaac 180
gtgttcttgc ccgcgaccac aacgcgactg ccacgtgact cggtcgtcaa cgtcacggcg 240
attgtcacgc tcaacaagac tgacctcacc gaccgagttg gggaggtgcc agcgagcttg 300
atgcacgagg ttgaccgagg acttcgtcgc gtactggacc tttga 345

<210> SEQ ID NO 72
<211> LENGTH: 309
<212> TYPE: DNA
<213> ORGANISM: Mycobacterium tuberculosis

<400> SEQUENCE: 72
atgcggcgcg gtgaattgtg gtttgccgcc acacctggtg gtgacagacc agtacttgtc 60
cttaccagag atccggtggc agaccgcatc ggcgcggtcg ttgtggtggc cctaacccgc 120
acccgccgag gcctggtgtc ggaattggag ctcacggccg tcgaaaaccg tgttccgagc 180
gactgcgtcg tcaacttcga caacattcat acgttgccac gcaccgcatt ccgacgccgc 240
atcacccggc tgtccccggc ccgcctgcac gaagcctgtc aaacactccg ggcgagcacg 300
gggtgttga 309

<210> SEQ ID NO 73
<211> LENGTH: 330
<212> TYPE: DNA
<213> ORGANISM: Mycobacterium tuberculosis

<400> SEQUENCE: 73
gtgaccgcac ttccggcgcg cggagaggtg tggtggtgtg agatggctga gatcggtcgg 60
cgaccagtcg tcgtgctgtc gcgcgatgcc gcgatccctc ggctgcgacg cgcacttgtc 120
gcgccctgca ccacgaccat ccgagggcta gccagtgagg ttgttcttga acccggttcc 180
gacccgatcc cgcgccgttc cgcggtgaat ttggactcag tcgaaagtgt ctcggtcgcg 240
gtattggtga atcggcttgg ccgcctcgcc gacatccgga tgcgcgccat ctgcacggcc 300
ctcgaggtcg ccgtcgattg ctctcgatga 330

<210> SEQ ID NO 74
<211> LENGTH: 118

<212> TYPE: PRT
<213> ORGANISM: Mycobacterium tuberculosis

<400> SEQUENCE: 74

Met Met Arg Arg Gly Glu Ile Trp Gln Val Asp Leu Asp Pro Ala Arg
1 5 10 15

Gly Ser Glu Ala Asn Asn Gln Arg Pro Ala Val Val Val Ser Asn Asp
20 25 30

Arg Ala Asn Ala Thr Ala Thr Arg Leu Gly Arg Gly Val Ile Thr Val
35 40 45

Val Pro Val Thr Ser Asn Ile Ala Lys Val Tyr Pro Phe Gln Val Leu
50 55 60

Leu Ser Ala Thr Thr Thr Gly Leu Gln Val Asp Cys Lys Ala Gln Ala
65 70 75 80

Glu Gln Ile Arg Ser Ile Ala Thr Glu Arg Leu Leu Arg Pro Ile Gly
85 90 95

Arg Val Ser Ala Ala Glu Leu Ala Gln Leu Asp Glu Ala Leu Lys Leu
100 105 110

His Leu Asp Leu Trp Ser
115

<210> SEQ ID NO 75
<211> LENGTH: 93
<212> TYPE: PRT
<213> ORGANISM: Mycobacterium tuberculosis

<400> SEQUENCE: 75

Met Leu Arg Gly Glu Ile Trp Gln Val Asp Leu Asp Pro Ala Arg Gly
1 5 10 15

Ser Ala Ala Asn Met Arg Arg Pro Ala Val Ile Val Ser Asn Asp Arg
20 25 30

Ala Asn Ala Ala Ala Ile Arg Leu Asp Arg Gly Val Val Pro Val Val
35 40 45

Pro Val Thr Ser Asn Thr Glu Lys Val Pro Ile Pro Gly Val Val Ala
50 55 60

Gly Ser Glu Arg Trp Pro Gly Arg Arg Phe Glu Gly Ala Gly Pro Ala
65 70 75 80

Gly Trp Ile Arg Arg Cys Ala Thr Ser Pro Leu Pro Ser
85 90

<210> SEQ ID NO 76
<211> LENGTH: 114
<212> TYPE: PRT
<213> ORGANISM: Mycobacterium tuberculosis

<400> SEQUENCE: 76

Met Val Ile Ser Arg Ala Glu Ile Tyr Trp Ala Asp Leu Gly Pro Pro
1 5 10 15

Ser Gly Ser Gln Pro Ala Lys Arg Arg Pro Val Leu Val Ile Gln Ser
20 25 30

Asp Pro Tyr Asn Ala Ser Arg Leu Ala Thr Val Ile Ala Ala Val Ile
35 40 45

Thr Ser Asn Thr Ala Leu Ala Ala Met Pro Gly Asn Val Phe Leu Pro
50 55 60

Ala Thr Thr Thr Arg Leu Pro Arg Asp Ser Val Val Asn Val Thr Ala
65 70 75 80

Ile Val Thr Leu Asn Lys Thr Asp Leu Thr Asp Arg Val Gly Glu Val
85 90 95

```
Pro Ala Ser Leu Met His Glu Val Asp Arg Gly Leu Arg Arg Val Leu
            100                 105                 110

Asp Leu
```

<210> SEQ ID NO 77
<211> LENGTH: 102
<212> TYPE: PRT
<213> ORGANISM: Mycobacterium tuberculosis

<400> SEQUENCE: 77

```
Met Arg Arg Gly Glu Leu Trp Phe Ala Ala Thr Pro Gly Gly Asp Arg
 1               5                  10                  15

Pro Val Leu Val Leu Thr Arg Asp Pro Val Ala Asp Arg Ile Gly Ala
            20                  25                  30

Val Val Val Val Ala Leu Thr Arg Thr Arg Arg Gly Leu Val Ser Glu
        35                  40                  45

Leu Glu Leu Thr Ala Val Glu Asn Arg Val Pro Ser Asp Cys Val Val
    50                  55                  60

Asn Phe Asp Asn Ile His Thr Leu Pro Arg Thr Ala Phe Arg Arg Arg
65                  70                  75                  80

Ile Thr Arg Leu Ser Pro Ala Arg Leu His Glu Ala Cys Gln Thr Leu
                85                  90                  95

Arg Ala Ser Thr Gly Cys
            100
```

<210> SEQ ID NO 78
<211> LENGTH: 109
<212> TYPE: PRT
<213> ORGANISM: Mycobacterium tuberculosis

<400> SEQUENCE: 78

```
Met Thr Ala Leu Pro Ala Arg Gly Glu Val Trp Trp Cys Glu Met Ala
 1               5                  10                  15

Glu Ile Gly Arg Arg Pro Val Val Val Leu Ser Arg Asp Ala Ala Ile
            20                  25                  30

Pro Arg Leu Arg Arg Ala Leu Val Ala Pro Cys Thr Thr Thr Ile Arg
        35                  40                  45

Gly Leu Ala Ser Glu Val Val Leu Glu Pro Gly Ser Asp Pro Ile Pro
    50                  55                  60

Arg Arg Ser Ala Val Asn Leu Asp Ser Val Glu Ser Val Ser Val Ala
65                  70                  75                  80

Val Leu Val Asn Arg Leu Gly Arg Leu Ala Asp Ile Arg Met Arg Ala
                85                  90                  95

Ile Cys Thr Ala Leu Glu Val Ala Val Asp Cys Ser Arg
            100                 105
```

<210> SEQ ID NO 79
<211> LENGTH: 351
<212> TYPE: DNA
<213> ORGANISM: Bacillus anthracis

<400> SEQUENCE: 79

```
ttgattgtaa aacgcggcga cgtgtatttt gcagaccttt ccccagttgt tggttctgag      60

caaggaggtg ttcgtccggt tcttgtcatt caaaatgaca tcggaaatcg ttttagtcca     120

acggtgattg tagcggctat tactgcacag attcaaaaag cgaaattacc cactcatgtg     180

gaaattgatg cgaaaaagta cggttttgag agagattctg ttattttact tgagcagatt     240
```

-continued cgaacaatcg ataagcagcg cttaacggac aaaatcactc acttagatga agtgatgatg 300
attcgtgtag atgaagcgct acaaattagt ttaggactaa tagattttta a 351

<210> SEQ ID NO 80
<211> LENGTH: 116
<212> TYPE: PRT
<213> ORGANISM: Bacillus anthracis

<400> SEQUENCE: 80

Met Ile Val Lys Arg Gly Asp Val Tyr Phe Ala Asp Leu Ser Pro Val
1 5 10 15

Val Gly Ser Glu Gln Gly Gly Val Arg Pro Val Leu Val Ile Gln Asn
20 25 30

Asp Ile Gly Asn Arg Phe Ser Pro Thr Val Ile Val Ala Ala Ile Thr
35 40 45

Ala Gln Ile Gln Lys Ala Lys Leu Pro Thr His Val Glu Ile Asp Ala
50 55 60

Lys Lys Tyr Gly Phe Glu Arg Asp Ser Val Ile Leu Leu Glu Gln Ile
65 70 75 80

Arg Thr Ile Asp Lys Gln Arg Leu Thr Asp Lys Ile Thr His Leu Asp
85 90 95

Glu Val Met Met Ile Arg Val Asp Glu Ala Leu Gln Ile Ser Leu Gly
100 105 110

Leu Ile Asp Phe
115

<210> SEQ ID NO 81
<211> LENGTH: 348
<212> TYPE: DNA
<213> ORGANISM: Pseudomonas putida

<400> SEQUENCE: 81
gtgaaacggt tgaaattcgc caggggtgat attgttcgcg tcaacctgga cccaacagtc 60
gggcgggaac agcagggctc cggccgacct gcactggtac ttactccggc tgcgttcaat 120
gcttcaggcc tggctgtaat catcccgatc actcaaggtg gggatttcgc gaggcatgcg 180
ggtttcgctg tcacgctcag cggtgcgggc acgcagactc agggggtgat gctttgcaac 240
caggtgcgca cagtcgacct tgaagcacga tttgccaagc gcatagagtc ggtgcctgaa 300
gctgtcatcc tggatgcact ggcgcgtgtg caaaccctat tcgattaa 348

<210> SEQ ID NO 82
<211> LENGTH: 345
<212> TYPE: DNA
<213> ORGANISM: Mycobacterium celatum

<400> SEQUENCE: 82
tgaattgctc tgacggaacg cggcgacatc tacatcgttt cgcttgaccc gacgtcggga 60
catgagcaga gcggcacgcg cccagtattg gtcgtgtccc cgggcgcgtt taatcgcctg 120
acgaaaacac cggtcgtgct acctataaca cgcggcggga actttgcccg aacggcaggg 180
ttcgctgtct cgctgaccga tgcgggtact cgcaccgccg gcgtaatacg ctgcgatcag 240
cctcgctcga ttgatatccg cgcccgtaaa ggccgcaagg ttgaacgtgt gccgtctggg 300
gttcttgacg aagcgttggc caagctcgcc acgatcttga cttga 345

<210> SEQ ID NO 83
<211> LENGTH: 366
<212> TYPE: DNA

<213> ORGANISM: Shigella flexneri 2a str. 301

<400> SEQUENCE: 83

```
atggtaaagg cacggacgcc acatcgtggt gagatctggt attttaaccc tgatccggtt     60

gccgggcatg aacttcaggg gccacattat tgcattgtgg taacggacaa aaaactcaac    120

aatgttttaa aagttgctat gtgctgcccg atttcaacag gggcaaatgc agcacgttcc    180

acaggggtga cggtgaacgt cctccccgt gatacgcaaa ccggtaacct gcatggcgtt    240

gtactttgtc accagctaaa agccgtcgat cttattgccc gtggcgctaa atttcatacc    300

gttgccgatg aaaaattgat tagtgaagtt atcagtaaac tggtgaattt aatcgaccca    360

caataa                                                              366
```

<210> SEQ ID NO 84
<211> LENGTH: 351
<212> TYPE: DNA
<213> ORGANISM: E. coli

<400> SEQUENCE: 84

```
atggtaaaga aaagtgaatt tgaacgggga gacattgtgc tggttggctt tgatccagca     60

agcggccatg aacagcaagg tgctggtcga cctgcgcttg tgctctccgt tcaagccttt    120

aatcaactgg gaatgacgct ggtggccccc attacgcagg gcggaaattt tgcccgttat    180

gccggattta gcgttccttt acattgcgaa gaaggcgatg tgcacggcgt ggtgctggtg    240

aatcaggtgc ggatgatgga tctacacgcc cggctggcaa agcgtattgg tctggctgcg    300

gatgaggtgg tggaagaggc gttattacgc ttgcaggcgg tggtggaata a            351
```

<210> SEQ ID NO 85
<211> LENGTH: 115
<212> TYPE: PRT
<213> ORGANISM: Pseudomonas putida

<400> SEQUENCE: 85

```
Met Lys Arg Leu Lys Phe Ala Arg Gly Asp Ile Val Arg Val Asn Leu
 1               5                  10                  15

Asp Pro Thr Val Gly Arg Glu Gln Gln Gly Ser Gly Arg Pro Ala Leu
            20                  25                  30

Val Leu Thr Pro Ala Ala Phe Asn Ala Ser Gly Leu Ala Val Ile Ile
        35                  40                  45

Pro Ile Thr Gln Gly Gly Asp Phe Ala Arg His Ala Gly Phe Ala Val
    50                  55                  60

Thr Leu Ser Gly Ala Gly Thr Gln Thr Gln Gly Val Met Leu Cys Asn
65                  70                  75                  80

Gln Val Arg Thr Val Asp Leu Glu Ala Arg Phe Ala Lys Arg Ile Glu
                85                  90                  95

Ser Val Pro Glu Ala Val Ile Leu Asp Ala Leu Ala Arg Val Gln Thr
            100                 105                 110

Leu Phe Asp
        115
```

<210> SEQ ID NO 86
<211> LENGTH: 111
<212> TYPE: PRT
<213> ORGANISM: Mycobacterium celatum

<400> SEQUENCE: 86

```
Met Thr Glu Arg Gly Asp Ile Tyr Ile Val Ser Leu Asp Pro Thr Ser
 1               5                  10                  15
```

```
Gly His Glu Gln Ser Gly Thr Arg Pro Val Leu Val Val Ser Pro Gly
            20                  25                  30

Ala Phe Asn Arg Leu Thr Lys Thr Pro Val Val Leu Pro Ile Thr Arg
        35                  40                  45

Gly Gly Asn Phe Ala Arg Thr Ala Gly Phe Ala Val Ser Leu Thr Asp
    50                  55                  60

Ala Gly Thr Arg Thr Ala Gly Val Ile Arg Cys Asp Gln Pro Arg Ser
65                  70                  75                  80

Ile Asp Ile Arg Ala Arg Lys Gly Arg Lys Val Glu Arg Val Pro Ser
                85                  90                  95

Gly Val Leu Asp Glu Ala Leu Ala Lys Leu Ala Thr Ile Leu Thr
            100                 105                 110


<210> SEQ ID NO 87
<211> LENGTH: 121
<212> TYPE: PRT
<213> ORGANISM: Shigella flexneri 2a str. 301

<400> SEQUENCE: 87

Met Val Lys Ala Arg Thr Pro His Arg Gly Glu Ile Trp Tyr Phe Asn
 1               5                  10                  15

Pro Asp Pro Val Ala Gly His Glu Leu Gln Gly Pro His Tyr Cys Ile
            20                  25                  30

Val Val Thr Asp Lys Lys Leu Asn Asn Val Leu Lys Val Ala Met Cys
        35                  40                  45

Cys Pro Ile Ser Thr Gly Ala Asn Ala Ala Arg Ser Thr Gly Val Thr
    50                  55                  60

Val Asn Val Leu Pro Arg Asp Thr Gln Thr Gly Asn Leu His Gly Val
65                  70                  75                  80

Val Leu Cys His Gln Leu Lys Ala Val Asp Leu Ile Ala Arg Gly Ala
                85                  90                  95

Lys Phe His Thr Val Ala Asp Glu Lys Leu Ile Ser Glu Val Ile Ser
            100                 105                 110

Lys Leu Val Asn Leu Ile Asp Pro Gln
        115                 120


<210> SEQ ID NO 88
<211> LENGTH: 116
<212> TYPE: PRT
<213> ORGANISM: E. coli

<400> SEQUENCE: 88

Met Val Lys Lys Ser Glu Phe Glu Arg Gly Asp Ile Val Leu Val Gly
 1               5                  10                  15

Phe Asp Pro Ala Ser Gly His Glu Gln Gln Gly Ala Gly Arg Pro Ala
            20                  25                  30

Leu Val Leu Ser Val Gln Ala Phe Asn Gln Leu Gly Met Thr Leu Val
        35                  40                  45

Ala Pro Ile Thr Gln Gly Gly Asn Phe Ala Arg Tyr Ala Gly Phe Ser
    50                  55                  60

Val Pro Leu His Cys Glu Glu Gly Asp Val His Gly Val Val Leu Val
65                  70                  75                  80

Asn Gln Val Arg Met Met Asp Leu His Ala Arg Leu Ala Lys Arg Ile
                85                  90                  95

Gly Leu Ala Ala Asp Glu Val Val Glu Glu Ala Leu Leu Arg Leu Gln
            100                 105                 110
```

```
Ala Val Val Glu
        115


<210> SEQ ID NO 89
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 89

aatgatgaca ctggaag                                                17


<210> SEQ ID NO 90
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 90

gtcgttgaca ttgatgg                                                17


<210> SEQ ID NO 91
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 91

atctcgaaca cgcagcc                                                17


<210> SEQ ID NO 92
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 92

tcgttttaca cccttga                                                17


<210> SEQ ID NO 93
<211> LENGTH: 24
<212> TYPE: RNA
<213> ORGANISM: Artificial Sequence
<220> FEATURE:
<223> OTHER INFORMATION: synthetic RNA substrate

<400> SEQUENCE: 93

cuuuaagaag gagauauaca uaug                                        24


<210> SEQ ID NO 94
<211> LENGTH: 23
<212> TYPE: RNA
<213> ORGANISM: Artificial Sequence
<220> FEATURE:
<223> OTHER INFORMATION: synthetic RNA substrate

<400> SEQUENCE: 94

uugaagaaac cuacgaaguc gug                                         23


<210> SEQ ID NO 95
<211> LENGTH: 24
<212> TYPE: RNA
<213> ORGANISM: Artificial Sequence
```

<220> FEATURE:
<223> OTHER INFORMATION: synthetic RNA substrate

<400> SEQUENCE: 95
auaaaaguua cugcggauuu auug 24

<210> SEQ ID NO 96
<211> LENGTH: 25
<212> TYPE: RNA
<213> ORGANISM: Artificial Sequence
<220> FEATURE:
<223> OTHER INFORMATION: synthetic RNA substrate

<400> SEQUENCE: 96
aacgcggugg uuaugacauc aacgg 25

<210> SEQ ID NO 97
<211> LENGTH: 25
<212> TYPE: RNA
<213> ORGANISM: Artificial Sequence
<220> FEATURE:
<223> OTHER INFORMATION: synthetic RNA substrate

<400> SEQUENCE: 97
aggagauaua cauaugaauc aaauc 25

<210> SEQ ID NO 98
<211> LENGTH: 26
<212> TYPE: RNA
<213> ORGANISM: Artificial Sequence
<220> FEATURE:
<223> OTHER INFORMATION: synthetic RNA substrate

<400> SEQUENCE: 98
cgauaaaagu uacugcggau uuauug 26

<210> SEQ ID NO 99
<211> LENGTH: 24
<212> TYPE: RNA
<213> ORGANISM: Artificial Sequence
<220> FEATURE:
<223> OTHER INFORMATION: synthetic RNA substrate

<400> SEQUENCE: 99
ggacaacaug gcuacuaaau accg 24

<210> SEQ ID NO 100
<211> LENGTH: 20
<212> TYPE: PRT
<213> ORGANISM: Artificial Sequence
<220> FEATURE:
<223> OTHER INFORMATION: synthetic peptide tag

<400> SEQUENCE: 100

Met Gly Ser Ser His His His His His His Ser Ser Gly Leu Val Pro
1 5 10 15

Arg Gly Ser His
20

<210> SEQ ID NO 101
<211> LENGTH: 41
<212> TYPE: DNA
<213> ORGANISM: Artificial Sequence
<220> FEATURE:
<223> OTHER INFORMATION: synthetic combined DNA/RNA substrate

<400> SEQUENCE: 101

-continued aucuaccuga agcgacucau cacuucccgg aagauuacau c 41

<210> SEQ ID NO 102
<211> LENGTH: 336
<212> TYPE: RNA
<213> ORGANISM: E. coli

<400> SEQUENCE: 102
augguaagcc gauacguacc cgauaugggc gaucugauuu ggguugauuu ugacccgaca 60
aaagguagcg agcaagcugg acaucgucca gcuguugucc ugaguccuuu cauguacaac 120
aacaaaacag guaugugucu guguguuccu uguacaacgc aaucaaaagg auauccguuc 180
gaaguuguuu uauccgguca ggaacgugau ggcguagcgu uagcugauca gguaaaaagu 240
aucgccuggc gggcaagagg agcaacgaag aaaggaacag uugccccaga ggaauuacaa 300
cucauuaaag ccaaaauuaa cguacugauu ggguag 336

<210> SEQ ID NO 103
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 103
uuuuaacuuu aagaaggaga 20

<210> SEQ ID NO 104
<211> LENGTH: 20
<212> TYPE: DNA
<213> ORGANISM: Artificial Sequence
<220> FEATURE:
<223> OTHER INFORMATION: synthetic combined DNA/RNA substrate

<400> SEQUENCE: 104
aaggagauau acauaugaat 20

<210> SEQ ID NO 105
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 105
gaagaaaccu acgaagugcu 20

<210> SEQ ID NO 106
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 106
gugguguuuu acgcgcaaau 20

<210> SEQ ID NO 107
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 107
cuuugacuuu aaugauauuu 20

<210> SEQ ID NO 108
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 108
cuuuaaugau auuugcgcug 20

<210> SEQ ID NO 109
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 109
cgcauguuuu gcugauaguu 20

<210> SEQ ID NO 110
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 110
gaggugaugu acgaagcgcg 20

<210> SEQ ID NO 111
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 111
ugccacgguu aaucuggcuc 20

<210> SEQ ID NO 112
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 112
aguggagcgu auuguugccg 20

<210> SEQ ID NO 113
<211> LENGTH: 20
<212> TYPE: DNA
<213> ORGANISM: Artificial Sequence
<220> FEATURE:
<223> OTHER INFORMATION: synthetic combined DNA/RNA substrate

<400> SEQUENCE: 113
gataaaaguu acugcggauu 20

<210> SEQ ID NO 114
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 114
ggggauccau acugaaggcg 20

<210> SEQ ID NO 115
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 115
caggcgaucu acgucgauac 20

<210> SEQ ID NO 116
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 116
guaagcaucu accugaagcg 20

<210> SEQ ID NO 117
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 117
ccggaagauu acaucaccga 20

<210> SEQ ID NO 118
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 118
gaacugccgu acuccgugac 20

<210> SEQ ID NO 119
<211> LENGTH: 20
<212> TYPE: RNA
<213> ORGANISM: Artificial Sequence
<220> FEATURE:
<223> OTHER INFORMATION: synthetic RNA substrate

<400> SEQUENCE: 119
cgcggugguu augacaucaa 20

<210> SEQ ID NO 120
<211> LENGTH: 20
<212> TYPE: DNA
<213> ORGANISM: Artificial Sequence
<220> FEATURE:
<223> OTHER INFORMATION: synthetic combined DNA/RNA substrate

<400> SEQUENCE: 120
caacauggcu actaaatacc 20

RNA INTERFERASES AND METHODS OF USE THEREOF

CROSS REFERENCE TO RELATED APPLICATIONS

The present application is a National Stage Application claiming the priority of co-pending PCT Application No. PCT/US2004/018571 filed 14 Jun. 2004, which in turn, claims priority from Provisional Application Ser. Nos. 60/543,693, filed 11 Feb. 2004, and 60/478,515, filed 13 Jun. 2003. Applicants claim the benefits of 35 U.S.C. §120 as to the PCT application and priority under 35 U.S.C. §119 as to the said provisional applications, and the entire disclosures of these applications are incorporated herein by reference in their entireties.

FIELD OF THE INVENTION

The present invention relates to the field of molecular biology, and particularly to the discovery of a novel enzymatic activity. Specifically, the invention pertains to the identification of a novel family of proteins designated herein as mRNA Interferases. Exemplary members of the family described herein include MazF and PemK, and homologs and orthologs thereof. More specifically, the invention relates to the biochemical characterization of MazF and PemK polypeptides as endoribonucleases or mRNA interferases. Also encompassed are analyses of associated proteins which serve to inhibit activities ascribed to mRNA interferases. Specifically, a characterization of MazE protein function and effects thereto on MazF activity and a characterization of PemI protein function and effects thereto on PemK activity are described herein. Methods of use for novel mRNA interferases, such as MazF and PemK, and modulators of MazF and PemK activity, such as MazE and PemI, are also provided which are of utility in research and therapeutic applications.

BACKGROUND OF THE INVENTION

In *Escherichia coli* (*E. coli*), programmed cell death is mediated through “addiction modules” consisting of two genes, one of which encodes a stable toxic protein (toxin) and the other encodes a short-lived antitoxin (Engelberg-Kulka and Glaser, *Annu Rev Microbiol* 53, 43-70 (1999)). The toxin and the antitoxin are coexpressed from an operon and interact with each other to form a stable complex and their expression is auto-regulated either by the toxin-antitoxin complex or by the antitoxin alone. When their co-expression is inhibited by stress conditions, for example, the antitoxin is degraded by proteases, enabling the toxin to act on its target. Such genetic systems for bacterial programmed cell death have been reported in a number of *E. coli* extrachromosomal elements for the so-called postsegregational killing effect (Tsuchimoto et al., *J Bacteriol* 170, 1461-6 (1988); Roberts and Helinski, *J Bacteriol* 174, 8119-32 (1992)). When bacteria lose the plasmids or other extrachromosomal elements, the cells are selectively killed because unstable antitoxins are degraded faster than their cognate stable toxins. Thus, the cells are addicted to the short-lived antitoxins since their de novo synthesis is essential for cell survival.

Among the known addiction modules found on the *E. coli* chromosome (Gotfredsen and Gerdes, *Mol Microbiol* 29, 1065-76 (1998); Mittenhuber, *J Mol Microbiol Biotechnol* 1, 295-302 (1999)), the *E. coli* MazEF system is the first known prokaryotic chromosomal addiction module (Aizenman et al., *Proc Natl Acad Sci USA* 93, 6059-63 (1996)). The mazEF module consists of two overlapping genes mazE and mazF, located downstream of the relA gene. MazF is a stable toxin, whereas MazE is a labile antitoxin, which is readily degraded in vivo by an ATP-dependent ClpPA serine protease (Aizenman et al., *Proc Natl Acad Sci USA* 93, 6059-63 (1996)). mazEF expression is negatively regulated by guanosine 3',5'-bispyrophosphate (ppGpp) synthesized by RelA under severe amino acid starvation (Aizenman et al., *Proc Natl Acad Sci USA* 93, 6059-63 (1996)). Moreover, mazEF-mediated cell death can be triggered by several antibiotics, including rifampicin, chloramphenicol and spectinomycin (Sat et al., *J Bacteriol* 183, 2041-5 (2001)). Results from in vivo experiments using *E. coli* cells have suggested that MazF inhibits both protein synthesis and DNA replication (Pedersen et al., *Mol Microbiol* 45, 501-10 (2002)). Thymineless death has recently been reported to be mediated by the mazEF module (B. Sat, M. Reches, H. Engelberg-Kulka, *J Bacteriol* 185, 1803-7 (2003)).

In *E. coli*, some extrachromosomal elements are known to contain addiction modules and cause bacterial programmed cell death via the so-called postsegregational killing effect. The best studied extrachromosomal addiction modules include the phd-doc system on bacteriophage P1 (Lehnherr et al. (1993) *J Mol Biol* 233, 414-428; Gazit and Sauer. (1999) *J Biol Chem* 274, 16813-16818; Magnuson et al. (1996) *J Biol Chem* 271, 18705-18710; Lehnherr and Yarmolinsky. (1995) *Proc Natl Acad Sci USA* 92, 32743277), the ccdA-ccdB system on factor F (Tam and Kline. (1989) *J Bacteriol* 171, 2353-2360; Bahassi et al. (1999) *J Biol Chem* 274, 10936-10944; Afif et al. (2001) *Mol Microbiol* 41, 73-82; Dao-Thi et al. (2002) *J Biol Chem* 277, 3733-3742), the kis-kid system on plasmid R1 (Ruiz-Echevarria et al. (1991) *Mol Microbiol* 5, 2685-2693; Hargreaves et al. (2002) *Structure* (Camb) 10, 1425-1433; Ruiz-Echevarria et al. (1995) *J Mol Biol* 247, 568-577; Santos-Sierra et al. (2003) *Plasmid* 50, 120-130), and the pemI-pemK system on plasmid R100 (Tsuchimoto et al. (1992) *J Bacteriol* 174, 42054211; Tsuchimoto et al. (1988) *J Bacteriol* 170, 1461-1466; Tsuchimoto and Ohtsubo. (1993) *Mol Gen Genet.* 237, 81-88; Tsuchimoto and Ohtsubo. (1989) *Mol Gen Genet.* 215, 463-468). Interestingly, the *E. coli* chromosome also contains several addiction module systems, such as the relBE system (Gotfredsen and Gerdes. (1998) *Mol Microbiol* 29, 1065-1076; Christensen et al. (2001) *Proc Natl Acad Sci USA* 98, 14328-14333; Christensen and Gerdes. (2003) *Mol Microbiol* 48, 1389-1400; Pedersen et al. (2003) *Cell* 112, 131-140), the mazEF system (Aizenman et al. (1996) *Proc Natl Acad Sci USA* 93, 6059-6063; Marianovsky et al. (2001) *J Biol Chem* 276, 5975-5984; Kamada et al. (2003) *Mol Cell* 11, 875-884; Zhang et al. (2003) *J Biol Chem* 278, 32300-32306) and the chpB system (Santos Sierra et al. (1998) *FEMS Microbiol Lett* 168, 51-58; Masuda et al. (1993) *J Bacteriol* 175, 6850-6856; Christensen et al. (2003) *J Mol Biol* 332, 809-819).

The cellular effects of toxins associated with addiction modules have been studied quite extensively. CcdB, the toxin in the ccdA-ccdB system, interacts with DNA gyrase to block DNA replication (Bahassi et al. (1999) supra; Kampranis et al. (1999) *J Mol Biol* 293, 733-744), and RelE, the toxin in the relBE system cleaves mRNA in the ribosome A site with high codon-specificity, but is not able to degrade free RNA (Pedersen et al. (2003) supra). It was recently demonstrated, however, that the A-site mRNA cleavage can occur in the absence of RelE (Hayes and Sauer. (2003) *Mol Cell* 12, 903-911). The exact mechanism of the A-site mRNA cleavage, therefore, is still unknown. It has been proposed that MazF (ChpAK), the toxin encoded by the mazEF system, and ChpBK, the toxin encoded by chpB system, inhibit translation by a mechanism very similar to that of RelE in a ribosome-dependent and codon-specific manner (Christensen et al. (2003) supra). The present inventors have, however, recently demonstrated that MazF is a sequence-specific endoribonuclease functional only for single-stranded RNA, which preferentially cleaves mRNAs at the ACA sequence in a manner independent of ribosomes and codons, and is, therefore, functionally distinct from RelE (Zhang et al. (2003) *Mol Cell* 12, 913-923).

The pemI-pemK system and the kis-kid system are involved in the stable maintenance of two closely related incFII low-copy plasmids, plasmid R100 (Tsuchimoto et al. (1992) supra; Tsuchimoto et al. (1988) supra) and plasmid R1 (Ruiz-Echevarria et al. (1991) supra; Bravo et al. (1987) *Mol Gen Genet* 210, 101-110), respectively. These two systems are now known to be identical (Engelberg-Kulka and Glaser. (1999) supra). It has been demonstrated that Kid (PemK) inhibits ColE1 plasmid replication acting at the initiation of DNA synthesis, but does not inhibit P4 DNA replication in vitro (Ruiz-Echevarria et al. (1995) supra). To date, there is no evidence that Kid (PemK) inhibits chromosomal DNA replication. Toxin Kid (PemK) and antidote Kis (PemI) not only function in bacteria, but also function efficiently in a wide range of eukaryotes. Kid (PemK) inhibits proliferation in yeast, *Xenopus laevis* and human cells, wherein Kis (PemI) abrogates this inhibition (de la Cueva-Mendez et al. (2003) *Embo J* 22, 246-251). It has also been demonstrated that Kid (PemK) triggers apoptosis in human cells (de la Cueva-Mendez et al. (2003) supra). These results suggest that there is a common target for Kid (PemK) in both prokaryotes and eukaryotes.

The citation of references herein shall not be construed as an admission that such is prior art to the present invention.

Other features and advantages of the invention will be apparent from the detailed description, the drawings, and the claims.

SUMMARY OF THE INVENTION

In a first aspect, the present invention relates to the discovery of a novel family of enzymes, also referred to herein as "RNA Interferases". As described herein, exemplary endoribonucleases of the mRNA interferase family include MazF and PemK, and homologs and orthologs thereof. The invention, therefore, encompasses endoribonucleases having either sequence and/or structural homology to either MazF or PemK polypeptides.

Of note, prior to the discovery of the present invention, the cellular target(s) of MazF had not been identified. Moreover, the present invention is also directed to the discovery that PemK effectively blocks protein synthesis by cleaving cellular mRNAs in a sequence specific manner. A novel finding of the present inventors, therefore, presents new applications for which mRNA interferase (e.g., MazF and/or PemK) nucleic and amino acid sequences and compositions thereof may be used to advantage. Such utilities include, but are not limited to, various research and therapeutic applications as described hereinbelow. Also provided is a kit comprising mRNA interferase (e.g., MazF and/or PemK) nucleic and/or amino acid sequences, mRNA interferase activity compatible buffers, and instruction materials.

The invention also provides a method for detecting an activity of an mRNA interferase or functional fragment thereof, wherein said activity is endoribonuclease activity, said method comprising:

(a) providing a nucleic acid sequence encoding said mRNA interferase or a functional fragment thereof;

(b) expressing the nucleic acid sequence of step (a);

(c) incubating the expressed nucleic acid sequence of step (b) with an endoribonuclease substrate; and (d) measuring cleavage of said substrate, wherein cleavage of said substrate indicates endoribonuclease activity and provides means to detect or is a positive indicator of endoribonuclease activity of an mRNA interferase or a functional fragment thereof.

Also encompassed by the present invention is a method for screening to identify an agent capable of modulating an activity of an mRNA interferase or functional fragment thereof, wherein said activity is endoribonuclease activity, said method comprising:

(a) providing a nucleic acid sequence encoding said mRNA interferase or a functional fragment thereof;

(b) expressing the nucleic acid sequence of step (a);

(c) incubating the expressed nucleic acid sequence of step (b) with an endoribonuclease substrate under conditions capable of promoting endoribonuclease activity;

(d) adding at least one agent potentially capable of modulating endoribonuclease activity of an mRNA interferase or functional fragment thereof; and (e) measuring cleavage of said substrate, wherein cleavage of said substrate indicates endoribonuclease activity and provides means to detect endoribonuclease activity or is a positive indicator of an mRNA interferase or a functional fragment thereof, and wherein a change in an amount of cleaved substrate in the presence of the at least one agent capable of modulating endoribonuclease activity of an mRNA interferase or functional fragment thereof identifies an agent capable of modulating an activity of an mRNA interferase or functional fragment thereof. Such methods are performed in vitro or in a cell.

Such an agent identified using the methods of the invention, which is capable of modulating an endoribonuclease activity of an mRNA interferase or a functional fragment thereof may effectuate either an increase or a decrease in substrate cleavage. The present invention also encompasses agents identified using the methods of the invention.

In another aspect, a method is presented for modulating an activity of an mRNA interferase or functional fragment thereof, wherein said activity is endoribonuclease activity, said method comprising:

(a) providing a nucleic acid sequence encoding said mRNA interferase or a functional fragment thereof;

(b) expressing the nucleic acid sequence of step (a);

(c) incubating the expressed nucleic acid sequence of step (b) with an endoribonuclease substrate under conditions capable of promoting endoribonuclease activity;

(d) adding an agent capable of modulating the endoribonuclease activity of an mRNA interferase or functional fragment thereof; and (e) measuring cleavage of said substrate, wherein cleavage of said substrate indicates endoribonuclease activity and provides means to detect endoribonuclease activity or is a positive indicator of an mRNA interferase or a functional fragment thereof, and wherein a change in an amount of cleaved substrate in the presence of the agent provides means to modulate endoribonuclease activity of an mRNA interferase or functional fragment thereof.

Exemplary nucleic acid sequences encoding an mRNA interferase include, but are not limited to, SEQ ID NO: 1 or 3, and nucleic acid sequences that encode SEQ ID NO: 2 or 4, and homologs and orthologs thereof as described herein below. An exemplary homolog/ortholog thereof is MazF-mt1, comprising a nucleic and amino acid sequence comprising SEQ ID NO: 69 and 74, respectively.

In another embodiment, a method is provided for detecting an activity of an mRNA interferase or functional fragment thereof, wherein said activity is endoribonuclease activity, said method comprising:

(a) providing an amino acid sequence comprising an mRNA interferase;

(b) incubating the amino acid sequence of step (a) with an endoribonuclease substrate under conditions capable of promoting endoribonuclease activity; and (c) measuring cleavage of said substrate, wherein cleavage of said substrate indicates endoribonuclease activity and provides means to detect or is a positive indicator of endoribonuclease activity of an mRNA interferase or a functional fragment thereof.

The present invention also encompasses a method for screening to identify an agent capable of modulating an activity of an mRNA interferase or functional fragment thereof, wherein said activity is endoribonuclease activity, said method comprising:

(a) providing an amino acid sequence comprising an mRNA interferase;

(b) incubating the amino acid sequence of step (a) with an endoribonuclease substrate under conditions capable of promoting endoribonuclease activity;

(c) adding at least one agent potentially capable of modulating endoribonuclease activity of an mRNA interferase or functional fragment thereof; and (d) measuring the cleavage of said substrate, wherein cleavage of said substrate indicates endoribonuclease activity and provides means to detect endoribonuclease activity of an mRNA interferase or a functional fragment thereof, and wherein a change in an amount of cleaved substrate in the presence of the at least one agent identifies an agent capable of modulating an activity of an mRNA interferase or functional fragment thereof. Such methods may be performed, for example, in vitro or in a cell.

Agents identified using these methods, which are capable of modulating an endoribonuclease activity of mRNA interferase or a functional fragment thereof, can effectuate either an increase or a decrease in substrate cleavage. Such modulatory agents are within the scope of the invention. It is to be understood that such agents may, for example, modulate endoribonuclease activity of an mRNA interferase (e.g., PemK, Maze, or functional and/or structural homologs or orthologs) by acting on the mRNA interferase (toxin) or its antitoxin (e.g., PemI, MazE, respectively, or an antitoxin of a functional and/or structural homolog or ortholog of either), or by altering the autoregulatory feedback mechanism whereby toxin-antitoxin complexes downregulate expression of the toxin and antitoxin genes. An agent capable of altering the autoregulatory feedback mechanism whereby toxin-antitoxin complexes downregulate expression of toxin and antitoxin genes could alter the coordinate regulation of these genes. In an aspect of this embodiment, an agent that is capable of reducing toxin-antitoxin complex formation inhibits the effect of antitoxin, which results in increased toxin activity that eventually leads to cell death. In another aspect, an agent that is capable of blocking expression of antitoxin and toxin genes is envisioned, wherein this agent leads to an increase in toxin levels relative to those of antitoxin due to the stable nature of the toxins. Such an imbalance also results in cellular toxicity.

Accordingly, such agents may be used advantageously for treating a subject with a bacterial infection, particularly those with antibiotic resistant strains of bacteria. Such agents are within the scope of the present invention and may be used alone or in combination.

Also provided is a method for modulating an activity of an mRNA interferase or functional fragment thereof, wherein said activity is endoribonuclease activity, said method comprising:

(a) providing an amino acid sequence of an mRNA interferase;

(b) incubating the amino acid sequence of step (a) with an endoribonuclease substrate under conditions capable of promoting endoribonuclease activity;

(c) adding an agent capable of modulating the endoribonuclease activity of an mRNA interferase or functional fragment thereof; and (d) measuring cleavage of said substrate, wherein cleavage of said substrate indicates endoribonuclease activity and provides means to detect endoribonuclease activity or is a positive indicator of an mRNA interferase or a functional fragment thereof, and wherein a change in an amount of cleaved substrate in the presence of the agent provides means to modulate endoribonuclease activity of an mRNA interferase or functional fragment thereof. Such methods may be performed, for example, in cell-based assays (in culture or in a subject such as a non-human animal or a human patient) or in vitro.

In accordance with the present invention, exemplary amino acid sequences comprising an mRNA interferase include, but are not limited to, SEQ ID NO: 2 or 4, and homologs and orthologs thereof as described herein below. An exemplary homolog/ortholog thereof is MazF-mt1, comprising an amino acid sequence of SEQ ID NO: 74.

The invention also includes a method for detecting an activity of an mRNA interferase or functional fragment thereof in a cell, wherein said activity is endoribonuclease activity, said method comprising:

(a) providing a cell comprising an expression vector, which vector comprises a nucleic acid sequence encoding an mRNA interferase, and/or which encodes an amino acid sequence comprising an mRNA interferase, and which optionally includes at least one regulatory sequence;

(b) incubating the cell of step (a) under conditions capable of promoting endoribonuclease activity of at least one cellular substrate; and (c) measuring cleavage of said at least one cellular substrate, wherein cleavage of said at least one cellular substrate indicates endoribonuclease activity and provides means to detect endoribonuclease activity of an mRNA interferase or a functional fragment thereof in a cell.

In an aspect, a method for modulating an activity of an mRNA interferase or functional fragment thereof in a cell is presented, wherein said activity is endoribonuclease activity, said method comprising:

(a) providing a cell comprising an expression vector, which vector comprises a nucleic acid sequence encoding an mRNA interferase, and/or which encodes an amino acid sequence comprising an mRNA interferase, and which optionally includes at least one regulatory sequence;

(b) incubating the cell of step (a) under conditions capable of promoting endoribonuclease activity of at least one cellular substrate;

(c) adding an agent capable of modulating endoribonuclease activity of an mRNA interferase or functional fragment thereof; and (d) measuring cleavage of said at least one cellular substrate, wherein cleavage of said at least one cellular substrate indicates endoribonuclease activity and provides means to detect endoribonuclease activity of an mRNA interferase or a functional fragment thereof in a cell, and wherein a change in an amount of at least one cleaved substrate in the presence of the agent provides means to modulate endoribonuclease activity of an mRNA interferase or functional fragment thereof.

Also presented is a method for screening to identify an agent capable of modulating an activity of an mRNA interferase or functional fragment thereof in a cell, wherein said activity is endoribonuclease activity, said method comprising:

(a) providing a cell comprising an expression vector, which vector comprises a nucleic acid sequence encoding an mRNA interferase, and/or which encodes an amino acid sequence comprising an mRNA interferase, and which optionally includes at least one regulatory sequence;
(b) incubating the cell of step (a) under conditions capable of promoting endoribonuclease activity of at least one cellular substrate;
(c) adding at least one agent potentially capable of modulating endoribonuclease activity of an mRNA interferase or functional fragment thereof; and
(d) measuring cleavage of said at least one cellular substrate, wherein cleavage of said at least one cellular substrate indicates endoribonuclease activity and provides means to detect endoribonuclease activity of an mRNA interferase or a functional fragment thereof in a cell, and wherein a change in an amount of at least one cleaved substrate in the presence of the agent identifies an agent capable of modulating an activity of an mRNA interferase or functional fragment thereof.

In accordance with the present invention, a cell comprising an expression vector which comprises a nucleic acid sequence encoding an mRNA interferase encompasses nucleic acid sequences that include, but are not limited to, SEQ ID NO: 1 or 3, and homologs and orthologs thereof as described herein; and nucleic acid sequences that encode SEQ ID NO: 2 or 4, and homologs and orthologs thereof as described herein. An exemplary homolog/ortholog thereof is MazF-mt1, comprising a nucleic and amino acid sequence comprising SEQ ID NO: 69 and 74, respectively.

Also provided is a composition comprising at least one mRNA interferase or functional fragment thereof, an mRNA interferase encoding nucleic acid sequence, and/or an mRNA interferase modulatory agent identified using the methods of the invention and a pharmaceutically acceptable buffer.

In an aspect, a method is presented for treating a patient with a disorder, said method comprising administering to said patient a therapeutically effective amount of a composition of the invention to alleviate symptoms of said disorder. The composition comprises at least one agent capable of either increasing or decreasing endoribonuclease substrate cleavage, depending on the disorder afflicting the patient, to alleviate symptoms of the disorder.

Accordingly, the invention includes use of a therapeutically effective amount of an mRNA interferase or functional fragment thereof, an mRNA interferase encoding nucleic acid sequence, or an mRNA interferase modulatory agent in the preparation of a medicament for use in the treatment of a patient having a disorder to alleviate symptoms of said disorder. Such medicaments may further comprise a pharmaceutically acceptable buffer.

A disorder such as a bacterial infection, for example, is treatable by administering a composition of the invention comprising a therapeutically effective amount of at least one molecule or agent capable of increasing endoribonuclease substrate cleavage to a patient to alleviate symptoms of the bacterial infection by reducing the number of bacteria in the patient. Such methods are used to particular advantage when the bacterial infection comprises at least one antibiotic resistant bacterial strain.

The methods of the invention are also useful for the treatment of a hyperproliferative disorder, wherein administering a composition of the invention comprising a therapeutically effective amount of at least one molecule or agent capable of increasing endoribonuclease substrate cleavage to a patient alleviates symptoms of the hyperproliferative disorder by reducing the number of hyperproliferative cells in the patient. Hyperproliferative disorders, which are characterized by unregulated cell proliferation, treatable using the compositions and methods of the invention include, but are not limited to, dysplasias and metaplasias of different tissues, inflammatory conditions, autoimmune diseases, hyperproliferative skin disorders, psoriasis, allergy/asthma, atherosclerosis, restenosis after angioplastic surgery, and cancer.

Also encompassed is a method for treating a patient with a disorder, said method comprising administering to the patient a therapeutically effective amount of a composition of the invention, wherein at least one agent of said composition effectuates a decrease in endoribonuclease substrate cleavage, to alleviate symptoms of said disorder.

Also encompassed is a method for making a polypeptide in a cell, said method comprising:

(a) transfecting said cell with a nucleic acid sequence encoding said polypeptide, wherein the nucleic acid sequence encoding said polypeptide is mutated to replace mRNA interferase recognition sequences with an alternate triplet codon, wherein amino acid sequences of said polypeptide encoded by said mutated nucleic acid sequence are not altered by said mutating;
(b) transfecting said cell with a nucleic acid sequence encoding an mRNA interferase, wherein said mRNA interferase recognizes said mRNA interferase recognition sequences; and
(c) expressing the nucleic acid sequences of step (a) and (b) in said cell, wherein expressing the nucleic acid sequences of step (a) and (b) in said cell provides means to produce the polypeptide in said cell.

In accordance with the invention, the nucleic acid sequences encoding either the polypeptide or the mRNA interferase may be included in a first and a second expression vector, respectively. Moreover, the transfecting steps of step (a) and (b) may be performed separately or simultaneously (e.g., by co-transfection). As indicated herein above, mutation of the mRNA interferase recognition sequences in a nucleic acid sequence to a different triplet sequence or codon does not alter the amino acid sequence of the polypeptide encoded by the mutated nucleic acid sequence. The mutation is, therefore, silent with respect to the amino acid sequence of the encoded polypeptide. The purpose of mutating the nucleic acid sequence is to dramatically reduce the susceptibility of the RNA message transcribed therefrom to the endoribonucleolytic activity of the mRNA interferase in question. Expression of a nucleic acid of step (b) (e.g., a nucleic acid sequence encoding, e.g., a PemK polypeptide or functional fragment thereof, or a MazF polypeptide or functional fragment thereof, or a homolog or ortholog of either MazF or PemK) reduces or inhibits synthesis of cellular polypeptides encoded by nucleic acid sequences comprising the mRNA interferase recognition sequences. Thus, the method produces a desired polypeptide essentially in the absence of cellular proteins whose RNA transcripts comprise the mRNA interferase recognition sequence recognized by the expressed mRNA interferase. The method, therefore, provides for making a "purified" polypeptide in a cell. For some applications, the method further comprises incubating the cell prior to or during step (c) in media comprising at least one radioactively labeled isotope. Such applications include, but are not limited to, the generation of labeled polypeptides for subsequent analyses using nuclear magnetic resonance (NMR) technology.

In a particular embodiment, the method for making a polypeptide in a cell utilizes the mRNA recognition sequence Adenine-Cytosine-Adenine (ACA) and the mRNA interferase MazF comprising SEQ ID NO: 2 or a functional fragment thereof. In this embodiment, expression of a nucleic acid encoding MazF or a functional fragment thereof reduces or inhibits synthesis of cellular polypeptides encoded by nucleic acid sequences comprising ACA sequences.

In another embodiment, the method for making a polypeptide in a cell utilizes the mRNA recognition sequence Uracil-Adenine-X (UAX), wherein X is a Cytosine (C), A, or U, and the mRNA interferase PemK comprising SEQ ID NO: 4 or a functional fragment thereof. In this embodiment, expression of a nucleic acid encoding PemK or a functional fragment thereof reduces or inhibits synthesis of cellular polypeptides encoded by nucleic acid sequences comprising UAX sequences.

In yet another embodiment, the method for making a polypeptide in a cell utilizes the mRNA recognition sequence Uracil-Adenine-C (UAC), and the mRNA interferase MazF-mt1 comprising SEQ ID NO: 74 or a functional fragment thereof. In this embodiment, expression of a nucleic acid encoding MazF-mt1 or a functional fragment thereof reduces or inhibits synthesis of cellular polypeptides encoded by nucleic acid sequences comprising UAC sequences.

In one aspect of the present invention, a method for making a polypeptide is presented comprising:

(a) providing a nucleic acid sequence encoding said polypeptide, wherein the nucleic acid sequence encoding said polypeptide is mutated to replace mRNA interferase recognition sequences with an alternate triplet codon, wherein amino acid sequences of said polypeptide encoded by said mutated nucleic acid sequence are not altered by said mutating;

(b) providing a nucleic acid sequence encoding an mRNA interferase, wherein said mRNA interferase recognizes said mRNA interferase recognition sequences; and (c) expressing the nucleic acid sequences of step (a) and (b), wherein expressing the nucleic acid sequences of step (a) and (b) provides means to produce the polypeptide. This method may be performed in vitro, for example, in a test tube or the like. Suitable in vitro transcription/translation systems or cell-free expression systems are known in the art and described herein below. The mRNA interferase or fragment thereof may optionally be provided as an expressed protein, rather than in the form of a nucleic acid sequence requiring expression therefrom.

In a particular embodiment, the method for making a polypeptide utilizes the mRNA recognition sequence ACA and the mRNA interferase MazF comprising SEQ ID NO: 2 or a functional fragment thereof.

In an alternative embodiment, the method for making a polypeptide utilizes the mRNA recognition sequence UAX, wherein X is a C, A, or U, and the mRNA interferase PemK comprising SEQ ID NO: 4 or a functional fragment thereof.

In yet another embodiment, the method for making a polypeptide utilizes the mRNA recognition sequence UAC, and the mRNA interferase MazF-mt1 comprising SEQ ID NO: 74 or a functional fragment thereof.

The present invention is also directed to a method for making a plurality of polyribonucleotide sequences using mRNA interferases of the invention. The method comprises:

(a) providing a first and a second nucleic acid sequence, wherein a region of said first nucleic acid sequence is complementary to a region of said second nucleic acid sequence and neither complementary region of said first or second nucleic acid sequence comprises a sequence complementary to an mRNA interferase recognition site, and each of said first and second nucleic acid sequences is phosphorylated at its 5' terminus;

(b) annealing said first and second nucleic acid sequences via a complementary region of said first and second nucleic acid sequences to form a double stranded nucleic acid sequence comprising a complementary region flanked by single stranded overhangs, wherein each of said single stranded overhangs comprises at least one sequence complementary to an mRNA interferase recognition site and said single stranded overhangs are complementary to each other;

(c) ligating annealed first and second nucleic acid sequences via complementary single stranded overhangs to form a concatamer comprising a plurality of tandem repeats of annealed first and second nucleic acid sequences;

(d) amplifying said concatamer using a first primer comprising a T7 promoter and a region complementary to said first nucleic acid sequence and a second primer complementary to said second nucleic acid sequence, wherein said amplifying produces a plurality of concatamers comprising a T7 promoter;

(e) transcribing RNA molecules from said plurality of concatamers using T7 RNA polymerase, wherein each of said RNA molecules comprises a plurality of tandem repeats of a polyribonucleotide sequence flanked by mRNA interferase recognition sites; and (f) digesting said RNA molecules with an mRNA interferase capable of cleaving RNA at said interferase recognition sites, wherein said digesting produces a plurality of said polyribonucleotide sequences.

In a particular aspect of the method for making a plurality of polyribonucleotide sequences, the mRNA recognition sequence is an ACA sequence and the mRNA interferase is MazF comprising SEQ ID NO: 2 or a functional fragment thereof.

In another aspect of the method for making a plurality of polyribonucleotide sequences, the mRNA recognition sequence is a UAX sequence, wherein X is a C, A, or U, and the mRNA interferase is PemK comprising SEQ ID NO: 4 or a functional fragment thereof.

In yet another aspect of the method for making a plurality of polyribonucleotide sequences, the mRNA recognition sequence is a UAC sequence, and the mRNA interferase is MazF-mt1 comprising SEQ ID NO: 74 or a functional fragment thereof.

The invention is also directed to an isolated nucleic acid sequence which encodes a polypeptide having sequence and/or structural homology to either SEQ ID NO: 2 or SEQ ID NO: 4, or a functional fragment thereof, wherein said polypeptide is capable of exhibiting endoribonuclease activity. In one embodiment, a polypeptide having sequence and/or structural homology to SEQ ID NO: 2 or a functional fragment thereof is a MazF ortholog capable of exhibiting endoribonuclease activity. Polypeptides capable of exhibiting endoribonuclease activity include, but are not limited to, *Bacillus halodurans* MazF (NP_244588.1), *Staphylococcus epidermidis* MazF (AAG23809.1), *Staphylococcus aureus*

MazF (NP_372592.1), *Bacillus subtilis* MazF (1NE8_A), *Neisseria meningitides* MazF (NP_266040.1), *Morganella morgani* MazF (AAC82516.1) and *Mycobacterium tuberculosis* MazF (NP_217317.1).

In another embodiment, a polypeptide having sequence and/or structural homology to SEQ ID NO: 4 or a functional fragment thereof is a PemK homolog or ortholog capable of exhibiting endoribonuclease activity. Polypeptides capable of exhibiting endoribonuclease activity include, but are not limited to, the 73 known members of the PemK protein family, which includes MazF (ChpAK), ChpBK and other PemK-like proteins. The following is a list of designations for these proteins found in web site (http://pfam.wustl.edu/cgi-bin/getdesc?acc=PF02452): Q9RX98; Q8F5A3; Q9K6K8; CHPA_ECOLI; Q7NPF9; Q88TP7; Q7WWW1; Q8YS80; Q8DW95; Q82YR2; Q7X3Y1; Q93S64; Q8PRN1; Q8GFY1; O52205; PEMK_ECOLI Q7N4H2; Q88PS7; Q8XCF2 CHPB_ECOLI; Q82VU0; Q8UGU5; Q9RWK4; Q9PHH8; Q7TXU4; P71650; Q7U1Y5; P96295; Q9JWF2; Q9JXI1; Q8E882; Q82VB5; Q8KJS3; Q7NMY4; Q9KFF7; P96622; Q81IT4; Q81VF4; Q8ESK5; Q92DC7; Q8Y8L0; Q97LR0; Q8XNN7; Q8R861; Q88Z43; O07123; Q83719; Q9F7V5; Q8CRQ1; O05341; P95840; Q9FCV0; Q837L1; Q93M89; Q99IU9; Q82UB5; Q93MT8; YJ91_MYCTU; Q97MV8; Q7NHW0; Q7NI95; Q8YML2; Q7NHR3; YE95_MYCTU; Q9PCB9; Q8YZW8; Q7TZ90; P95272; Q8VJR1; Q7U0N2; O53450; O06780; and Q7U1I8.

Also encompassed by the invention are expression vectors comprising an isolated nucleic acid sequence which encodes a polypeptide having sequence and/or structural homology to either SEQ ID NO: 2 or SEQ ID NO: 4, or a functional fragment thereof, wherein said polypeptide is capable of exhibiting endoribonuclease activity. Cells comprising these expression vectors are also envisioned, as are transgenic animals comprising an isolated nucleic acid sequence of the invention, wherein a nucleic acid sequence is expressed in at least one cell of the transgenic animal.

In another aspect of the invention, an isolated amino acid sequence comprising a polypeptide having sequence and/or structural homology to either SEQ ID NO: 2 or SEQ ID NO: 4, or a functional fragment thereof, wherein said polypeptide is capable of exhibiting endoribonuclease activity, is presented. Also included are expression vectors encoding an amino acid sequence of the invention, wherein expression of the amino acid sequence is controlled by regulatory sequences in the expression vector, cells comprising such expression vectors, and transgenic animals comprising an amino acid sequence of the invention, wherein the amino acid sequence is expressed in at least one cell in the transgenic animal.

In another aspect of the invention, an isolated nucleic acid sequence comprising SEQ ID NO: 1 or SEQ ID NO: 3, wherein the nucleic acid sequence encodes an mRNA interferase or functional fragment thereof capable of exhibiting endoribonuclease activity is provided.

Also described is an expression vector comprising a nucleic acid sequence of SEQ ID NO: 1 or SEQ ID NO: 3, wherein the nucleic acid sequence encodes an mRNA interferase or functional fragment thereof capable of exhibiting endoribonuclease activity, and SEQ ID NO: 1 or SEQ ID NO: 3 is operably linked to a regulatory sequence. Moreover, a cell comprising such an expression vector is also within the scope of the invention.

In another aspect, a transgenic animal comprising a nucleic acid sequence comprising SEQ ID NO: 1 or SEQ ID NO: 3, wherein the nucleic acid sequence encodes an mRNA interferase or functional fragment thereof capable of exhibiting endoribonuclease activity, and wherein the nucleic acid sequence is expressed in at least one cell of the transgenic animal is presented.

Also provided is an isolated nucleic acid sequence encoding a polypeptide comprising SEQ ID NO: 2 or SEQ ID NO: 4, wherein the polypeptide is an mRNA interferase or functional fragment thereof, capable of exhibiting endoribonuclease activity.

In another aspect, an expression vector is presented comprising an isolated nucleic acid sequence encoding a polypeptide comprising SEQ ID NO: 2 or SEQ ID NO: 4, wherein the polypeptide is an mRNA interferase or functional fragment thereof, capable of exhibiting endoribonuclease activity, and the nucleic acid sequence is operably linked to regulatory sequence. Cells comprising such expression vectors are also encompassed.

In yet another aspect, a transgenic animal comprising an isolated nucleic acid sequence encoding a polypeptide comprising SEQ ID NO: 2 or SEQ ID NO: 4 is presented, wherein the polypeptide is an mRNA interferase or functional fragment thereof, capable of exhibiting endoribonuclease activity, and the nucleic acid sequence is expressed in at least one cell of the transgenic animal In an embodiment of the invention, an isolated amino acid sequence comprising SEQ ID NO: 2 or SEQ ID NO: 4, wherein the amino acid sequence is an mRNA interferase or functional fragment thereof, and the mRNA interferase or functional fragment thereof is capable of exhibiting endoribonuclease activity is provided.

Also described is an expression vector encoding an isolated amino acid sequence comprising SEQ ID NO: 2 or SEQ ID NO: 4, wherein the amino acid sequence is an mRNA interferase or functional fragment thereof, and the mRNA interferase or functional fragment thereof is capable of exhibiting endoribonuclease activity, and expression of the amino acid sequence is controlled by regulatory sequences in the expression vector. A cell comprising such an expression vector is also encompassed by the invention.

In another aspect, a transgenic animal comprising an isolated polypeptide comprising SEQ ID NO: 2 or SEQ ID NO: 4, wherein the polypeptide is an mRNA interferase or functional fragment thereof, capable of exhibiting endoribonuclease activity, and the polypeptide is expressed in at least one cell in the transgenic animal is presented.

The present invention also includes a kit comprising an isolated nucleic acid sequence comprising SEQ ID NO: 1 or SEQ ID NO: 3, wherein the nucleic acid sequence encodes an mRNA interferase or functional fragment thereof; an isolated amino acid sequence comprising SEQ ID NO: 2 or SEQ ID NO: 4, wherein the amino acid sequence is an mRNA interferase or functional fragment thereof; an mRNA interferase activity compatible buffer; and instructional materials.

The present invention also encompasses the use of mRNA interferases of the invention in applications directed to gene therapy. Cells that are engineered to express a molecule, which is defective or deficient in a subject (e.g., a human subject), can also be designed to self destruct via the incorporation of an mRNA interferase of the invention, the expression of which is controlled by an inducible regulatory element(s). Incorporation of an inducible means for the destruction of cells used for gene therapy applications provides a fail-safe mechanism whereby such cells can be eliminated after they have conferred beneficial effects to a subject and/or before they can cause deleterious effects.

BRIEF DESCRIPTION OF THE DRAWINGS

FIGS. 1A and 1B show cellular proliferation on different solid media and sequence alignments of different members of the MazF family of RNA Interferases. FIG. 1A shows growth properties of *E. coli* BW25113(ΔaraBAD) cells transformed with pBAD-MazF, pBAD-MazF R29S or pBAD-MazF R86G plasmid, respectively. FIG. 1B depicts sequence alignments of MazF of *Escherichia coli* (GenBank Accession No. NP_289336.1; SEQ ID NO: 2) with that of *Bacillus halodurans* (GenBank Accession No. NP_244588.1; SEQ ID NO: 46), *Staphylococcus epidermidis* (GenBank Accession No. AAG23809.1; SEQ ID NO: 47), *Staphylococcus aureus* (GenBank Accession No. NP_372592.1; SEQ ID NO: 48), *Bacillus subtilis* (GenBank Accession No. 1NE8_A; SEQ ID NO: 49), *Neisseria meningitides* (GenBank Accession No. NP_266040.1; SEQ ID NO: 50), *Morganella morgani* (GenBank Accession No. AAC82516.1; SEQ ID NO: 51) and *Mycobacterium tuberculosis* (GenBank Accession No. NP_217317.1; SEQ ID NO: 52).

FIGS. 3A-C show a line trace depicting a densitometric analysis of polysome profiles (FIG. 3A), which reveals the effect of MazF on polysome profiles, and show protein gels demonstrating the effect of MazF(His)$_6$ on prokaryotic (FIG. 3B) and eukaryotic (FIG. 3C) cell-free protein synthesis.

FIG. 4A shows toeprinting of the mazG mRNA in the presence of MazF. FIG. 4B shows toeprinting of the mazG mRNA after phenol extraction. FIG. 4C shows an effect of MazE on MazF cleavage of mazG mRNA. FIG. 4D shows a Northern blot analysis of total cellular mRNA extracted from *E. coli* BW25113 cells containing pBAD-MazF at various time points after the addition of arabinose (as indicated) and probed with radiolabeled ompA and lpp ORF DNA.

FIG. 15 shows alignments of the amino acid sequences of MazE homologs. Sequence alignments of eight MazE family proteins are shown. The amino acid sequences shown therein (as presented from top to bottom) are designated SEQ ID NO: 60; SEQ ID NO: 61; SEQ ID NO: 62; SEQ ID NO: 63; SEQ ID NO: 6; SEQ ID NO: 64; SEQ ID NO: 65; and SEQ ID NO: 66.

As shown in FIGS. 16A and 16B, a MazE N-terminal domain mediates DNA binding of MazE-MazF (His)$_6$ complex and (His)$_6$MazE protein, respectively.

FIGS. 20A and 20B show a nucleic (SEQ ID NO: 1) and amino acid (SEQ ID NO: 2) sequence of *E. coli* MazF.

FIGS. 21A and 21B show a nucleic (SEQ ID NO: 5) and amino acid (SEQ ID NO: 6) sequence of *E. coli* MazE.

FIGS. 22A-22H show nucleic acid sequences of orthologs of *E. coli* MazF.

FIGS. 23A-23H show amino acid sequences of orthologs of *E. coli* MazF.

FIGS. 24A-24G show nucleic acid sequences of orthologs of *E. coli* MazE.

FIGS. 25A-25G show amino acid sequences of orthologs of *E. coli* MazE.

FIGS. 26A and 26B are line graphs depicting the effect of PemK on (A) DNA and (B) protein synthesis in vivo. FIG. 26C shows an SDS-PAGE analysis of total cellular proteins following PemK induction.

FIGS. 31A and 31B show a nucleic (SEQ ID NO: 3) and amino acid (SEQ ID NO: 4) sequence of *E. coli* PemK.

FIGS. 32A and 32B show a nucleic (SEQ ID NO: 7) and amino acid (SEQ ID NO: 8) sequence of *E. coli* PemI.

FIG. 34 shows sequence alignments of PemK, ChpBK, MazF and three PemK-like proteins from *Mycobacterium celatum, Pseudomonas putida* KT2440 and *Shigella flexneri* 2a str. 301. The amino acid sequences shown therein (as presented from top to bottom) are designated SEQ ID NO: 4; SEQ ID NO: 86; SEQ ID NO: 85; SEQ ID NO: 88; SEQ ID NO: 87; and SEQ ID NO: 2.

FIG. 35 shows a nucleic and amino acid sequence of mature human eotaxin (SEQ ID NOs: 67 and 68, respectively).

FIGS. 41A-B show sequence alignments of (A) *E. coli* MazF and its homologs in *M. tuberculosis* and (B) *E. coli* MazF and its homologs in *B. subtilis, B. anthracis* and *S. aureus*. The amino acid sequences shown in FIG. 41A (as presented from top to bottom) are designated SEQ ID NO: 75; SEQ ID NO: 74; SEQ ID NO: 2; SEQ ID NO: 76; SEQ ID NO: 77; and SEQ ID NO: 78. The amino acid sequences shown in FIG. 41B (as presented from top to bottom) are designated SEQ ID NO: 49; SEQ ID NO: 80; SEQ ID NO: 48; and SEQ ID NO: 2.

FIG. 42 shows an RNA sequence of the mazF open reading frame (ORF). All ACA sequences are shown in gray, and base changes that replace ACA sequences without altering the MazF amino acid sequence encoded therefrom are shown on top of the RNA sequence. The MazF amino acid sequence shown therein is designated SEQ ID NO: 2 and the MazF RNA sequence shown therein is designated SEQ ID NO: 102.

FIGS. 43A-E show nucleic acid sequences of *E. coli* MazF homologs in *M. tuberculosis.*

FIGS. 44A-E show amino acid sequences of *E. coli* MazF homologs in *M. tuberculosis.*

FIGS. 45A-D show nucleic acid sequences of three PemK-like proteins from *Mycobacterium celatum, Pseudomonas putida* KT2440 and *Shigella flexneri* 2a str. 301 and ChpBK.

FIGS. 46A-D show amino acid sequences of three PemK-like proteins from *Mycobacterium celatum, Pseudomonas putida* KT2440 and *Shigella flexneri* 2a str. 301 and ChpBK.

DETAILED DESCRIPTION OF THE INVENTION

Figure 1A:
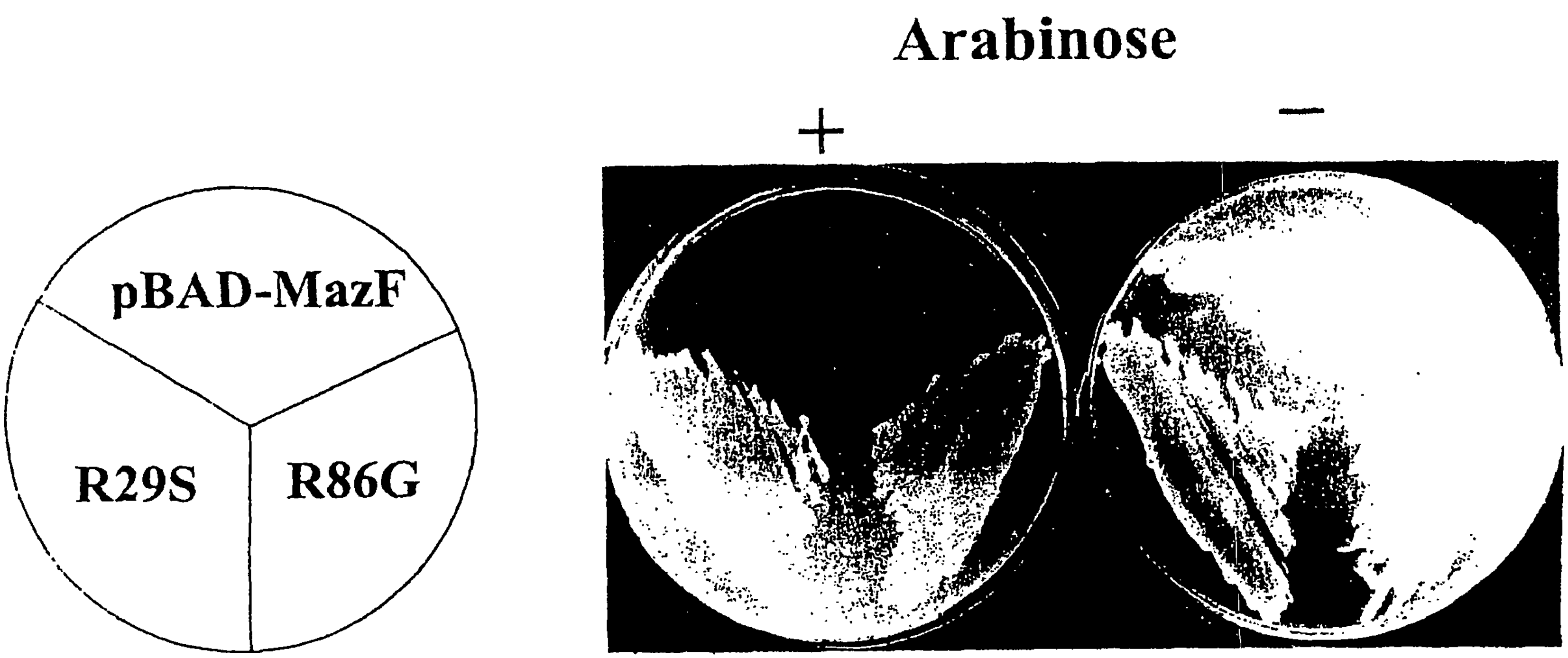

Before the present discovery and methods of use thereof are described, it is to be understood that this invention is not limited to particular assay methods, or test compounds and experimental conditions described, as such methods and compounds may vary. It is also to be understood that the terminology used herein is for the purpose of describing particular embodiments only, and is not intended to be limiting, since the scope of the present invention will be limited only the appended claims.

Accordingly, the term "MazF" or "PemK" as used in the specification and claims refers both to the general class of endoribonucleases, and to the particular enzyme bearing the particular name, and is intended to include enzymes having structural and sequence homology thereto. Likewise, the family of enzymes encompassed by the present invention is referred to herein as "RNA Interferases," a novel family identified herein by the inventors. Moreover, it is intended that the invention extends to molecules having structural and functional similarity consistent with their role in the invention.

Moreover, the term "MazE" or "PemI" as used in the specification and claims refers both to the general class of MazE (or MazF modulatory molecules) or PemI (or Pem K modulatory molecules, and to a particular molecule bearing this name, and is intended to include MazE (or MazF modulatory molecules) or PemI (or PemK modulululatory molecules) having structural and/or sequence homology to SEQ ID NO: 6 or SEQ ID NO: 8. Indeed, it is intended that the invention extends to molecules having structural and functional similarity consistent with their role in the invention.

Bacterial cell-death and growth inhibition are triggered by endogenous toxic genes in bacterial genomes in response to certain stress conditions. MazF is an endogenous toxin which causes cell-death and is encoded by an operon called "MazEF addiction module" in *Escherichia coli*. MazE is a labile antitoxin against MazF. As described herein, the effects of MazF on DNA, RNA and protein synthesis were examined in permeabilized cells. Briefly, at ten minutes after MazF induction, ATP-dependent $^{35}$S-methionine incorporation was completely inhibited, whereas [α-$^{32}$P]dTTp and [α-$^{32}$P]UTP incorporation were not, indicating that MazF is a specific inhibitor of protein synthesis. Moreover, purified MazF inhibited protein synthesis in both prokaryotic and eukaryotic cell-free systems, and this inhibition was blocked in the presence of MazE. When analyzed by sucrose density-gradient centrifugation, MazF induction blocked the formation of polysomes with a concomitant increase of the 70S ribosomal fraction, while the 50S and 30S ribosomal fractions were unaffected by expression of MazF.

Of note, toeprinting analysis revealed that MazF is a sequence specific endoribonuclease that recognizes ACA sequences and functions independently of the ribosome. Moreover, Northern blot analysis indicated that whole cellular mRNAs were degraded upon MazF induction. The present inventors have therefore made the surprising discovery that MazF is the first defined member of a novel family of endoribonucleases and, in view of its ability to interfere with the function of cellular mRNA, have designated it herein an "mRNA interferase". As shown herein, the interferase function results from the cleavage of mRNA transcripts at a specific sequence (ACA), which leads to rapid cell growth arrest and/or cell death. As demonstrated herein, the role of mRNA interferases has broad implications in normal cellular physiology and/or distressed cellular physiology induced by conditions of stress.

The present inventors have also discovered that purified PemK, the toxin encoded by the "pemI-pemK addiction module", inhibits protein synthesis in an *E. coli* cell-free system, while the addition of PemI, the antitoxin against PemK, restores protein synthesis. Additional studies described herein reveal that PemK is a sequence-specific endoribonuclease that cleaves mrRNAs and thereby inhibits protein synthesis. PemI blocks PemK mediated endoribonuclease activity and thus restores protein synthesis. PemK is shown to cleave only single-stranded RNA, preferentially at the 5' or 3' side of the A residue in a "UAX (X is C, A or U)" recognition site. Upon induction, PemK cleaves cellular mRNAs to effectively block protein synthesis in *E. coli*. pemK homologs have been identified on the genomes of a wide range of bacteria and the present inventors propose herein that PemK and its homologues form a novel endoribonuclease family that interferes with mRNA function by cleaving cellular mRNAs in a sequence-specific manner.

In order to more clearly set forth the parameters of the present invention, the following definitions are used:

The phrase "flanking nucleic acid sequences" refers to those contiguous nucleic acid sequences that are 5' and 3' to the endonuclease cleavage site. As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure and so forth.

The term "endonuclease" refers to an enzyme that can cleave DNA internally.

The term "endoribonuclease" refers to an enzyme that can cleave RNA internally.

The term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 60%, but often, more than 85%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program and are known in the art.

The present invention also includes active portions, fragments, derivatives and functional or non-functional mimetics of MazF polypeptides or proteins of the invention. An "active portion" of a MazF polypeptide means a peptide that is less than the full length MazF polypeptide, but which retains measurable biological activity.

A "fragment" or "portion" of an mRNA interferase means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. A "derivative" of an mRNA interferase or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of the original mRNA interferase.

Different "variants" of an mRNA interferase exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to an mRNA interferase, (c) variants in which one or more amino acids include a substituent group, and (d) variants in which an mRNA interferase is fused with another peptide or polypeptide such as a fusion partner, a protein tag or other chemical moiety, that may confer useful properties to an mRNA interferase, such as, for example, an epitope for an antibody, a polyhistidine sequence, a biotin moiety and the like. Other mRNA interferases of the invention include variants in which amino acid residues from one species are substituted for the corresponding residue in another species, either at conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to a person having ordinary skill in the art.

To the extent such allelic variations, analogues, fragments, derivatives, mutants, and modifications, including alternative nucleic acid processing forms and alternative post-translational modification forms result in derivatives of an mRNA interferase that retain any of the biological properties of the mRNA interferase, they are included within the scope of this invention.

The terms "ortholog" or "homolog" as used herein refer to nucleases encoded by nucleic acid sequences whose polypeptide product has greater than 60% identity to a MazF encoding sequence and/or whose gene products have similar three dimensional structure and/or biochemical activities of MazF. Exemplary orthologs/homologs include, without limitation, MazF of *Bacillus halodurans* (GenBank Accession No. NP_244588.1), *Staphylococcus epidermidis* (GenBank Accession No. AAG23809.1), *Staphylococcus aureus* (GenBank Accession No. NP_372592.1), *Bacillus subtilis* (GenBank Accession No. 1NE8_A), *Neisseria meningitides* (GenBank Accession No. NP_266040.1), *Morganella morgani* (GenBank Accession No. AAC82516.1) and *Mycobacterium tuberculosis* (GenBank Accession No. NP_217317.1). See FIGS. 22 and 23. The terms "ortholog" and "homolog" may be used to refer to orthologs/homologs of a MazF nucleic or amino acid sequence of any species. Such species include, but are not limited to, *E. coli, Bacillus halodurans, Staphylococcus epidermidis, Staphylococcus aureus, Bacillus subtilis, Neisseria meningitides, Morganella morgani, Mycobacterium tuberculosis, Mus musculus*, and *Homo sapiens*. The use of nucleases encoded by such orthologs/homologs in the methods of the invention is contemplated herein.

The term "ortholog" or "homolog" as used herein also refers to nucleases encoded by nucleic acid sequences whose polypeptide product has greater than 60% identity to a PemK encoding sequence and/or whose gene products have similar three dimensional structure and/or biochemical activities of PemK. The terms "ortholog" and "homolog" may be used to refer to orthologs/homologs of a PemK nucleic or amino acid sequence of any species.

Figure 33:
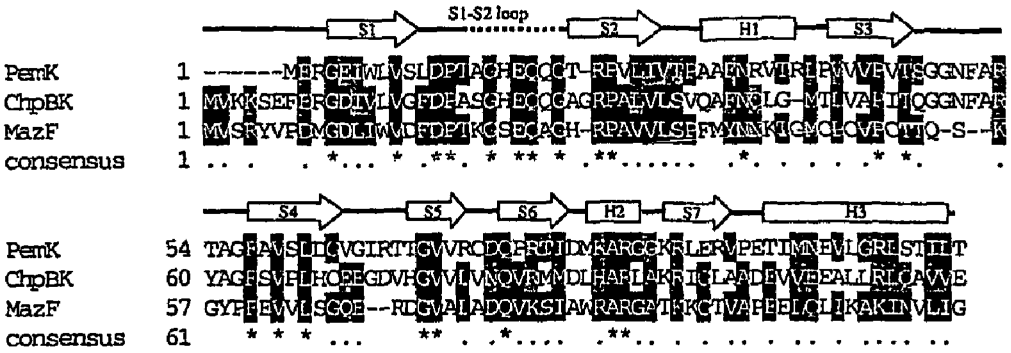
FIG. 33 shows sequence alignments of PemK, ChpBK and MazF polypeptides. The amino acid sequences shown therein (as presented from top to bottom) are designated SEQ ID NO: 4; SEQ ID NO: 88; and SEQ ID NO: 2.

The use of nucleases encoded by homologs or orthologs of PemK in the methods of the invention is contemplated herein. Exemplary homologs and orthologs include, without limitation, the 73 known members of the PemK protein family, which includes MazF (ChpAK), ChpBK and other PemK-like proteins. The following is a list of designations for these proteins found in web site pfam.wustl.edu/cgi-bin/getdesc?acc=PF02452): Q9RX98; Q8F5A3; Q9K6K8; CHPA_ECOLI; Q7NPF9; Q88TP7; Q7WWW1; Q8YS80; Q8DW95; Q82YR2; Q7X3Y1; Q93S64; Q8PRN1; Q8GFY1; O52205; PEMK_ECOLI Q7N4H2; Q88PS7; Q8XCF2 CHPB_ECOLI; Q82VU0; Q8UGU5; Q9RWK4; Q9PHH8; Q7TXU4; P71650; Q7U1Y5; P96295; Q9JWF2; Q9JXI1; Q8E882; Q82VB5; Q8KJS3; Q7NMY4; Q9KFF7; P96622; Q81IT4; Q81VF4; Q8ESK5; Q92DC7; Q8Y8L0; Q97LR0; Q8XNN7; Q8R861; Q88Z43; O07123; Q83719; Q9F7V5; Q8CRQ1; O05341; P95840; Q9FCV0; Q837L1; Q93M89; Q99IU9; Q82UB5; Q93MT8; YJ91_MYCTU; Q97MV8; Q7NHW0; Q7NI95; Q8YML2; Q7NHR3; YE95_MYCTU; Q9PCB9; Q8YZW8; Q7TZ90; P95272; Q8VJR1; Q7U0N2; O53450; O06780; and Q7U1I8. See FIGS. 33 and 34.

Swiss-Protein Number Followed by NCBI Number:

Q9RX98 NP_294140 Q8F5A3 NP_711962 Q9K6K8 NP_244588 CHPA_ECOLI NP_417262 Q7NPF9 NP_923042 Q88TP7 NP_786238 Q7WWW1 NP_943016 Q8YS80 NP_487251 Q8DW95 NP_720642 Q82YR2 NP_816992 Q7X3Y1 NP_857606 Q93S64 NP_862570 Q8PRN1 NP_644713 Q8GFY1AAN87626. O52205 AAC82516 PEMK_ECOLI NP_957647 Q7N4H2 NP_929611 Q88PS7 NP_742932 Q8XCF2 NP_290857 CHPB_ECOLI D49339 Q82VU0 NP_841047 Q8UGU5 NP_531638 Q9RWK4 AAF10240 Q9PHH8 NP_061683 Q7TXU4 NP_856470 P71650 NP_217317 Q7U1Y5 NP_854128 P96295 CAB03645 Q9JWF2 NP_283229 Q9JXI1 AAF42359 Q8E882 NP_720377 Q82VB5 NP_841237 Q8KJS3 CAA70141 Q7NMY4 NP_923577 Q9KFF7 NP_241388 P96622 NP_388347 Q81IT4 NP_830134 Q81VF4 NP_842807 Q8ESK5 NP_691544 Q92DC7 NP_470228 Q8Y8L0 NP_464414 Q97LR0 NP_347134 Q8XNN7 NP_561211 Q8R861NP_623721 Q88Z43 NP_784302 O07123 CAA70141 Q837I9 NP_814592 Q9F7V5 NP_765227 Q8CRQ1 AA005271 O05341 NP_646809 P95840 BAB95857 Q9FCV0 CAC03499 Q837L1 NP_814568 Q93M89 NP_150051 Q82UB5 NP_841618 Q93MT8 NP_713024 YJ91_MYCTU NP_216507 Q99IU9 P_856470 Q97MV8 NP_346728 Q7NHW0 NP_925371 Q7NI95 NP_925234 Q8YML2 NP_488961 Q7NHR3 NP_925418 YE95_MYCTU CAA17218 Q9PCB9 NP_299148 Q8YZW8 NP_484381 Q7TZ90 NP_855627 P95272 NP_216458 Q8VJR1 NP_336589Q7U0N2 NP_854788 O53450 NP_216458 O06780 NP_215173 Q7U1I8 NP_854336.

The term "ortholog" or homolog as used herein also refers to binding partners of nucleases (antitoxins or modulators of nucleases) encoded by nucleic acid sequences whose polypeptide product has greater than 60% identity to a MazE encoding sequence and/or whose gene products have similar three dimensional structure and/or biochemical activities of MazE. Exemplary orthologs/homologs include, without limitation, MazE, *Deinococcus radiodurans* (GenBank Accession No. NP_294139); MazE, *Bacillus halodurans* (GenBank Accession No. NP_244587); PemI, plasmid R100 (GenBank Accession No. NP_052993); PemI, plasmid R466b (GenBank Accession No. AAC82515); ChpS, *Escherichia coli* (GenBank Accession No. NP_290856); MazE, *Pseudomonas putida* KT2440 (GenBank Accession No. NP_742931); MazE, *Photobacterium profundum* (AAG34554). See FIGS. 24 and 25. The terms "ortholog" and "homolog" may be used to refer to orthologs/homologs of a MazE nucleic or amino acid sequence of any species. Such species include, but are not limited to, *E. coli, Deinococcus radiodurans, Bacillus halodurans, Pseudomonas putida, Photobacterium profundum, Staphylococcus epidermidis, Staphylococcus aureus, Bacillus subtilis, Neisseria meningitides, Morganella morgani, Mycobacterium tuberculosis, Mus musculus*, and *Homo sapiens*. The use of nuclease modulatory molecules (antitoxin) encoded by such homologs/orthologs in the methods of the invention is contemplated herein.

The term "ortholog" or homolog as used herein also refers to binding partners of nucleases (antitoxins or modulators of nucleases) encoded by nucleic acid sequences whose polypeptide product has greater than 60% identity to a PemI encoding sequence and/or whose gene products have similar three dimensional structure and/or biochemical activities of PemI. Exemplary orthologs/homologs of PemI include, without limitation, the known members of the MazE (antitoxin) protein family, which includes MazE (ChpAI), ChpBI and other MazE homologues. The terms "ortholog" and "homolog" may be used to refer to orthologs/homologs of a PemI nucleic or amino acid sequence of any species. The use of nuclease modulatory molecules encoded by such homologs in the methods of the invention is contemplated herein. The use of nuclease modulatory molecules (antitoxin) encoded by such homologs/orthologs in the methods of the invention is contemplated herein.

The term "functional" as used herein implies that the nucleic or amino acid sequence is functional for the recited assay or purpose.

The term "functional fragment" as used herein implies that the nucleic or amino acid sequence is a portion or subdomain of a full length polypeptide and is functional for the recited assay or purpose.

The phrase "consisting essentially of" when referring to a particular nucleotide or amino acid means a sequence having the properties of a given SEQ ID No. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which are placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of predetermined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers may be labeled fluorescently with 6-carboxyfluorescein (6-FAM). Alternatively primers may be labeled with 4,7,2',7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

The compositions containing the molecules or compounds of the invention can be administered for prophylactic and/or therapeutic treatments. In one therapeutic application, for example, compositions are administered to a patient already suffering from a hyperproliferative disorder (such as, e.g., cancer) in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

As used herein, the term "cancer" refers to an abnormal growth of tissue resulting from uncontrolled progressive multiplication of cells. Examples of cancers that can be treated according to a method of the present invention include, without limitation, sarcomas, blastomas, and carcinomas such as: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastic cancer, pancreatic cancer, breast cancer, meningeal carcinomatosis (which is most commonly associated with disseminated breast or lung cancer), ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular cancer, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Examples of hematologic malignancies that can be treated according to a method of the present invention include: acute myeloid leukemia (AML), chronic myeloid leukemia (CML), acute lymphocytic leukemia (ALL), chronic lymphocytic leukemia (CLL), multiple myeloma, non-Hodgkin's lymphoma (NHL), Hodgkin's disease and lymphoma (HD), prolymphocytic leukemia (PLL), and myelodysplastic syndrome (MDS).

An "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunloglobulin molecule such as those portions known in the art as Fab, Fab', F(ab')2 and F(v).

The term "cellular substrate" refers to a molecule in a cell which is an enzymatic target of an enzyme or family of related enzymes. With regard to mRNA interferases, "cellular substrates" include polyribonucleotides in a cell, which are expressed from endogenous or exogenous nucleic acid sequences.

As used herein, the phrase "under conditions that promote endoribonuclease activity" includes any condition in a cell (in cell culture or in vivo) or in vitro (in a test tube or other similar vessel) wherein an mRNA interferase of the invention exhibits endoribonuclease activity. Such conditions are described in the Examples presented herein. Similarly, an "mRNA interferase compatible buffer" is a buffer wherein an mRNA interferase of the invention exhibits endoribonuclease activity.

The term "mRNA interferase modulatory agent" as used herein refers to an agent that is capable of modulating (e.g., increasing or decreasing) the endoribonuclease activity of an mRNA interferase. Methods for screening/identifying such agents are presented herein below. Exemplary endogenous mRNA interferase modulatory agents include MazE (which inhibits MazF activity) and PemI (which inhibits PemK activity). Functional fragments of MazE and PemI, which are capable of inhibiting MazF and PemK activity, respectively, are also described herein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

I. Preparation of mRNA Interferase-Encoding Nucleic Acid Molecules and mRNA Interferases Nucleic Acid Molecules Nucleic acid molecules encoding an endoribonuclease of the invention (e.g., MazF or PemK) may be prepared by two general methods: (1) Synthesis from appropriate nucleotide triphosphates; or (2) Isolation from biological sources. Both methods utilize protocols well known in the art.

The availability of nucleotide sequence information, such as a full length cDNA of SEQ ID NOs: 1 or 3 (See FIGS. 20A and 31A), enables preparation of an isolated nucleic acid molecule of the invention by oligonucleotide synthesis. Synthetic oligonucleotides may be prepared by the phosphoramidite method employed in the Applied Biosystems 380A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Synthetic DNA molecule constructed by such means may then be cloned and amplified in an appropriate vector. Nucleic acid sequences encoding an mRNA interferase may be isolated from appropriate biological sources using methods known in the art. In a preferred embodiment, a cDNA clone is isolated from a cDNA expression library of bacterial origin. In an alternative embodiment, utilizing the sequence information provided by the cDNA sequence, genomic clones encoding an mRNA interferase may be isolated. Alternatively, cDNA or genomic clones having homology to an mRNA interferase may be isolated from other species, using oligonucleotide probes corresponding to predetermined sequences within the mRNA interferase gene.

In accordance with the present invention, nucleic acids having the appropriate level of sequence homology with the protein coding region of either SEQ ID NOs: 1 or 3 may be identified by using hybridization and washing conditions of appropriate stringency. For example, hybridizations may be performed using a hybridization solution comprising: 5×SSC, 5×Denhardt's reagent, 0.5-1.0% SDS, 100 micrograms/ml denatured, fragmented salmon sperm DNA, 0.05% sodium pyrophosphate and up to 50% formamide. Hybridization is generally performed at 37-42° C. for at least six hours. Following hybridization, filters are washed as follows: (1) 5 minutes at room temperature in 2×SSC and 0.5-1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. \; 16.6 \, \text{Log} \, [Na+] + 0.41(\% \, G+C) - 0.63(\% \, \text{formamide}) - 600/\#bp \, \text{in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

As can be seen from the above, the stringency of the hybridization and wash depend primarily on the salt concentration and temperature of the solutions. In general, to maximize the rate of annealing of the two nucleic acid molecules, the hybridization is usually carried out at 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 micrograms/ml denatured salmon sperm DNA at 42° C. and wash in 2×SSC and 0.5% SDS at 55° C. for 15 minutes. A high stringency hybridization is defined as hybridization in 6×SSC, 5×Denhardt's solution, 0.5% SDS and 100 micrograms/ml denatured salmon sperm DNA at 42° C. and wash in 1×SSC and 0.5% SDS at 65° C. for 15 minutes. A very high stringency hybridization is defined as hybridization in 6×SSC, 5×Denhardt's solution, 0.5% SDS and 100 micrograms/ml denatured salmon sperm DNA at 42° C. and wash in 0.1×SSC and 0.5% SDS at 65° C. for 15 minutes.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Genomic clones of the invention encoding an mRNA interferase gene may be maintained in lambda phage FIX II (Stratagene).

mRNA interferase-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of a cDNA of either SEQ ID NO: 1 or 3. Such oligonucleotides are useful as probes for detecting or isolating mRNA interferase genes.

It will be appreciated by persons skilled in the art that variants (e.g., allelic variants) of these sequences exist in bacterial populations and/or species, and must be taken into account when designing and/or utilizing oligonucleotides of the invention. Accordingly, it is within the scope of the present invention to encompass such variants, with respect to the mRNA interferase sequences disclosed herein or the oligonucleotides targeted to specific locations on the respective genes or RNA transcripts. With respect to the inclusion of such variants, the term "natural allelic variants" is used herein to refer to various specific nucleotide sequences and variants thereof that would occur in a given DNA population. Genetic polymorphisms giving rise to conservative or neutral amino acid substitutions in the encoded protein are examples of such variants. Additionally, the term "substantially complementary" refers to oligonucleotide sequences that may not be perfectly matched to a target sequence, but the mismatches do not materially affect the ability of the oligonucleotide to hybridize with its target sequence under the conditions described.

Thus, the coding sequence may be that shown in, for example, SEQ ID NO: 1 or 3, or it may be a mutant, variant, derivative or allele of either of these sequences. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in SEQ ID NO: 1 or 3, but which encodes a polypeptide with the same amino acid sequence.

On the other hand, the encoded polypeptide may comprise an amino acid sequence which differs by one or more amino acid residues from the amino acid sequence shown in either SEQ ID NO: 2 or 4. See FIGS. 20B and 31B. Nucleic acid encoding a polypeptide which is an amino acid sequence mutant, variant, derivative or allele of the sequence shown in SEQ ID NO: 2 or 4 is further provided by the present invention. Nucleic acid encoding such a polypeptide may show greater than 60% identity with the coding sequence shown in SEQ ID NO: 1 or 3, greater than about 70% identity, greater than about 80% identity, greater than about 90% identity or greater than about 95% identity.

The present invention provides a method of obtaining a nucleic acid of interest, the method including hybridization of a probe having part or all of the sequence shown in either SEQ ID NO: 1 or 3, or a complementary sequence thereto, to target nucleic acid. Successful hybridization leads to isolation of nucleic acid which has hybridized to the probe, which may involve one or more steps of polymerase chain reaction (PCR) amplification.

Such oligonucleotide probes or primers, as well as the full-length sequence (and mutants, alleles, variants, and derivatives) are useful in screening a test sample containing nucleic acid for the presence of alleles, mutants or variants of an mRNA interferase, the probes hybridizing with a target sequence from a sample obtained from a cell, tissue, or organism being tested. The conditions of the hybridization can be controlled to minimize non-specific binding. Preferably stringent to moderately stringent hybridization conditions are used. The skilled person is readily able to design such probes, label them and devise suitable conditions for hybridization reactions, assisted by textbooks such as Sambrook et al (1989) and Ausubel et al (1992).

In some preferred embodiments, oligonucleotides according to the present invention that are fragments of the sequences shown in either SEQ ID NO: 1 or 3, or any allele associated with endoribonuclease activity, are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence encoding a homolog or ortholog of an mRNA interferase.

B. Proteins

MazF is the first nuclease identified which cleaves RNA with high specificity at a specific nucleic acid sequence (i.e., ACA). PemK is the first nuclease identified which cleaves RNA with high specificity at a specific nucleic acid sequence (i.e., UAX, wherein X is C, A, or U). A full-length mRNA interferase protein of the present invention (e.g., MazF or PemK) may be prepared in a variety of ways, according to known methods. The protein may be purified from appropriate sources. This is not, however, a preferred method due to the low amount of protein likely to be present in a given cell type at any time. The availability of nucleic acid molecules encoding MazF and PemK enables production of either of these proteins using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of an mRNA interferase may be produced by expression in a suitable prokaryotic or eukaryotic system. For example, part or all of a DNA molecule, such as a cDNA of SEQ ID NO: 1 or 3, may be inserted into a plasmid vector adapted for expression in a bacterial cell, such as *E. coli*. Such vectors comprise regulatory elements necessary for expression of the DNA in a host cell (e.g. *E. coli*) positioned in such a manner as to permit expression of the DNA in the host cell. Such regulatory elements required for expression include promoter sequences, transcription initiation sequences and, optionally, enhancer sequences.

An mRNA interferase produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

mRNA interferases of the invention, prepared by the aforementioned methods, may be analyzed according to standard procedures. For example, such proteins may be subjected to amino acid sequence analysis, according to known methods.

Polypeptides which are amino acid sequence variants, alleles, derivatives or mutants are also provided by the present invention. A polypeptide which is a variant, allele, derivative, or mutant may have an amino acid sequence that differs from that given in SEQ ID NO: 2 by one or more of addition, substitution, deletion and insertion of one or more amino acids. Preferred such polypeptides have MazF function, that is to say have one or more of the following properties: ability to cleave ACA sequences in RNA; immunological cross-reactivity with an antibody reactive with the polypeptide for which the sequence is given in SEQ ID NO: 2; sharing an epitope with the polypeptide for which the sequence is given in SEQ ID NO: 2 (as determined for example by immunological cross-reactivity between the two polypeptides.

Alternatively, a polypeptide which is a variant, allele, derivative, or mutant may have an amino acid sequence that differs from that given in SEQ ID NO: 4 by one or more of addition, substitution, deletion and insertion of one or more amino acids. Preferred such polypeptides have PemK function, that is to say have one or more of the following properties: ability to cleave UAX sequences (wherein X is C, A, or U) in RNA; immunological cross-reactivity with an antibody reactive with the polypeptide for which the sequence is given in SEQ ID NO: 4; sharing an epitope with the polypeptide for which the sequence is given in SEQ ID NO: 4 (as determined for example by immunological cross-reactivity between the two polypeptides.

A polypeptide which is an amino acid sequence variant, allele, derivative or mutant of the amino acid sequence shown in SEQ ID NO: 2 or 4 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO: 2 or 4 by insertion, addition, substitution or deletion of 1 amino acid, 2, 3, 4, 5-10, 10-20, 20-30, 30-40, 40-50, 50-100, 100-150, or more than 150 amino acids. For amino acid "homology", this may be understood to be identity or similarity (according to the established principles of amino acid similarity, e.g., as determined using the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used including without limitation, BLAST (Altschul et al. (1990 J. Mol. Biol. 215:405-410); FASTA (Pearson and Lipman (1998) PNAS USA 85:2444-2448) or the Smith Waterman algorithm (Smith and Waterman (1981) J. Mol. Biol. 147:195-197) generally employing default parameters. Use of either of the terms "homology" and "homologous" herein does not imply any necessary evolutionary relationship between the compared sequences. The terms are used similarly to the phrase "homologous recombination", i.e., the terms merely require that the two nucleotide sequences are sufficiently similar to recombine under appropriate conditions.

A polypeptide according to the present invention may be used in screening for molecules which affect or modulate its activity or function. Such molecules may be useful for research purposes.

The present invention also provides antibodies capable of immunospecifically binding to proteins of the invention. Polyclonal antibodies directed toward an mRNA interferase (e.g., MazF or PemK) may be prepared according to standard methods. In a preferred embodiment, monoclonal antibodies are prepared, which react immunospecifically with various epitopes of an mRNA interferase. Monoclonal antibodies may be prepared according to general methods of Kohler and Milstein, following standard protocols. Polyclonal or monoclonal antibodies that immunospecifically interact with an mRNA interferase can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-mRNA interferase antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

II. Uses of mRNA Interferase-Encoding Nucleic Acids, mRNA Interferases and Antibodies Thereto MazF and PemK, for example, are RNA endonucleases which may be used to advantage to reduce or inhibit protein synthesis in a cell, tissue, or organism. Moreover, an mRNA interferase of the invention may be specifically targeted to a particular tissue or tissues in a subject so as to specifically reduce or inhibit protein synthesis in the targeted tissue(s). For some applications, it is advantageous to target specific RNA transcripts for endonucleolytic cleavage by MazF. Such sequences may comprise an elevated frequency of ACA sequences and, therefore, are native preferred targets for MazF activity. Alternatively, RNA transcripts may be targeted for MazF cleavage by altering a MazF polypeptide to specifically or preferentially bind and/or cleave the transcript(s) targeted for cleavage. Alternatively, it may be advantageous to target specific RNA transcripts for endonucleolytic cleavage by PemK. Such sequences may comprise an elevated frequency of UAX sequences (wherein X is a C, A, U) and, therefore, are native preferred targets for PemK activity. Alternatively, RNA transcripts may be targeted for PemK cleavage by altering a PemK polypeptide to specifically or preferentially bind and/or cleave the transcript(s) targeted for cleavage.

Specifically, mRNA interferase molecules (such as MazF and PemK) and compositions of the invention may be used to advantage to treat a patient with a hyperproliferative disorder. Such disorders include, without limitation, dysplasias and metaplasias of different tissues, inflammatory conditions, autoimmune diseases, hyperproliferative skin disorders, psoriasis, allergy/asthma, atherosclerosis, restenosis after angioplastic surgery, and cancer. mRNA interferase molecules (such as MazF and PemK) and compositions of the invention may also be used to advantage to treat a patient with a bacterial infection.

Additionally, mRNA interferase nucleic acids, proteins and antibodies thereto, according to this invention, may be used as a research tool to identify other proteins that are intimately involved in RNA recognition and cleavage reactions.

A. mRNA Interferase-Encoding Nucleic Acids

MazF- and PemK-encoding nucleic acids may be used for a variety of purposes in accordance with the present invention. MazF- and PemK-encoding DNA, RNA, or fragments thereof may be used as probes to detect the presence of and/or expression of genes encoding MazF-like and PemK-like proteins. Methods in which MazF- and PemK-encoding nucleic acids may be utilized as probes for such assays include, but are not limited to: (1) in situ hybridization; (2) Southern hybridization (3) northern hybridization; and (4) assorted amplification reactions such as PCR.

mRNA interferase-encoding nucleic acids of the invention may also be utilized as probes to identify related genes from other bacterial, plant, or animal species. As is well known in the art, hybridization stringencies may be adjusted to allow hybridization of nucleic acid probes with complementary sequences of varying degrees of homology. Thus, MazF- and PemK-encoding nucleic acids may be used to advantage to identify and characterize other genes of varying degrees of relation to MazF and/or PemK, thereby enabling further characterization of RNA degradative systems. Additionally, they may be used to identify genes encoding proteins that interact with MazF and/or PemK (e.g., by the "interaction trap" technique), which should further accelerate identification of the components involved in RNA cleavage.

Nucleic acid molecules, or fragments thereof, encoding MazF or PemK may also be utilized to control the production of MazF or PemK, thereby regulating the amount of protein available to participate in RNA cleavage reactions. Alterations in the physiological amount of MazF or PemK protein may dramatically affect the activity of other protein factors involved in RNA cleavage.

B. mRNA Interferases and Antibodies Thereto

Purified mRNA interferases, such as isolated MazF or PemK proteins, or fragments thereof, produced via expression of MazF or PemK encoding nucleic acids of the present invention may be used to produce polyclonal or monoclonal antibodies which also may serve as sensitive detection reagents for the presence and accumulation of MazF (or complexes containing MazF) or PemK (or complexes containing PemK) in bacterial cells. Recombinant techniques enable expression of fusion proteins containing part or all of the MazF or PemK protein. The full length protein or fragments of the protein may be used to advantage to generate an array of monoclonal antibodies specific for various epitopes of the protein, thereby providing even greater sensitivity for detection of the protein in cells.

Polyclonal or monoclonal antibodies immunologically specific for an mRNA interferase (e.g., MazF or PemK) may be used in a variety of assays designed to detect and quantitate the protein. Such assays include, but are not limited to: (1) flow cytometric analysis; (2) immunochemical localization of an mRNA interferase in, for example, bacterial cells; and (3) immunoblot analysis (e.g., dot blot, Western blot) of extracts from various cells. Additionally, as described above, anti-MazF and anti-PemK antibodies, for example, can be used for purification of MazF and orthologs thereof or PemK and orthologs thereof (e.g., affinity column purification, immunoprecipitation).

mRNA interferases, such as MazF or PemK protein, may also be used to advantage to reduce or inhibit protein synthesis in a cell, tissue, or organism, as discussed above.

From the foregoing discussion, it can be seen that mRNA interferase-encoding nucleic acids, mRNA interferase expressing vectors, and anti-mRNA interferase antibodies of the invention can be used to produce large quantities of mRNA interferase protein, detect mRNA interferase gene expression and alter mRNA interferase accumulation for purposes of assessing the genetic and protein interactions involved in the RNA cleavage.

The present inventors have made the surprising discovery that stable toxin MazF derived from bacteria is an endoribonuclease. As described herein, MazF has been designated the first member of a novel family of enzymes referred to as "RNA Interferases". Moreover, it is proposed that MazF exemplifies this new family of "RNA Interferases". Of note, prior to the discovery of the present invention, the cellular target(s) of MazF had not been identified. As shown herein, MazF functions as a highly sequence-specific endoribonuclease, which cleaves cellular mRNAs at ACA sites. Such activity may effectuate a partial or total inhibition of protein synthesis in a cell. The predicted frequency of an ACA sequence in an RNA transcript is one in 64, based on standard calculations predicated on an equal probability that any one of the four nucleotides will be incorporated at each one of the three nucleotide positions. It is to be understood that some RNA transcripts comprise a lower or higher frequency of ACA sequences as compared to the predicted frequency. Accordingly, the sensitivity of a specific RNA transcript or a family of related RNA transcripts to cleavage by a MazF endoribonuclease is dependent upon the frequency of ACA sequences or MazF target sequences in the transcript. Moreover, one of ordinary skill in the art could predict, based on the sequence of an RNA transcript, the sensitivity of the transcript to MazF mediated cleavage.

The present inventors have also discovered that PemK is a member of the novel family of enzymes designated herein as "RNA Interferases". As shown herein, PemK functions as a highly sequence-specific endoribonuclease, which cleaves cellular mRNAs at UAX sites, wherein X is a C, A, or U. Such activity may effectuate a partial or total inhibition of protein synthesis in a cell. The predicted frequency of a UAX site, wherein X is a C, A, or U sequence in an RNA transcript is three in 64, based on standard calculations predicated on an equal probability that any one of the four nucleotides will be incorporated at each one of the three nucleotide positions. It is to be understood that some RNA transcripts comprise a lower or higher frequency of UAX sequences as compared to the predicted frequency. Accordingly, the sensitivity of a specific RNA transcript or a family of related RNA transcripts to cleavage by a PemK endoribonuclease is dependent upon the frequency of UAX sequences (wherein X is a C, A, or U) or PemK target sequences in the transcript. Moreover, one of ordinary skill in the art could predict, based on the sequence of an RNA transcript, the sensitivity of the transcript to PemK mediated cleavage.

The novel findings of the present inventors, therefore, present new applications for which mRNA interferase (e.g., MazF and PemK) nucleic and amino acid sequences and compositions thereof may be used to advantage. Such utilities include, but are not limited to, various research and therapeutic applications as described herein. Also provided is a kit comprising MazF and PemK nucleic and/or amino acid sequences, MazF and/or PemK-activity compatible buffers, and instruction materials.

III. Preparation of mRNA Interferase Inhibitor-Encoding Nucleic Acid Molecules and mRNA Interferase Inhibitor Proteins MazE- and PemI-encoding nucleic acid molecules and MazE and PemI polypeptides, and functional fragments thereof, are generated essentially as described above for MazF- and PemK-encoding nucleic acid sequences and MazF and PemK polypeptides. In accordance with the present invention, a nucleic acid sequence encoding MazE protein and comprising SEQ ID NO: 5 is provided. See FIG. 21A. Also provided is an amino acid sequence comprising SEQ ID NO: 6 and functional fragments thereof. See FIG. 21B. Accordingly, a nucleic acid sequence encoding PemI protein and comprising SEQ ID NO: 7 is provided. See FIG. 32A. Also provided is an amino acid sequence comprising SEQ ID NO: 8 and functional fragments thereof. See FIG. 32B.

IV. Uses of mRNA Interferase Inhibitor-Encoding Nucleic Acids and mRNA Interferase Inhibitor Proteins MazE polypeptides encoded by SEQ ID NO: 5, nucleic acid sequences encoding MazE polypeptides comprising SEQ ID NO: 6 and functional fragments thereof, and MazE polypeptides comprising SEQ ID NO: 6 and functional fragments thereof are encompassed by the invention. As described herein, MazE polypeptides and functional fragments thereof exhibit the ability to modulate MazF activity. See Example III and summary below.

Briefly, and as demonstrated herein, the binding of purified $(His)_6$MazE to mazEF promoter DNA was enhanced by MazF. Site-directed mutations at conserved amino acid residues K7A, R8A, S12A and R16A) in the N-terminal region of MazE disrupted the DNA-binding ability of both $(His)_6$MazE and the MazE-MazF$(His)_6$ complex, suggesting that MazE binds to mazEF promoter DNA through the N-terminal domain. In solution, the ratio of MazE to MazF$(His)_6$ in the MazE-MazF$(His)_6$ complex is about 1:2. Since both MazE and MazF$(His)_6$ exist as homodimers, the MazE-MazF$(His)_6$ complex (76.9 kDa) is predicted to consist of one MazE dimer and two MazF$(His)_6$ dimers. The interaction between MazE and MazF was also characterized using the yeast two-hybrid system. It was found that the region from residue 38 to 75 of MazE was required for binding to MazF. Site-directed mutagenesis at this region revealed that Leu55 and Leu58 play an important role in MazE-MazF complex formation but not in MazE-binding to the mazEF promoter DNA. The present results demonstrate that MazE is composed of two domains, an N-terminal DNA-binding domain and a C-terminal MazF interacting domain.

Thus, in one embodiment, MazE polypeptides and MazE functional fragments of the invention inhibit MazF activity. In a particular aspect, MazE polypeptides or MazE functional fragments of the invention inhibit MazF endoribonuclease activity or effectuate a decrease in endoribonuclease activity. Indeed, MazE and functional fragments thereof are the first molecules characterized by the present invention and demonstrated herein to be capable of effectuating a decrease in endoribonuclease activity and thereby effectuating a decrease in endoribonuclease substrate cleavage. Exemplary MazE functional fragments capable of effectuating a decrease in endoribonuclease substrate cleavage include, but are not limited to, a C-terminal MazF interacting domain. In a specific embodiment, a C-terminal MazF interacting domain comprises a region from residue 38 to 75 of MazE. As described herein, critical residues identified in this region include Leu55 and Leu58. In another embodiment, a C-terminal MazF interacting domain comprises an Hp-Box of a MazE molecule and critical residues identified therein.

In a particular aspect of the invention, two C-terminal peptides of MazE can be chemically synthesized, one with T54-K77 (24 amino acid residues; TLAELVNDITPENLHENIDWGEPK; SEQ ID NO: 9) and the other with N60-K77 (18 a.a. residues; NDITPENLHENIDWGEPK; SEQ ID NO: 10). These peptides are expected to form stable inhibitory complexes with the MazF dimer on the basis of the X-ray structure of the MazE-MazF complex. The former peptide contains both helix 2 and the C-terminal acidic tail, while the latter peptide lacks helix 2. These peptides will be examined for their abilities to inhibit the mRNA interferase activity of MazF using a synthetic 30-base RNA (5'-UAAGAAGGAGAUAUACAUAUGAAUCAAAUC-3'; SEQ ID NO: 11) as a substrate. Their inhibitory activities will be compared with the intact MazE as a control.

In another embodiment, MazE polypeptides and MazE functional fragments of the invention enhance or increase MazF activity. In a particular aspect, MazE polypeptides or MazE functional fragments of the invention enhance MazF endoribonuclease activity or effectuate an increase in endoribonuclease activity. Indeed, MazE polypeptide mutants and functional fragments thereof are the first molecules characterized by the present invention to be capable of effectuating an increase in endoribonuclease activity and thereby effectuating an increase in endoribonuclease substrate cleavage. Exemplary MazE polypeptides capable of effectuating an increase in endoribonuclease substrate cleavage include, but are not limited to, a MazE polypeptide comprising mutations in a C-terminal MazF interacting domain, a region from MazE residue 38 to 75, an Hp-box, or at Leu55 or Leu 58 (or homologous positions thereof), wherein such a mutation(s) reduces or inhibits the ability of MazE to bind to MazF. Exemplary MazE fragments capable of effectuating an increase in endoribonuclease substrate cleavage include, but are not limited to, a MazE fragment comprising a mutation(s) that reduces or inhibits the ability of the MazE fragment to bind MazF. Such MazE fragments comprising such mutations include, but are not limited to, a C-terminal MazF interacting domain or a region from residue 38 to 75 of MazE. Exemplary mutations in residues known to reduce or inhibit the ability of a MazE fragment to bind MazF include mutations at Leu55 and Leu58. Such MazE mutant polypeptides and fragments may be referred to herein as having dominant negative activity. In general, dominant negative polypeptides serve to reduce or inhibit the activity of the corresponding wild type polypeptide because they are still capable of binding to and, therefore, competing for substrates and/or interacting proteins or molecules, but are at least partially impaired with respect to wild type function.

PemI polypeptides encoded by SEQ ID NO: 7, nucleic acid sequences encoding PemI polypeptides comprising SEQ ID NO: 8 and functional fragments thereof, and PemI polypeptides comprising SEQ ID NO: 8 and functional fragments thereof are also encompassed by the invention. As described herein, PemI polypeptides and functional fragments thereof exhibit the ability to modulate PemK activity. Exemplary PemI functional fragments capable of modulating PemI activity and, by extension, that of PemK, include the N-terminal DNA binding domain and the C-terminal PemK interacting domain. See Example IV herein below.

Thus, in one embodiment, PemI polypeptides and PemI functional fragments of the invention inhibit PemK activity. In a particular aspect, PemI polypeptides or PemI functional fragments of the invention inhibit PemK endoribonuclease activity or effectuate a decrease in endoribonuclease activity. Indeed, PemI and functional fragments thereof are the first molecules characterized by the present invention and demonstrated herein to be capable of effectuating a decrease in endoribonuclease activity and thereby effectuating a decrease in endoribonuclease substrate cleavage.

In another embodiment, a mutated form or derivative of a PemI polypeptide or a fragment thereof which is capable of inhibiting PemI activity is envisioned. Such PemI mutant polypeptides and fragments may be referred to herein as having dominant negative activity. In general, dominant negative polypeptides serve to reduce or inhibit the activity of the corresponding wild type polypeptide because they are still capable of binding to and, therefore, competing for substrates and/or interacting proteins or molecules, but are at least partially impaired with respect to wild type function. Since PemI normally binds to PemK, thereby inhibiting its toxic effects, prevention of PemI-mediated inhibition of PemK serves to release PemK from this negative regulation. Inhibiting PemI activity, therefore, leads to an increase in PemK activity.

C. General Methods for Identifying Compounds Capable of Modulating MazF Activity A structure of the *Escherichia coli* chromosomal MazE/MazF addiction module has been determined to a 1.7 Å resolution (Kamada et al., *Mol Cell* 11, 875-884(2003)). As described herein, addiction modules consist of stable toxin and unstable antidote proteins that govern bacterial cell death. MazE (antidote) and MazF (toxin) form a linear heterohexamer composed of alternating toxin and antidote homodimers ($MazF_2$-$MazE_2$-$MazF_2$). Kamada et al. show that the MazE homodimer contains a β barrel from which two extended C termini project that interact with flanking MazF homodimers. Such interactions resemble those of the plasmid-encoded toxins CcdB and Kid. The MazE/MazF heterohexamer structure documents that the mechanism of antidote-toxin recognition is common to both chromosomal and plasmid-borne addiction modules, and provides general molecular insights into toxin function, antidote degradation in the absence of toxin, and promoter DNA binding by antidote/toxin complexes.

Based on information presented herein, suitable peptide targets in MazE include, but are not limited to, those residues and regions listed below. Suitable peptide targets in MazE include the N-box, the highly conserved N-terminal region in MazE from residue 7 to 18 which mediates DNA-binding, and critical residues therein. Critical residues in the N-box of MazE include K7A, R8A, S12A and R16A, mutation of which disrupts the DNA-binding ability of both MazE and the MazE-MazFcomplex. The Hp-Box, the conserved C-terminal region in MazE from residue 53 to 64, which is rich in hydrophobic residues, is also a suitable target for peptide-based therapeutics. The Hp-box region is involved in the seemingly most stable interface between MazE and MazF. The side-chains of hydrophobic amino acid residues (Leu55, Leu58, Val59 and Ile62) in the Hp-box interact with a cluster of hydrophobic residues in the MazF homodimer.

Based on information presented herein, suitable peptide targets in MazF include, but are not limited to, those residues and regions listed below. Suitable peptide targets in MazF include R29S, N40D, T52K, Q77H, R86G, I110N, E24A and K79A residues and small peptides encompassing these critical residues (e.g. 5-10 residue peptides comprising these residues and flanking residues thereof).

In one embodiment of the invention, the crystal structure of the 2:4 MazE/MazF complex (Kamada et al., supra), structural components thereof, and interfaces identified between MazE and MazF are used as targets in a virtual ligand screening procedure that seeks to identify, via computer docking methods, candidate compounds from a vast compound library which bind with high affinity to the target site.

In another embodiment, the structural information of the MazE/MazF complex Kamada et al., supra), components thereof, and interfaces identified between MazE and MazF are used to design compounds predicted to bind to MazF and/or MazE/MazF interfaces, and such compounds are tested for high affinity binding.

In specific embodiments, candidate compounds and "designed compounds" are selected which modulate binding of MazF to RNA. Such compounds may either enhance or inhibit binding of MazF to RNA. Such compounds may, in turn, effectuate an increase or a decrease in substrate (i.e., RNA) cleavage. Compounds derived or obtained from either approach scoring the highest in the docking procedure are then tested in cell-based and cell-free assays (described below) to determine their efficacy in modulating MazF activity.

Any compounds which show efficacy in biological assays may then be co-crystallized with MazF to identify the binding site. In a further embodiment of the invention, candidate compounds able to bind MazF are modified by methods known in the art to further improve specific characteristics, e.g., to increase efficacy and/or specificity and/or solubility. Selected compounds exhibiting the most desired characteristics are designated lead compounds, and further tested in, for example, animal models of hyperproliferative disorders to measure their efficacy.

D. General Methods for Identifying Compounds Capable of Modulating PemK Activity Based on information presented herein, suitable peptide targets in PemI include, but are not limited to, those residues and regions listed below. Suitable peptide targets in PemI include regions conserved among members of the PemI family of polypeptides.

Based on information presented herein, suitable peptide targets in PemK include, but are not limited to, those residues and regions listed below. The conserved loop between β strands S1 and S2 (designated the S1-S2 loop) and residues therein are suitable peptide targets. See FIGS. 33 and 34 for amino acid sequence alignment of conserved regions and amino acid sequences therein.

In one embodiment of the invention, the crystal structure of the 2:4 MazE/MazF complex (Kamada et al., supra), structural components thereof, and interfaces identified between MazE and MazF can be applied to the examination of PemI/PemK complexes. Accordingly, such extrapolations can be used to identify targets in a virtual ligand screening procedure that seeks to identify, via computer docking methods, candidate compounds from a vast compound library which bind with high affinity to the target site.

In another embodiment, the structural information of the MazE/MazF complex (Kamada et al., supra), components thereof, and interfaces identified between MazE and MazF can be applied to the examination of PemI/PemK complexes. Accordingly, such extrapolations can be used to design compounds predicted to bind to PemK and/or PemI/PemK interfaces, and such compounds can be tested for high affinity binding.

In specific embodiments, candidate compounds and "designed compounds" are selected which modulate binding of PemK to RNA. Such compounds may either enhance or inhibit binding of PemK to RNA. Such compounds may, in turn, effectuate an increase or a decrease in substrate (i.e., RNA) cleavage. Compounds derived or obtained from either approach scoring the highest in the docking procedure are subsequently tested in cell-based and cell-free assays (described below) to determine their efficacy in modulating PemK activity.

Any compounds which show efficacy in biological assays may then be co-crystallized with PemK to identify the binding site(s). In a further embodiment of the invention, candidate compounds able to bind PemK are modified by methods known in the art to further improve specific characteristics, e.g., to increase efficacy and/or specificity and/or solubility.

Selected compounds exhibiting the most desired characteristics are designated lead compounds, and further tested in, for example, animal models of hyperproliferative disorders to measure their efficacy.

Virtual Ligand Screening Via Flexible Docking Technology

Current docking and screening methodologies can select small sets of likely lead candidate ligands from large libraries of compounds using a specific protein structure. Such methods are described, for example, in Abagyan and Totrov (2001) Current Opinion Chemical Biology 5:375-382, herein specifically incorporated by reference in its entirety.

Virtual ligand screening (VLS) based on high-throughput flexible docking is useful for designing and identifying compounds able to bind to a specific protein structure. VLS can be used to virtually sample a large number of chemical molecules without synthesizing and experimentally testing each one. Generally, the methods start with polypeptide modeling which uses a selected protein structure derived by conventional means, e.g., X-ray crystallography, NMR, homology modeling. A set of compounds and/or molecular fragments are then docked into the selected binding site using any one of the existing docking programs, such as for example, MCDOCK (Liu et al. (1999) J. Comput. Aided Mol. Des. 13:435-451), SEED (Majeux et al. (1999) Proteins 37:88-105; DARWIN (Taylor et al. (2000) Proteins 41:173-191; MM (David et al. (2001) J. Comput. Aided Mol. Des. 15:157-171. Compounds are scored as ligands, and a list of candidate compounds predicted to possess the highest binding affinities generated for further in vitro and in vivo testing and/or chemical modification.

In one approach of VLS, molecules are "built" into a selected binding pocket prior to chemical generation. A large number of programs are designed to "grow" ligands atom-by-atom [see, for example, GENSTAR (Pearlman et al. L (1993) J. Comput. Chem. 14:1184), LEGEND (Nishibata et al. (1993) J. Med. Chem. 36:2921-2928), MCDNLG (Rotstein et al. (1993) J. Comput-Aided Mol. Des. 7:23-43), CONCEPTS (Gehlhaar et al. (1995) J. Med. Chem. 38:466-472] or fragment-by-fragment [see, for example, GROUP-BUILD (Rotsein et al. (1993) J. Med. Chem. 36:1700-1710), SPROUT (Gillet et al. (1993) J. Comput. Aided Mol. Des. 7:127-153), LUDI (Bohm (1992) J. Comput. Aided Mol. Des. 6:61-78), BUILDER (Roe (1995) J. Comput. Aided Mol. Des. 9:269-282), and SMOG (DeWitte et al. (1996) J. Am. Chem. Soc. 118:11733-11744].

Methods for scoring ligands for a particular protein are known which allow discrimination between the small number of molecules able to bind the protein structure and the large number of non-binders. See, for example, Agagyan et al. (2001) supra, for a report on the growing number of successful ligands identified via virtual ligand docking and screening methodologies.

For example, Nishibata et al. (1993) J. Med. Chem. 36:2921-2928, describe the ability of a structure construction program to generate inhibitory molecules based on the three-dimension structure of the active site of a molecule, dihydrofolate reductase. The program was able to predict molecules having a similar structure to four known inhibitors of the enzyme, providing strong support that new lead compounds can be obtained with knowledge of the target three dimensional structure. Similarly, Gillet et al. (1993) J. Computer Aided Mol. Design. 7:127-153 describe structure generation through artificial intelligence techniques based on steric constrains (SPROUT).

Agents Identified by the Screening Methods of the Invention

The invention provides methods for identifying agents (e.g., candidate compounds or test compounds) that bind with high affinity to mRNA interferases (e.g., MazF or PemK) or mRNA interferase inhibitors, (e.g., MazE or PemI). Agents identified by the screening method of the invention are useful as candidate anti-hyperproliferative disorder and anti-bacterial therapeutics.

Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233, each of which is incorporated herein in its entirety by reference.

Libraries of compounds may be presented, e.g., presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or phage (Scott and Smith (19900 Science 249:386-390; Devlin (1990) Science 249:404-406; Cwirla et al. (1990) Proc. Natl. Acad. Sci. USA 87:6378-6382; and Felici (1991) J. Mol. Biol. 222:301-310), each of which is incorporated herein in its entirety by reference.

Screening Assays

Small molecules identified through the above described virtual ligand docking and screening methodologies are further tested in in vitro and in vivo assays. In one embodiment, agents that interact with (i.e., bind to) an mRNA interferase, such as MazF or PemK, or mRNA interferase inhibitors, such as MazE or PemI, are identified in a cell-based assay system. For the purposes of clarity and brevity, the remainder of these assays is described with regard to MazF and MazF fragments, but it is to be understood that such assays/methods are also applicable to other mRNA interferases and fragments thereof, such as MazE and MazE fragments, PemK and PemK fragments, and PemI and PemI fragments.

In accordance with this embodiment, cells expressing a MazF or a functional fragment thereof, are contacted with a candidate compound or a control compound and the ability of the candidate compound to interact with MazF is determined. If desired, this assay may be used to screen a plurality (e.g. a library) of candidate compounds. The cell, for example, can be of prokaryotic origin (e.g., *E. coli*) or eukaryotic origin (e.g., yeast or mammalian). Further, the cells can express MazF or a fragment thereof endogenously or be genetically engineered to express MazF or a MazF fragment. In certain instances, MazF or a MazF fragment is labeled, for example with a radioactive label (such as $^{32}P$, $^{35}S$ or $^{125}I$, or a fluorescent label (such as fluorescein isothiocyanate, rhodamine, phycoerythrin, phycocyanin, allophycocyanin, o-phthaldehyde or fluorescamine) to enable detection of an interaction between MazF and a candidate compound. The ability of the candidate compound to bind to MazF can be determined by methods known to those of skill in the art. For example, the interaction between a candidate compound and MazF can be determined by flow cytometry, a scintillation assay, immunoprecipitation or western blot analysis.

In another embodiment, agents that interact with (i.e., bind to) MazF, or a relevant fragment thereof, are identified in a cell-free assay system. In accordance with this embodiment, a native or recombinant MazF or fragment thereof is contacted with a candidate compound or a control compound and the ability of the candidate compound to interact with MazF is determined. If desired, this assay may be used to screen a plurality (e.g. a library) of candidate compounds. In one embodiment, MazF or fragment thereof is first immobilized, by, for example, contacting with, for example, an immobilized antibody which specifically recognizes and binds it, or by contacting a purified preparation of MazF or fragment thereof, with a surface designed to bind proteins. MazF or a fragment thereof may be partially or completely purified (e.g., partially or completely free of other polypeptides) or part of a cell lysate. Further, MazF or a fragment thereof may be a fusion protein comprising MazF or a biologically active portion thereof, and a domain such as glutathionine-S-transferase. Alternatively, MazF or a fragment thereof can be biotinylated using techniques well known to those of skill in the art (e.g., biotinylation kit, Pierce Chemicals; Rockford, Ill.). The ability of the candidate compound to interact with MazF can be determined by methods known to those of skill in the art.

In another embodiment, agents that modulate the MazF activity are identified in an animal model. Examples of suitable animals include, but are not limited to, mice, rats, rabbits, monkeys, guinea pigs, dogs and cats. Preferably, the animal used represents a model of a hyperproliferative disorder. In accordance with this embodiment, the test compound or a control compound is administered (e.g., orally, rectally or parenterally such as intraperitoneally or intravenously) to a suitable animal and the effect on the level of activity is determined.

E. Therapeutic Uses of Agents Able to Bind mRNA Interferases or mRNA Interferase Inhibitors The invention provides for treatment of hyperproliferative disorders by administration of a therapeutic compound identified using the above-described methods. Such compounds include, but are not limited to proteins, peptides, protein or peptide derivatives or analogs, antibodies, nucleic acids, and small molecules.

The invention provides methods for treating patients afflicted with a hyperproliferative disorder comprising administering to a subject an effective amount of a compound identified by the method of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu (1987) J. Biol. Chem. 262:4429-4432), and construction of a nucleic acid as part of a retroviral or other vector. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally, e.g., by local infusion during surgery, topical application, e.g., by injection, by means of a catheter, or by means of an implant, said implant being of a porous, non-porous, or gelatinous material, including membranes, such as sialastic membranes, or fibers. In one embodiment, administration can be by direct injection into CSF or at the site of a tumor, for example, in CNS tissue.

In another embodiment, the compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., a target tissue or tumor, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

F. Pharmaceutical Compositions

The present invention also provides pharmaceutical compositions. Such compositions comprise a therapeutically effective amount of an agent, and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, incorporated in its entirety by reference herein. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc The amount of the compound of the invention which will be effective in the treatment of a hyperproliferative disorder (e.g., cancer) can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Suppositories generally contain active ingredient in the range of 0.5% to 10% by weight; oral formulations preferably contain 10% to 95% active ingredient. Effective doses may be extrapolated from dose-response curves derived from in vitro or animal model test systems.

Nucleic Acids

The invention provides methods of identifying agents capable of binding an mRNA interferase (e.g., MazF or PemK) to effectuate an increase in the riboendonucleolytic activity of the mRNA interferase. Accordingly, the invention encompasses administration of a nucleic acid encoding a peptide or protein activator of an mRNA interferase or an ortholog thereof, as well as antisense sequences or catalytic RNAs capable of interfering with the expression of an endogenous inhibitor of an mRNA interferase (e.g., MazE or PemI) or an ortholog thereof.

In one embodiment, a nucleic acid comprising a sequence encoding a peptide or protein capable of competitively binding to an mRNA interferase is administered. Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; and Morgan and Anderson (1993) Ann. Rev. Biochem. 62:191-217; May (1993) TIBTECH 11(5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In a particular aspect, the compound comprises a nucleic acid encoding a peptide or protein capable of binding an mRNA interferase to effectuate an increase in the riboendonucleolytic activity of the mRNA interferase, such nucleic acid being part of an expression vector that expresses the peptide or protein in a suitable host. In particular, such a nucleic acid has a promoter operably linked to the coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller and Smithies (1989) Proc. Natl. Acad. Sci. USA 86:8932-8935; Zijlstra et al. (1989) Nature 342:435-43.8).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu and Wu, 1987, J. Biol. Chem. 262:4429-4432), which can be used to target cell types specifically expressing the receptors.

In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al. (1989) Nature 342:435-438).

In a further embodiment, a retroviral vector can be used (see Miller et al. (1993) Meth. Enzymol. 217:581-599). These retroviral vectors have been modified to delete retroviral sequences that are not necessary for packaging of the viral genome and integration into host cell DNA. The nucleic acid encoding an mRNA interferase to be used in gene therapy is cloned into the vector, which facilitates delivery of the gene into a subject. More detail about retroviral vectors can be found in Boesen et al. (1994) Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al. (1994) J. Clin. Invest. 93:644-651; Kiem et al. (1994) Blood 83:1467-1473; Salmons and Gunzberg (1993) Human Gene Therapy 4:129-141; and Grossman and Wilson (1993) Curr. Opin. in Genetics and Devel. 3:110-114.

Adenoviruses may also be used effectively in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993) Current Opinion in Genetics and Development 3:499-503 present a review of adenovirus-based gene therapy. Bout et al. (1994) Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al. (1991) Science 252:431-434; Rosenfeld et al. (1992) Cell 68:143-155; Mastrangeli et al. (1993) J. Clin. Invest. 91:225-234; PCT Publication WO94/12649; and Wang, et al. (1995) Gene Therapy 2:775-783. Adeno-associated virus (AAV) has also been proposed for use in gene therapy (Walsh et al. (1993) Proc. Soc. Exp. Biol. Med. 204:289-300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr (1993) Meth. Enzymol. 217:599-618; Cohen et al. (1993) Meth. Enzymol. 217:618-644; Cline (1985) Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. In a preferred embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The amount of cells envisioned for use depends on the desired effect, the condition of the subject, etc., and can be determined by one skilled in the art.

Cells into which a nucleic acid can be introduced for purposes of gene therapy encompass any desired, available cell type, and include but are not limited to neuronal cells, glial cells (e.g., oligodendrocytes or astrocytes), epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood or fetal liver. In a preferred embodiment, the cell used for gene therapy is autologous to the subject that is treated.

In another embodiment, the nucleic acid to be introduced for purposes of gene therapy may comprise an inducible promoter operably linked to the coding region, such that expression of the nucleic acid is controllable by adjusting the concentration of an appropriate inducer of transcription.

Direct injection of a DNA coding for a peptide or protein capable of binding to an mRNA interferase or an agent capable of interfering with the expression of an endogenous inhibitor of an mRNA interferase (e.g., MazE or PemI, or an ortholog thereof) may also be performed according to, for example, the techniques described in U.S. Pat. No. 5,589,466. These techniques involve the injection of "naked DNA", i.e., isolated DNA molecules in the absence of liposomes, cells, or any other material besides a suitable carrier. The injection of DNA encoding a protein and operably linked to a suitable promoter results in the production of the protein in cells near the site of injection.

G. Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

The following examples are put forth so as to provide those of ordinary skill in the art with a complete disclosure and description of how to make and use the assay, screening, and therapeutic methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The following protocols are provided to facilitate the practice of the present invention.

Example I

As described herein, *E. coli* cells permeabilized by toluene treatment were used to demonstrate that MazF inhibits translation, but not RNA synthesis or DNA replication. Moreover, MazF was shown to cleave mRNA specifically between A and C residues at ACA sequences in a manner independent of ribosomes. Thus, the present invention demonstrates that MazF interferes with mRNA function by cleaving it at specific sites. Accordingly, the present inventors have discovered that MazF is a novel endoribonuclease and have designated it herein an “mRNA interferase”.

Methods and Materials

Strains and Plasmids. *E. coli* BL21(DE3), BW25113 (Datsenko and Wanner, *Proc Natl Acad Sci USA* 97, 6640-5 (2000)) and MRE600 (Swaney et al., *Antimicrob Agents Chemother* 42, 3251-5 (1998)) were used. Plasmid pET-21 cc-MazEF was constructed from pET-21 cc (Novagen), which was modified to express both MazE and MazF(His)$_6$ under the control of a T7 promoter. The Shine-Dalgarno (SD) sequence, however, was derived from the mazEF operon. Plasmid pET-28a-MazE was constructed using pET-28a (Novagen) to express (His)$_6$MazE. pBAD-MazF was constructed using pBAD (Guzman et al., *J Bacteriol* 177, 4121-30 (1995)) to tightly regulate mazF expression following addition of arabinose (0.2%).

Assay of protein, DNA and RNA synthesis in toluene-treated cells. A 50-ml culture of *E. coli* BW25113 containing pBAD-MazF plasmid was grown at 37° C. in glycerol-M9 medium. When the $OD_{600}$ of the culture reached 0.6, arabinose was added to a final concentration of 0.2%. After incubation at 37° C. for 10 minutes, the cells were treated with 1% toluene (Halegoua et al., *Eur J Biochem* 69, 163-7 (1976)). Using toluene-treated cells, protein synthesis was carried out with $^{35}$S-methionine as described previously (Halegoua et al., *J Bacteriol* 126, 183-91 (1976)). The toluene-treated cells were washed once with 0.05 M potassium phosphate buffer (pH 7.4) at room temperature, and then resuspended in the same buffer to examine DNA synthesis using [α-$^{32}$P]UTP as described previously (Moses and Richardson, *Proc Natl Acad Sci USA* 67, 674-81 (1970)). For assaying RNA synthesis, the toluene-treated cells were washed once with 0.05 M Tris-HCl buffer (pH 7.5) at room temperature, and then resuspended into the same buffer to measure [α-$^{32}$P]UTP incorporation into RNA as described previously (Peterson et al., *J Bacteriol* 107, 585-8 (1971)).

Assay of in vivo protein synthesis. *E. coli* BW25113 cells containing pBAD-MazF were grown in glycerol-M9 medium. When the $OD_{600}$ of the culture reached 0.6, the culture was divided into two equal parts. To one part, arabinose was added to a final concentration of 0.2%, and to the second part, water was added. At different time intervals as indicated in FIG. 2D, 1 ml of the culture was removed to a test tube containing 2 μCi $^{35}$S-methionine, and the mixture was incubated for 1 min at 37° C. 50 μl of the reaction mixture was then applied to a filter paper disk (Whatman 3 mm, 2.3 cm diameter). Filters were treated in 5% TCA solution as described previously (Hirashima and Inouye, *Nature* 242, 405-7 (1973)) and radioactivity was quantitated using a liquid scintillation counter. The remaining 500 μl of the reaction mixture was put into a chilled test tube containing 25 μl of 100% TCA solution and 100 μg/ml non-radioactive methionine. The mixture was incubated in an ice bath for 60 minutes. The pellets were collected following centrifugation and dissolved in 50 μl SDS-PAGE loading buffer by incubating the mixture in a boiling water bath for 30 minutes. After removing insoluble materials, the supernatant (10 μl) was analyzed by SDS-PAGE.

Purification of MazF(His)$_6$ and (His)$_6$MazE proteins. MazF(His)$_6$ tagged at the C-terminal end was purified from strain BL21(DE3) carrying pET-21 cc-MazEF. The complex of MazF(His)$_6$ and MazE was first purified on Ni-NTA resin. After dissociating MazE from MazF(His)$_6$ in 6M guanidine-HCl, MazF(His)$_6$ was re-purified over Ni-NTA resin and refolded by step-step dialysis. (His)$_6$MazE tagged at the N-terminal end was purified from strain BL21(DE3) carrying pET-28a-MazE.

Effect of MazF on Protein Synthesis in Prokaryotic and Eukaryotic Cell Free Systems.

Prokaryotic cell-free protein synthesis was carried out with the *E. coli* T7 S30 extract system (Promega). The reaction mixture consisted of 10 μl of S30 premix, 7.5 μL of S30 extract and 2.5 μl of an amino acid mixture (1 mM each of all amino acids but methionine), 1 μl of $^{35}$S-methionine, and different amounts of MazF(His)$_6$ and (His)$_6$MazE in a final volume of 24 μl. The reaction mixture was incubated for 10 min at 37° C. and the assay initiated by adding 1 μl of pET-11a-MazG plasmid-DNA (0.16 μg/μl) (Zhang and Inouye, *J Bacteriol* 184, 5323-9 (2002)). The reaction was performed for 1 h at 37° C., and proteins were precipitated with acetone and analyzed by SDS-PAGE. Eukaryotic cell-free protein synthesis was carried out with the rabbit reticulocyte lysates system TNT® T7 Quick for PCR DNA (Promega). A DNA fragment encoding a human protein under the control of a T7 promoter was used as template for mRNA transcription. The reaction was performed for 1 h at 37° C., and proteins were precipitated with acetone and analyzed by SDS-PAGE.

Polysome profiles. An overnight culture of *E. coli* BW25113 containing pBAD-MazF plasmid was diluted 50 times in fresh glycerol-M9 medium. After 5 h incubation at 37° C., arabinose was added to a final concentration of 0.2%. After MazF was induced for 10 minutes, chloramphenicol was added to a final concentration of 100 μg/ml. The cell pellets were collected by centrifugation and resuspended in 1 ml of 10 mM Tris-HCl (pH 7.8) containing 10 mM $MgCl_2$, 60 mM $NH_4Cl$, 1 mM DTT and 1 mg/ml lysozyme. After freezing and thawing two times using liquid nitrogen, the lysates were centrifuged at 24,000 rpm for 20 minutes in a Beckman TLA 100.3 rotor. The supernatant (300 μl) was loaded onto a 5 to 40% sucrose gradient for polysome profiling. A similar experiment was carried out without the addition of arabinose. Ribosome patterns were detected by $OD_{280}$ and the gradient was run from left (40%) to right (5%). Kasugamycin was added to a final concentration of 500 μg/ml where indicated.

Preparation of *E. coli* 70S ribosomes. 70S ribosomes were prepared from *E. coli* MRE 600 as described previously (Aoki et al., *Antimicrob Agents Chemother* 46, 1080-5 (2002); Du and Babitzke, *J Biol Chem* 273, 20494-503 (1998); Hesterkamp et al., *J Biol Chem* 272, 21865-71 (1997)) with minor modification. Bacterial cells (2 g) were suspended in buffer A [10 mM Tris-HCl (pH 7.4) containing 10 mM $MgCl_2$, 60 mM $NH_4Cl$ and 6 mM 2-mercaptoethanol]. Cells were lysed using a French Press. After incubation with RNase-free DNase (30 min at 0° C.), cell debris was removed by two rounds of centrifugation at 30,000 rpm for 30 min at 4° C. in a Beckman 50Ti rotor. The supernatant (the top three-fourths) was then layered over an equal volume of 1.1 M sucrose in buffer B (buffer A containing 0.5 M $NH_4Cl$) and centrifuged at 45,000 rpm for 15 h at 4° C. in a Beckman 50Ti rotor. After washing with buffer A, the ribosome pellets were resuspended in buffer A and applied to a linear 10 to 30% (wt/vol) sucrose gradient prepared in buffer A, and centrifuged at 20,000-rpm for 15 h at 4° C. in a Beckman SW40Ti rotor. Gradients were fractionated and the 70S ribosome fractions were pooled and pelleted at 45,000 rpm for 20 h at 4° C. in a Beckman 50Ti rotor. The 70S ribosome pellets were resuspended in buffer A and stored at −80° C.

Primer extension inhibition (toeprinting) assays. Toeprinting was carried out as described previously (Moll and Blasi, Biochem Biophys Res Commun 297, 1021-1026 (2002)) with minor modification. The mixture for primer-template annealing containing the mazG mRNA and $^{32}$P-end-labeled DNA primer complementary to bases 65 to 85 of the mazG mRNA was incubated at 65° C. for 5 minutes, and then cooled slowly to room temperature. The ribosome-binding mixture contained 2 μl of 10× buffer [100 mM Tris-HCl (pH 7.8) containing 100 mM $MgCl_2$, 600 mM $NH_4Cl$ and 10 mM DTT], different amounts of MazF$(His)_6$, 0.375 mM dNTP, 0.5 μM 70S ribosomal subunits, 2.5 μM $tRNA^{fmet}$ and 2 μl of the annealing mixture in a final volume of 20 μl. The final mRNA concentration was 0.05 μM. This ribosome-binding mixture was incubated at 37° C. for 10 minutes, and then reverse transcriptase (2 U) was added. cDNA synthesis was carried out at 37° C. for 15 minutes. The reaction was terminated by adding 12 μl of the sequencing loading buffer. The sample was incubated at 90° C. for 5 minutes prior to electrophoresis on a 6% polyacrylamide sequencing gel. The mazG mRNA was synthesized in vitro from a 173-bp DNA fragment containing a T7 promoter using T7 RNA polymerase. The DNA fragment consisting of T7 promoter and the mazG mRNA from +1 to +153 was obtained by PCR amplification using pET-11a-MazG plasmid as DNA template.

Toeprinting of the mazG mRNA after phenol extraction. The experiment was carried out in the same way as described above except that 70S ribosomes and $tRNA^{fmet}$ were omitted. The reaction mixtures were phenol-extracted to remove proteins before primer extension.

Construction of Mutant Plasmids. Site-directed mutagenesis was performed with pET-11a-MazG plasmid as DNA template. The mutations were confirmed by DNA sequence analysis.

RNA isolation and Northern blot analysis. *E. coli* BW25113 containing pBAD-MazF were grown at 37° C. in glycerol-M9 medium. When the $OD_{600}$ value reached 0.8, arabinose was added to a final concentration of 0.2%. The samples were removed at different intervals as indicated in FIG. 4D. Total RNA was isolated using the hot-phenol method as described previously (Sarmientos et al., *Cell* 32, 1337-46 (1983)). Northern blot analysis was carried out as described previously (Baker and Mackie, *Mol Microbiol* 47, 75-88 (2003)).

Specific Methodological Details Pertaining to Drawings

As shown in FIG. 1A, MazF expression has a toxic effect on cells. *E. coli* BW25113(ΔaraBAD) cells were transformed with pBAD-MazF, pBAD-MazF R29S or pBAD-MazF R86G plasmid, respectively. The cells were spread on glycerol-M9 plates with and without arabinose (0.2%) and the inoculated plates were incubated at 37° C. for 24 h. FIG. 1B shows sequence alignments of MazF of *Escherichia coli* (NP_289336.1) with that of *Bacillus halodurans* (NP_244588.1), *Staphylococcus epidermidis* (AAG23809.1), *Staphylococcus aureus* (NP_372592.1), *Bacillus subtilis* (1NE8_A), *Neisseria meningitides* (NP_266040.1), *Morganella morgani* (AAC82516.1) and *Mycobacterium tuberculosis* (NP_217317.1).

Figure 2A:
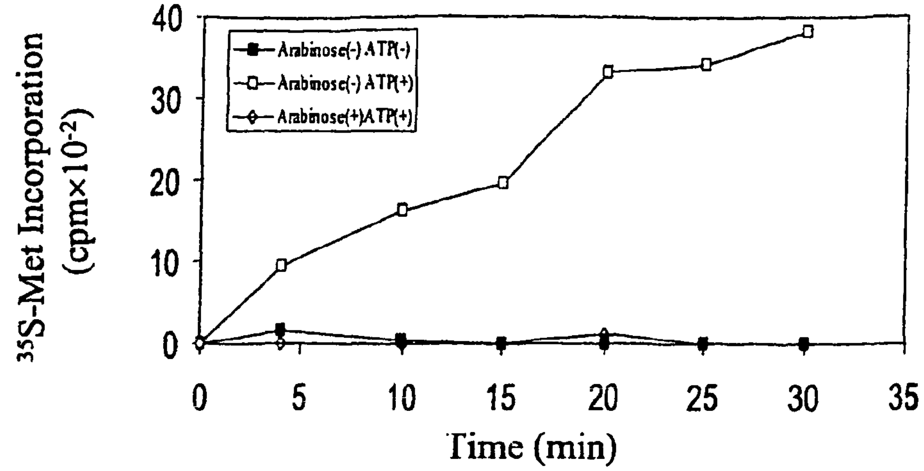
FIGS. 2A-E show line graphs depicting the effect of MazF on $^{35}$S-Met incorporation (FIG. 2A); on [α-$^{32}$P]dTTP incorporation (FIG. 2B); and on [α-$^{32}$P]UTP incorporation (FIG. 2C) in toluene-treated *E. coli* cells; and the effect of MazF on $^{35}$S-Met incorporation into *E. coli* cells in vivo (FIG. 2D); and SDS-PAGE analysis of in vivo protein synthesis after the induction of MazF (FIG. 2E).
Figure 2B:
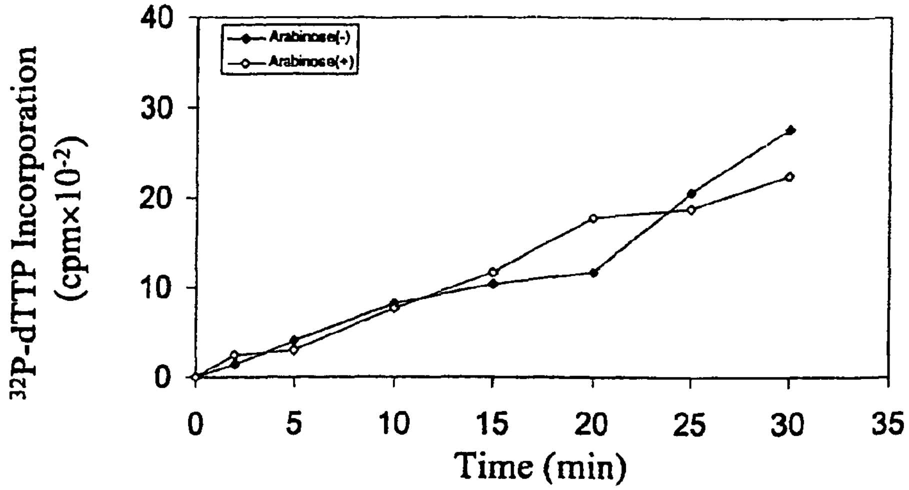
Figure 2C:
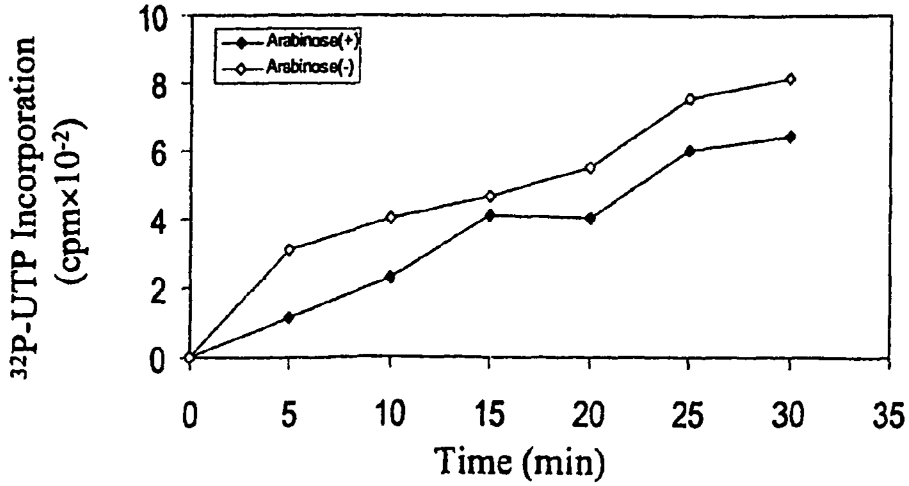
Figure 2E:
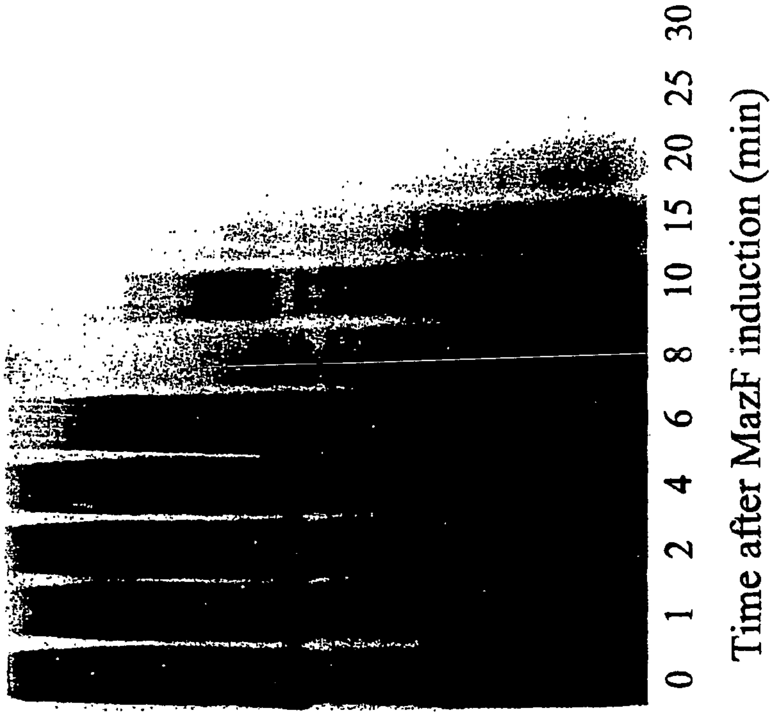
Figure 2D:
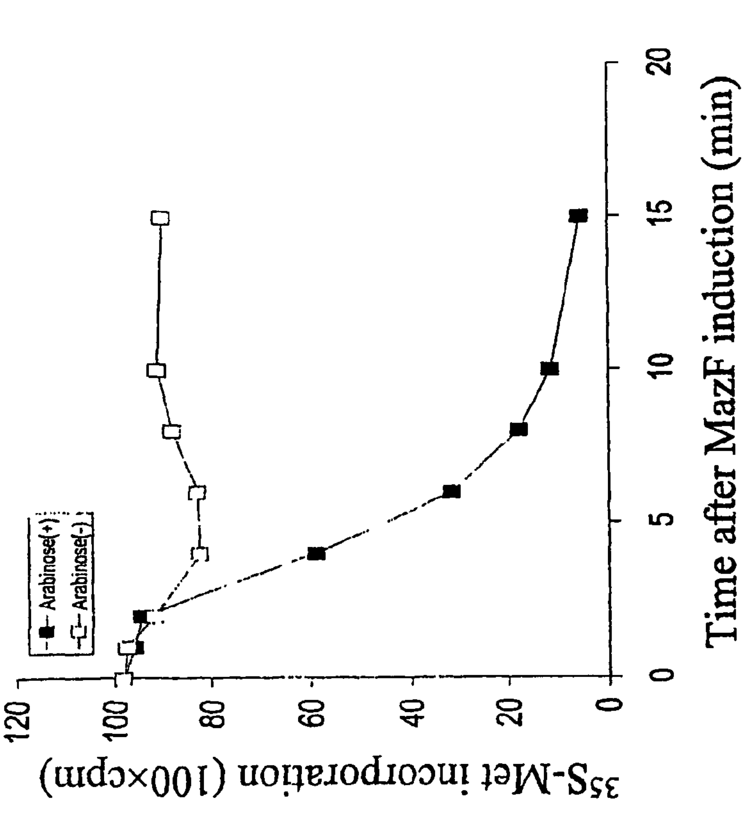

FIG. 2A reveals the effect of MazF expression on $^{35}$S-Met incorporation in toluene-treated cells. Specifically, *E. coli* BW25113 cells containing pBAD-MazF were grown at 37° C. in glycerol-M9 medium. When the $OD_{600}$ of the culture reached 0.6, arabinose was added to a final concentration of 0.2%. After incubation at 37° C. for 10 minutes, the cells were treated with toluene (Halegoua et al., *J Bacteriol* 126, 183-91 (1976)). Using toluene-treated cells, protein synthesis was carried out with $^{35}$S-methionine as described previously (Halegoua et al., *Eur J Biochem* 69, 163-7 (1976)). FIG. 2B shows the effect of MazF on [α-$^{32}$P]dTTP incorporation in toluene-treated cells (Moses and Richardson, *Proc Natl Acad Sci USA* 67, 674-81 (1970)). FIG. 2C shows the effect of MazF on [α-$^{32}$P]UTP incorporation in toluene-treated cells (Peterson et al., *J Bacteriol* 107, 585-8 (1971)). FIG. 2D reveals the effect of MazF on $^{35}$S-Met incorporation in vivo. $^{35}$S-Met incorporation into *E. coli* BW25113 cells containing pBAD-MazF was measured at various time points after MazF induction as indicated. FIG. 2E shows an SDS-PAGE analysis of in vivo protein synthesis after the induction of MazF. The cultures used in FIG. 2E are the same as those shown in FIG. 2D.

Figure 3A:
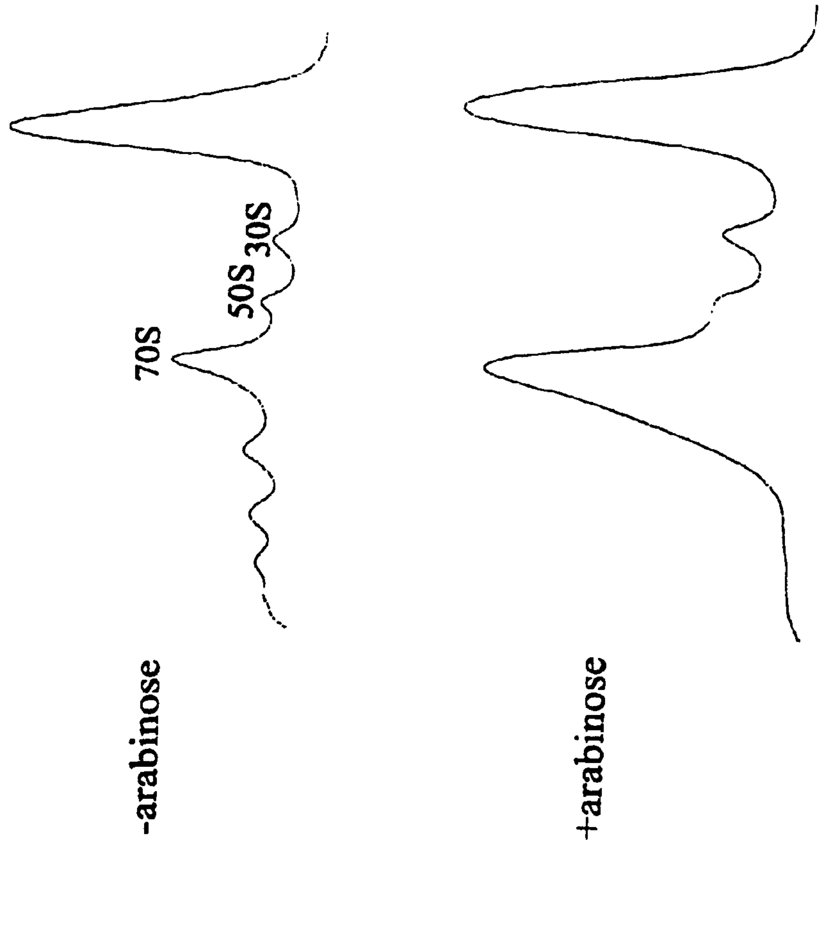

FIG. 3A shows the effect of MazF on polysome profiles. Ribosome patterns were detected by $OD_{260}$ and the gradient was run from left (40%) to right (5%). The position of 70, 50 and 30S ribosomes are indicated. FIG. 3B illustrates the effect of MazF$(His)_6$ on prokaryotic cell-free protein synthesis using an *E. coli* T7 S30 extract system (Promega). Lane C, without MazF$(His)_6$; lanes 1 to 5: 77, 154, 231, 308 and 384 nM MazF$(His)_6$ were added, respectively; lanes 6 to 10: 384 nM MazF$(His)_6$ and the ratios of $(is)_6$MazE to MazF$(His)_6$ were 0.1, 0.2, 0.4, 0.8 and 1.2, respectively. FIG. 3C reveals the effect of MazF$(His)_6$ on eukaryotic cell-free protein synthesis using a rabbit reticulocyte lysate system TNT® T7 Quick for PCR DNA (Promega). Lane 1, without $(His)_6$MazE and MazF$(His)_6$; lane 2, with 0.66 μM MazF$(His)_6$; and lane 3, with 0.9 μM $(His)_6$MazE and 0.66 μM MazF$(His)_6$, the ratio of $(His)_6$MazE to MazF$(His)_6$ was 1.2:1.

Figures 4A, 4B, 4C:
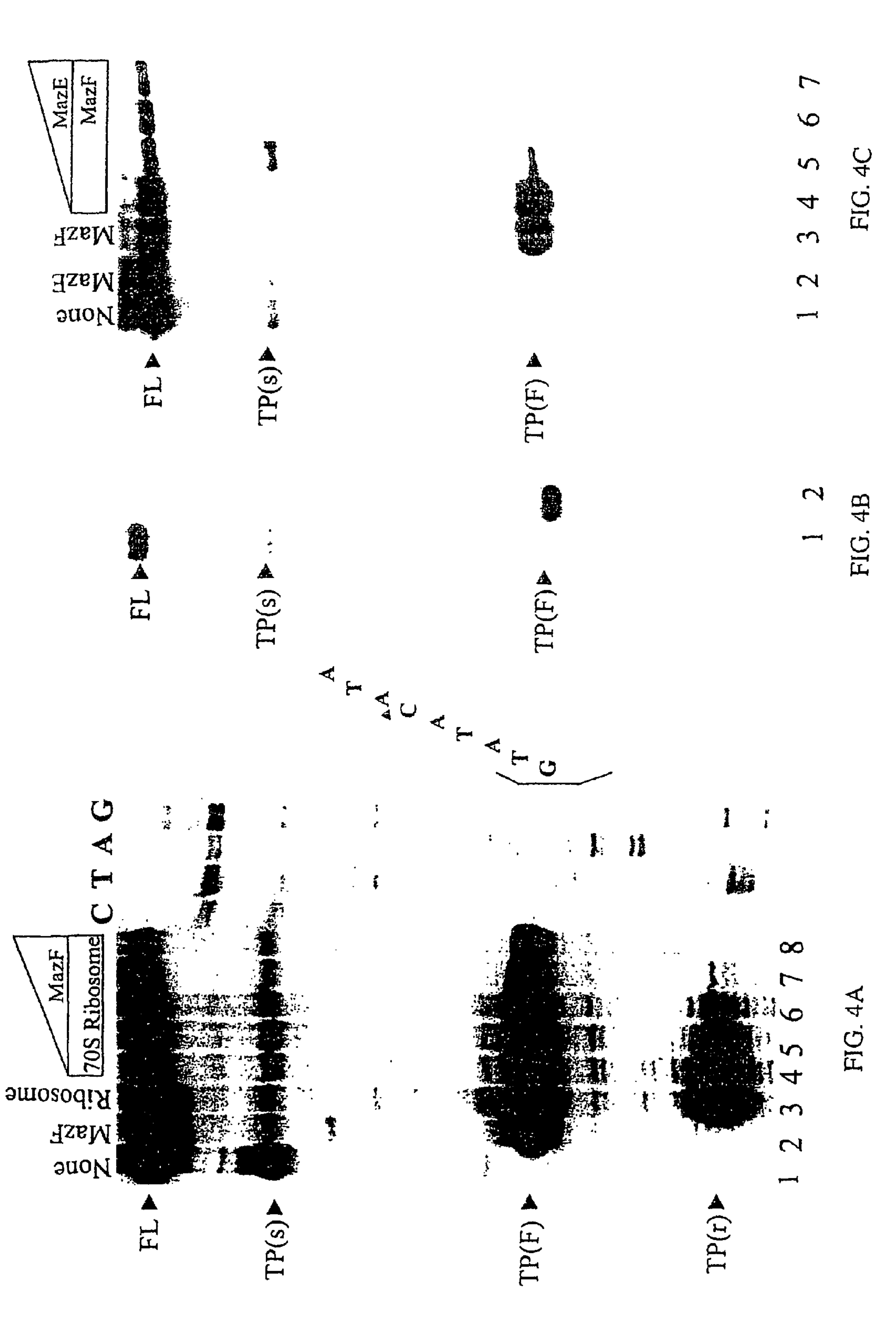
FIG. 4A-D show the effects of MazF on mRNA synthesis.
Figure 4D:
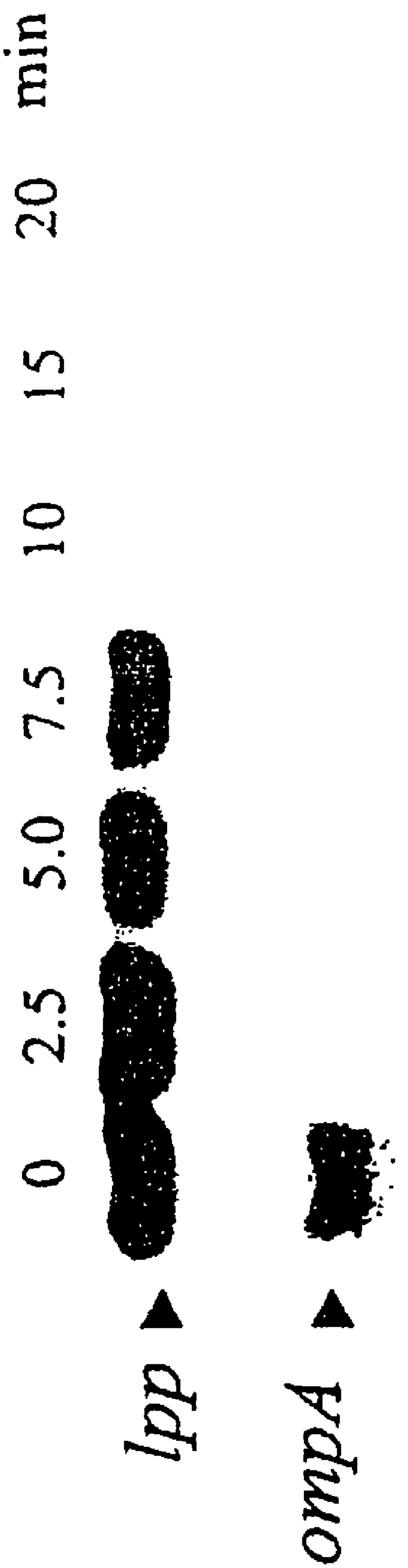

FIG. 4A shows toeprinting of the mazG mRNA in the presence of MazF. The mRNAs were synthesized in vitro from a 173-bp DNA fragment containing a T7 promoter using T7 RNA polymerase. The DNA fragment (T7 promoter and the mazG mRNA from +1 to +153) was obtained by PCR amplification using pET-11a-MazG plasmid DNA. Lane 1, without MazF$(His)_6$ and 70S ribosome; lane 2, with 2.6 μM MazF$(His)_6$ and no 70S ribosome; lane 3, with 0.5 μM 70S ribosome and no MazF$(His)_6$ and lanes 4 to 8, with 0.5 μM 70S ribosome and 0.35 μM, 0.7 μM, 1.4 μM, 2.1 μM and 2.6 μM MazF$(His)_6$, respectively. FIG. 4B reveals toeprinting of the mazG mRNA after phenol extraction. The experiment was performed in the same manner as described in lane 1 and lane 2 of FIG. 4A, except that reaction products were phenol extracted to remove proteins before primer extension. Lane 1, without MazF(His)$_6$ and lane 2, with 2.6 μM MazF(His)$_6$. FIG. 4C illustrates the effect of MazE on MazF cleavage of mazG mRNA. Lane 1, without MazF(His)$_6$ and (His)$_6$MazE; lane 2, with 8.8 μM (His)$_6$MazE; lane 3, with 2.2 μM MazF (His)$_6$ and lanes 4 to 7, with 2.2 μM MazF(His)$_6$ and the ratios of (His)$_6$MazE to MazF(His)$_6$ were 0.25, 0.4, 0.8 and 1.0, respectively. FIG. 4D shows the effect of MazF on cellular mRNAs in vivo. Total cellular RNA was extracted from *E. coli* BW25113 cells containing pBAD-MazF at various time points after the addition of arabinose (as indicated) and subjected to Northern blot analysis using radiolabeled ompA and lpp ORF DNA as probes.

Figures 5A, 5B:
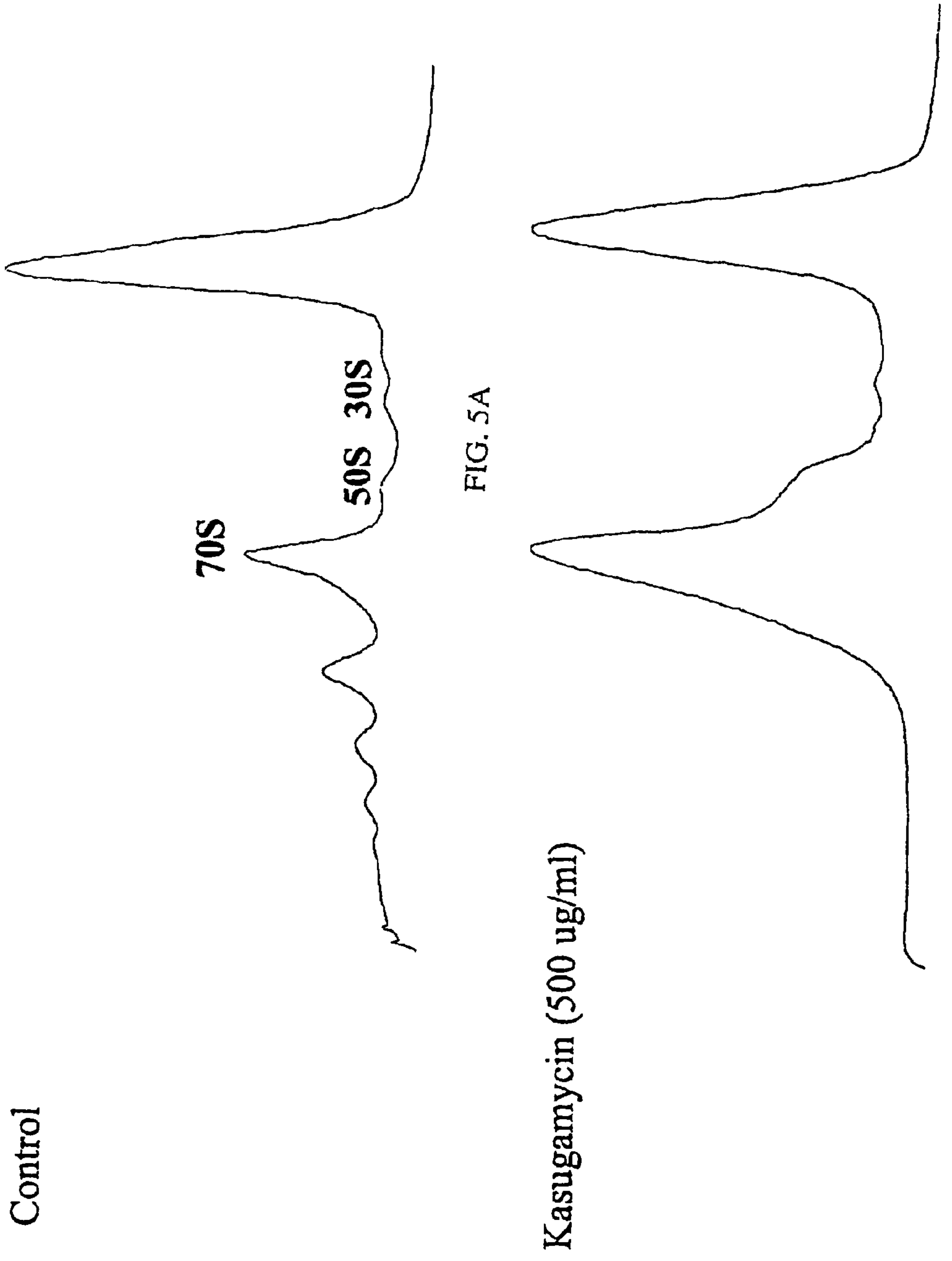
FIGS. 5A and B show line traces depicting a densitometric analysis of polysome profiles in the absence (FIG. 5A) and presence (FIG. 5B) of kasugamycin. The positions of 70, 50 and 30S ribosomes are indicated.

FIG. 5 demonstrates the effect of kasugamycin on polysome profile. Experiments were carried out as described above. Ribosome patterns were detected by $OD_{260}$ and the gradient was run from left (40%) to right (5%). The positions of 70, 50 and 30S ribosomes are indicated.

Figure 6:
FIG. 6 shows a toeprinting analysis depicting the inhibition of MazF cleavage of the mazG mRNA by ribosomes.
Figure 7:
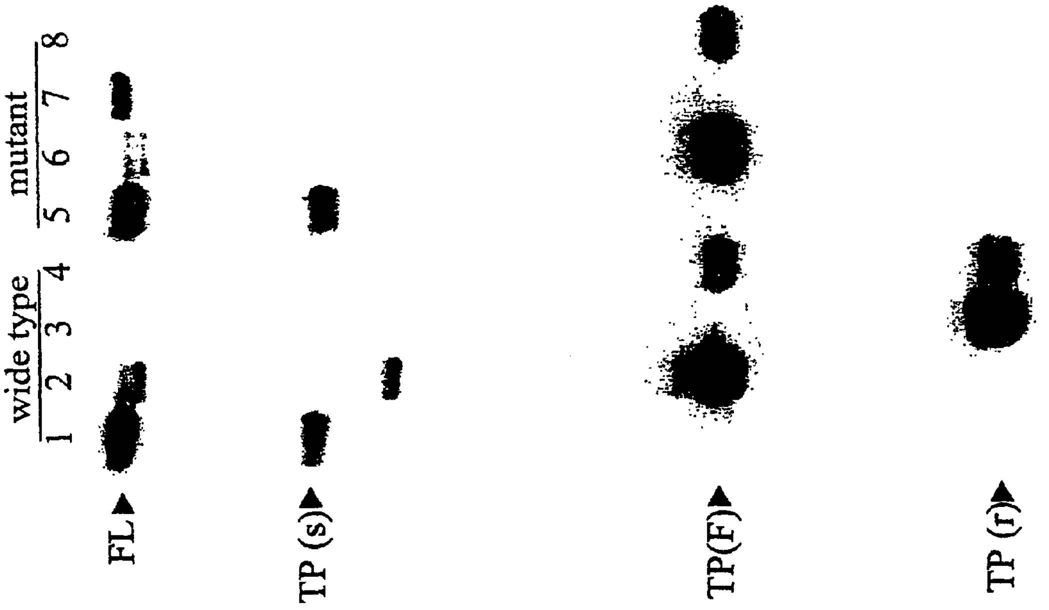
FIG. 7 shows a toeprinting analysis illustrating the effect of the GGAG to UUUG mutation of the Shine-Dalgarno sequence of the mazG mRNA on MazF function.

FIG. 6 shows the inhibition of MazF cleavage of the mazG mRNA by ribosomes. The reaction was carried out as described above. Lane 1, without MazF(His)$_6$ and 70S ribosomes; lane 2, with 2.6 μM MazF(His)$_6$ but no 70S ribosomes; lane 3, with 0.5 μM 70S ribosomes but no MazF (His)$_6$; lane 4, mazG mRNA and 70S ribosomes were incubated at 37° C. for 10 minutes and 2.2 μM MazF(His)$_6$ was then added to the mixture for another 10 minutes at 37° C. prior to primer extension; lane 5, 70S ribosomes and MazF (His)$_6$ were first mixed and incubated at 37° C. for 10 minutes before addition of the mazG mRNA and an additional 10 minute incubation at 37° C. followed by primer extension; lane 6, after the mazG mRNA and MazF(His)$_6$ were mixed and incubated at 37° C. for 10 minutes, 70S ribosomes were added to the mixture, which was incubated at 37° C. for another 10 minutes before primer extension. FL, the full-length mazG mRNA; TP(s), a paused site due to a secondary structure; TP(F), the toeprint site due to MazF cleavage; and TP(r), the toeprint site due to ribosome binding to the mazG mRNA FIG. 7 illustrates the effect of the GGAG to UUUG mutation of the Shine-Dalgarno sequence of the mazG mRNA on MazF function. The reaction was carried out as described above. Lanes 1 to 4, with wild-type mazG mRNA; lanes 5 to 8, with a mutant mazG mRNA having the GGAG to UUUG mutation at the Shine-Dalgarno sequence. Lanes 1 and 5, without MazF(His)$_6$ and 70S ribosomes; lanes 2 and 6, with 2.6 μM MazF(His)$_6$ but without 70S ribosomes; lanes 3 and 7, with 0.5 μM 70S ribosomes but without MazF(His)$_6$ and lanes 4 and 8, with 0.5 μM 70S ribosomes plus 2.2 μM MazF(His)$_6$. Notations of the markers at the left-hand side are the same as in FIG. 6.

Figure 8:
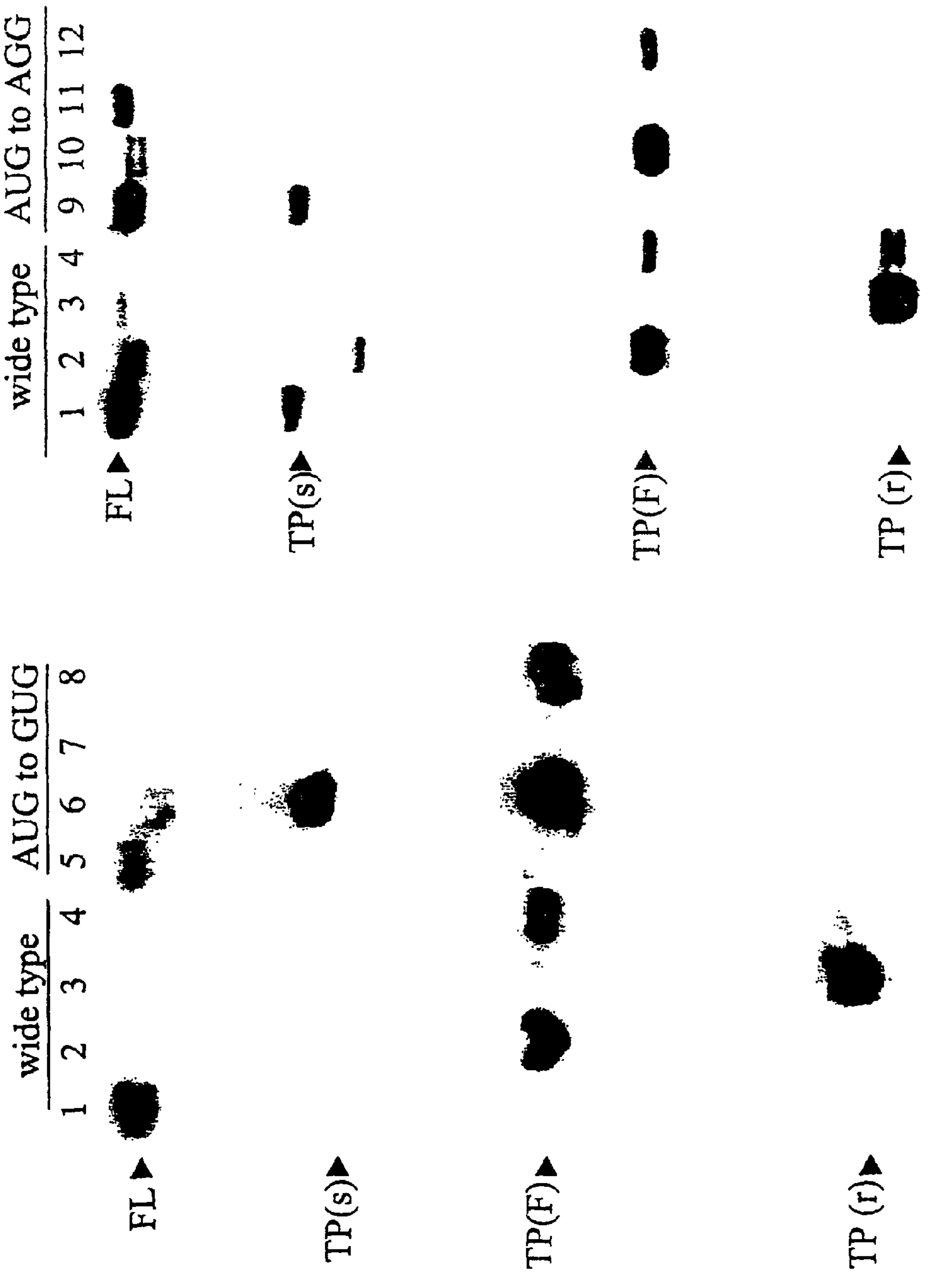
FIG. 8 shows a toeprinting analysis revealing the effect of mutations at the initiation codon of the mazG mRNA on MazF function.

FIG. 8 shows the effect of mutations at the initiation codon of the mazG mRNA on MazF function. The reaction was carried out as described above. Lanes 1 to 4, with the wild-type mazG mRNA; lanes 5 to 8, with a mutant mazG mRNA whose initiation codon was changed to GUG; lanes 9 to 12, with a mutant mazG mRNA whose initiation codon was changed to AGG. Lanes 1, 5 and 9, without MazF(His)$_6$ and 70S ribosomes; lanes 2, 6 and 10, with 2.6 μM MazF(His)$_6$ but without 70S ribosomes; lanes 3, 7 and 11, with 0.5 μM 70S ribosomes but without MazF(His)$_6$; and lanes 4, 8 and 12, with 0.5 μM 70S ribosomes plus 2.2 μM MazF(His)$_6$. Notations of the markers at the left-hand side are the same as in FIG. 6.

Figure 9:
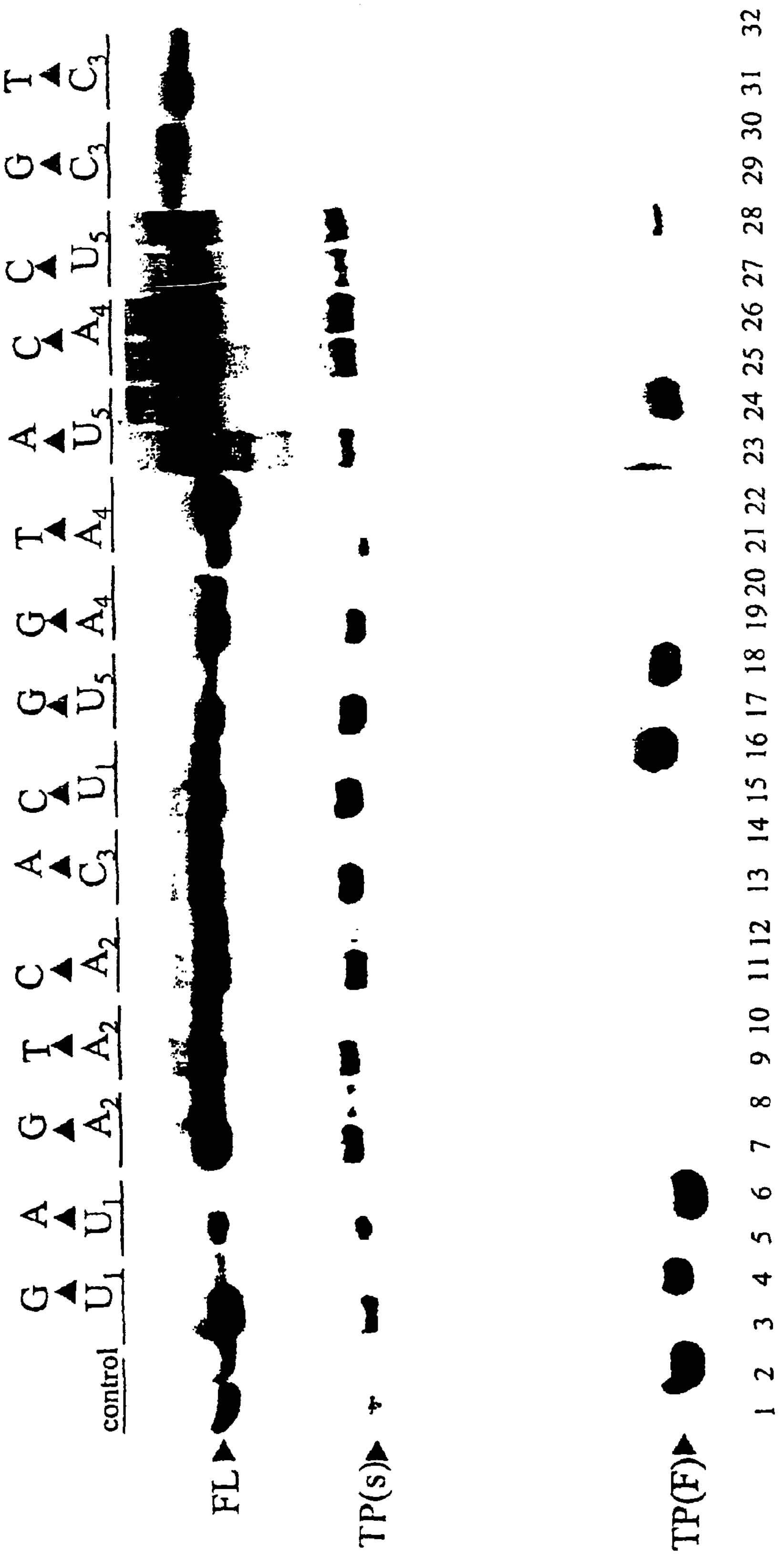
FIG. 9 shows a toeprinting analysis depicting the effects of mutations at the UACAU ($U_1A_2C_3A_4U_5$) cleavage sequences on MazF function.

FIG. 9 reveals the effects of mutations at the UACAU ($U_1A_2C_3A_4U_5$) cleavage sequences on MazF function. The reaction mixture was carried out as described above. Lanes 1 and 2 are with wild-type mazG mRNA as a control. All the mutations are indicated by the arrow. Lanes 1, 3, 5, 7, 9, 11, 13, 15, 17, 19, 21, 23, 25, 27, 29 and 31, without MazF(His)$_6$; lanes 2, 4, 6, 8, 10, 12, 14, 16, 18, 20, 22, 24, 26, 28, 30 and 32, with 2.6 μM MazF(His)$_6$. Notations of the markers at the left-hand side are the same as in FIG. 6.

Figure 10:
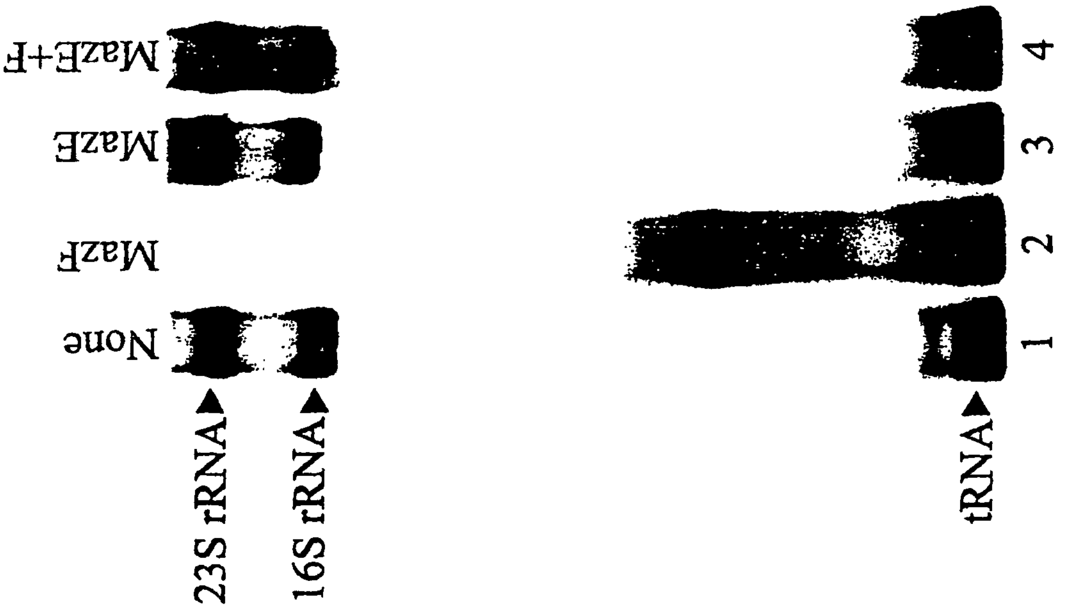
FIG. 10 shows an acrylamide gel revealing the effect of MazF and MazE on the cleavage of 16S and 23S rRNA.

FIG. 10 shows the effect of MazF and MazE on the cleavage of 16S and 23S rRNA. The reaction was carried out in 10 mM Tris-HCl (pH 7.8) containing 10 mM $MgCl_2$, 60 mM $NH_4Cl$, 1 mM DTT, 0.5 μl human placenta RNase inhibitor (Roche), 5.6 μM MazF(His)$_6$ and/or 17.6 μM (His)$_6$MazE and in a total volume of 10 μl. After incubating at 37° C. for 10 minutes, 2 μl of loading buffer was added to stop the reaction. The sample was analyzed on a 3.5% acrylamide gel. Lane 1, without MazF(His)$_6$; lane 2, with 5.2 μM MazF (His)$_6$; lane 3, with 17.6 μM (His)$_6$MazE; and lane 4, with 5.2 μM MazF(His)$_6$ and 17.6 μM (His)$_6$MazE. The positions of 23S and 16S rRNA and tRNA are indicated by the arrows.

Results

The mazF gene was cloned into an arabinose inducible pBAD plasmid (Guzman et al., *J Bacteriol* 177, 4121-30 (1995)). *E. coli* BW25113 carrying pBAD-MazF did not grow on a glycerol-M9 plate in the presence of arabinose (0.2%) (See FIG. 1A). The arabinose sensitivity was eliminated (FIG. 1A) when either Arg29 or Arg86, highly conserved residues among MazF homologues, was replaced with Ser or Gly, respectively (FIG. 1B). This result indicated that the cell growth inhibition observed was due to the presence of wild-type MazF. In liquid medium, cell viability was reduced by $10^4$ after the addition of arabinose for a period of 5 minutes.

Tto identify the cellular function inhibited by MazF, a cell-free system prepared from *E. coli* BW25113 carrying pBAD-MazF permeabilized by toluene treatment was used (Halegoua et al., *J Bacteriol* 126, 183-91 (1976); Halegoua et al., *Eur J Biochem* 69, 163-7 (1976). ATP-dependent $^{35}S$-methionine incorporation was completely inhibited when cells were preincubated for 10 minutes in the presence of arabinose before toluene treatment (FIG. 2A). The incorporation of [α-$^{32}P$]dTTP (Moses and Richardson, *Proc Natl Acad Sci USA* 67, 674-81 (1970)) (FIG. 2B) and [α-$^{32}P$]UTP (Peterson et al., *J Bacteriol* 107, 585-8 (1971)) (FIG. 2C), however, was not affected under similar conditions. These results demonstrated that MazF inhibits protein synthesis, but not DNA replication or RNA synthesis. The in vivo incorporation of $^{35}S$-methionine (Hirashima and Inouye, *Nature* 242, 405-7 (1973) was dramatically inhibited after the addition of arabinose using cells not treated with toluene (FIG. 2D). SDS-PAGE analysis of total cellular protein synthesis at different time points after arabinose addition (FIG. 2E) showed that MazF is a general inhibitor of protein synthesis, which affects essentially all cellular proteins. Interestingly, the synthesis of larger proteins was more susceptible to MazF toxicity than that of smaller proteins.

Analysis of the polysome pattern of *E. coli* BW25113 cells carrying pBAD-MazF cells was performed by sucrose density gradient after 10 minutes of arabinose induction. As shown in FIG. 3A, the polysomes completely disappeared in such cells, with a concomitant increase of the 70S ribosomal fraction and no significant change in either the 30S or the 50S ribosomal fraction. A similar change in the polysome pattern was observed when cells were treated with kasugamycin, an antibiotic that inhibits translation initiation (FIG. 5). These findings suggest that MazF causes the release of ribosomes from mRNA either by inhibiting translation initiation or by degrading mRNA.

The effect of purified MazF(His)$_6$ on the synthesis of a candidate protein, MazG, was also examined in an *E. coli* cell-free RNA/protein synthesis system. MazF(His)$_6$ was purified from cells co-expressing both MazE and MazF (His)$_6$. The synthesis of MazG (30 kD) (Hirashima and Inouye, *Nature* 242, 405-7 (1973)) from plasmid pET-11a-MazG was carried out at 37° C. for 1 hr using an *E. coli* T7

S30 extract system (Promega) in the absence and presence of increasing concentrations of MazF(His)$_6$ (FIG. 3B). MazG synthesis was completely blocked at MazF(His)$_6$ concentrations above 231 nM. The effect of MazE antitoxin on this observed MazF-mediated inhibition of MazG synthesis was also assessed in parallel. Interestingly, the co-addition of the antitoxin (His)$_6$MazE rescued MazG synthesis in a dose-dependent manner (FIG. 3B). MazF(His)$_6$ was also able to inhibit eukaryotic cell-free protein synthesis (FIG. 3C, lane 2), which was also recovered upon co-addition of (His)$_6$ MazE (lane 3).

Since MazF inhibited MazG synthesis (FIG. 3B), an analysis of the timing of inhibition was executed. To determine if the inhibition affected the translation initiation step, toeprinting (TP) techniques were utilized using 70S ribosomes and the mazG mRNA (Moll and Blasi, *Biochem Biophys Res Commun* 297, 1021-1026 (2002)). Toeprinting of the mazG mRNA alone yielded the full-length band (FL) and band TP(s) presumably due to a secondary structure at the 5' end of the mazG mRNA (FIG. 4A, lane 1). In the presence of 70S ribosomes, the toeprinting band [TP(r)] downstream of the initiation codon was detected (lane 3). When MazF(His)$_6$ was added together with 70S ribosomes, a new band TP(F) appeared, which corresponded to the region between the Shine-Dalgarno (SD) sequence and the initiation codon (lanes 4-8). With increasing MazF(His)$_6$ concentrations, the TP(r) band intensities were gradually reduced, and at 3.75 μM MazF(His)$_6$, the TP(r) band almost completely disappeared (lane 7).

Surprisingly, the TP(F) band was detected even in the absence of 70S ribosomes (lane 2), indicating that MazF was able to bind to the mRNA independent of 70S ribosomes or alternatively that MazF is an endoribonuclease cleaving between A and C residues (FIG. 4A).

To differentiate between these possibilities, the mazG mRNA was incubated with MazF(His)$_6$, phenol-extracted to remove protein, and used for primer extension as shown in FIG. 4B. The TP(F) band was also observed even after phenol extraction (lane 2), indicating that MazF(His)$_6$ indeed cleaved the mazG mRNA. The cleavage of the mazG mRNA was again blocked when MazE was co-added (FIG. 4C, lanes 4-7). Note that (His)$_6$MazE alone had no detectable effect on the mRNA (lane 2). This result indicated that the antitoxic effect of MazE was due to an inhibition of MazF endoribonuclease activity. The addition of 70S ribosomes before MazF (His)$_6$ inhibited mRNA cleavage by MazF(His)$_6$ probably because the SD sequence and the ACA sequence in the mazG mRNA are closely located (FIG. 6). In contrast, the toxic function of RelE requires ribosomes (Pedersen et al., supra, (2003)).

Table I shows the MazF cleavage sequences in different mRNA transcripts examined.

The conserved cleavage sequences are underlined.

| Gene Name | Sequence |
|---|---|
| yeeW | A A T G A T G A C A C T G G A A G |
| | G T C G T T G A C A T T G A T G G |
| EnvZ | A T C T C G A A C A C G C A G C C |
| lacZ | T C G T T T T A C A C C C T T G A |

(YeeW first line: SEQ ID NO: 84; YeeW second line: SEQ ID NO: 90; EnvZ: SEQ ID NO: 91; lacZ: SEQ ID NO: 92) In order to determine the specificity of MazF cleavage, the mazG-mRNA SD sequence was mutated from GGAG to UUUG, and the AUG initiation codon to GUG or AGG. None of these mutations affected mazG mRNA cleavage by MazF (His)$_6$ (FIGS. 7 and 8). When mRNA for yeeW, envZ and lacZ were used as substrates, each was cleaved at the expected ACA sequences in the mRNA transcripts independent of the SD sequence and the initiation codon (Table I). In these mRNAs, the ACA sequences are flanked by G, A or T at the 5' end and by C or T at the 3' end. In view of this finding, a mazG mRNA having the UACAU sequence at the cleavage site was mutated such that the U residues at the 5' and 3' ends were mutated to G, A, or C. None of these mutations had any effect on the cleavage (FIG. 9). However, when the central ACA sequence was changed to GCA, CCA, TCA; AGA, ATA, AAA; ACC, ACG or ACT, no cleavage was observed (FIG. 9), indicating that MazF is a highly sequence specific endoribonuclease recognizing the ACA sequence.

In summary, the above results indicate that MazF functions as a highly sequence-specific endoribonuclease, which cleaves cellular mRNAs at ACA sites and thereby blocks whole protein synthesis in the cell (FIG. 2E). To further test this finding, Northern blot analysis was performed using total cellular RNA extracted at different time intervals (Baker and Mackie, Mol Microbiol 47, 75-88 (2003); Sarmientos et al., *Cell* 32, 1337-46 (1983)) after arabinose induction of MazF. Both ompA and lpp mRNAs were degraded (FIG. 4C). The observed differences in the half-lives of these two mRNAs correlated with the total number of ACA sequences present in the mRNA and to the mRNA length. The 322 bp lpp mRNA (Nakamura and Inouye, *Cell* 18, 1109-17 (1979)), for example, has only one ACA sequence, while the 1229 bp ompA mRNA (Movva et al., *J Mol Biol* 143, 317-28 (1980)) has twenty-one ACA sequences. This correlation suggests that longer mRNAs may be more sensitive than smaller mRNAs to cleavage mediated by MazF.

Interestingly, within the mazF ORF there are a total of nine ACA sequences, four of which are clustered in the middle of the ORF, suggesting that mazF expression may be negatively autoregulated by its own gene product. It should also be noted that MazF(His)$_6$ was capable of cleaving 16S and 23S rRNA to smaller fragments, but not in the presence of (His)$_6$MazE (FIG. 10).

In conclusion, MazF is a novel endoribonuclease which specifically inhibits mRNA function by cleaving at the unique triplet sequence, ACA. Because of its ability to interfere with mRNA function, this category of endoribonuclease is designated herein as an "mRNA interferase". As underscored by the results presented herein, additional mRNA interferases having different sequence specificities are likely to exist.

In addition to the newly discovered category of endoribonucleases, there are several other mechanisms known to effect interference of mRNA function. One such mechanism involves micRNA (mRNA-interfering-complementary RNA), which was originally characterized as an RNA repressor for specific gene expression in *E. coli* (Mizuno et al, *Proc Natl Acad Sci USA* 81, 1966-70 (1984)). More recently, similar RNA elements have been discovered in eukaryotes as miRNA (Zeng and Cullen, *Rna* 9, 112-23 (2003) and siRNA (Billy et al., *Proc Natl Acad Sci USA* 98, 14428-33 (2001)). The intriguing possibility exists that this new mechanism of disrupting mRNA function by mRNA interferases, as demonstrated for *E. coli* in the present study, may also pertain to eukaryotes. This would have numerous implications for the cellular physiology of many, if not all, living organisms. Furthermore, highly sequence-specific mRNA interferases may be used as therapeutic tools for treating human diseases, as well as biochemical tools for structural studies of RNA. Notably, the crystal structure of the 2:4 MazE/MazF complex was recently published (Kamada et al., *Mol Cell* 11, 875-884 (2003)). The information garnered from the crystal structure may assist in the determination of how MazF specifically recognizes an ACA sequence and cleaves it.

Example II

Of note, prior to the discovery of the present invention, the cellular target(s) of MazF had not been identified. As shown herein, MazF functions as a highly sequence-specific endoribonuclease, which cleaves cellular mRNAs at ACA sites. Such activity may effectuate a partial or total inhibition of protein synthesis in a cell. The predicted frequency of an ACA sequence in an RNA transcript is one in 64, based on standard calculations predicated on an equal probability that any one of the four nucleotides will be incorporated at each one of the three nucleotide positions. It is to be understood that some RNA transcripts comprise a lower or higher frequency of ACA sequences as compared to the predicted frequency. Accordingly, the sensitivity of a specific RNA transcript or a family of related RNA transcripts to cleavage by a MazF endoribonuclease is dependent upon the frequency of ACA sequences or MazF target sequences in the transcript. Moreover, one of ordinary skill in the art could predict, based on the sequence of an RNA transcript, the sensitivity of the transcript to MazF mediated cleavage.

Example III

As described above, programmed cell death is proposed to be mediated in *E. coli* through "addiction module" systems, each of which consists of a pair of genes encoding a stable toxin and an unstable antitoxin which are co-expressed. Their expression is auto-regulated either by a toxin/antitoxin complex or by antitoxin alone. When co-expression is inhibited, the antitoxin is rapidly degraded by protease, enabling the toxin to act on its target. In *E. coli*, extrachromosomal elements are the main genetic system for bacterial programmed cell death. The most studied extrachromosomal addiction modules are the phd-doc on bacteriophage P1 (Lehnherr et al. (1993) *J Mol Biol* 233, 414-428; Lehnherr and Yarmolinsky (1995) *Proc Natl Acad Sci USA* 92, 3274-3277; Magnuson and Yarmolinsky (1998) *J Bacteriol* 180, 6342-6351; Gazit and Sauer (1999) *J Biol Chem* 274, 16813-16818; Gazit and Sauer (1999) *J Biol Chem* 274, 2652-2657), the ccdA-ccdB on factor F (Tam and Kline (1989) *J Bacteriol* 171, 2353-2360; Van Melderen et al. (1994) *Mol Microbiol* 11, 1151-1157; Bahassi et al. (1999) *J Biol Chem* 274, 10936-10944; Loris et al. (1999) *J Mol Biol* 285, 1667-1677; Afif et al. (2001) *Mol Microbiol* 41, 73-82; Dao-Thi et al. (2002) *J Biol Chem* 277, 3733-3742; Van Melderen (2002) *Int J Med Microbiol* 291, 537-544), and the pemI-pemK on plasmid R100 (Tsuchimoto et al. (1988) *J Bacteriol* 170, 1461-1466; Tsuchimoto and Ohtsubo. (1989) *Mol Gen Genet* 215, 463-468; Tsuchimoto et al. (1992) *J Bacteriol* 174, 4205-4211; Tsuchimoto and Ohtsubo. (1993) *Mol Gen Genet* 237, 81-88. Interestingly, the *E. coli* chromosome also contains several addiction module systems, such as the relBE system and the mazEF system, which are described hereinabove.

The mazEF system, which consists of two adjacent genes, mazE and mazF, is located downstream from the relA gene on the *E. coli* chromosome. Sequence analysis revealed that they are partly homologous to the pemI and pemK genes on plasmid pR100 (Masuda et al. (1993) *J Bacteriol* 175, 6850-6856). As described above, the mazEF system exhibits properties of an addiction module: MazF is toxic and MazE is antitoxic; MazF is stable, while MazE is a labile protein degraded in vivo by the ATP dependent ClpPA serine protease (Aizenman et al. (1996) supra); MazE and MazF are coexpressed and interact with each other to form a complex; and the expression of mazEF is negatively auto-regulated by MazE and the MazE-MazF complex (Marianovsky et al. (2001) *J Biol Chem* 276, 5975-5984). As described hereinabove, mazEF-mediated cell death can be triggered by extreme amino acid starvation and thymine starvation (Sat et al. (2003) supra), by toxic protein Doc (Hazan et al. (2001) *J Bacteriol* 183, 2046-2050), and by some antibiotics that are general inhibitors of transcription and/or translation, such as rifampicin, choramphenicol, and spectinomycin) (Sat et al. (2001) supra).

As described hereinbelow, the interactions between MazE, MazF, and the mazEF promoter DNA were investigated to identify the functional domains in MazE responsible for binding to the mazEF promoter DNA and for interacting with MazF. It is demonstrated that MazE has a DNA-binding domain in its N-terminal region, and that the region from residue 38 to 75 in MazE is required for binding to MazF, of which Leu55 and Leu58 residues are essential. The data presented herein also suggest that the MazE-MazF complex in solution can comprise one MazE dimer and two MazF dimers.

Methods and Materials

Reagents and enzymes—Nucleotides, ampicillin and kanamycin were from Sigma. The restriction enzymes and DNA modifying enzymes used for cloning were from New England Biolabs. Pfu DNA polymerase was from Stratagene. The radioactive nucleotides were from Amersham Pharmacia Biotech.

Constructions of plasmid—The mazEF gene (including its Shine-Dalgarno sequence region) was amplified by PCR using *E. coli* genomic DNA as template, and cloned into the XbaI-NheI sites of pET11a, creating the plasmid pET11a-EF. The mazEF gene (including its Shine-Dalgarno sequence region) was amplified by PCR, and cloned into the XbaI-XhoI sites of pET21 cc to create an in-frame translation with a $(His)_6$ tag at the MazF C-terminus. The plasmid was designated as pET21 cc-EF$(His)_6$. The mazE gene was amplified by PCR and cloned into the NdeI-HindIII sites of pET28a. This plasmid was designated as pET28a-$(His)_6$E. MazE was expressed as a fusion with an N-terminal $(His)_6$ tag (designated $(His)_6$MazE) followed by a thrombin cleavage site. The full-length mazE gene and various N-terminal and C-terminal deletion constructs of the mazE gene (See FIG. 17), were generated by PCR and cloned into EcoRI-PstI sites of pGAD-C1 vector to create in-frame translation fusions with the Gal4 transcriptional activation domain. These plasmids were designated as pGAD-MazE, pGAD-MazEΔ(1-13), pGAD-MazEΔ(1-24), pGAD-MazEΔ(1-37), pGAD-MazEΔ(1-46), pGAD-MazEΔ(68-82) and pGAD-MazEΔ(76-82).

The full-length mazF gene and various N-terminal and C-terminal deletion constructs of the mazF gene were generated by PCR and cloned into EcoRI-BglII sites of pGBD-C1 vector to create in-frame translation fusions with the Gal4 DNA binding domain. These plasmids were designated as pGBD-MazF, pGBD-MazFΔ(1-14), pGBD-MazFΔ(1-25), pGBD-MazFΔ(72-111) and pGBD-MazFΔ(97-111).

Protein purification—pET11a-EF was introduced into *E. coli* BL21(DE3) strain. The coexpression of MazE and MazF was induced for 4 h in the presence of 1 mM isopropyl-β-thiogalactopyranoside (IPTG). The cells were harvested by centrifugation and lysed using a French press. The cell lysate was maintained at 37° C. for 30 minutes to degrade MazE maximally, and cell debris and unlysed cells were pelleted by centrifugation 8,000×g for 10 minutes followed by ultracentrifugation at 10,000×g for 1 hour to remove membrane and insoluble fractions. MazF was subsequently purified by ammonium sulfate fractionation, gel filtration on Sephadex G-100 column, DEAE-Sepharose and hydroxyapatite column chromatography. The fractions containing MazF protein were pooled and concentrated. MazF was further purified by gel filtration with a Superdux™ 200 column (Pharmacia Biotech).

For purification of $(His)_6$MazE, pET28a-$(His)_6$E was introduced into *E. coli* BL21DE3) strain, and $(His)_6$ MazE expression was induced with 1 mM IPTG for 4 hours. $(His)_6$ MazE protein was immediately purified by Ni-NTA (QIAGEN) affinity chromatography.

pET21 cc-EF$(His)_6$ was also introduced into *E. coli* BL21 (DE3) strain. Coexpression of MazE and MazF$(His)_6$ was induced in the presence of 1 mM IPTG for 4 hours. The MazE-MazF$(His)_6$ complex was immediately purified by Ni-NTA (QIAGEN) affinity chromatography, and further purified by gel filtration. To purify MazF$(His)_6$ from the purified MazE-MazF$(His)_6$ complex, MazE in the purified MazE-MazF$(His)_6$ complex was dissociated from MazF$(His)_6$ in 6M guanidine-HCl. MazF$(His)_6$ was retrapped by Ni-NTA resin (QIAGEN) and refolded by step-wise dialysis. The yield of refolding is approximately 80%. The biochemical activity of MazF$(His)_6$ was determined with *E. coli* T7 S30 extract system (Promega) for the protein synthesis inhibition.

Electrophoretic mobility shift assays (EMSA)—Two single-stranded oligonucleotides 5'-GCTCGTATCTACAATGTAGATTGATATATACTGTATCrACATATGATAGC-3' (SEQ ID NO: 12) and 3'-CGAGCATAGATGTTACATCTAACTATATATGACATAGATGTATACTATCG-5' (SEQ ID NO: 13) were synthesized and annealed to generate the 50-bp double-stranded DNA containing the mazEF promoter sequence. The 50-bp DNA fragment was end-labeled by T4 polynucleotide kinase with [γ-$^{32}$P]ATP and used to detect the protein-DNA binding by EMSA. Binding reactions (20 μl) were carried out at 4° C. for 30 minutes with purified proteins, 2 μl 100 μg/ml poly(dI-dC) and 2 μl labeled DNA fragment in the binding buffer [50 mM Tris-HCl (pH 7.5), 5 mM $MgCl_2$, 1 mM dithiotheritol and 5% glycerol]. Electrophoresis was performed in TAE buffer at 100 V in 6% native polyacrylamide gel. After electrophoresis, the gel was dried and then exposed to X-ray film.

Native PAGE—Different amounts of $(His)_6$MazE and MazF were mixed in binding buffer [50 mM Tris-HCl (pH 7.5), 5 mM $MgCl_2$, 1 mM dithiotheritol and 5% glycerol] at 4° C. for 30 minutes, and then 2× loading solution [40 mM Tris-HCl (pH7.5), 80 mM β-mercaptoethanol, 0.08% bromophenol blue and 8% glycerol] was added to the mixtures before loading on a native gel. The composition of the stacking gel was 5% acrylamide-bis(29:1) in 62.5 mM Tris-HCl (pH 7.5), and the composition of the separation gel was 10% acrylamide-bis (29:1) in 187.5 mM Tris-HCl (pH8.9). The running buffer contained 82.6 mM Tris-HCl (pH 9.4) and 33 mM glycine. Electrophoresis was performed at constant voltage (150 V) at 4° C. Protein bands were visualized by Coomassie brilliant blue.

Resolution of low molecular weight proteins by tricine SDS-PAGE—Tricine SDS-PAGE was carried out according to the method described previously (Schagger and von Jagow, G. (1987) *Anal Biochem* 166, 368-379) with some modifications as following: stacking gel, 5% acrylamide-bis(48:1.5) in 0.75 M Tris-HCl (pH 8.45) and 0.075% SDS; spacer gel, 10% acrylamide-bis(48:1.5) in 1.0 M Tris-HCl (pH 8.45) and 0.1% SDS; resolving gel: 16.5% acrylamide-bis(48:1.5) in 1.0 M Tris-HCl (pH 8.45) and 0.1% SDS. The anode running buffer was 0.2 M Tris-HCl (pH 8.9), and the cathode running buffer was 0.1 M Tris base, 0.1 M tricine and 0.1% SDS. After running the gel at constant current (20 mAmp) at room temperature, protein bands were visualized by Coomassie brilliant blue.

Assays of MazE-MazF interaction in the yeast two-hybrid system—The yeast two-hybrid reporter strain PJ69-4A [MATa trp1-901 leu2-3,112 ura3-52 his3-200 gal4 gal80LYS2::GAL1-HIS3 GAL2-ADE2 met::GAL7-lacZ] and vectors pGAD-C1 and pGBD-C1 were was used for two-hybrid assays (James et al. (1996) Genetics 144, 1425-1436). In order to localize the MazF-binding region in MazE, a series of N- and C-terminal deletions of the mazE gene were constructed in pGAD-C1, and cotransformed with the pGBD-MazF plasmid into the PJ69-4A cells. See FIG. 17. In order to localize the MazE-binding region in MazF proteins, a series of N- and C-terminal deletions of the mazF gene were constructed in pGBD-C1, and cotransformed with the pGAD-MazE plasmid into the PJ69-4A cells. Assays of the interactions were performed by monitoring growth of cotransformants on synthetic dropout (SD) minimal medium (Clontech) lacking Trp, Leu, His and adenine (Ade). The medium was supplemented with 1 mM 3-amino-1,2,4-triazole (3-AT) and incubated at 30° C. for 5 days.

Specific Methodological Details Pertaining to Drawings

Figure 11:
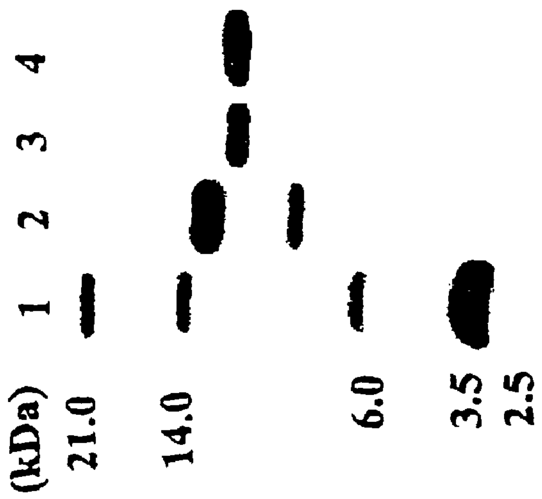
FIG. 11 shows an analysis of purified MazE-MazF(His)$_6$ complex, MazF, and (His)$_6$MazE proteins by tricine SDS-PAGE separation and visualization by staining with Coomassie brilliant blue.

In FIG. 11, the lanes were loaded as follows: Lane 1, protein molecular weight markers; lane 2, MazE-MazF$(s)_6$ complex; lane 3, MazF; and lane 4, $(His)_6$MazE.

Figure 12B:
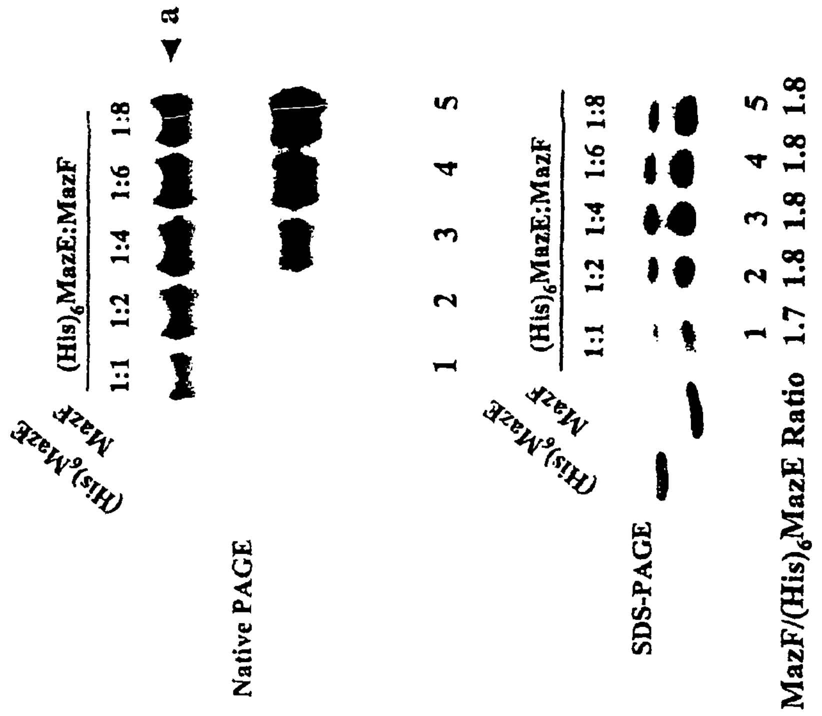
FIGS. 12A and 12B show a native polyacrylamide gel demonstrating stoichiometric complex formation between (His)$_6$MazE and MazF.
Figure 12A:
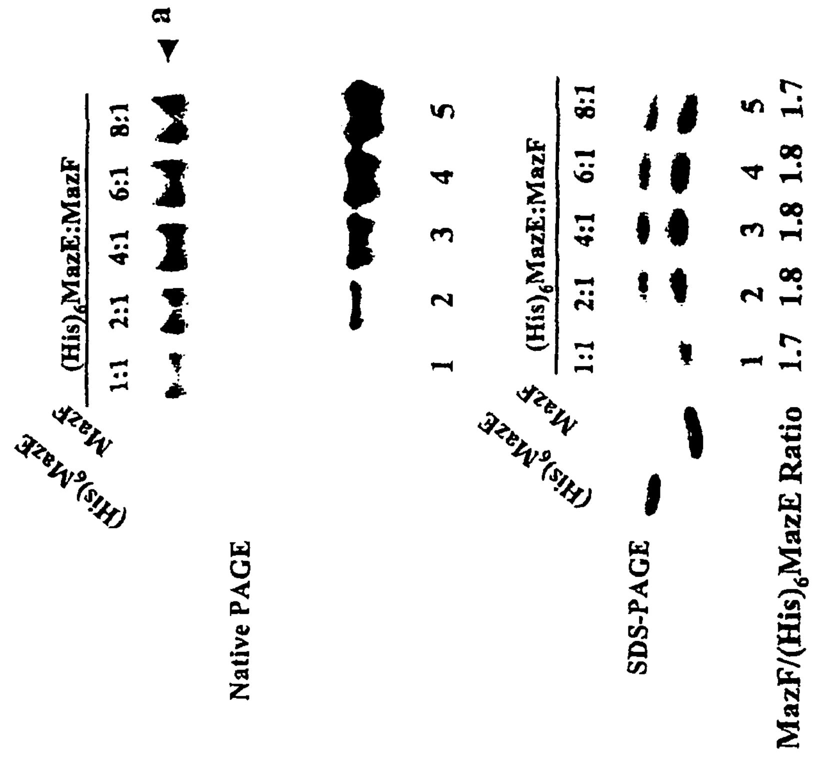

In FIGS. 12A and 12B, $(His)_6$MazE and MazF were mixed at the indicated molar ratios. The mixtures were incubated for 30 minutes at 4° C., and then subjected to native PAGE. The gel corresponding to the band of the complex was excised and incubated in reducing buffer [20 mM Tris-HCl (pH 7.5), 100 mM NaCl and 50 mM β-ME] for 30 minutes at room temperature and subjected to 15% SDS-PAGE for second dimensional electrophoresis. $(His)_6$MazE and MazF in the complex were separated as shown in the gels in the lower panel. Relative protein amounts in each lane were determined by densitometry with $(His)_6$MazE and MazF as controls. In FIG. 12A, different amounts of $(His)_6$MazE were added to 20-μl of a 2 μM MazF solution. Lanes 1-5, the $(His)_6$MazE:MazF ratios are 1:1, 2:1, 4:1, 6:1 and 8:1, respectively. In FIG. 12B, different amounts of MazF were added to 20-μl of a 2 μM $(His)_6$MazE solution. Lanes 1-5, the $(His)_6$MazE:MazF ratios are 1:1, 1:2, 1:4, 1:6 and 1:8, respectively. The upper panels in FIG. 12A and FIG. 12B show the results of native PAGE. The position of the $(His)_6$MazE-MazF complex is indicated by an arrow a. The lower panels in FIG. 12A and FIG. 12B show the results of SDS-PAGE for the second dimensional electrophoresis. Purified $(His)_6$MazF (40 pmol) and MazF (40 pmol) were applied to the first and the second lanes as controls.

Figure 13:
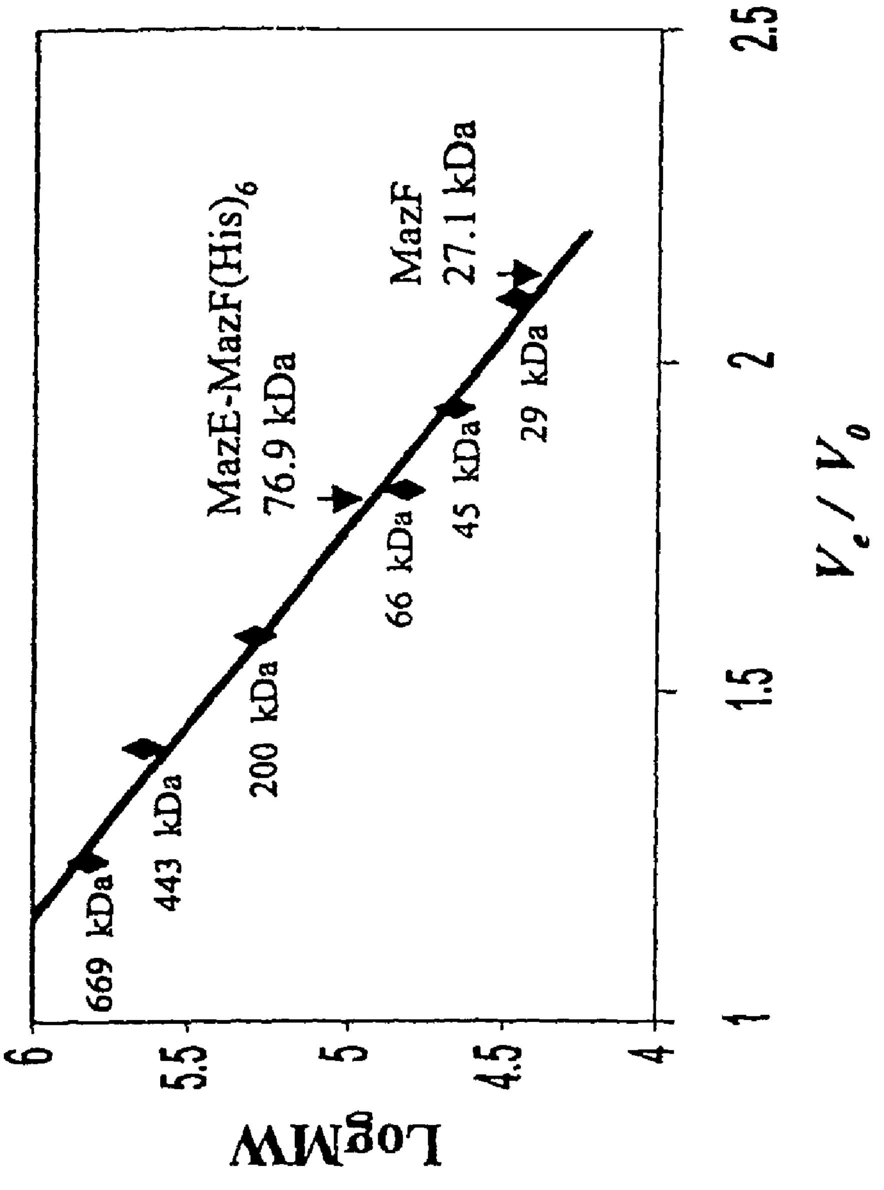
FIG. 13 shows a line graph of a protein molecular weight standard curve which depicts the determined molecular masses of MazF and the MazE-MazF(His)$_6$ complex.

In FIG. 13, the molecular masses of MazF and the MazE-MazF$(His)_6$ complex were determined by gel filtration with a Superdex 200 column. The protein molecular weight standard curve includes Thyroglobulin (669 kDa), Apoferritin (443 kDa), β-Amylase (200 kDa), BSA (66 kDa), Ovalbumin (45 kDa) and Carbonic Anhydrase (29 kDa). The vertical arrows on the standard curve indicate the positions of MazF and the MazE-MazF$(His)_6$ complex.

Figure 14B:
FIGS. 14A, 14B, and 14C show EMSA gels depicting binding of (His)$_6$MazE and/or MazF to the mazEF promoter DNA.
Figure 14A:
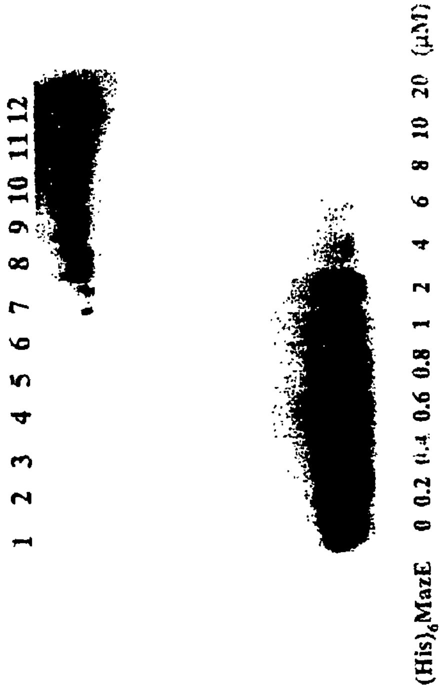
Figure 14C:
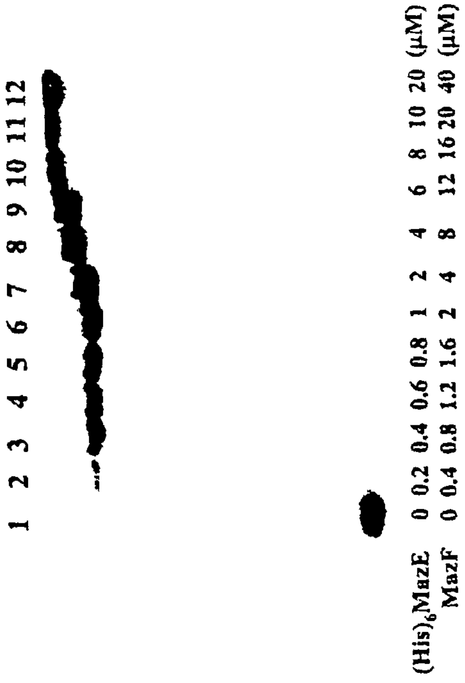

In FIGS. 14A, 14B, and 14C, a 50-bp [$^{32}$P]-labeled DNA fragment containing the mazEF promoter region was incubated with increasing concentrations of $(His)_6$MazE (FIG. 14A), with increasing concentrations of MazF (FIG. 14B), or with increasing concentrations of both $(His)_6$MazE and MazF at the constant $(His)_6$MazE/MazF ratio of 1:2 (FIG. 14C).

In FIG. 15, the ClustalW program was used for alignment analysis. Identical residues among eight different proteins are shown by black boxes. Similar residues are indicated by gray boxes. Gaps (indicated by dashes) are introduced to optimize the alignment. The sequences are: MazE in *Deinococcus radiodurans* (GenBank Accession No. NP_294139); MazE in *Bacillus halodurans* (GenBank Accession No. NP_244587); PemI on plasmid R100 (GenBank Accession No. NP_052993); PemI on plasmid R466b (GenBank Accession No. AAC82515); MazE in *Escherichia coli* (GenBank Accession No. NP_289337); ChpB in *Escherichia coli* (GenBank Accession No. NP_290856); MazE in *Pseudomonas putida* KT2440 (GenBank Accession No. NP_742931); MazE in *Photobacterium profundum* (GenBank Accession No. AAG34554). The numbers correspond to amino acid residue position.

Figure 16B:
FIGS. 16A and 16B show EMSA gels depicting protein-DNA interactions.
Figure 16A:

In FIGS. 16A and 16B, DNA binding of the proteins was determined by EMSA with a 50-bp [$^{32}$P]-labeled DNA fragment containing the mazEF promoter region. In FIG. 16A, the DNA fragment was incubated with 1 μM of each complex as indicated in a 20-μl mixture at 4° C. for 30 minutes. Lane 1, control without protein; lane 2, MazE-MazF(His)$_6$ complex; lane 3, MazE(K7A)-MazF(His)$_6$ complex; lane 4, MazE (R8A)-MazF(His)$_6$ complex; lane 5, MazE(S12A)-MazF (His)$_6$ complex; lane 6, MazE(R16A)-MazF(His)$_6$ complex; lane 7, MazE(I43N)-MazF(His)$_6$ complex; and lane 8, MazE (E57Q)-MazF(His)$_6$ complex. In FIG. 16B, the DNA fragment was incubated with 4 μM (His)$_6$MazE or (His)$_6$MazE mutant as indicated in a 20-μl mixture at 4° C. for 30 minutes. Lane 1, control without protein; lane 2, wild-type (His)$_6$ MazE protein; lane 3, (His)$_6$MazE(K7A) mutant; lane 4, (His)$_6$MazE(R8A) mutant; lane 5, (His)$_6$MazE(S12A) mutant; and lane 6, (His)$_6$MazE(R16A) mutant.

Figure 17:
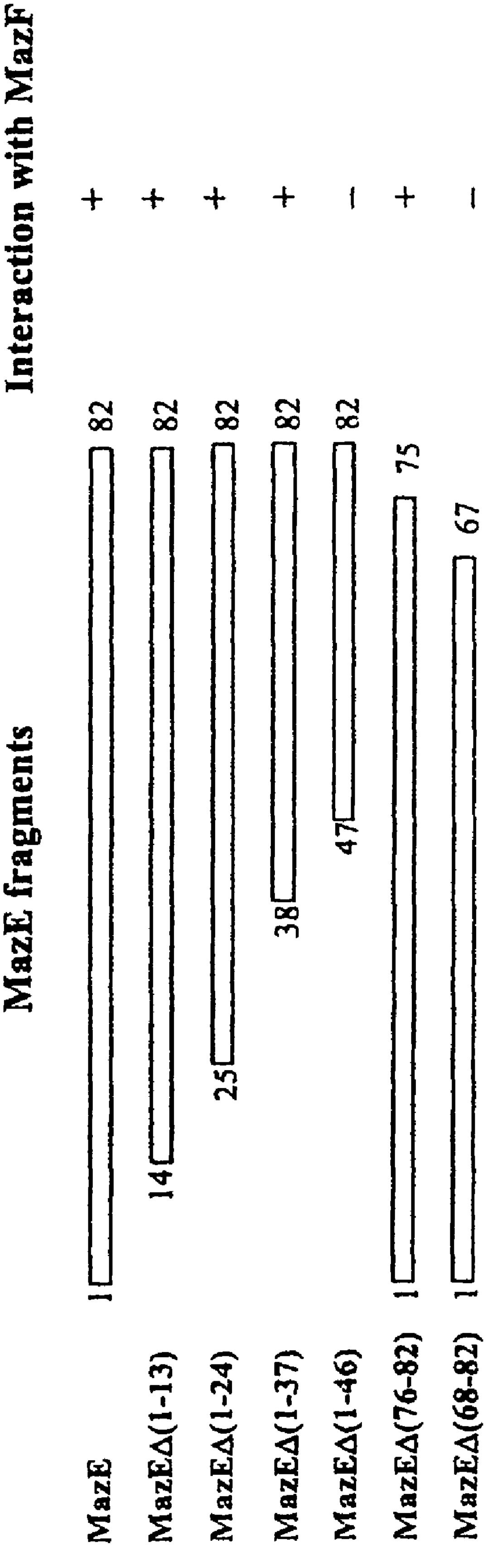
FIG. 17 depicts MazE and truncations thereof and the results of yeast two-hybrid assays indicating interactions between MazF and MazE or truncates/fragments thereof.

In FIG. 17, the full-length mazE gene and the truncated mazE genes were constructed in pGAD-C1. Numbers refer to the amino acid positions in MazE. The plasmids were cotransformed with pGBD-MazF into yeast PJ69-4A cells. Protein-protein interactions were tested on SD medium (Clontech) plates containing 1 mM 3-AT in the absence of Trp, Leu, His and Ade. +, indicates visible colonies formed in 5 days; –, indicates no visible colonies formed in 5 days.

Figure 18B:
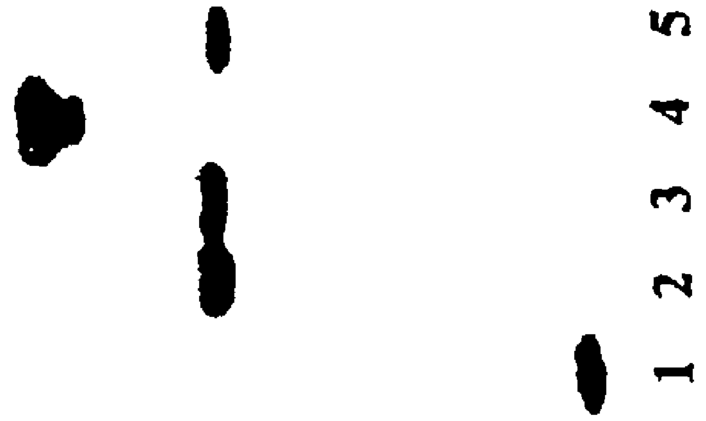
FIGS. 18A and 18B show native polyacrylamide gels depicting protein interactions and EMSA gels depicting protein-DNA interactions, respectively.
Figure 18A:
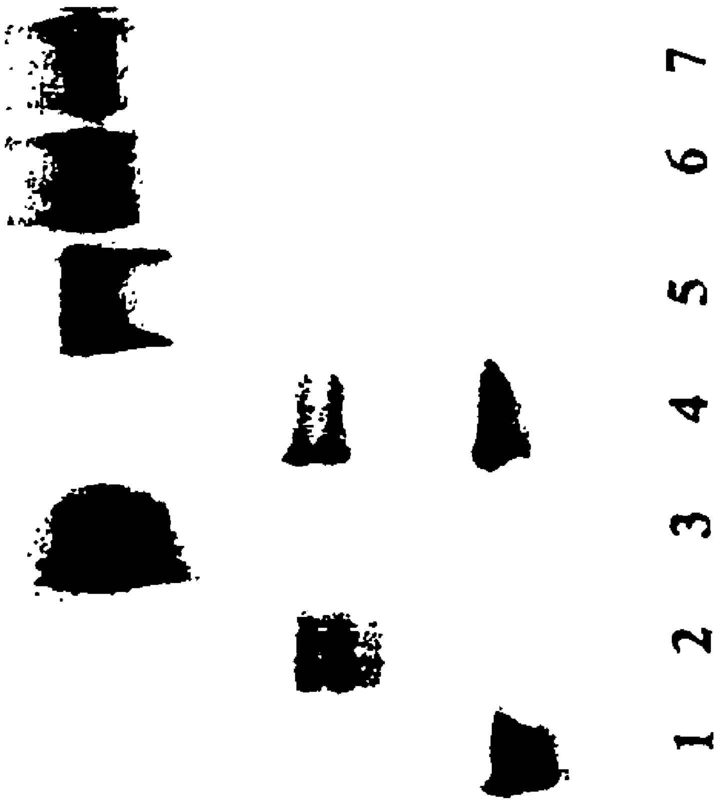

In FIG. 18A, interactions between MazF and (His)$_6$MazE or (His)$_6$MazE mutants were determined by native PAGE. Lane 1, wild-type (His)$_6$MazE; lane 2, MazF; lane 3, wild-type (His)$_6$MazE and MazF; lane 4, (His)$_6$MazE L55A/L58A mutant and MazF; lane 5, (His)$_6$MazE R48A mutant and MazF; lane 6, (His)$_6$MazE E57Q mutant and MazF; and lane 7, (His)$_6$MazE F53A mutant and MazF.

In FIG. 18B, interactions between MazF and (His)$_6$MazE or (His)$_6$MazE L55A/L58A mutant were determined by EMSA with the 50-bp [$^{32}$P]-labeled DNA fragment containing the mazEF promoter region. Lane 1, control without protein; lane 2, 4 μM wild-type (His)$_6$MazE; lane 3, 4 μM (His)$_6$MazE L55A/L58A mutant; lane 4, 2 μM wild-type (His)$_6$MazE and 4 μM MazF; and lane 5, 2 μM (His)$_6$MazE L55A/L58A mutant and 4 μM MazF.

Figure 19:
FIG. 19 depicts an X-ray structure of the MazE-MazF complex.

In FIG. 19, which depicts an X-ray structure of the MazE-MazF complex, conserved amino acid residues essential for MazE function(s) are indicated. Only a portion of the MazF$_2$-MazE$_2$-MazF$_2$ complex is shown, in which one MazE molecule (blue) is interacting with two MazF molecules of the MazF homodimer (purple and red). In the MazE molecule, the N-box and the Hp-box are shown in green and yellow, respectively. Positions of Lys7, Arg8, Ser12 and Arg16 in the N-box and Leu55 and Leu58 in the Hp-box are shown. As shown herein, these substitution mutations which resulted in the loss of MazE function(s).

Results

MazE and MazF can form a complex in a 1:2 ratio-Tricine SDS-PAGE patterns of purified MazE-MazF(His)$_6$, MazF and (His)$_6$MazE are shown in FIG. 11, lanes 2, 3 and 4, respectively. The sizes of (His)$_6$MazE and MazF agree with theoretical molecular weights of 11.4 kDa and 12.0 kDa, respectively (FIG. 11, lanes 3 and 4). The MazE-MazF(His)$_6$ complex was separated into 9.3 kDa MazE and 13.2 kDa MazF(His)$_6$ (FIG. 11, lane 2), and the ratio of MazF(His)$_6$ to MazE was determined to be approximately two (2) using a densitometer.

When (His)$_6$MazE and MazF were mixed together and the mixture was subjected to native PAGE, a new band appeared at a position a near the top of the gel (position a in FIG. 12). The gel corresponding to the new band was cut out and incubated in a reducing buffer [20 mM Tris-HCl (pH 7.5), 100 mM NaCl and 50 mM β-ME] for 30 minutes at room temperature, and then the gel was placed on the top of SDS-PAGE gel to run a second dimensional electrophoresis to analyze the protein components. After staining the gel with Coomassie brilliant blue, two bands corresponding to (His)$_6$MazE and MazF were observed, while (His)$_6$MazE moved slower than MazF on the SDS-PAGE. These results demonstrated that the new band was complex comprising (His)$_6$MazE and MazF. When the gel cut from the native PAGE was not treated in the reducing buffer, three protein bands were observed after it was subjected to the SDS-PAGE, (His)$_6$MazE, MazF and the MazF dimer (data not shown). Three bands appeared for the purified MazF on the native PAGE, but only one peak was observed when the purified MazF protein was assayed by HPLC (data not shown).

Additional experiments were performed to determine if the ratio of (His)$_6$MazE to MazF in the complex was stable. As shown in FIG. 12A, different amounts of (His)$_6$MazE were added to identical solutions containing a constant concentration of MazF (2 μM) to generate a series of solutions in which the (His)$_6$MazE:MazF ratios varied from 1:1, to 2:1, to 4:1, to 6:1, to 8:1. As shown in FIG. 12B, different amounts of MazF were also added to identical solutions containing a constant concentration of (His)$_6$MazE (2 μM) to generate a series of solutions in which the (His)$_6$MazE:MazF ratio was 1:1, 1:2, 1:4, 1:6 and 1:8. The above mixtures were incubated for 30 minutes at 4° C. and analyzed by native PAGE. The gel corresponding to the new band (at position a) was cut out and incubated in the reducing buffer for 30 minutes at room temperature and subjected to 15% SDS-PAGE. The second dimensional gel was stained with Coomassie brilliant blue to detect protein bands. Relative protein amounts in each lane were determined by densitometer using purified (His)$_6$MazE and MazF as controls. The ratios of MazF to (His)$_6$MazE in the complex were maintained almost constant at 1.8 when (His)$_6$MazE or MazF was added in excess in the mixtures (FIG. 12). As mentioned above, the MazE-MazF(His)$_6$ complex was separated to MazE and MazF(His)$_6$ by tricine SDS-PAGE, and the ratio of MazF(His)$_6$ to MazE was approximately 2 (FIG. 11, lane 2). The molecular masses of the purified MazE-MazF(His)$_6$ complex and MazF were determined to be 76.9 kDa and 27.1 kDa by gel filtration with a Superdux™ 200 column (Pharmacia Biotech) (FIG. 13). MazF(His)$_6$ was purified from the MazE-MazF(His)$_6$ complex. MazF(His)$_6$ was able to inhibit the protein synthesis in an *E. coli* cell-free system (*E. coli* T7 S30 extract system, Promega), and the protein synthesis was rescued by the co-addition of (His)$_6$MazE (data not shown). The molecular mass of MazF(His)$_6$ was determined to be 28.3 kDa with light scattering, suggesting MazF(His)$_6$ exists as dimer. The structure of MazE has been demonstrated as a dimer (Lah et al. (2003) *J Biol Chem* 278, 14101-14111). Therefore, the MazE-MazF(His)$_6$ complex (76.9 kDa) may consist of one MazE dimer (predicted to be around 18.6 kDa as the MazE molecular weight is 9.3 kDa) and two MazF$(His)_6$ dimers (56.6 kDa).

MazF enhances MazE binding to the mazEF promoter—The 50-bp mazEF promoter fragment was prepared as described herein and end-labeled by T4 polynucleotide kinase with [γ-$^{32}$P]ATP. Using electrophoretic mobility shift assays (EMSA), $(His)_6$MazE, MazF and MazE-MazF$(His)_6$ complex were tested separately for their ability to bind to the mazEF promoter DNA fragment. $(His)_6$MazE was able to shift the mazEF promoter fragment at a concentration of 2 μM or higher (FIG. 14A, lane 7). At 0.4 to 1.0 μM $(His)_6$MazE, no discrete mobility-shifted bands were observed, although the signals of the DNA fragment started to smear upward (FIG. 14A, lanes 3-6), indicating that some unstable $(His)_6$MazE-DNA complexes were formed at these concentrations. At 2 to 20 μM $(His)_6$MazE, discrete mobility-shifted complexes were observed, which moved more slowly at higher concentrations of $(His)_6$MazE (FIG. 14A, lanes 7-12), suggesting that the number of $(His)_6$MazE molecules bound to the DNA fragment increased at higher MazE concentrations. It is possible that there are more than one $(His)_6$MazE binding sites in the 50-bp mazEF promoter fragment.

In contrast, MazF protein could not bind to the 50-bp mazEF promoter DNA even at a concentration of 20 μM (FIG. 14B). Increasing amounts of both $(His)_6$MazE and MazF proteins were added with a constant $(His)_6$MazE/MazF ratio of 1:2. Compared with $(His)_6$MazE alone, MazF significantly enhances $(His)_6$MazE binding to the mazEF promoter. Under these conditions, the 50-bp mazEF promoter fragment was shifted at a $(His)_6$MazE concentration of as low as 0.2 μM (FIG. 14C), and supershifting was observed at higher concentrations of the $(His)_6$MazE-MazF complex, which indicates that more $(His)_6$MazE-MazF complexes bind to the DNA fragment at higher concentrations, demonstrating there are multiple binding sites for the $(His)_6$MazE-MazF complex in the mazEF promoter.

Conserved amino acid sequences in MazE homologs-MazE homologs were identified by BLAST search, and their amino acid sequence alignments are shown in FIG. 15. Although generally MazE is not highly conserved in bacteria, there are conserved regions in MazE homologs. First, the N-terminal region of MazE is more conserved than other regions in MazE. MazE is an acidic protein with a pI of 4.7, but there are a few conserved basic residues (K7, R8 and R16) in its N-terminal region, designated the N-box (FIG. 15). Since MazE is able to bind the mazEF promoter DNA, the N-box may be responsible for the DNA binding. Secondly, there is a conserved C-terminal region, named the Hp-box (FIG. 15), which contains several conserved hydrophobic residues.

The N-box of MazE is responsible for the DNA-binding of both MazE and the MazE-MazF complex—Various site-directed mutations were constructed in the mazE gene in the pET21 cc-EF$(His)_6$ plasmid, converting the conserved amino acid residues in the N-box to Ala. The complexes formed by MazE mutant proteins and MazF$(His)_6$ were purified. These complexes were tested for their ability to bind to the mazEF promoter by EMSA respectively. As shown in FIG. 16A, the complexes formed by MazE mutants with a mutation in the N-box (K7A, R8A, S12A or R16A) and MazF$(His)_6$ were unable to bind to the mazEF promoter DNA (FIG. 16A, lanes 3, 4, 5 and 6). The substitution mutations on the conserved amino acids outside the N-box, however, such as MazE I43N and E57Q, did not affect the DNA binding capacity of complex comprising such mutated proteins (FIG. 16A, lanes 7 and 8, respectively). Additional substitution mutations were also constructed in the mazE gene in the pET28a-$(His)_6$E plasmid. All of the $(His)_6$MazE mutants with a substitution mutation in the N-box (K7A, R8A, S12A and R16A) lost their DNA-binding ability (FIG. 16B, lanes 3, 4, 5 and 6, respectively), while the wild-type $(His)_6$MazE retained the ability to bind to the mazEF promoter (FIG. 16B, lane 2). In contrast, the $(His)_6$MazE mutants with a substitution mutation outside the N-box (R48A, F53A, L55A/L58A and E57Q) were able to bind the mazEF promoter DNA (data not shown). These results indicate that the DNA-binding ability of the MazE-MazF complex is due to MazE protein in the complex, and that the N-box is responsible for the DNA binding of MazE.

Interaction between MazE and MazF-Yeast two-hybrid assays were performed to examine the interaction between MazE and MazF. In order to demonstrate which region of MazE is required for its interaction with MazF, the full-length mazE gene and various N-terminal and C-terminal deletion constructs of the mazE gene were generated by PCR (see FIG. 17) and cloned into the EcoRI-PstI sites of pGAD-C1 vector to create in-frame translation fusions with the Gal4 transcriptional activation domain, and then each of these plasmids was cotransformed with the pGBD-MazF plasmid into PJ69-4A yeast cells. The cotransformants harboring pGAD-MazE, pGAD-MazEΔ(1-13), pGAD-MazEΔ(1-24), pGAD-MazEΔ(1-37) or pGAD-MazEΔ(76-82) with pGBD-MazF were able to grow on a synthetic medium (SD medium, Clontech) lacking Trp, Leu, His and Ade, while the cotransformants harboring pGAD-MazEΔ(1-46) or pGAD-MazEΔ(68-82) with pGBD-MazF were not able to grow. These data demonstrated that the full length MazE, MazEΔ(1-13), MazEΔ(1-24), MazEΔ(1-37) and MazEΔ(76-82) were capable of interacting with MazF, while the further N-terminal deletion mutant MazEΔ(1-46) and the further C-terminal deletion mutant MazEΔ(68-82) was not. These results indicate that the region from residue 38 to 75 of MazE is responsible for the interaction with MazF.

A series of truncation mutations from the N- and C-terminal ends of MazF were constructed in pGBD-C1 and cotransformed with pGAD-MazE into PJ69-4A cells. All of these cotransformed yeast cells were unable to grow on a complete synthetic medium in the absence of Trp, Leu, His, and Ade, indicating that all of these MazF mutants were unable to interact with MazE. Therefore both N- and C-terminal regions of MazF may be involved in the interaction with MazE, or the deletion mutations generated disrupt a structural conformation of MazF favorable to interaction with MazE.

Site-directed mutations were also created on plasmid pET28a-$(His)_6$E to construct $(His)_6$MazE R48A, F53A, L55A/L58A and E57Q mutants. The complex formations with these $(His)_6$MazE mutants and MazF were examined by native PAGE. As shown in FIG. 18A, $(His)_6$MazE mutants R48A, F53A and E57Q were able to form complexes with MazF (FIG. 18A, lanes 5, 6 and 7, respectively), while the $(His)_6$MazE L55A/L58A mutant was not (FIG. 18A, lane 4). EMSA were utilized to demonstrate that both the wild-type $(His)_6$MazE and $(His)_6$MazE L55A/L58A mutant were capable of binding to the mazEF promoter DNA (FIG. 18B, lanes 2 and 3, respectively). When MazF was added, the wild-type $(His)_6$MazE was able to interact with MazF to form a complex resulting in a supershifted band near the top of the gel (FIG. 18B, lane 4), as compared to the lane with wild-type $(His)_6$MazE alone (FIG. 18B, lane 2). The addition of MazF to $(His)_6$MazE L55A/L58A did not, however, result in the appearance of a supershifted species of the DNA fragment, confirming that the $(His)_6$MazE L55A/L58A mutant cannot interact with MazF to form a complex.

Discussion

The mazEF addiction system in *E. coli* consists of two genes, mazE and mazF, encoding labile antitoxin MazE and stable toxin MazF, respectively. The toxic effect of MazF is activated by ppGpp, the signal produced by RelA protein in response to amino acid starvation (Aizenman et al. (1996) supra), by certain antibiotics (Sat et al. (2001) supra), and by the toxic protein Doc (Hazan et al. (2001) supra). Under these circumstances, the degradation of labile MazE results in the appearance of free stable MazF, which can exert a toxic effect on the cell. The regulation of MazE cellular concentration is, therefore, a major determinant of cell death. In brief, by forming a complex with MazF, MazE inhibits its toxic effect. Moreover, MazE is also involved in the autoregulation of mazEF expression by binding to the mazEF promoter (Marianovsky et al. (2001) supra). As shown herein, MazE comprises at least two functional domains: a DNA-binding domain and a MazF-binding domain.

The fusion protein $(His)_6$MazE is capable of interacting with MazF and binding to the mazEF promoter. MazF$(His)_6$, like MazF, forms a dimer and inhibits in vitro protein synthesis, and such inhibition of protein synthesis is rescued by co-addition of $(His)_6$MazE (data not shown). Thus, the His-tagged fusion proteins appear to exhibit similar functional activity as compared to that of the wild type MazE and MazF in vitro. Using highly purified $(His)_6$MazE and MazF, $(His)_6$ MazE was demonstrated to be capable of binding to the mazEF promoter by itself, an interaction which was enhanced by the addition of MazF. Indeed, MazF enhanced $(His)_6$ MazE-binding to the mazEF promoter DNA by more than ten-fold. At higher concentrations of either $(His)_6$MazE or $(His)_6$MazE-MazF complex, supershifted complexes comprising the mazEF promoter DNA were observed in the electrophoretic mobility shift assays, indicating that both $(His)_6$ MazE and the $(His)_6$MazE-MazF complex have more than one binding site on the mazEF promoter DNA. Notably, a previous study suggested that there may be three MazE-binding sides in the mazEF promoter region (Lah et al. (2003) *J Biol Chem* 278, 14101-14111). It is interesting to note that the bands observed by EMSA were not shifted in a step-wise manner.

The site-directed mutations in the conserved N-box of MazE (K7A, R8A, S12A and R16A) disrupted the DNA-binding ability of both $(His)_6$MazE and the MazE-MazF $(His)_6$ complex (FIG. 16), suggesting that MazE is responsible for the DNA-binding ability of the MazE-MazF$(His)_6$ complex, and that the highly conserved N-terminal region in MazE is the DNA-binding domain.

Yeast two-hybrid assays were performed to identify the region(s) responsible for MazE-MazF interactions. It was found that the region from residue 38 to 75 in the carboxy terminus of MazE was required for binding to MazF. Of note, there is a conserved C-terminal region in MazE named the Hp-box, which is rich in hydrophobic residues. Mutations in the MazE Hp-box at the conserved amino acids of Leu55 and Leu58 (L55A/L58A) disrupted the interaction between $(His)_6$MazE and MazF. Yeast two-hybrid experiments also indicated that the entire structure of MazF protein may be required for its interaction with MazE, since deletions from either the N- or C-terminal end of MazF disrupted the interaction between MazE and MazF.

The molecular mass of the MazE-MazF$(His)_6$ complex was determined to be 76.9 kDa by gel filtration. When the purified MazE-MazF$(s)_6$ complex was subjected to tricine SDS-PAGE, the ratio of MazE to MazF$(His)_6$ was found to be approximately 1:2 (FIG. 11, lane 2). Even in the presence of excess amounts of $(His)_6$MazE or MazF, the ratio of $(His)_6$MazE to MazF in the $(His)_6$MazE-MazF complex was stably maintained at around 1:1.8 (FIG. 12). Since both MazE (Lah et al. (2003) supra) and MazF$(His)_6$ exist as dimers, the MazE-MazF$(His)_6$ complex (76.9 kDa) may consist of one MazE dimer (predicted to be around 18.6 kDa as the molecular weight of MazE is 9.3 kDa) and two MazF$(His)_6$ dimers (predicted to be around 56.6 kDa as the molecular mass of MazF$(His)_6$ dimer is 28.3 kDa).

As described above, the crystal structure of the MazE-MazF complex was determined by Kamada et al ((2003) supra). The crystal structure of the MazE-MazF complex corroborated the results set forth herein in several aspects, including: 1) the finding that MazE and MazF form a 2:4 heterohexamer, consisting of alternating MazF and MazE homodimers ($MazF_2$-$MazE_2$-$MazF_2$). It is important to note that the 2:4 stoichiometric complex formation between MazE and MazF appears to be very stable, since the ratio between $(His)_6$MazE and MazF in the $(His)_6$MazE-MazF complex was found irrespective of which protein was added in large excess (FIG. 12). 2) The C-terminal region of MazE interacts with MazF homodimer in the structure of MazE-MazF complex. The Hp-box region identified in this study is involved in the seemingly most stable interface between MazE and MazF (FIG. 19). 3) Based on the similarity between MazE and other addiction module antidotes and the distribution of the basic regions on the electrostatic surfaces of MazE and MazF, Kamada et al ((2003) supra) proposed that Lys7 and Arg8 in MazE serve as the primary DNA anchoring sites in the MazE-MazF complex. As demonstrated herein, the DNA-binding abilities of $(His)_6$MazE and the MazE-MazF$(His)_6$ complex were disrupted not only by the site-directed mutations at Lys7 and Arg8 but also by mutations at other conserved amino acid residues (Ser12 and Arg16) in the N-box (FIG. 19). It is possible that, since MazE exists as a dimer, the two N-boxes in the MazE dimer may be involved together in DNA-binding.

Example IV

As shown herein, purified PemK, the toxin encoded by the "pemI-pemK addiction module", inhibits protein synthesis in an *E. coli* cell-free system, while the addition of PemI, the antitoxin against PemK, restores protein synthesis. Further studies reveal that PemK is a sequence-specific endoribonuclease that cleaves mRNAs to inhibit protein synthesis, while PemI blocks the endoribonuclease activity of PemK. As described herein, PemK cleaves single-stranded RNA preferentially at the 5' or 3' side of the A nucleotide in "UAX" sequences, wherein X is C, A or U. Upon induction, PemK cleaves cellular mRNAs to effectively block protein synthesis in *E. coli*. Thus, the present invention demonstrates that PemK interferes with mRNA function by cleaving it at specific sites. Accordingly, the present inventors have discovered that PemK is a novel endoribonuclease and have designated it herein an "mRNA interferase". pemK homologues have been identified on the genomes of a wide range of bacteria. It is proposed that PemK and its homologues form a novel endoribonuclease family that interferes with mRNA function by cleaving cellular mRNAs in a sequence-specific manner. See also FIGS. 33 and 34.

Methods and Materials

Strains and plasmids: *E. coli* BL21(DE3) and BW25113 cells were used as described herein. The pemIK gene was amplified by PCR with plasmid R100 as template, and cloned into the NdeI-XhoI sites of pET21 cc (Novagen) to create an in-frame translation with a $(His)_6$ tag at the PemK C-terminus. The plasmid was designated pET21 cc-IK$(His)_6$. The pemI gene was cloned into the NdeI-BamHI sites of pET28a (Novagen), creating plasmid pET28a-$(His)_6$I. PemI was expressed as a fusion with an N-terminal $(His)_6$ tag followed by a thrombin cleavage site, named $(His)_6$PemI. The pemK gene was cloned into pBAD (Guzman et al. (1995) *J Bacteriol* 177, 4121-4130), creating plasmid pBAD-K. *E. coli* mazG gene was cloned into NdeI-BamHI sites of pET11a (New England Biolabs), creating plasmid pET11a-MazG. The mazG gene was cloned into a pINIII vector (Nakano et al. (1987) *J Virol* 61, 302-307), creating plasmid pIN-MazG. *E. coli* era gene was cloned into the ScaI-AhoI sites of pET28a, creating plasmid pET28a-Era. The era gene was also cloned into pINIII vector to create plasmid pIN-Era.

Protein purification: For purification of $(His)_6$PemI, pET28a-$(His)_6$I was introduced into *E. coli* BL21(DE3) strain, and $(His)_6$PemI expression was induced with 1 mM IPTG for 4 h. $(His)_6$PemI protein was purified using Ni-NTA (QIAGEN). pET21 cc-IK$(His)_6$ was also introduced into the *E. coli* BL21(DE3) strain. The coexpression of PemI and PemK$(His)_6$ was induced in the presence of 1 mM IPTG for 4 h. The PemI-PemK$(His)_6$ complex was purified using Ni-NTA (QIAGEN). To purify PemK$(His)_6$ from the purified PemI-PemK$(His)_6$ complex, the PemI-PemK$(His)_6$ complex was dissociated in 5 M guanidine-HCl to release PemI from PemK$(His)_6$. PemK$(His)_6$ was retrapped on Ni-NTA resin (QIAGEN), and then eluted and refolded by step-wise dialysis.

Assays of protein and DNA synthesis in vivo: *E. coli* BW25113 cells containing pBAD-K were grown in modified M9 medium with 0.5% glycerol (no glucose) and an amino acid mixture (1 mM each) without methionine. When the $OD_{600}$ of the culture reached 0.6, arabinose was added to a final concentration of 0.2% to induce PemK expression. Cell cultures (1 ml) were taken at the time points indicated and mixed with 5 μCi [±S]-methionine (for protein synthesis analysis) or 2 μCi methyl-$^3$H-thymidine (for DNA synthesis analysis). After 1 minute incorporation time at 37° C., the rates of DNA replication and protein synthesis were determined as described previously (Pedersen et al. (2002) *Mol Microbiol* 45, 501510). To prepare the samples for SDS-PAGE analysis of the total cellular protein synthesis, [$^{35}$S]-methionine incorporation reaction mixture (500 μl) was removed at the time points indicated and added to a chilled test tube containing 25 μl of 100% TCA solution and 100 μg/ml non-radioactive methionine. Cell pellets were collected by centrifugation and subjected to SDS-PAGE followed by autoradiography.

Primer extension analysis: A DNA fragment containing a T7 promoter and the mazG gene was obtained by PCR amplification with T7 primer (5'-AGATCTCGATCCCGCA AATTAAT-3') (SEQ ID NO: 14) and primer G6 (5'-TTAGAGATCAATTTCCTGCCGTTTTAC-3') (SEQ ID NO: 15) with pET11a-MazG as a template. Another DNA fragment comprising a T7 promoter and the era gene was obtained by PCR amplification with the same T7 primer above and primer E5 (5'-TTAAAGATCGTCAACGTAACCG-3') (SEQ ID NO: 16) with pET28a-Era as template. The mazG mRNA and era mRNA were prepared from these two DNA fragments, respectively, using the T7 large-scale transcription kit (Promega). RNA substrates were partially digested with PemK$(His)_6$ at 37° C. for 15 min. The digestion reaction mixture (20 μl) contained 4 μg RNA substrate, 0.2 μg PemK $(His)_6$, 1 μl RNase inhibitor, 20 mM Tris-HCl (pH 8.0), 100 mM NaCl and 1 mM DTT. Partial digestion products were purified with the RNAeasy column (QIGENE) to remove PemK$(His)_6$ protein. The primers G1 (5'-TGCTCTTTATCCCACGGGCAGC-3') (SEQ ID NO: 17), G2 (5'-GCCCAGTTCACCGCGAAGATC GTC-3') (SEQ ID NO: 18), G3 (5'-GGTTTTGATTTGCTCCCAACGGGCAAG-3') (SEQ ID NO: 19), G4 (5'-CATTTCCT CCTCCAGTTTAGCCTGGTC-3') (SEQ ID NO: 20), and G5 (5'-TTGCCAGACTTCTTCCATTGTTTCG AG-3') (SEQ ID NO: 21) were used for primer extension analyses of the mazG RNA; the primers E1 (5'-GATCCCCACAATGCGGTGACGAGT-3') (SEQ ID NO: 22), E2 (5'-CACGTTGTCCACTTTGTTCACC GC-3') (SEQ ID NO: 23), E3 (5'-CAGTTCAGCGCCGAGGAAACGCAT-3') (SEQ ID NO: 24), and E4 (5'-GCGTTCGTCG TCGGCCCAACCGGA-3') (SEQ ID NO: 25) were used for primer extension analyses of the era RNA. The primers were 5'-labeled with [γ-$^{32}$P]ATP using T4 polynucleotide kinase. Primer extension reactions were performed at 42° C. for 1 hr. Control experiments were performed using the same conditions except that PemK$(His)_6$ was not added to the digestion reaction mixture. The primer extension product was analyzed on a 6% sequencing gel on which it was run alongside the DNA sequencing ladder prepared with the same primer.

Cleavage of Synthesized RNA by PemK: The 30-base RNA 5'-UAAGAAGGAGAUA UACAUAUGAAUCAAAUC-3' (SEQ ID NO: 11), antisense RNA 5'-GAUUUGAUUCAUAUGUAUAU CUCCUUCUUA-3' (SEQ ID NO: 26), and the complementary DNA 5'-GATTTGATTCATATGTATATC TCCTTCTTA-3' (SEQ ID NO: 27) were commercially synthesized. The 30-base RNA was 5'-end labeled with [γ-$^{32}$P]ATP using T4 polynucleotide kinase and used as a substrate for PemK$(His)_6$. The cleavage products of the 30-base RNA were applied to a 20% sequencing gel (with 7M Urea) along with an RNA ladder, which was prepared by partial alkaline hydrolysis of the 5'-end labeled 30-base RNA as described previously (Smith and Roth. (1992) *J Biol Chem* 267, 15071-15079). The effects of the RNA-RNA duplex and RNA-DNA duplex formation on the PemK-mediated RNA cleavage were determined as described previously (Zhang et al. (2003) supra).

Northern blot and primer extension analyses of the PemK effects on mRNAs in vivo: pIN-MazG plasmid and pIN-Era plasmid were transformed into *E. coli* BW25113 cells comprising pBAD-K, creating the BW25113/pBAD-K/pIN-MazG and BW25113/pBAD-K/pIN-Era strains, respectively. Cells were grown at 37° C. in LB medium containing ampicillin (50 μg/ml) and chloramphenicol (20 μg/ml). When the $OD_{600}$ value reached 0.4, IPTG was added to a final concentration of 1 mM to induce the synthesis of the mazG or era mRNA. After another 30 minute incubation at 37° C., arabinose was added to a final concentration of 0.2% to induce the expression of PemK. The samples were removed at different time intervals after the induction of PemK. Total cellular RNA was isolated using the hot-phenol method as described previously (Sarmientos et al. (1983) *Cell* 32, 1337-1346). The DNA fragment containing the full-length ORF of the mazG or era gene was used to prepare each of the radioactively labeled probes, which were used in Northern blot analyses. Primer extension analysis was performed with primer G2 (for the mazG mRNA) or E1 (for the era mRNA). To detect the lpp mRNA, total cellular RNA was extracted from *E. coli* BW25113/pBAD-K at various time points, after the addition of arabinose and subjected to Northern blot analysis using the radiolabeled lpp ORF DNA fragment as a probe. The primer extension analysis of the lpp mRNA was performed with primer lpp-C (5'-AGAATGTGCGCC ATTTTTCACT-3') (SEQ ID NO: 28).

Specific Methodological Details Pertaining to Drawings

FIG. 26. Effects of PemK on DNA and protein synthesis in vivo. (A) Effect of PemK on DNA synthesis. *E. coli* BW25113 cells containing pBAD-K were grown at 37° C. in M9 medium with glycerol as a carbon source. When the $OD_{600}$ of the culture reached 0.6, arabinose was added to a final concentration of 0.2% to induce PemK expression. The rates of DNA replication were measured by detecting the methyl-$^3$H-thymidine incorporation at various time points after the induction of PemK as described in Materials and Methods. (B) Effect of PemK on protein synthesis. The rates of protein synthesis were measured by detecting the [$^{35}$S]-methionine incorporation at various time points after the induction of PemK as described in Materials and Methods. (C) SDS-PAGE analysis of the total cellular protein synthesis after the induction of PemK. Cell culture (1 ml) was taken at the time point after the induction of PemK as indicated and mixed with 5 μCi [$^{35}$S]-methionine. After 1 minute of incorporation at 37° C., the [$^{\pm}$S]-methionine incorporation reaction mixture (500 μl) was placed in a chilled test tube containing 25 μl of 100% TCA solution and 100 μg/ml non-radioactive methionine. Cell pellets were collected by centrifugation and subjected to SDS-PAGE followed by autoradiography. The band indicated with an arrow is PemK.

FIG. 27. Effects of PemK and PemI on the cell-free protein synthesis. (A) Inhibition of cell-free protein synthesis by PemK. Protein synthesis was performed at 37° C. for 1 hr in the *E. coli* T7 S30 extract system (Promega). MazG was expressed from pET11a-MazG, and $(His)_6$Era was expressed from plasmid pET28a-Era. Lane 1, control without the addition of PemK; lanes 2 to 5, 0.125, 0.25, 0.5, and 1 μg PemK $(His)_6$ were added, respectively. (B) Release of PemK-mediated inhibition of protein synthesis in the cell-free system by PemI. Lane 1, control without the addition of PemK$(His)_6$; lane 2, with 1 μg PemK$(His)_6$; lanes 3 to 5; 0.5, 1, 2 μg $(his)_6$PemI were added together with 1 μg PemK$(His)_6$, respectively. (C) Effect of preincubation of the cell-free system with PemK on protein synthesis. The cell-free system was preincubated with or without PemK$(His)_6$ for 15 minutes at 37° C. before the addition of pET28a-Era plasmid. The protein synthesis was perpetuated for another 1 hr incubation at 37° C. Reaction products were analyzed by SDS-PAGE followed by autoradiography. Lane 1, control preincubated without PemK$(His)_6$; lane 2, preincubated with 1 μg PemK $(His)_6$ followed by adding pET28a-Era plasmid; lane 3, preincubated with 1 μg PemK$(His)_6$ followed by adding pET28a-Era plasmid and 1 μg $(His)_6$PemI together; lane 4, preincubated with 1 μg PemK$(His)_6$ and 1 μg $(His)_6$PemI together followed by the addition of pET28a-Era plasmid.

FIG. 28. Endoribonuclease activity of PemK. (A) Cleavage of the mazG mRNA by PemK and the inhibitory effect of PemI on the PemK-mediated RNA cleavage. Lane 1, control, the mazG mRNA alone; lane 2, the mazG mRNA (1.5 μg) incubated with 0.2 μg PemK$(His)_6$; lanes 3 to 6, the mazG mRNA (1.5 μg) incubated with 0.2 μg PemK$(His)_6$ together with 0.05, 0.1, 0.2 and 0.4 μg $(His)_6$PemI, respectively; lane 7, the mazG mRNA (1.5 μg) incubated with 0.4 μg $(His)_6$ PemI. The reactions were performed at 37° C. for 15 minutes, and the reaction products were analyzed by 3.5% native PAGE with TAE buffer. (B), (C), (D) and (E), primer extension analyses of PemK cleavage sites in the mazG mRNA and the era mRNA. Primer extension experiments were performed as described in Materials and Methods. Each primer extension product was analyzed on a 6% sequencing gel running alongside a DNA sequencing ladder prepared with the same primer. The RNA sequences complementary to the DNA sequence ladders around the PemK$(His)_6$ cleavage sites are shown at the right-hand side, and the cleavage sites are shown by arrows. Shown in this figure are the PemK$(His)_6$ cleavage sites in the mazG mRNA detected with primers G1 (B) and G2 (C), and the PemK$(His)_6$ cleavage sites in the era mRNA detected with primers E1 (D) and E4 (E).

FIG. 29. Inhibition of PemK endoribonuclease activity by RNA/RNA formation. A 30 base RNA was synthesized with the identical sequence around a PemK$(His)_6$ cleavage site in the mazG mRNA (Table II, row 2). (A) PemK cleavage sites on the 30-base RNA. The 30-base RNA was 5'-end labeled with [γ-$^{32}$P]-ATP using T4 polynucleotide kinase, and then incubated with PemK$(His)_6$ at 37° C. for 15 minutes. The cleavage products were analyzed on a 20% sequencing gel. Lane 1, 5'-end [$^{32}$P]-labeled 11-base RNA size maker; lane 2, RNA ladder prepared from the 5'-end [$^{32}$P]-labeled 30-base RNA by partial alkaline hydrolysis as described previously (Smith and Roth. (1992) *J Biol Chem* 267, 15071-15079); lane 3,5'-end [$^{32}$P]-labeled 30-base RNA untreated by PemK $(His)_6$; and lane 4, the cleavage products of the 5'-end [$^{32}$P]-labeled 30-base RNA by PemK$(His)_6$. The size of each band in lanes 1 and 4 is shown with the number of its total nucleotides. (B) The effects of RNA-RNA duplex formation on the endoribonuclease activity of PemK. Lane 1, the [$^{32}$P]-labeled 30-base RNA alone (1 pmol); lane 2, the [$^{32}$P]-labeled 30-base RNA (1 pmol) was incubated with 0.2 μg PemK $(His)_6$ at 37° C. for 15 minutes; lanes 3 to 7, the [$^{32}$P]-labeled 30-base RNA (1 pmol) was annealed with its 30-base antisense RNA in different ratios as indicated, and then incubated with 0.2 μg PemK$(His)_6$ at 37° C. for 15 minutes. The reaction products were analyzed by 15% PAGE followed by autoradiography.

FIG. 30. Northern blot and primer extension analyses of the effects of PemK on various mRNAs in vivo. (A) Northern blot analyses of the effects of PemK on mazG, era and lpp mRNAs in vivo. The mazG mRNA and the era mRNA were produced respectively from pIN-MazG and pIN-Era in the presence of 1 mM IPTG for 30 minutes before the addition of arabinose (to a final concentration of 0.2%) to induce PemK expression. The lpp mRNA was transcribed from the *E. coli* chromosome. Total cellular RNA was extracted at various time points as indicated after the induction of PemK and used for Northern blot analysis. The control experiments were carried out under the same condition without the induction of PemK. (B), (C) and (D) Primer extension analyses of PemK cleavage sites in the mazG, era and lpp mRNAs in vivo. Total cellular RNA was extracted at each time point as indicated and used for the primer extension experiments. Primer extension products were analyzed on a 6% sequencing gel running alongside a DNA sequencing ladder prepared with the same primer. The RNA sequences complementary to the DNA sequence ladders around the PemK cleavage sites are shown at the right-hand side, and the cleavage sites are indicated by arrows. Shown are in vivo PemK cleavage sites in the mazG mRNA detected with primer G2 (B), in the era mRNA detected with primer E1 (C), and in the lpp mRNA detected with primer lpp-C (D).

Results

Figure 26A:
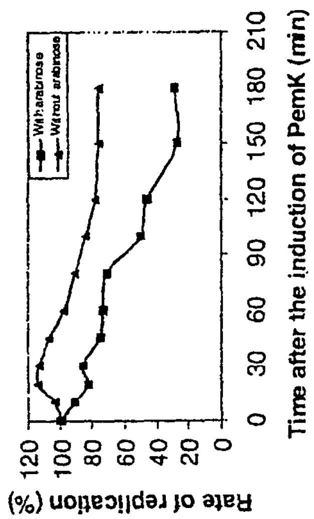
FIGS. 26A-C show the effects of PemK on DNA and protein synthesis.
Figure 26B:
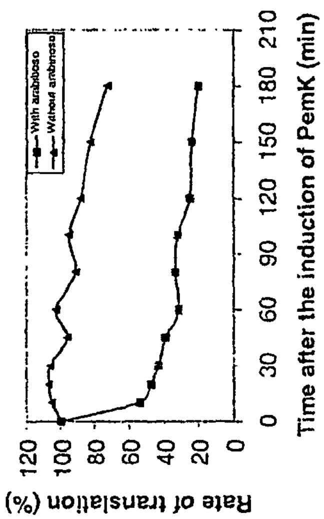
Figure 26C:
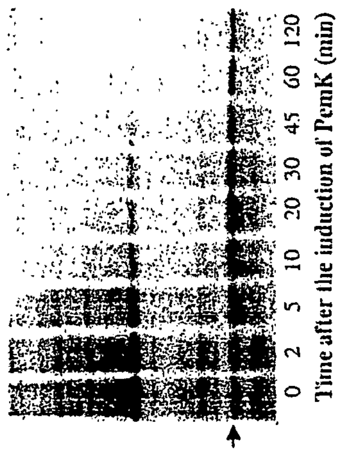

The effects of PemK on DNA and protein syntheses in vivo: The pemK gene was cloned into the pBAD vector (Guzman et al. (1995) *J Bacteriol* 177, 4121-4130) creating plasmid pBAD-K, which was transformed into *E. coli* BW25113. The expression of PemK in BW25113/pBAD-K was induced by the addition of arabinose to a final concentration of 0.2%. After the induction of PemK, the rates of DNA replication and protein synthesis were measured at various time points as indicated in FIGS. 26A and B, respectively. Both DNA replication and protein synthesis were affected by the induction of PemK, but DNA replication was inhibited to a significantly lesser degree than protein synthesis. Protein synthesis was rapidly reduced by approximately 50% at 10 minutes after the induction of PemK, while it took about 100 minutes for similar inhibition of DNA replication. As shown in FIG. 26C, SDS-PAGE analysis of total cellular protein synthesis at different time points after the induction of PemK indicates that PemK is a general inhibitor of cellular protein synthesis. After the induction of PemK, the intensity of a band (indicated by an arrow) increased from 0 to 30 minutes and then decreased. On the basis of its molecular mass and kinetics of induction, this band represents the induced PemK protein.

Figure 27A:
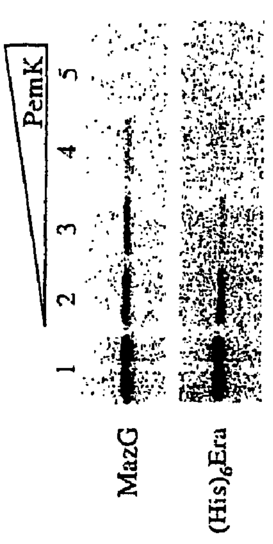
FIGS. 27A-C show autoradiograms of proteins separated by SDS-PAGE. The results demonstrate the effects of PemK and PemI on cell-free protein synthesis.
Figure 27B:
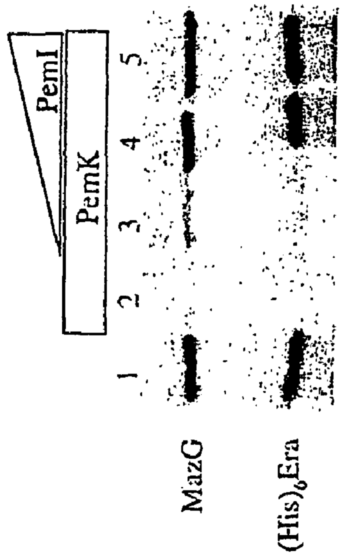
Figure 27C:

PemK inhibits protein synthesis in a cell-free system: PemK$(His)_6$ (C-terminally tagged) was purified from *E. coli* strain BL21(DE3)/pET21 cc-IK$(His)_6$ co-expressing both PemI and PemK$(His)_6$ as described in Methods and Materials. $(His)_6$PemI (N-terminally tagged) was purified from *E. coli* strain BL21(DE3)/pET28a-$(His)_6$I. PemK$(His)_6$ and $(His)_6$PemI are referred to as PemK and PemI, respectively in the following in vitro experiments. In order to determine if PemK inhibits protein synthesis, the effects of purified PemK on the synthesis of MazG and $(His)_6$Era in an *E. coli* cell-free RNA/protein synthesis system were examined. The synthesis of MazG from plasmid pET11a-MazG and the synthesis of $(His)_6$Era from plasmid pET28a-Era were carried out at 37° C. for 1 hr using the *E. coli* T7 S30 extract system (Promega) in the absence of PemK (FIG. 27A, lane 1) or in the presence of increasing amounts of PemK (FIG. 27A, lanes 2 to 5). Both MazG and $(His)_6$Era synthesis were blocked by PemK in a dose-dependent manner (FIG. 27A). These results demonstrate that PemK inhibits protein synthesis, consistent with the PemK-mediated inhibition of protein synthesis observed in vivo (FIGS. 26B and 26C). The delayed PemK-mediated inhibition of DNA replication observed in vivo (FIG. 26A) is thus speculated to be due to a secondary effect of the inhibition of cellular protein synthesis. Interestingly, the addition of the antitoxin PemI blocked the PemK-mediated inhibition of protein synthesis and restored MazG and $(His)_6$Era synthesis in a PemI-dose-dependent manner (FIG. 27B). It should be noted that pre-incubation of the *E. coli* cell-free system with PemK for 15 minutes at 37° C. did not have a significant adverse effect on $(His)_6$Era synthesis, if PemI was added together with the plasmid DNA after the 15 minute pre-incubation (compare lanes 1 and 3 in FIG. 27C). In the absence of PemI, however, no protein was produced (FIG. 27C, lane 2). Notably, $(His)_6$Era synthesis was restored regardless of whether PemI was added after the 15 minute pre-incubation with PemK (FIG. 27C, lane 3) or it was added together with PemK during the 15 minute pre-incubation (FIG. 27C, lane 4). These results suggest that the primary target of PemK is mRNA, and not tRNA, ribosomes and any other factors that are required for protein synthesis in a cell-free system.

Figure 28E:
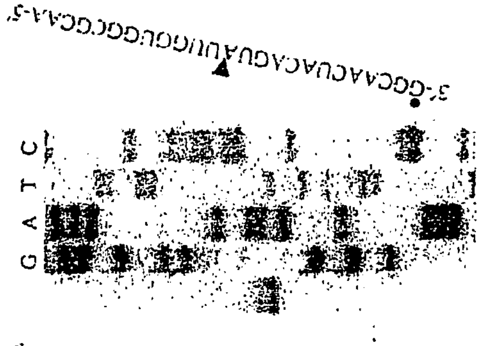
FIGS. 28A-E show a photograph of a polyacrylamide gel (A) or autoradiograms of polyacrylamide gels (B-E) that illustrate PemK mediated endoribonuclease activity. The RNA sequences complementary to the DNA sequence ladders around the PemK(His)$_6$ cleavage sites are shown at the right-hand side and are designated SEQ ID NO: 93 (FIG. 28B); SEQ ID NO: 94 (FIG. 28C); SEQ ID NO: 95 (FIG. 28D); and SEQ ID NO: 96 (FIG. 28E).
Figure 28D:
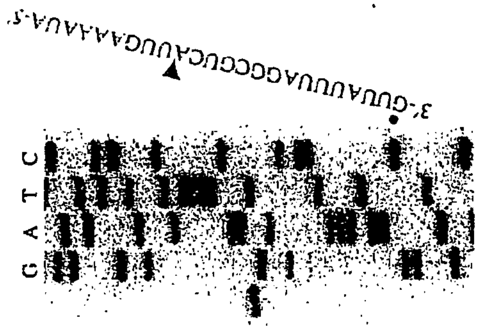
Figure 28C:
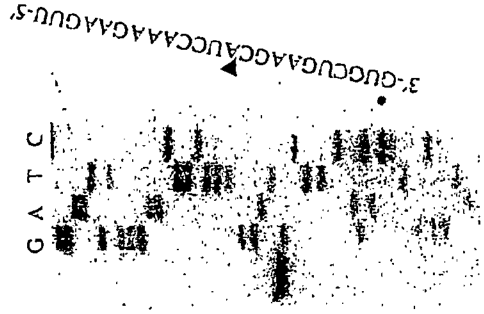
Figure 28B:
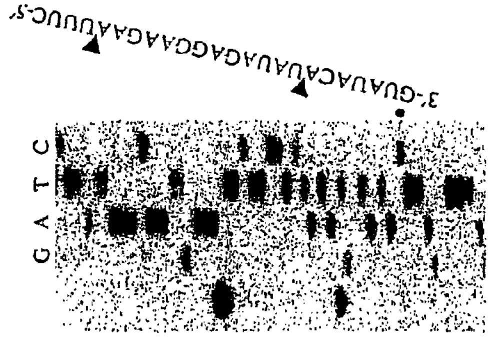
Figure 28A:

Endoribonuclease activity of PemK: A DNA fragment comprising a T7 promoter and the mazG gene was obtained by PCR amplification using the plasmid pET11a-MazG as a template as described in Methods and Materials. Similarly another DNA fragment containing a T7 promoter and the era gene was obtained using the plasmid pET28a-Era as a template. The mazG mRNA and the era mRNA were then prepared from these two DNA fragments respectively using the T7 large-scale transcription kit (Promega). The mazG mRNA was digested into smaller fragments after incubation with PemK at 37° C. for 15 minutes (FIG. 28A, lane 2), while the addition of PemI inhibited the cleavage of mazG mRNA in a dose-dependent manner (FIG. 28A, lanes 3 to 6). PemI alone had no effect on the mazG mRNA (FIG. 28A, lane 7). A similar result was obtained with the era mRNA as a substrate. These results demonstrate that PemK is an endoribonuclease that cleaves mRNA to inhibit protein synthesis, and that PemI functions as an antitoxin to block the endoribonuclease activity of PemK.

The finding that the digestion products of mazG mRNA cleaved by PemK form distinct bands on a 3.5% polyacrylamide gel (FIG. 28A) indicates that PemK cleaves RNA at specific sites. The mazG mRNA was partially digested by PemK and then subjected to primer extension using five different oligodeoxyribonucleotide primers, G1 to G5, as described in Materials and Methods. A number of specific cleavage sites along the mazG mRNA were detected on a 6% sequence gel as compared to controls treated in parallel, but without PemK treatment. Partially digested era mRNA by PemK was also subjected to primer extension using four different primers, E1 to E4, as described in Materials and Methods to detect the PemK cleavage sites along the era mRNA. To determine the exact sequence around the PemK cleavage sites, each primer extension product was analyzed on a 6% sequencing gel with the DNA sequencing ladder prepared with the same primer (FIG. 28B to E).

Table II shows mRNA sequences around the PemK cleavage sites. The mRNA sequences around PemK cleavage sites (indicated by arrows) in the mazG mRNA (from pET11a-MazG), The era mRNA (from pET28a-Era) and the 1 pp mRNA (from *E. coli* chromosomal DNA, see FIG. 30D) are shown. The conserved UA dinucleotides are shown in bold. The numbers show the positions of the nucleotides in mRNA taking the A residue in the initiation codon AUG as +1.

| Gene Names | Primer | | mRNA sequences around the cleavage sites | | |
|---|---|---|---|---|---|
| mazG | G1 | (-27) | UUUUAACUU**U**↓**A**AGAAGGAGA | (-8) | (SEQ ID NO: 103) |
| | | (-14) | AAGGAGAUA**U**↓**A**CAUAUGAAT | (+6) | (SEQ ID NO: 104) |
| | G2 | (+112) | GAAGAAACC**UA**↓CGAAGUGCU | (+131) | (SEQ ID NO: 105) |
| | G3 | (+196) | GUGGUGUUU**U**↓**A**CGCGCAAAU | (+215) | (SEQ ID NO: 106) |
| | | (+234) | CUUUGACUU**U**↓**A**AUGAUAUUU | (+253) | (SEQ ID NO: 107) |
| | | (+240) | CUUUAAUGA**U**↓**A**UUUGCGCUG | (+259) | (SEQ ID NO: 108) |
| | | (+290) | CGCAUGUUU**U**↓**G**CUGAUAGUU | (+309) | (SEQ ID NO: 109) |
| | G4 | (+523) | GAGGUGAUG**UA**↓CGAAGCGCG | (+542) | (SEQ ID NO: 110) |
| | G5 | (+597) | UGCCACGGU**U**↓**A**AUCUGGCUC | (+616) | (SEQ ID NO: 111) |
| | | (+684) | AGUGGAGCG**U**↓**A**UUGUUGCCG | (+703) | (SEQ ID NO: 112) |

-continued

| Gene Names | Primer | | mRNA sequences around the cleavage sites | | |
|---|---|---|---|---|---|
| era | E1 | (+10) | GATAAAAGU**U**↓**A**CUGCGGAUU | (+29) | (SEQ ID NO: 113) |
| | E2 | (+144) | GGGGAUCCA**U**↓**A**CUGAAGGCG | (+163) | (SEQ ID NO: 114) |
| | | (+169) | CAGGCGAUC**U**↓**A**CGUCGAUAC | (+188) | (SEQ ID NO: 115) |
| | E3 | (+509) | GUAAGCAUC**U**↓**A**CCUGAAGCG | (+528) | (SEQ ID NO: 116) |
| | | (+541) | CCGGAAGAU**U**↓**A**CAUCACCGA | (+560) | (SEQ ID NO: 117) |
| | E4 | (+625) | GAACUGCCG**UA**↓CUCCGUGAC | (+644) | (SEQ ID NO: 118) |
| | | (+676) | CGCGGUGGU**U**↓**A**UGACAUCAA | (+695) | (SEQ ID NO: 119) |
| lpp | lppC | (+210) | CAACAUGGC**U**↓**A**CTAAAUACC | (+229) | (SEQ ID NO: 120) |

Table II shows the sequences around the major cleavage sites in the mazG mRNA, the era mRNA and the lpp mRNA (see FIG. 30D for the lpp mRNA), as determined by the primer extension experiments. These findings reveal that a UA dinucleotide is common in all but one cleavage site, and that the primary cleavages occur at the 5' or 3' side of the A residue in the UAX (X is C, A or U) sequence, with only one exception in which the cleavage occurs between U and G residues in the UGC sequence (Table II, row 7). The UAC sequence appears in 11 out of the 18 cleavage sites determined.

Figure 29B:
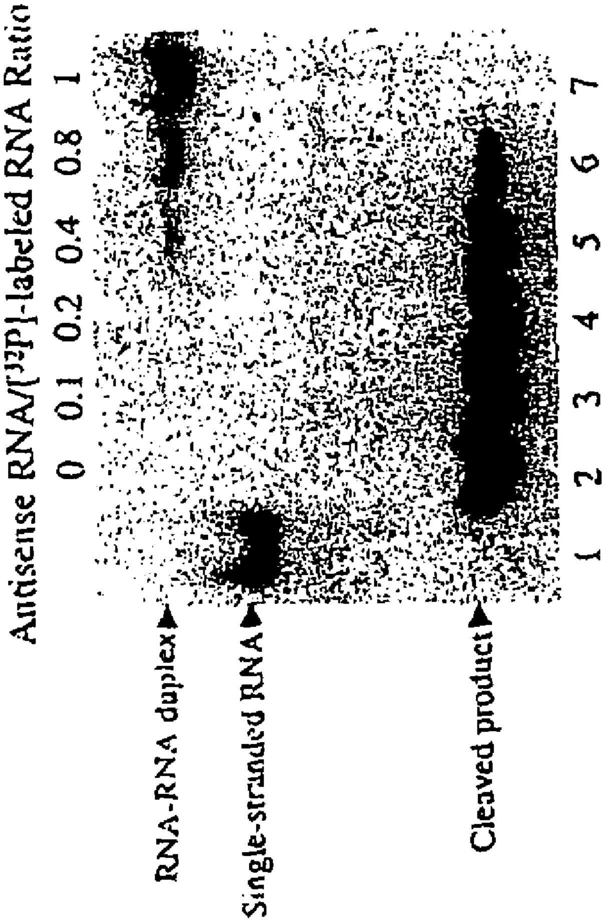
FIGS. 29A-B show a photograph of a polyacrylamide sequencing gel (A) and an autoradiogram of a polyacrylamide gel (B) that reveal the specificity of PemK mediated endoribonuclease activity for single stranded RNA. The RNA sequence shown therein is designated SEQ ID NO: 97.
Figure 29A:
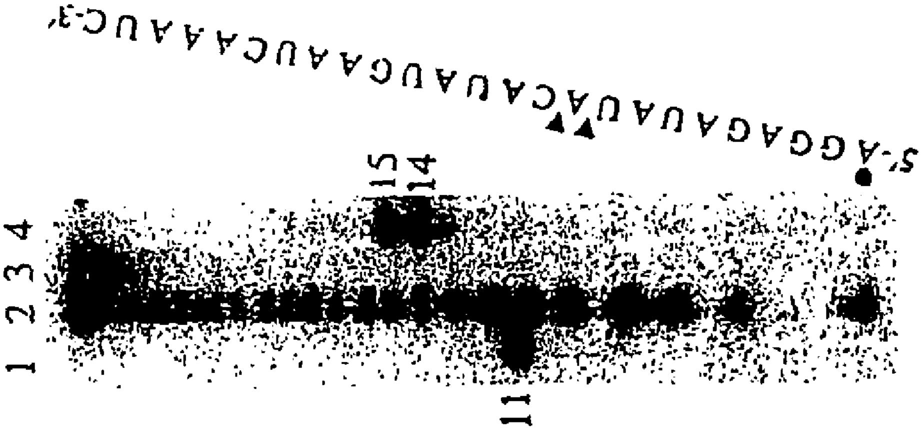

A 30-base RNA substrate was designed on the basis of the sequence around one PemK cleavage site in the mazG mRNA that comprises a UAC sequence (Table II, row 2). The RNA was labeled at the 5' end with [$\gamma$-$^{32}$P]ATP using T4 polynucleotide kinase. In the primer extension experiment using the full-length mazG mRNA, the UAC sequence was cleaved only at the 5' side of the A residue (FIG. 28B). The 30-base RNA, however, was cleaved equally well at either 5' side or 3' side of the A residue (nucleotide 15 in the 30 base RNA) in the UAC sequence (FIG. 29A). On a 15% native PAGE, the cleavage products from the 30-base RNA migrated as a single band (FIG. 29B, lane 2). When the antisense RNA was annealed with the 30-base RNA substrate in different ratios before the addition of PemK, it blocked the RNA cleavage in a dose-dependent manner (FIG. 29B, lanes 3 to 7). A similar result was obtained when the 30-base RNA substrate formed a duplex with its complementary DNA. These results indicate that the PemK cleavage sites in the 30-base RNA substrate are protected in the RNA-RNA and RNA-DNA duplexes. It can, therefore, be concluded that PemK is a sequence-specific endoribonuclease for single-stranded RNA.

Figure 30A:
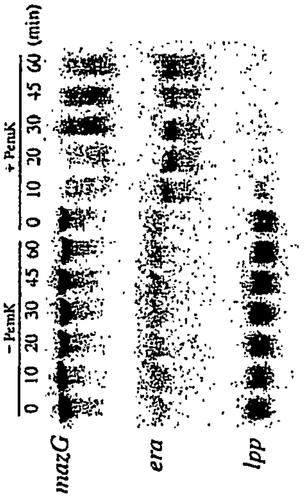
FIGS. 30A-D show a Northern blot analysis (A) or autoradiograms of polyacrylamide gels (B-D) that depict PemK mediated endonucleolytic activity on various mRNAs in vivo. The RNA sequences shown therein are designated SEQ ID NO: 94 (FIG. 30B); SEQ ID NO: 98 (FIG. 30C); and SEQ ID NO: 99 (FIG. 30D).

In vivo mRNA cleavage upon the induction of PemK To examine the effect of PemK on mRNAs in vivo, Northern blot and primer extension analyses were performed with total cellular RNA extracted at different time points after the induction of PemK as described in Methods and Materials. The 16S and 23S rRNAs were stable against PemK in vivo, as no significant changes were observed in their band intensities as revealed by visualization on 1% agarose gels of total cellular RNA samples during a 60 minute period after the induction of PemK. This indicates that in vivo both 16S and 23S rRNA are well protected from PemK cleavage. FIG. 30A shows the Northern blot analyses of the mazG, era and lpp mRNAs at the various time points with or without the induction of PemK. The mazG mRNA and the era mRNA were produced respectively from pIN-MazG and pIN-Era in the presence of 1 mM IPTG for 30 minutes before the addition of arabinose (the final concentration of 0.2%) to induce PemK expression. The lpp mRNA was transcribed from the *E. coli* chromosome. All three of these mRNAs were degraded after 10 minutes of induction of PemK expression, while no changes were observed during a 60 minute incubation without the induction of PemK (FIG. 30A). In comparison with the mazG and lpp mRNAs, the era mRNA was mostly converted to a smaller distinct band, which was comparatively stable during the 60 minute induction of PemK. The nature of this stable mRNA cleavage product is unknown.

Figure 30B:
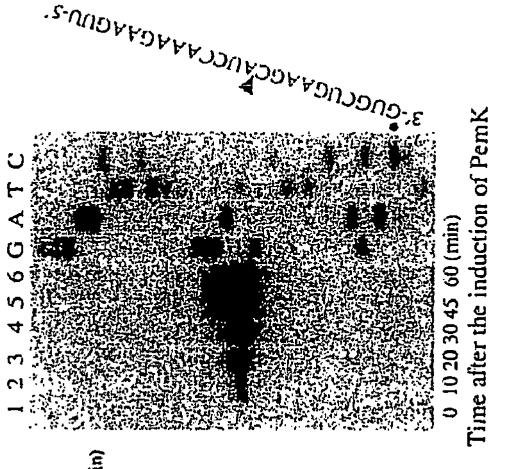
Figure 30C:
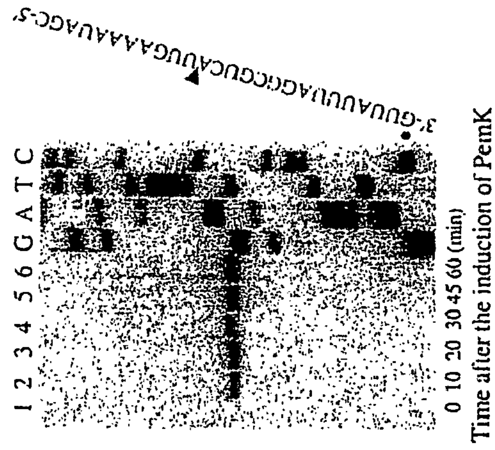
Figure 30D:
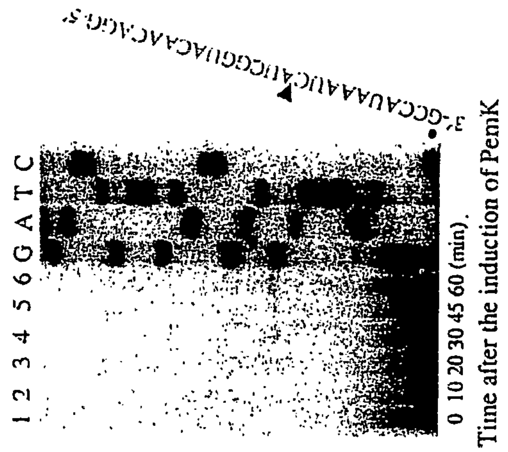

Primer extension experiments were also performed to determine the PemK cleavage sites in mRNAs in vivo. One cleavage site for each mRNA is shown in FIGS. 30B, C, and D for mazG, era and lpp, respectively. In all cases, a band appeared at 10 minutes after the induction of PemK (lane 2 in FIGS. 30B, C and D), whose intensity further increased during the 60 minute induction of PemK (lanes 2 to 6). Of note, the band was barely detectable at 0 minutes (lane 1), clearly demonstrating that the observed cleavages were caused by the induction of PemK. Both the mazG and lpp mRNAs were cleaved between the A and C residues in the UAC sequence, while the era mRNA was cleaved between the U and A residues. The mazG mRNA was cleaved at the identical site in vivo and in vitro (compare FIG. 28C and FIG. 30B). The in vivo cleavage of the era mRNA also occurred at the same site as detected in vitro with use of the same primer (compare FIG. 28D and FIG. 30C). The cleaved-UAC sequences in the mazG and the era RNAs are in the reading frame of both ORFs, encoding Tyr41 in MazG and Tyr7 in Era, while the cleaved UAC sequence in the lpp mRNA is between two adjacent codons, GCU for Ala73 and ACU for Thr74. In vivo mRNA cleavage by PemK was very specific as no other cleavage events were detected, as shown in FIGS. 30B, C and D. Therefore, unlike RelE which stimulates codon-specific mRNA cleavage at the A site on ribosomes (Pedersen et al. (2003) *Cell* 112, 131-140; Hayes and Sauer. (2003) *Mol Cell* 12, 903-911), PemK is a sequence-specific endoribonuclease capable of inhibiting protein synthesis by cleaving mRNA in a manner independent of ribosomes and codon-reading.

Conclusion

The present invention is directed, in part, to the novel discovery that PemK, the toxin encoded by the pemI-pemK addiction module, is a sequence-specific endoribonuclease. Both in vitro and in vivo studies demonstrate that PemK inhibits protein synthesis by cleaving mRNAs at specific sites. Purified PemK inhibits protein synthesis in an *E. coli* cell-free system, while the addition of PemI is able to block the inhibitory effect of PemK and restore protein synthesis. Furthermore, it is demonstrated herein that mRNAs are degraded by PemK, and that the PemK mediated mRNA cleavage is inhibited by PemI. PemI, therefore, functions as an antitoxin that inhibits the endoribonuclease activity of PemK by forming a complex with PemK. With respect to endoribonuclease activity, PemI-PemK complexes are inactive.

PemK is shown herein to be highly specific for single-stranded RNA, as PemK mediated RNA cleavage is blocked when an RNA substrate is annealed to its antisense RNA or complementary DNA to form an RNA-RNA or RNA-DNA duplex. The present results also demonstrate that PemK cleaves preferentially at the 5' or 3' side of the A residue in UAX (X is C, A or U) sequences. The results presented herein also reveal that RNA cleavage by PemK is independent of ribosomes, which is distinctly different from RelE, the toxin encoded by the relBE addiction module. RelE is not able to cleave free RNA but stimulates mRNA cleavage at the ribosome A site with high codon-specificity (Christensen and Gerdes. (2003) *Mol Microbiol* 48, 1389-1400; Pedersen et al. (2003) *Cell* 112, 131-140; Hayes and Sauer. (2003) *Mol Cell* 12, 903-911).

In a previous study on the kis-kid system, which is an addiction module identical to the pemI-pemK system, it has been reported that Kid (PemK) inhibits in vitro ColE1 replication at the initiation stage but has no significant effect on P4 DNA replication. DnaB has been proposed as the target for the inhibitory action of Kid (PemK) (Ruiz-Echevarria et al. (1995) *J Mol Biol* 247, 568-577). There is, however, no data to support the interaction between Kid (PemK) and DnaB. It is interesting to note that ColE1 replication is initiated by RNA II and inhibited by RNA I (Cesareni et al. (1991) *Trends Genet.* 7, 230-235; Davison. (1984) *Gene* 28, 1-15), while P4 DNA replication is mainly regulated by a protein (Briani et al. (2001) *Plasmid* 45, 1-17). RNases involved in the metabolism of RNA I and RNA II are expected to play a key role in the control of the ColE1 plasmid replication (Jung and Lee. (1995) *Mol Biol Rep* 22, 195-200). RNA II contains several UAC sequences, two of which exist in the loop regions of the first and second stem-loop structure (Tomizawa and Itoh. (1982) *Cell* 31, 575-583; Tomizawa. (1984) *Cell* 38, 861-870). The inhibition of ColE1 DNA replication by Kid (PemK), therefore, is likely due to degradation of RNA II by its endoribonuclease activity. Furthermore, the fact that Kid (PemK), a toxin in bacteria, inhibits the growth of various eukaryotic cells (de la Cueva-Mendez et al. (2003) *Embo J* 22, 246-251) can be readily explained by virtue of its endoribonuclease activity against cellular mRNAs rather than by its interaction with DnaB.

PemK homologues have been identified in a wide range of bacteria. MazF (ChpAK) and ChpBK are the two PemK-like proteins in *E. coli* (Santos Sierra et al. (1998) *FEMS Microbiol Lett* 168, 51-58; Masuda et al. (1993) *J Bacteriol* 175, 6850-6856; Christensen et al. (2003) *J Mol Biol* 332, 809-819). MazF (ChpAK), the toxin encoded by the mazEF addiction module is 25% identical to PemK; ChpBK, the toxin encoded by the chpB addiction module is 41% identical to PemK. Notably, MazF (ChpAK) and ChpBK are known to inhibit translation by cleaving mRNAs in a manner similar to RelE (Christensen et al. (2003) supra). The present inventors have recently demonstrated, however, that MazF is an endoribonuclease that acts independently of ribosomes and inhibits protein synthesis by cleaving single-stranded mRNA at specific sequences (Zhang et al. (2003) *Mol Cell* 12, 913-923). MazF preferentially cleaves mRNA between A and C residues at the ACA sequence (Zhang et al. (2003) supra).

The crystal structure of Kid (PemK) protein has been determined as a homodimer (Hargreaves et al. (2002) *Structure* (Camb) 10, 1425-1433; Hargreaves et al. (2002) *Acta Crystallogr Biol Crystallogr* 58, 355-358). Although the structure of MazF has not been determined, Kamada et al (2003) have reported the crystal structure of the MazE-MazF complex (MazF2-MazE2-MazF2), which was formed by two MazF homodimers and one MazE homodimer. Interestingly, the structure of the Kid (PemK) homodimer and that of the MazF homodimer in the MazE-MazF complex are similar. The conserved loops between β strands S1 and S2 (termed the S1-S2 loops) in the MazE-bound MazF homodimer, however, project into solvent and are mostly disordered, while the two corresponding loops are in a "closed" conformation in the Kid (PemK) homodimer (Kamada et al. (2003) *Mol Cell* 11, 875-884). The S1-S2 loops in the structure of the Kid (PemK) homodimer form a cavity-like structure covering a basic surface and a conserved hydrophobic pocket. The conserved hydrophobic pocket plays an essential role in the recognition of MazE in the MazE-MazF complex formation (Kamada et al. (2003) supra). The present inventors have proposed that the highly negatively charged C-terminal extension of MazE may mimic single-stranded RNA, which binds between the S1-S2 loops in the MazF homodimer (Zhang et al. (2003) supra). PemI is envisioned to bind to PemK in a very similar manner to block the endoribonuclease activity of PemK.

Both PemK and MazF have been characterized by the present inventors as sequence-specific endoribonucleases for single-stranded RNA, however, their physiological function appears to be distinct from other known endoribonucleases such as RNase E, A and T1. PemK and MazF function as general protein synthesis inhibitors by interfering with the function of cellular mRNAs. It is well known that the small RNAs, such as micRNA (mRNA-interfering-complementary RNA) (Mizuno et al. (1984) *Proc Natl Acad Sci USA* 81, 1966-1970), miRNA (Ambros. (2001) *Cell* 107, 823-826) and siRNA (Billy et al. (2001) *Proc Natl Acad Sci USA* 98, 14428-14433), interfere with the function of the specific target RNAs. The ribozyme also acts on the target RNA specifically and interferes with its function (Puerta-Femandez et al. (2003) *FEMS Microbiol Rev* 27, 75-97). The present inventors propose that PemK and PemK homologues (including MazF) form a novel endoribonuclease family with a new mRNA-interfering mechanism that effects cleavage of mRNAs at specific sequences. As such, they have been designated herein as "mRNA interferases". As reported previously, Kid (PemK) triggers apoptosis in human cancer cells, while Kis (PemI) inhibits the toxic effect of Kid (PemK) (de la Cueva-Mendez et al. (2003) supra). This new regulatable mRNA-interfering system may, therefore, be useful for therapeutic intervention (e.g., gene therapy) of human disease.

Example V

As shown herein, PemK functions as a highly sequence-specific endoribonuclease, which cleaves cellular mRNAs at UAX sequences, wherein X is C, A or U. Such activity may effectuate a partial or total inhibition of protein synthesis in a cell. The predicted frequency of an UAX sequence in an RNA transcript (wherein X is C, A, U) is three in 64, based on standard calculations predicated on an equal probability that any one of the four nucleotides will be incorporated at each one of the first two nucleotide positions and any one of the three indicated nucleotides will be incorporated into the third nucleotide position. It is to be understood that some RNA transcripts comprise a lower or higher frequency of UAX sequences as compared to the predicted frequency. Accordingly, the sensitivity of a specific RNA transcript or a family of related RNA transcripts to cleavage by a PemK endoribonuclease is dependent upon the frequency of UAX sequences or PemK target sequences in the transcript. Moreover, one of ordinary skill in the art could predict, based on the sequence of an RNA transcript, the sensitivity of the transcript to PemK mediated cleavage.

Example VI

RNA interferases, in general, and specific RNA interferases of the present invention may also be used to advantage as components of in vivo and in vitro protein production systems, wherein background (non-specific) protein production is dramatically reduced or eliminated so as to generate a "single-protein" synthesizing system. Proteins expressed using a "single-protein" synthesizing system are essentially free of contaminating proteins and are, therefore, useful for applications wherein "pure" protein preparations are advantageous or necessary. Such applications include, but are not limited to nuclear magnetic resonance (NMR) analysis of a protein without purification and other structural determinations of proteins, including those involving membrane proteins. With regard to structural analyses of membrane proteins, membrane protein preparations generated using a method of the present invention are well suited for protocols involving solid state NMR. In a preferred aspect, a method of the present invention can be used to advantage to exclusively label a specific membrane protein with radioactive isotope in a cellular context. The labeled membrane protein is subsequently incorporated via endogenous cellular machinery into an appropriate cellular membrane wherein it is readily detected by virtue of its label.

In order to construct a single-protein synthesizing system for either in vivo or in vitro applications, the system is pretreated with an mRNA interferase (e.g., PemK and/or MazF) which cleaves endogenous mRNAs to block protein synthesis from these mRNAs. To effect such pretreatment in vivo, a regulatable gene for an mRNA interferase is introduced into a cell or tissue and its expression induced. Methods for introducing and expressing exogenous genes into cells and/or tissues are described herein above and known in the art. To effect mRNA interferase pretreatment in vitro, a purified mRNA interferase is added to an in vitro translation system. Various in vitro translation systems are known in the art and consist of, but are not limited to, extracts derived from rabbit reticulocytes, wheat germ and *E. coli*. For production of a "single protein" in either of these in vivo or in vitro systems, a genetic construct encoding the desired protein is engineered to transcribe an mRNA from which all of the mRNA interferase-target sequences have been removed. This procedure generates an mRNA which is not susceptible to the endonuclease activity of the mRNA interferase added to the "single protein" expression system. Such an engineered mRNA transcript of the invention may be referred to herein as an "interferase resistant mRNA". Expression of an interferase resistant mRNA is carried out by inducing its expression from, for example, an engineered construct. The interferase resistant mRNA is translated into protein, essentially in the absence of translation of any other proteins that are susceptible to the activity of the mRNA interferase, thus producing, in essence, a single protein sample. This approach can be applied to either prokaryotic or eukaryotic systems.

It is to be understood that treatment with an mRNA interferase can also be rendered concomitantly with the expression/induction or addition of an interferase resistant mRNA. Such an approach may be used in conjunction with either in vitro or in vivo (cell-based) systems of the invention directed to single protein synthesis.

Cell-Based Expression Systems: In that MazF is a sequence specific (ACA) endoribonuclease, functional only for single-stranded RNA (Zhang et al. 2003, supra), a cell-based "single-protein" synthesizing system was developed to exemplify the utility of MazF in such applications.

Figure 36:
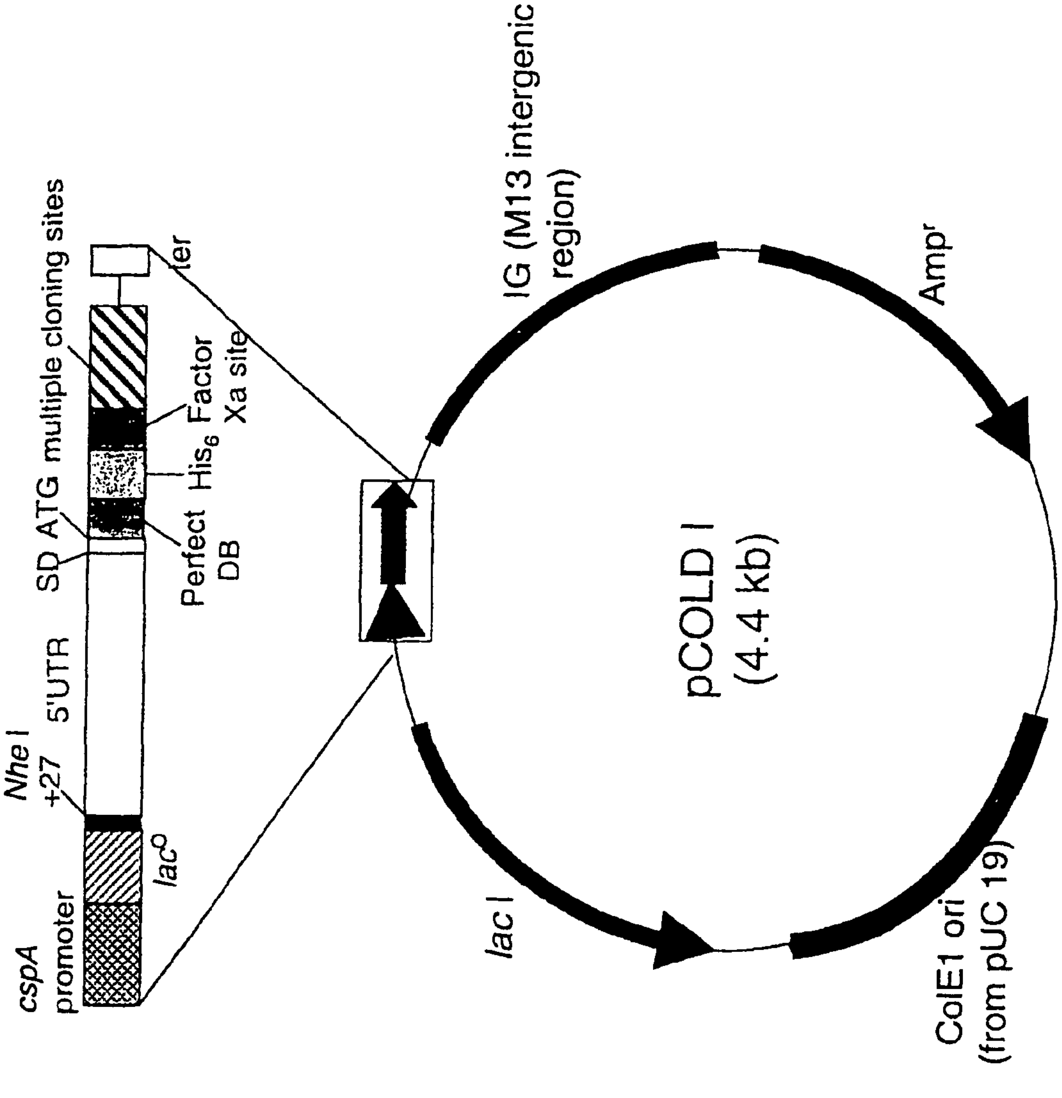
FIG. 36 is a schematic depicting the pCold I vector.

Accordingly, a single protein synthesizing system was developed to synthesize mature human eotaxin in bacterial cells. To achieve this end, a novel nucleic acid sequence that encodes the wild type eotaxin amino acid sequence was synthesized. RNA molecules transcribed from this novel nucleic acid sequence are devoid of ACA sequences. See FIG. 35; SEQ ID NOs: 30-31 (nucleic and amino acid sequences of mature human eotaxin, respectively). This novel nucleic acid sequence encoding mature human eotaxin was cloned into a cold-shock vector (pCOLDI), which expresses proteins when in the presence of IPTG induced by incubation at low temperature. See FIG. 36. A significant advantage of this expression system is a low background of non-specific protein expression.

It is to be understood that nucleic acid sequences encoding polypeptides of interest can be generated using a variety of approaches. Such approaches include: designing and generating a synthetic nucleic acid sequence capable of encoding a polypeptide of interest, wherein the nucleic acid sequence is devoid of ACA sequences; and isolating a nucleic acid sequence capable of encoding the polypeptide of interest and mutating each ACA sequence therein to an alternate triplet sequence, wherein such mutations are silent with regard to altering the amino acid sequence encoded therefrom.

Methods and Materials

Cold Shock Induction with pCold I Vector:

Since the pCold I vector comprises a lac operator, 1 mM IPTG is added to induce expression of genes controlled by this regulatory element. For some proteins, induction at 15° C. after the cells reach mid-log phase ($OD_{600}$=0.4-0.7) is preferred to achieve improved folding of the protein. To determine conditions best suited to optimal protein yield, samples are removed at different time intervals following induction and evaluated by SDS-PAGE analysis. □In general, cells are maintained in LB medium while expression induced, but when it is desirable to label a protein with a radioactive isotope, for example, $^{15}N$ or $^{13}C$ labeling, M9 or MJ9 medium is used.

The nucleotide sequence from the SD site to the multiple cloning site of the pCold I vector is shown herein below. The expressed protein comprises a 15-residue removable sequence at the N-terminus, consisting of a downstream box (DB), which is a translation enhancing cis-element, a $His_6$ tag and a factor Xa site followed by the multiple cloning sites.

| | |
|---|---|
| GAGG | SD |
| TAAT***ACA***CC | Sequences downstream of SD (SEQ ID NO: 29) |
| ATGAATC***ACA***AAGTG | DB (SEQ ID NO: 30) |
| CATCATCATCATCATCAT | $His_6$ (SEQ ID NO: 31) |
| ATCGAAGGTAGG | factor Xa site (SEQ ID NO: 32) |
| CATATGGAGCTCGGTACCCTCGAG GGATCC<br>NdeI SacI KpnI XhoI BamHI | |
| GAATTCAAGCTTGTCGACCTGCAGTCTAGA<br>EcoRI □HindIII SalI PstI XbaI | multiple cloning site (SEQ ID NO: 33) |

For constructing pCold(SP)eotaxin (also referred to herein as pSPSeotaxin), two ACA sequences indicated above in bold, italicized font are changed to ATA to remove recognition sites for MazF interferase.

It should be appreciated that the method of the present invention can be used with any expression vector or expression vector system (e.g., the pET vector). The pCold I vector is presented as an exemplary vector and the above example is not intended to limit the scope of the invention.

Specific Methodological Details Pertaining to Drawings

Figure 37:
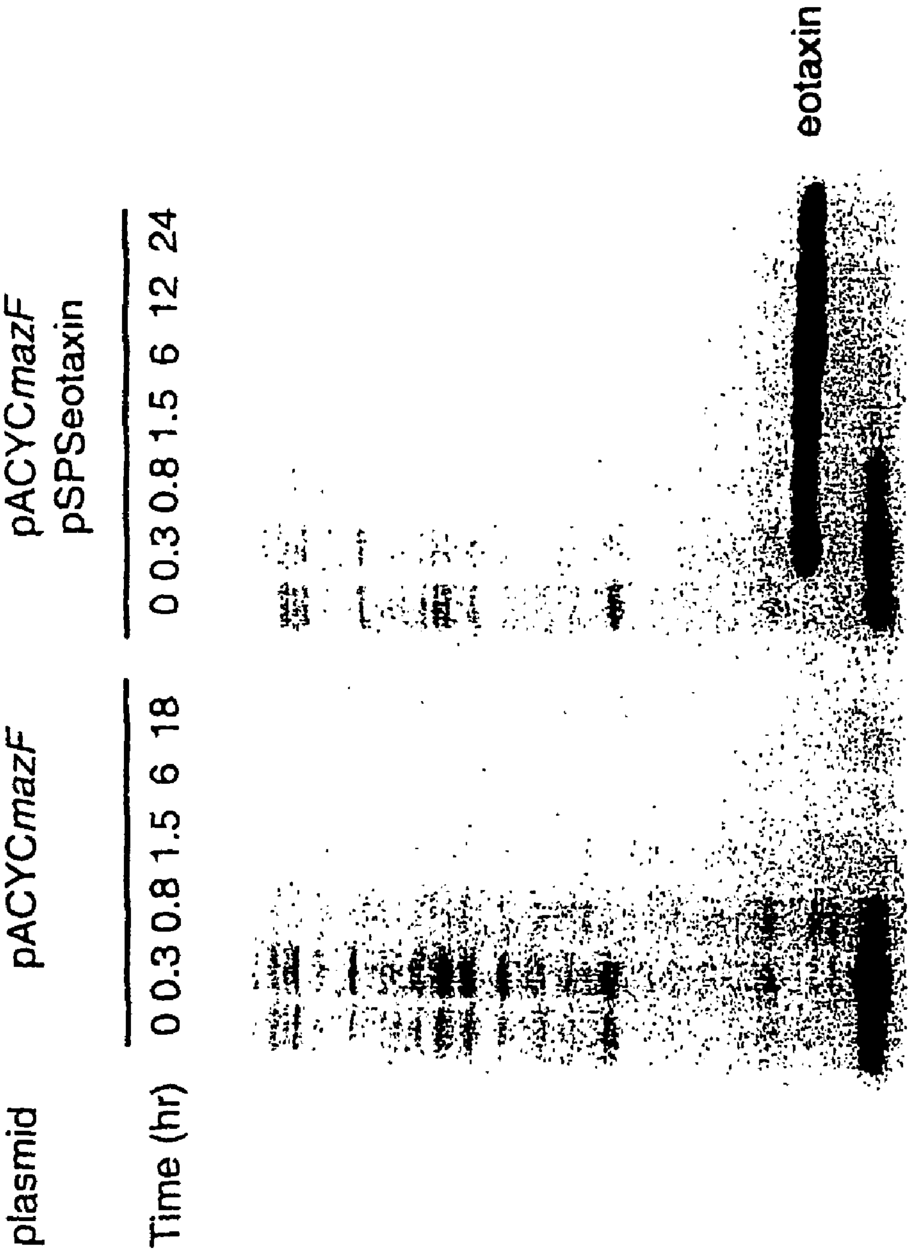
FIG. 37 shows an autoradiogram of a polyacrylamide gel revealing the production of mature human eotaxin in the absence of background protein synthesis.

FIG. 37. *E. coli* BL21(DE3) comprising pACYCmazF or BL21(DE3) comprising pACYCmazF and pCold(SP)eotaxin were grown in M9-glucose medium containing appropriate antibiotics. When the $OD_{600}$ of the culture reached 0.5, the culture was shifted to 15° C. for 15 minutes and 1 mM IPTG was added to the culture. At the indicated time intervals, 1 ml of culture was removed and added to a test tube containing 10 μCi $^{35}$S-methionine. After incubation for 15 minutes (pulse), 0.2 ml of 50 mg/ml methionine was added and incubated for 5 minutes (chase). The labeled cells were washed with M9-glucose medium and suspended in 100 μl of SDS-PAGE loading buffer. 10 μl of each sample was analyzed by SDS-PAGE followed by autoradiography.

Results pCOLDI comprising a novel nucleic acid sequence encoding mature human eotaxin was used as a template. See FIG. 36. The resultant plasmid was designated pCold(SP)eotaxin. Plasmid pACYCmazF comprising a mazF gene under the control of a T7 promoter was used for inducing expression of MazF. *E. coli* BL21(DE3) cells comprising either pACYC-mazF alone or pACYCmazF and pCold(SP)eotaxin were grown in M9-glucose medium containing appropriate antibiotics. When the $OD_{600}$ of the culture reached 0.5, the culture was shifted to 15° C. for 15 minutes and 1 mM of IPTG was added to the culture. At the indicated time intervals, 1 ml of culture was added to a test tube containing 10 μCi $^{35}$S-methionine. After a 15 minute incubation in the presence of label (pulse), 0.2 ml of 50 mg/ml methionine was added and the culture incubated for 5 minutes (chase). The labeled cells were washed with M9-glucose medium and suspended in 1001 of SDS-PAGE loading buffer. 10 μl of each sample was analyzed by SDS-PAGE followed by autoradiography. Expression of the mazF gene inhibited the protein synthesis in BL21(DE3) cells, as reported previously (Zhang et al. 2003, supra). Synthesis of mature human eotaxin, however, which is encoded by an mRNA which does not comprise an ACA sequence, was not inhibited by mazF expression. See FIG. 37. This result demonstrates that large quantities of a single protein can be obtained using the single-protein production method of the present invention.

Of note, parallel experiments have also been performed wherein *E. coli* BL21(DE3) cells comprising only pCold(SP) eotaxin were grown in M9-glucose medium containing appropriate antibiotics. Such experiments reveal the effect of MazF expression in this system. When cells carrying pCold (SP)eotaxin were cold-shocked in the absence of MazF induction, a large number of background *E. coli* proteins were also produced together with human eotaxin. As described herein above, when MazF is induced together with eotaxin, the cellular protein background is dramatically reduced. After 3 hours of MazF induction, background protein synthesis is almost completely eliminated, creating cells which are able to continue to produce only a single protein, namely human eotaxin.

The production of eotaxin lasts for at least 72 hours and the rate of eotaxin production is unchanged during the first 36 hours, indicating that the protein-synthesizing capacity of the cells is unaffected by MazF expression for almost 3 days. This demonstrates that ribosomes, tRNAs, all the other cellular components required for protein synthesis are not affected by MazF induction. These results also imply that energy metabolism and nucleotide synthesis, as well as amino acid biosynthesis, are largely unaffected by MazF expression.

It is also noteworthy that during the 72-hour incubation of the cell culture wherein MazF expression is induced, the $OD_{600}$ (0.5) did not increase, indicating that cell growth after MazF induction is completely inhibited, while the cells maintain full protein synthesis capacity. In the absence of MazF induction, however, the $OD_{600}$ increases from 0.5 to 1.2 during the 72-hour incubation at 15° C. as evidenced by the production of background cellular proteins.

In order to determine the production levels of eotaxin in the above expression system, the same amount of the culture is isolated and analyzed by SDS-PAGE. At 36 hr after cold shock, a clearly detectable, stained eotaxin band is evident and accounts for approximately 5% of total cellular protein. These results were obtained using M9 minimum medium as described above. The use of M9 medium is important for isotopic-enrichment of proteins with $^{13}$C-glucose and $^{15}$N—$NH_4Cl$. If it is, however, desirable to produce unlabeled proteins in a large quantity, a rich medium such as L-broth (LB) medium can alternatively be used. Indeed, the present inventors have found that eotaxin production can be as high as 20% of the total cellular protein or 40 mg/l of culture (1 g from 25 liter culture) in cultures incubated in LB medium. It is important to note that eotaxin produced in cells incubated in either M9 or LB medium is completely soluble and no inclusion forms are formed.

As indicated herein above, cell mass does not increase during the incubation period because cell growth is completely inhibited during the cold-shock incubation. The cellular machinery is, therefore, exclusively dedicated to the production of a cloned gene in a pCold vector upon cold shock in the present single protein production (SPP) system. Therefore, upon MazF induction, a cell culture can be concentrated to a degree not consistent with maintained viability under conditions wherein cell growth occurs. Indeed, the present inventors have determined that exponentially growing cultures can be concentrated at least 4 fold ($OD_{600}$ from 0.7 to 2.8) without affecting the yield of the cloned gene product. This means that one can use only 25% of the medium used for normal cultures wherein cell growth occurs. In other words, 1 g of human eotaxin can potentially be produced using only 6.5 liters of LB medium. This is a particularly relevant advantage of the SPP system of the present invention because this feature dramatically reduces the cost involved in expressing large amounts of proteins or isotope-enriched proteins for NMR structural study.

Cell-free Expression Systems: Extracts from rabbit reticulocytes, wheat germ and *E. coli* comprise the most frequently used cell-free translation systems. All are prepared as crude extracts which comprise the macromolecular components (70S or 80S ribosomes, tRNAs, aminoacyl-tRNA synthetases, initiation, elongation and termination factors, etc.) necessary for translation of exogenous RNA. Each extract is generally supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, K+, etc.) to ensure efficient translation.

The genetic material used (e.g., RNA or DNA) determines which of the two approaches to in vitro protein synthesis is of utility. Standard translation systems, such as reticulocyte lysates, use RNA as a template, whereas “coupled” and “linked” systems utilize DNA templates which are transcribed into RNA, which is subsequently translated.

Rabbit reticulocyte lysate: Rabbit reticulocyte lysate is an efficient in vitro eukaryotic protein synthesis system used for translation of exogenous RNAs (either natural or engineered). Reticulocytes are highly specialized enucleated cells whose in vivo function is primarily directed to the synthesis of hemoglobin, which comprises more than 90% of the protein synthesized by reticulocytes. These immature red cells possess all of the necessary machinery to produce large quantities of globin protein, including sufficient globin mRNA and components of the cellular translation system (as detailed herein above and known in the art). The endogenous globin mRNA can be eliminated by incubation with $Ca^{2+}$-dependent micrococcal nuclease, which is later inactivated by chelation of the $Ca^{2+}$ by EGTA. Such nuclease-treated lysates exhibit low background and efficient utilization of exogenous RNAs at even low concentrations. Exogenous proteins are synthesized at a rate close to that observed in intact reticulocyte cells. Either untreated or treated reticulocyte lysates may be used for the synthesis of larger proteins from either capped or uncapped RNAs (eukaryotic or viral).

Wheat germ extract: In that wheat germ extract has minimal background incorporation due to low levels of endogenous mRNA, it is a convenient alternative to rabbit reticulocyte extracts. Wheat germ extract efficiently translates exogenous RNA from a variety of different organisms, including those derived from viruses, yeast, higher plants, and mammals. It is a preferred system in which to translate RNA containing small fragments of double-stranded RNA or oxidized thiols, which inhibit rabbit reticulocyte lysate.

Capped or uncapped RNA templates: Both reticulocyte lysate and wheat germ extract are effective systems for translating in vitro transcribed RNA or RNA isolated from cells or tissue. The presence of a 5' cap structure may enhance translational activity when using RNA synthesized in vitro. Translation by wheat germ extracts is generally more cap-dependent than translation by reticulocyte lysate extracts. If determined to be desirable, RNA capping can be achieved by subcloning the coding sequence into a prokaryotic vector, which can be expressed directly from a DNA template in an *E. coli* cell-free system.

In standard translation reactions, purified RNA is used as a template for translation. "Linked" and "coupled" systems, on the other hand, use DNA as a template. RNA is transcribed from the DNA and subsequently translated without any purification. Such systems typically require template DNA with a prokaryotic phage polymerase promoter (T7, T3, or SP6). An RNA polymerase (e.g., that of a prokaryotic phage) transcribes the DNA into RNA, and eukaryotic or prokaryotic extracts translate the RNA into protein. DNA templates for transcription:translation reactions may be cloned into plasmid vectors or generated by PCR. The "linked" system is a two-step reaction, involving transcription using a bacteriophage polymerase and subsequent translation in a rabbit reticulocyte or wheat germ lysate. The transcription and translation reactions may be performed separately or may be coupled.

*E. coli* extracts: Unlike eukaryotic systems in which transcription and translation occur sequentially, transcription and translation occur simultaneously in *E. coli* cells. In vitro *E. coli* translation systems, therefore, involve a one-step reaction. During transcription, the 5' end of the RNA becomes available for ribosomal binding, and undergoes translation while its 3' end is still being transcribed. The early binding of ribosomes to the RNA maintains transcript stability and promotes efficient translation. Thus, bacterial translation systems are well suited for expeditious expression of either prokaryotic or eukaryotic gene products. In a preferred embodiment, a Shine-Dalgarno ribosome binding site is included upstream of the initiator codon of a DNA template used in order to promote high protein yield and optimal initiation fidelity. Capping of eukaryotic RNA is not required in *E. coli* translation systems.

*E. coli* extracts also confer additional benefits in that cross-reactivity or other problems associated with endogenous proteins in eukaryotic lysates are reduced or eliminated. Moreover, the *E. coli* S30 extract system enables expression from DNA vectors comprising natural *E. coli* promoter sequences (such as lac or tac). *E. coli* cell-free systems consist of a crude extract rich in endogenous mRNA. To prepare the extract for use in transcription/translation, it is incubated to effect translation of the endogenous mRNA, which is subsequently degraded. The resultant low levels of endogenous mRNA in such prepared lysates enable identification of the exogenous synthesized product.

Eukaryotic translation signals: Some significant differences exist between prokaryotic and eukaryotic mRNA transcripts that should be taken into consideration. Eukaryotic mRNAs are usually characterized by two post-transcriptional modifications: a 5'-7 methyl-GTP cap and a 3' poly(A) tail. Both of these modifications contribute to the stability of the mRNA by preventing premature degradation. The 5' cap structure also enhances the translation of mRNA by promoting binding to the eukaryotic ribosome and ensuring recognition of the proper AUG initiator codon. The consensus sequence, or "Kozak" sequence, is generally considered the strongest ribosomal binding signal in eukaryotic mRNA. For efficient translational initiation, the key elements are the G residue at the +1 position and the A residue at the −3 position of the Kozak sequence. An mRNA that lacks a Kozak consensus sequence may be translated efficiently in eukaryotic cell-free systems, if it comprises a moderately long 5'-untranslated region (UTR) that lacks stable secondary structure.

Prokaryotic translation signals: The ribosome is guided to the AUG initiation site by a purine-rich region referred to as the Shine-Dalgarno (SD) sequence in bacteria. This sequence is complementary to the 3' end of the 16S rRNA in the 30S ribosomal subunit. The SD region, which is located upstream of the initiation AUG codon, comprises a consensus sequence known in the art. Specific mRNAs vary considerably in the number of nucleotides that complement the anti-Shine-Dalgarno sequence of 16S rRNA, ranging from as few as 2 to 9 or more. The position of the ribosome binding site (RBS) in relation to the AUG initiator is very important for efficiency of translation (usually from −6 to −10 relative to the A of the initiation site).

Example VII

The present invention also encompasses a method for producing large quantities of small single-stranded RNA, which method involves simple biochemical procedures. Development of this method enables the production of large quantities of siRNA or miRNA, for example, which does not require expensive chemical synthetic procedures.

Briefly, RNA comprising a plurality of a short identical sequence, which is tandemly repeated in the RNA, is synthesized using T7 RNA polymerase. The tandemly-repeated sequences in the RNA are separated by a triplet sequence which can be specifically cleaved by an mRNA interferase of the invention, such as MazF (which cleaves specifically at ACA sequences) or PemK (which cleaves specifically at, for example, UAC sequences). Subsequent treatment of an RNA comprising tandemly-repeated sequences separated by an interferase recognition sequence (i.e., a specific triplet sequence) with an mRNA interferase which recognizes the incorporated sites will thus yield identical small RNAs.

Experimental Approach

The production of a 21 mer, CAGGAGAUACCU-CAAUGAUCA (SEQ ID NO: 34)

Step 1: Synthesis of the following two 21 mer DNA fragments (5'-ends are phosphorylated)

```
    11        211        10
5'p-CTCAATGATCACAGGAGATAC-3'    (SEQ ID NO: 35)

3'-TCCTCTATGGAGTTACTAGTG-p 5'   (SEQ ID NO: 36)
```

Step 2: Ligation to obtain multimers

Step 3: PCR with the following two primers:

```
#1
5'-(T7 promoter) -              (SEQ ID NO: 37)

    1         12
GGGACAGGAGATACCT-3'

#2
3'-TGTCCTCTATGGAGTTACTAGTG-5'   (SEQ ID NO: 38)
```

Step 4: RNA production with T7 RNA polymerase using the DNA fragment from (Step 3)

Step 5: MazF treatment of the RNA products from reaction (Step 4) and purification of the 21 mer product.

For some applications, it may be advantageous to use His-tagged T7 RNA polymerase and/or MazF to enable their removal from the reaction mixture using a nickel column.

A skilled artisan will appreciate that the presence of an ACA triplet in the nucleic acid sequence of a desired RNA sequence precludes use of MazF as the interferase for digesting the RNA. Under such circumstances, PemK, which is specific for UAC (U or A) triplet sequences, for example, may be used instead of MazF. In short, an analysis of the RNA sequence in question should be rendered to determine what, if any, recognition sites for known RNA interferases are present. Such an analysis is useful for assessing which RNA interferase(s) is of utility for applications involving a particular RNA.

The present invention, therefore, describes a method for producing large quantities of high quality small RNAs (e.g., siRNA or miRNA) that uses straightforward biochemical means. As such, the method provides a cost effective substitute for expensive and technically challenging protocols involving chemical synthesis of small RNAs.

Example VIII

Induction of cell death by an mRNA interferase: When induced, MazF and PemK cleave cellular mRNAs in a sequence-specific manner and effectively inhibit protein synthesis, leading to cell growth inhibition and cell death. It has been demonstrated that PemK (Kid) expression inhibits cell proliferation in yeast, *Xenopus laevis* and human cells. The co-expression of PemI (Kis) in these cells restores cellular proliferation, thereby releasing cells from the inhibitory effects of PemK (de la Cueva-Mendez et al., 2003, supra). As described herein below, the effects of MazF induction on human cells are examined. Although the T-Rex system (Invitrogen) was used to control induction of MazF in this example, a skilled artisan would appreciate that any inducible expression system may be used in the context of the present invention. The choice of the inducible system is based on several experimental considerations, including, but not limited to, the cell type in which the induction is effected, the level of expression desired, and the kinetics of induction.

Plasmids and cell lines: The *E. coli* mazF gene is cloned into the pcDNA4/TO vector (Invitrogen) under the control of a tetracycline operator TetO2, creating plasmid pcDNA4/TO-MazF. The pcDNA4/TO-MazF plasmid is transformed into the T-Rex-293 cells (Invitrogen), creating the T-Rex 293/MazF cell line, in which the expression of MazF is induced by the addition of tetracycline. The *E. coli* mazE gene is cloned into the pcDNA3 vector, creating plasmid pcDNA3-MazE. The pcDNA3-MazE is transformed into the T-Rex 293/MazF cells, creating the T-Rex 293/MazF/MazE cell line.

Figures 38A, 38B, 38C, 38D, 38E, 38F:
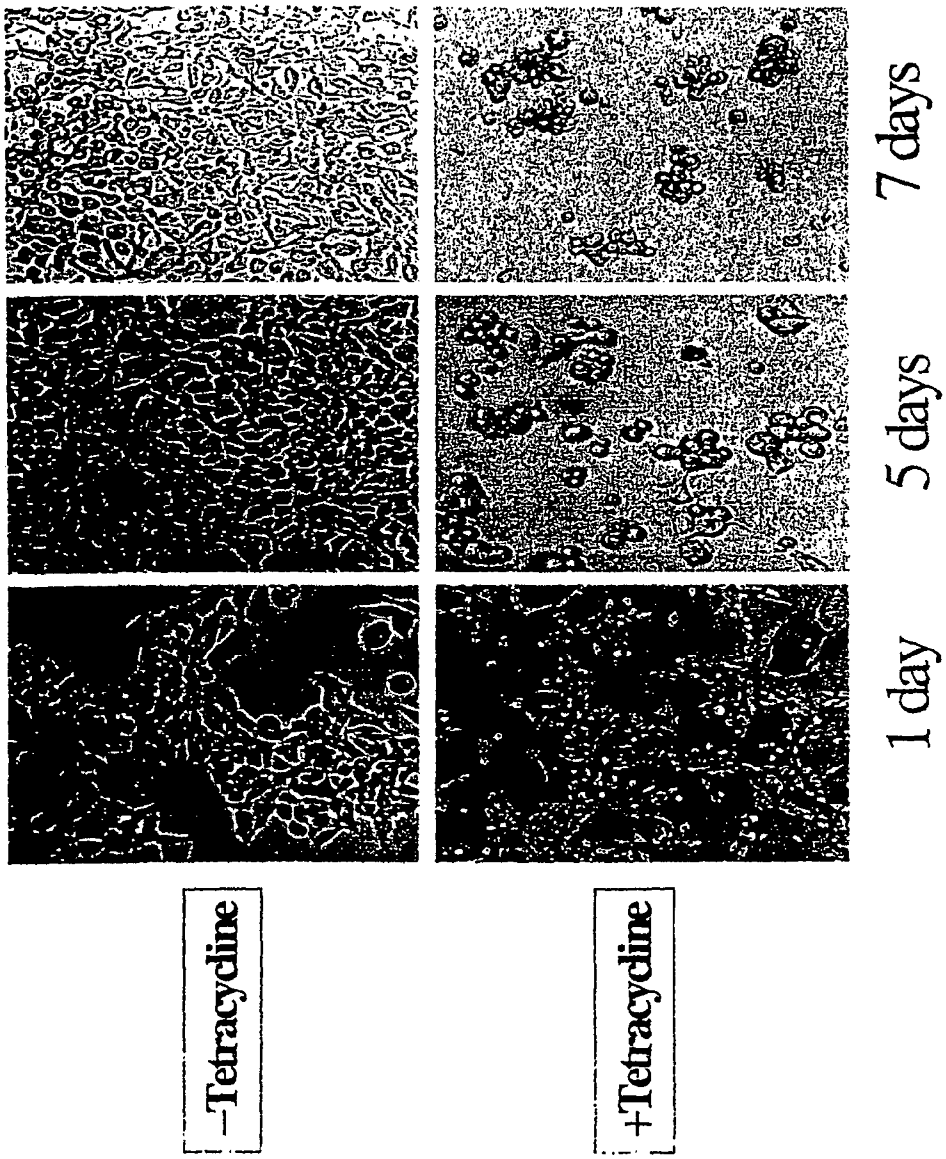
FIGS. 38A-F are micrographs showing the morphology of human cells induced to express MazF toxin (D-F) and uninduced (A-C).

The Toxic effect of MazF on human cells: MazF expression is induced in the T-Rex 293/MazF cells in the presence of tetracycline. At the various time points, dead cells in the cell population are counted by staining with a cellular viability dye comprised of Trypan Blue solution (0.4%) (Sigma). The control experiment is performed in parallel under the same conditions, but in the absence of tetracycline. As shown in FIG. 38, the cellular morphology of T-Rex 293/MazF cells induced to express MazF is dramatically altered by the first day of MazF induction as compared to that of control (uninduced) cells. Notably, about 50% of those cells induced to express MazF are dead by the fifth day, and 80% of induced cells are dead by the seventh day (FIG. 38). These results demonstrate that MazF is toxic to human cells.

The present invention encompasses the use of any suitable mRNA interferase whose expression is responsive to or controlled by an inducible regulatory element(s). Suitable mRNA interferases include those capable of mediating toxic effects when expressed in a cellular context, In a particular embodiment, the cell in which an mRNA interferase is expressed is a mammalian cell. Exemplary mRNA interferases of the invention include orthologs and homologs of *E. coli* MazF.

Accordingly, the present invention also encompasses the use of mRNA interferases of the invention in applications directed to gene therapy. Cells that are engineered to express a molecule, which is defective or deficient in a subject (e.g., a human subject), can also be designed to self destruct via the incorporation of an mRNA interferase of the invention, the expression of which is controlled by an inducible regulatory element(s). Incorporation of an inducible means for the destruction of cells used for gene therapy applications provides a fail-safe mechanism whereby such cells can be eliminated after they have conferred beneficial effects to a subject and/or before they can cause deleterious effects.

Example IX

Generation of a MazFmutants: A MazF mutant (E24A) has been generated in which the glutamic acid (Glu) at position 24 is substituted with an alanine (Ala). As a result of the mutation, the mRNA interferase activity as measured with a synthetic substrate is reduced approximately 10 fold. This reduction in MazF activity is important for a variety of reasons. First, as a result of the mutation, the toxicity to a host cell in which the MazF (E24A) mutant is expressed is significantly reduced. Reduced toxicity enables increased production levels of the MazF mutant in a cell. When using, for example, the pET 28a system, a reasonably high production of MazF has been achieved (approximately 15 mg/l after purification). This high level of expression is important for obtaining a reasonable amount of MazF, which may be doubly labeled with $^{15}N$ and $^{13}C$ for NMR structural determination. Second, the low mRNA interferase activity of the mutant MazF is important for determining the RNA interacting sites on the MazF dimer, which can be assessed by adding a substrate RNA to the $^{15}N$, $^{13}C$-labeled MazF sample. Third, since the mutant MazF retains mRNA interferase activity, the structure of the mutant MazF is likely to be similar to the three-dimensional structure of the wild-type MazF dimer, and its structure complexed with RNA is expected to provide insights into the molecular mechanism for the MazF mRNA interferase function.

Figures 39A, 39B:
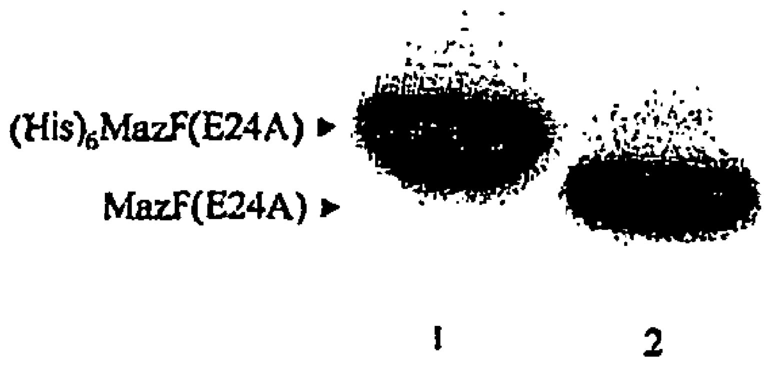
FIGS. 39A-B show (A) the amino acid sequence of the N-terminal extension of the MazF (E24A) mutant expressed with pET28a and (B) a photograph of a polyacrylamide gel showing a band corresponding to uncleaved MazF mutant fusion protein (lane 1) and thrombin cleaved MazF mutant fusion protein (lane 2). The amino acid sequence of the N-terminal extension is designated SEQ ID NO: 100.

The expression of the mutant MazF is carried out with pET 28a so that the product contains an N-terminal 20 residue extension (FIG. 39A), which contains the His-tag and a thrombin cleavage site. The N-terminal extension can be cleaved from the fusion protein as shown in FIG. 39B. The arrow in FIG. 39A indicates the thrombin cleavage site. To cleave the full length MazF(E24A) fusion protein, 0.04 units of thrombin is added to 10 μg Ni-NTA purified $(His)_6$MazF (E24A) and incubated at 4° C. for 8 hr. The cleaved N-terminal fragment is removed using a Ni-NTA column. FIG. 39 shows the successful cleavage and isolation of cleaved MazF fusion protein (lane 1, purified $(His)_6$MazF(E24A); lane 2, $(His)_6$MazF(E24A) after thrombin cleavage). Heteronuclear single quantum coherence (HSQC) spectra before and after the removal of the N-terminal extension reveal that the protein is stable for over a week at room temperature.

In addition, a MazF mutant in which Arg 29 is replaced with Ala has been generated. This (R29A) mutant was also found to be less toxic than wild type MazF, thus enabling its overexpression. Purified $^{15}N$-labeled MazF (R29A) has, for example, been produced at a level of 10 mg/L. This mutant also produced an excellent HSQC spectrum.

Example X

Identification and Characterization of MazF Homologs from Pathogenic Bacteria Identification and characterization of MazF homologs from *Mycobacterium tuberculosis* (*M. tuberculosis*): Tuberculosis (TB) is a chronically infectious disease that causes more than 2 million deaths every year. It is likely one of the oldest human diseases and is caused by *M. tuberculosis*. The present inventors have identified a gene (rv2801c) on the *M. tuberculosis* chromosome, which encodes a protein that is highly homologous to *E. coli* MazF. Specifically, the present inventors have cloned the rv2801c gene and determined that it encodes a protein of 118 amino acid residues having 40% identity to *E. coli* MazF. See FIG. 41A. This *M. tuberculosis* MazF gene (designated herein as MazF-mt1) has been cloned into pBAD; expression of MazF-mt1 from the pBAD vector in response to arabinose induction is toxic in *E. coli*. Of note, the cell colony-forming units (CFU) are decreased by about $10^4$ fold after 60 minutes of MazF-mt1 induction. MazF-mt1 has also been cloned into pET28a and a $(His)_6$-tagged MazF-mt1 has been successfully expressed and purified on a Ni-NTA column.

Figure 40:
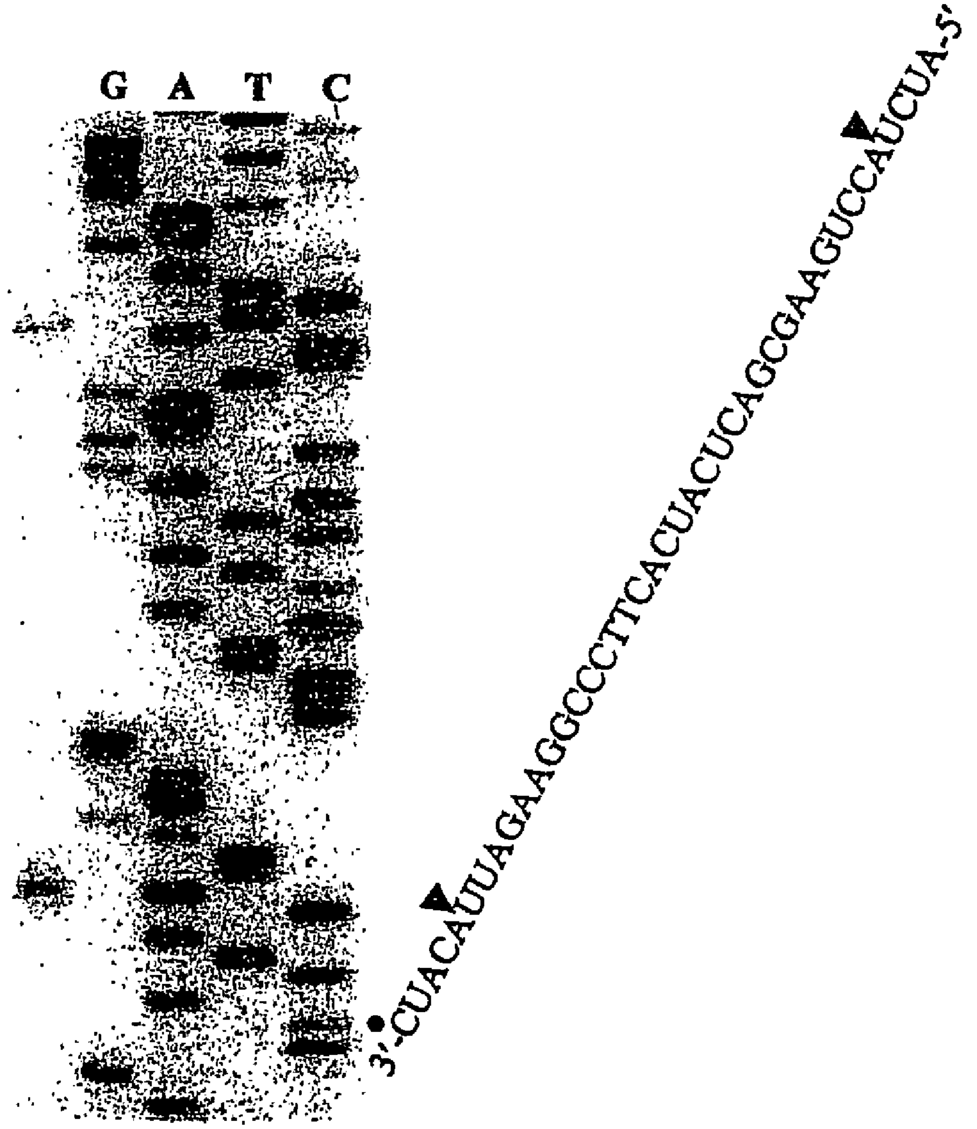
FIG. 40 shows a primer extension analysis of MazF-mt1 mRNA interferase activity. The RNA sequence shown therein is designated SEQ ID NO: 101.

As shown in FIG. 40, MazF-mt1 exhibits specificity for cleaving RNA at UAC sequences, a similar specificity to that of PemK. MazF-mt1 is, therefore, a bona fide member of the mRNA interferase family of proteins. In brief, era mRNA was synthesized by T7 RNA polymerase and the cleavage reaction was carried out as described herein above. The primer extension and the DNA ladder are obtained using the same primer. The MazF-mt1 cleavage sites are indicated by arrowheads.

In addition to the MazF-mt1 gene, the present inventors have also identified four additional MazF homologs encoded by the *M. tuberculosis* chromosome, genomic designations for which are Rv0456A, Rv1991C, Rv0659C and Rv1942C. See FIG. 41B. As shown by the sequence alignment of these genes with MazF, each of these sequences is homologous to *E. coli* MazF and has, therefore, been identified as an *M. tuberculosis* MazF homolog. MazF homologs encoded by Rv1991C, Rv0456a, Rv0659c and Rv1942c protein are designated MazF-mt2, -mt3, -mt4 and -mt5, respectively. Nucleic and amino acid sequences of MazF-mt1, -mt2, -mt3, -mt4 and -mt5 are shown in FIGS. 43A-E and 44A-E.

The genes encoding MazF-mt2, 3, 4 and 5 will be cloned into pBAD vector and their effects on *E. coli* cell growth examined upon induction of their expression in the presence of arabinose as described herein above for MazF-mt1. In vivo mRNA cleavage following induction of the *M. tuberculosis* MazF homologs will also be assessed as described in detail herein above, using Northern blot and primer extension analysis. The in vitro and in vivo protein synthesis will also be examined in the presence of *M. tuberculosis* MazF homologs.

Each of the five *M. tuberculosis* MazF genes will also be cloned into the mycobacterial expression vector pMIP12 (Picardeau et al. (2003) FEMS Microbiol Lett 229, 277-281) to enable their expression in *Mycobacterium smegmatis* (a model nonpathogenic, fast-growing species of the genus *Mycobacterium*) to test their toxic effects in this bacterium under different growth conditions. It is particularly interesting to elucidate how the genes for MazF-mt are regulated in *M. tuberculosis*. The pathogenesis of tuberculosis depends on the formation of lung granulomas, which are also the site of the organism's persistence in a non-growing state, brought about by oxygen and nutrient limitation. Understanding the physiology of the bacteria in this latent state is crucial to improving diagnosis and treatment of this devastating disease. DNA microarray analysis of *M. tuberculosis* genes will be performed under different growth conditions to determine how MazF-mt genes are regulated in response to such conditions.

The redundancy of bacterial toxin-antitoxin pairs suggests that they play an important role in cellular physiology. A variety of growth conditions have been explored to examine the in vitro conditions that induce expression of the genes encoding these molecules. A number of studies have suggested that one of the conditions for induction of mazF depends upon ppGppp and the stringent response. For example, one of the earliest observations was that a mutant mazEF null *E. coli* did not die after ppGppp levels were artificially increased (Aizenman et al., 1996, supra). The *M. tuberculosis* relA gene, encoding the ppGpp synthetase, has been cloned and characterized and shown to play a role in long-term survival in vitro (Primm et al., 2000, J Bacteriol 182, 4889-4898). These workers showed increased ppGpp(p) levels in all of the conditions listed below. To extend these findings to investigate the transcriptional response of MazF homologs to varied growth conditions, RNA will be prepared from virulent *M. tuberculosis* (strain H37Rv) subjected to the set of conditions listed below, and quantitative polymerase chain reaction (Q-PCR) will be used to evaluate the transcriptional response of the MazF homologs.

Growth Conditions

Stationary phase: H37Rv cells are grown in normal mycobacterial medium (Middlebrook 7H9 supplemented with 0.2% dextrose, 0.2% glycerol, 0.5% BSA fraction V and 0.1% Tween 80). After reaching an $OD_{600}$ (*M. tuberculosis* has a doubling time of approximately 24 hrs), a 3 day in stationary phase follows, after which total RNA is prepared from the cells. The control for this experiment is RNA from cells in the mid-logarithmic phase of growth.

Azide: H37Rv cells in mid-logarithmic growth are split into two cultures; one of which is treated with 5 mM sodium azide for 2 hr.

Carbon starvation: H37 Rv cells in early to mid-logarithmic phase are washed and resuspended in 7H9 medium without a carbon source for 24 hr.

Amino acid downshift: H37Rv are grown to mid-logarithmic phase in 7H9 medium, supplemented with 20 amino acids. The cultures are washed extensively in amino acid-free medium, split into two cultures and fresh medium, one with amino acids and one without, for 24 hours.

Amino acid starvation: *E. coli* cells when treated with serine hydroxymate, are starved for the amino acid L-serine, and have been shown to induce the expression of mazEF locus (Christensen et al., 2003, supra). *M. tuberculosis* showed no increase in ppGpp(p) when treated with serine hydroxymate suggesting that this species may be insensitive to the toxic effects of this amino acid analog (Primm et al., 2000, supra). Amino acid analogs with characterized toxic effects will be tested for the ability to induce the MazF-mt homologues.

Antibiotic treatment: Antibiotics known to affect protein synthesis (streptomycin) and RNA transcription (rifampin) in *M. tuberculosis*, are tested for the ability to induce the MazF homologues in H37Rv.

*M. tuberculosis* lies in a state of latency in about one-third of the world's population, sealed within granulomatous lesions, presumably without access to nutrients or oxygen (Flynn and Chan, 2001, Annu Rev Immunol 19, 93-129). Reactivation of disease occurs when the immune system of the host is somehow compromised (by, e.g., HIV status, poor nutrition, etc). Alarmingly, an increasing number of latent cases among HIV-ridden regions of the world are also multi-drug resistant and therefore difficult or impossible to treat. Understanding the mechanism for harnessing these endogenous mechanisms of direct bacterial growth control, therefore, holds great promise for developing novel therapies for this devastating disease. Accordingly, determining the role of endogenous MazF-mt genes in both latent and activated/re-activated states will offer insights useful for the design and/or identification of alternative therapeutic agents.

The present inventors have also utilized BLAST searches to reveal that MazF homologs exist in many prokaryotic organisms, including other pathogens such as *S. aureus* and *B. anthracis*. See FIG. 41. Specifically, the present inventors have identified MV1993 as a MazF homolog (MazF-sa1) in *S. aureus*. See FIG. 41B. *S. aureus* is a gram-positive bacterium that is the most common gram-positive pathogen causing nosocomial infection at hospitals. *E. coli* MazF and MazF-sa1 exhibit 25% identity and 44% similarity.

In addition, MazF homologues are also identified in *B. anthracis* and *B. subtilis*. See FIG. 41B. *E. coli* MazF and its homolog in *B. subtilis* (MazF-bs1) exhibit 32% identity and 48% similarity. *E. coli* MazF and its homolog in *B. anthracis* (MazF-ba1) exhibit 32% identity and 48% similarity. *B. anthracis* and *B. subtilis* are both gram-positive bacteria. There are only seven amino acid substitutions between MazF-bs1 and MazF-ba1. The differences in amino acid sequence and position are shown in FIG. 41B and are elaborated here, as indicated by the single letter abbreviation for the residue present in the MazF-bs1 gene first, then the numerical position, then the single letter abbreviation for the residue present in the MazF-ba1 (A42V, R66K, D97E, E98V, D101I, K102R and A112G). Nucleic and amino acid sequences of MazF (Pem-like) homologs in *S. aureus, B. subtilis, B. anthracis*, and *E. coli* ChpBK are shown in FIGS. 45A-D and 46A-D.

Example XI

Optimization of the SPP System in *E coli*

The *E. coli* SPP system of the present invention may be optimized for the expression of different proteins by varying, among other experimental parameters, various growth conditions. A skilled artisan would appreciate that the goals to be achieved in this regard pertain to: (a) prolonged maintenance of a cell's protein synthesizing capability after MazF induction; (b) reduction or elimination of background cellular protein synthesis; and (c) increased expression levels of a desired protein. It will also be appreciated that the SPP system of the present invention may involve the expression of mRNA interferases other than MazF. Co-expression of factors, which may assist expression and/or stability of products, may also be considered in the context of the SPP system to achieve improved or optimal expression levels of a polypeptide of choice.

The present inventors have varied a number of culture conditions following MazF induction to optimize for production of a protein of interest. Although these experiments are designed to optimize expression of the human eotaxin gene, the principles are equally well applied to the expression of other proteins. To begin, the eotaxin gene was synthesized using preferred codons for *E. coli* but eliminating all ACA sequences in the gene. The synthetic gene was cloned into pColdI vector to enable eotaxin expression following induction by cold shock or temperature downshift to 15° C. Using this eotaxin system, conditions are varied to prolong the synthesis of eotaxin after the induction of MazF as described below.

The present inventors have determined that MazF induction at 37° C. followed by eotaxin induction at 15° C. significantly affects eotaxin production. Specifically, a comparison of MazF induction at 15° C. with MazF induction at 37° C. revealed that MazF induction at a higher temperature substantially reduces background due to general cellular protein synthesis. This finding was evidenced by the near absence of detectable protein bands corresponding to expression of cellular proteins. Under these experimental conditions, however, eotaxin synthesis is also significantly reduced. At higher temperatures, MazF may cause damage to the cells due to, for example, increased susceptibility of ribosomes/tRNAs to ribonuclease activity of MazF at higher temperatures; and/or decreased stability of other cellular components, which are required for protein synthesis, nucleotide and amino acid biosynthesis, and energy production, at 37° C. Since these factors cannot be produced in the cells after MazF induction, their loss or reduction would lead to reduction in eotaxin production capacity.

In order to optimize protein expression, a number of experimental parameters can be varied, including those described below. It is to be understood that the following conditions are described with regard to MazF and eotaxin, but are applicable to other combinations of mRNA interferase and desired polypeptide. *E. coli* BL21(DE3) carrying both pACYCmazF and pCold(SP)eotaxin are cultured in M9 minimum medium (15-ml culture each) at 37° C. to mid-log phase ($OD_{600}$=0.5 to 0.8). Then, MazF induction is carried out at five different temperatures; 37, 30, 25, 20 and 15° C. After 10 minutes of pre-incubation at these different temperatures, 1 mM IPTG is added to induce MazF for 5, 10 and 15 minutes. Cultures are then maintained at 15° C. for eotaxin induction. The cells are labeled with $^{35}$S-methionine for 15 minutes at 0, 0.5, 1, 2, 4, 8, 12, 24, 36, 48, 72 and 96 hr after cold shock. The SDS-PAGE analysis of total cellular proteins reveals the preferred conditions for the SPP system in terms of background cellular protein synthesis, the rate of eotaxin production, and the duration of eotaxin production. For this determination and similar assessments for other polypeptides, the actual amount of eotaxin or other polypeptide produced at each time point is estimated by Coomassie blue staining.

The activity of intracellular proteases, such as Lon and ClpP, may also contribute to protein accumulation and stability. It has been shown, for example, that mutations in clpP and lon (single or double mutations) significantly reduce the degradation of cellular proteins in *E. coli* strains (Kandror et al., 1994, Proc Natl Acad Sci USA 94, 4978-4981). In keeping with these findings, the SPP system may be improved by constructing strains harboring these mutations (lon, clpP and lon-clpP) by transducing these mutations into BL21(DE3) cells by P1 transduction. Accordingly, an examination of polypeptide accumulation in BL21(DE3) cells, wherein one or more of these protease genes has been deleted, may reveal improved protein yield at 3-4 days after the eotaxin induction in the SPP system. In this fashion, particular conditions for the *E. coli* SPP system can be established to achieve the highest production of eotaxin with the lowest background of the cellular protein synthesis. Moreover, as described herein above, such an experimental approach is equally well applied to other SPP systems wherein a different mRNA interferase and polypeptide are utilized.

Another strategy for reducing levels of background cellular protein synthesis is to increase the production of MazF. This may be achieved by eliminating ACA sequences in the mazF gene, which may lead to degradation of MazF transcripts. Surprisingly, there are a total of nine ACA sequences in the mazF ORF which encodes a 111-residue protein. This frequency of ACA sequences is unusually high with respect to a predicted frequency based on random chance. These ACA sequences may play a role in MazF autoregulation, whereby MazF cleaves its own mRNA at these ACA sites, and thereby results in significant reduction of MazF protein production. On the basis of these considerations, removal of some or all of the ACA sequences in the mazF ORF is envisioned. See FIG. 42. Of note, the proposed base changes therein do not alter the amino acid sequence of MazF. To begin, the first 6 residues in the N-terminal half of MazF are altered using a PCR-based approach and the resultant gene designated mazFa. Independently, the three ACA sequences in the C-terminal half are altered, together with a change of the codon encoding Leu99 from UUA to CUG, which is a more preferred codon for leucine in *E. coli*. The resultant gene is designated mazFb. A combination of both mazFa and mazFb mutations serves to create mazFa,b in which all ACA sequences are removed.

Using the wild-type mazF, mazFa (-6ACA), mazFb (-3ACA) and mazFab (-9ACA), the effects of ACA removal from MazF can be determined in the SPP system. Experimentally, the wild-type mazF gene in pACYC mazF is replaced with mazFa, mazFb or mazFab. Using these four plasmids, it is possible to examine how effectively the removal of the ACA sequences from mazF reduces background protein synthesis.

To achieve a higher yield of a protein using the SPP system, the use of a rich media such as LB, rather than M9 medium, may be preferred. Therefore, experimental parameters are varied to optimize conditions for growth in LB medium. Various growth conditions can be optimized for culturing in LB media as described herein above. Such conditions include, but are not limited to, optimal temperature for MazF induction, the optimal time period for MazF induction, optimal temperature for eotaxin production, and optimal incubation time to maximize eotaxin production. Although these experiments are described as they pertain to eotaxin production as a model system, the optimal conditions for the highest yield of a different protein may vary. For each target protein, therefore, minor experimental changes may be required to achieve optimal expression levels. Other growth media, known to those skilled in the art, may also be used in conjunction with the SPP system and expression therein optimized as described herein above for M9 and LB media.

As described herein above, the present inventors have identified another mRNA interferase called PemK from plasmid R100 which cleaves mRNAs at UAC/A/U sequences. See Example IV. A number of other mRNA interferases have also been identified, including ChpBK from *E. coli*, five different mRNA interferases from *M. tuberculosis* and one from *Bacillus anthracis*. All of the above listed mRNA interferases are potential candidates that may be used advantageously to improve the SPP system. Upon characterization of their RNA-cleavage specificities, their effectiveness in the SPP system will be determined and compared to that of MazF. Since these mRNA interferases are expected to have different RNA cleavage specificities, they may be more effective in reducing background cellular protein synthesis and may cause less cellular damage than MazF. These mRNA interferases are useful tools not only for development of the SPP system in *E. coli*, but also for the development of SPP systems in other organisms, including yeast.

The *E. coli* SPP system described herein utilizes pColdI vectors, which induce protein production at low temperatures. Protein production at low temperatures is beneficial for many proteins, since they are frequently folded more efficiently and are stable at lower temperatures. Nevertheless, co-expression of molecular chaperones may further improve the yield of properly folded proteins in the SPP system. For this purpose, the gene for a cold-shock molecular chaperone known as trigger factor (Kandror and Goldberg, 1997, supra) has been cloned for use in the SPP system of the present invention. Since trigger factor is thought to assist protein folding at low temperatures, the effect of co-expression of trigger factor on expression of a desired protein may be used to advantage in the SPP system. The genes for trigger factor, as well as GroEL and GroES (heat shock molecular chaperones) will also be cloned into the pColdI vector to examine the protein yield and the effect on the solubility of expressed proteins.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method for making a polypeptide in a prokaryotic cell, said method comprising:

(a) transfecting said prokaryotic cell with a nucleic acid sequence encoding said polypeptide, wherein the nucleic acid sequence encoding said polypeptide is mutated to replace mRNA interferase recognition sequences with an alternate triplet codon, wherein amino acid sequences of said polypeptide encoded by said mutated nucleic acid sequence are not altered by said mutating;

(b) transfecting said prokaryotic cell with a nucleic acid sequence encoding an mRNA interferase, wherein said mRNA interferase recognizes said mRNA interferase recognition sequences; and (c) expressing the nucleic acid sequences of step (a) and (b) in said prokaryotic cell, wherein expressing the nucleic acid sequences of step (a) and (b) in said prokaryotic cell produces the polypeptide in said prokaryotic cell, wherein the mRNA recognition sequences are Adenine-Cytosine-Adenine (ACA) sequences and the mRNA interferase is MazF comprising SEQ ID NO: 2.

2. The method of claim 1, wherein expression of a nucleic acid of step (b) reduces or inhibits synthesis of cellular polypeptides encoded by nucleic acid sequences comprising ACA sequences.

3. The method of claim 1, wherein step (a) and step (b) are performed simultaneously.

4. The method of claim 1, further comprising incubating said cell prior to or during step (c) in media comprising at least one radioactively labeled isotope.

5. A method for making a polypeptide in a prokaryotic cell, said method comprising:

(a) transfecting said prokaryotic cell with a nucleic acid sequence encoding said polypeptide, wherein the nucleic acid sequence encoding said polypeptide is mutated to replace mRNA interferase recognition sequences with an alternate triplet codon, wherein amino acid sequences of said polypeptide encoded by said mutated nucleic acid sequence are not altered by said mutating;

(b) transfecting said prokaryotic cell with a nucleic acid sequence encoding an mRNA interferase, wherein said mRNA interferase recognizes said mRNA interferase recognition sequences; and (c) expressing the nucleic acid sequences of step (a) and (b) in said prokaryotic cell, wherein expressing the nucleic acid sequences of step (a) and (b) in said prokaryotic cell produces the polypeptide in said prokaryotic cell, wherein the mRNA recognition sequences are Uracil-Adenine-X (UAX) sequences, wherein X is a Cytosine (C), A, or U, and the mRNA interferase is PemK comprising SEQ ID NO: 4.

6. The method of claim 5, wherein step (a) and step (b) are performed simultaneously.

7. The method of claim 5, further comprising incubating said cell prior to or during step (c) in media comprising at least one radioactively labeled isotope.

8. The method of claim 5, wherein expression of a nucleic acid of step (b) reduces or inhibits synthesis of cellular polypeptides encoded by nucleic acid sequences comprising UAX sequences.

* * * * *